(12) United States Patent
Sunagawa et al.

(10) Patent No.: US 7,205,291 B2
(45) Date of Patent: Apr. 17, 2007

(54) CARBAPENEM COMPOUNDS

(75) Inventors: Makoto Sunagawa, Osaka (JP); Akira Sasaki, Osaka (JP)

(73) Assignee: Dainippon Sumitomo Pharma Co., Ltd., Osaka-Fu (JP)

( * ) Notice: Subject to any disclaimer, the term of this patent is extended or adjusted under 35 U.S.C. 154(b) by 58 days.

(21) Appl. No.: 10/494,603

(22) PCT Filed: Nov. 1, 2002

(86) PCT No.: PCT/JP02/11477

§ 371 (c)(1),
(2), (4) Date: May 4, 2004

(87) PCT Pub. No.: WO03/040146

PCT Pub. Date: May 15, 2003

(65) Prior Publication Data

US 2005/0020566 A1    Jan. 27, 2005

(30) Foreign Application Priority Data

Nov. 5, 2001 (JP) ............................. 2001-339195
May 20, 2002 (JP) ............................. 2002-145485

(51) Int. Cl.
*A61K 31/397* (2006.01)
*C07D 487/06* (2006.01)

(52) U.S. Cl. ................... 514/210.09; 540/302

(58) Field of Classification Search ........... 514/210.09; 540/302
See application file for complete search history.

(56) References Cited

U.S. PATENT DOCUMENTS

| | | | |
|---|---|---|---|
| 4,260,627 A | 4/1981 | Christensen et al. | 514/210.09 |
| 4,775,669 A | 10/1988 | Cama et al. | 514/20 |
| 5,034,385 A | 7/1991 | DiNinno et al. | 514/80 |
| 5,153,187 A | 10/1992 | Iwasaki et al. | 514/210 |
| 5,208,348 A | 5/1993 | Iwasaki et al. | 548/544 |
| 5,256,777 A | 10/1993 | DiNinno et al. | 540/302 |
| 5,258,509 A | 11/1993 | Nakagawa et al. | 540/302 |
| 5,338,875 A | 8/1994 | DeCamp et al. | 556/402 |
| 5,534,510 A | 7/1996 | Abe et al. | 514/210 |
| 5,583,218 A | 12/1996 | Takemura et al. | 540/350 |
| 5,587,374 A | 12/1996 | Perboni et al. | 514/210 |
| 5,679,790 A | 10/1997 | Abe et al. | 540/350 |
| 5,783,703 A | 7/1998 | Hayashi et al. | 548/193 |
| 5,821,362 A | 10/1998 | Kaneko et al. | 540/302 |
| 6,342,494 B1 | 1/2002 | Matsui et al. | 514/210.13 |
| 6,410,525 B1 | 6/2002 | Matsui | 514/210.13 |

FOREIGN PATENT DOCUMENTS

| | | |
|---|---|---|
| EP | 444889 | 9/1991 |
| JP | 2-49783 | 2/1990 |
| WO | 02/053566 | 7/2002 |

OTHER PUBLICATIONS

Cama et al., Total synthesis of thienamycin analogs-III. Syntheses of 2-aryl and 2-heteroaryl analogs of thienamycin. Tetrahedron, 39(15), pp. 2531-2549, (1983), Abstract.*
W. J. Weiss et al., "*In Vivo* Activities of Peptidic Prodrugs of Novel Aminomethyl Tetrahydrofuranyl-1 β-Methylcarbapenems", Antimicrobial Agents and Chemotherapy, vol. 43, No. 3, pp. 460-464, Mar. 1999.
L. D. Cama et al., "Total Synthesis of Thienamycin Analogs-III, Synthesis of 2-Aryl and 2-Heteroaryl Analogs of Thienamycin", Tetrahedron, vol. 39, No. 15, pp. 2531-2549, 1983.
R. N. Buthikonda et al., "Structure-Activity Relationships in the 2-Arylcarbapenem Series: Synthesis of 1-Methyl-2-Arylcarbapenems", J. Med. Chem., vol. 30, pp. 871-880, 1987.
L. D. Cama et al., "Total Synthesis of Thienamycin Analogs-III. Synthesis of 2-aryl and 2-heteroaryl analogs of thienamycin", Tetrahedron, vol. 39, No. 15, pp. 2531-2549, 1983.

* cited by examiner

*Primary Examiner*—James O. Wilson
*Assistant Examiner*—Ebenezer Sackey
(74) *Attorney, Agent, or Firm*—Wenderoth, Lind & Ponack, L.L.P.

(57) ABSTRACT

A compound or its pharmaceutically acceptable salt represented by the following formula:

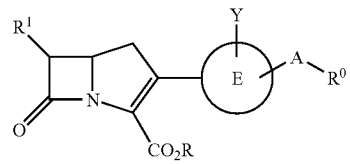

The invention is a carbapenem compound which has a potent antibacterial activity over a broad range of Gram negative and Gram positive bacteria, especially penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*, and has excellent oral absorbability.

13 Claims, No Drawings

CARBAPENEM COMPOUNDS

This application is a U.S. national stage of International Application No. PCT/JP02/11477 filed Nov. 1, 2002.

TECHNICAL FIELD

The present invention relates to a new carbapenem compound. In more detail, the present invention relates to a carbapenem compound, wherein a substituted phenyl or a substituted thienyl is directly substituted at position 3 of 7-oxo-1-azabicyclo[3.2.0]hept-2-ene which is a basic nucleus of the carbapenem compound. Furthermore, the present invention relates to an antibacterial agent containing such a compound.

BACKGROUND ART

The carbapenem compounds which have been developed and commercialized are poor in absorbability from the digestive tract and therefore, they are clinically used only in a form of injection, mainly intravenous injection. However, in the clinical field, it is desirable to select several administration routes from the viewpoint of circumstances or wishes of a patient, a therapeutic object, etc. Especially, oral administration of an antibacterial agent is easy and convenient for administration to a patient in comparison with injection. In view of the care of a patient at home, oral administration of the antibacterial agent is more convenient and the clinical usability is extremely high. It has been strongly desired in the clinical field to develop a carbapenem compound which has a potent antibacterial activity especially against penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*, and is rich in safety and is orally administrable. However none of such agents has been put on the market. Tricyclic carbapenem compounds which have been studied and developed until now are disclosed for example, in WO92/03437. These compounds have a characteristic structure in a side chain having a ring which is fused via C—C bond and they are modified to a prodrug thereof for increase of oral absorbability, but their safety in the clinical test is not reported. Besides, there are several known 1β methylcarbapenem compounds (Japanese patent publication 2-49783, Japanese patent publication 8-53453, Japanese patent publication 4-279588, Japanese patent publication 2-223587, WO98/34936, WO99/57121, Antimicrobial Agents and Chemotherapy, Mar. 1999, p460–464). All of them have a structural property having 1β-methyl group and a side chain via sulfide bond which are the said to contribute to an increase of chemical stability and in vivo (biological) stability, and are modified to a prodrug of them for increase of oral absorbability. Especially, the clinical trial was carried out on compounds disclosed in Japanese patent publication 2-49783 and Japanese patent publication 8-53453, but the safety of them and so on have been not clear.

On the other hand, carbapenem compounds having an aryl ring via C—C bond as a side chain structure were known since 1980s (U.S. Pat. No. 4,775,669, U.S. Pat. No. 5,258, 509, Tetrahedron, 1983, Vol. 39, p2531–2549, Journal of Medicinal Chemistry, 1987, Vol. 30, p871–880). Although there are many other reports on these compounds, these reports are concerned only to studies and developments on injections thereof, but not to studies for oral application thereof.

DISCLOSURE OF INVENTION

The object of the present invention is to provide a carbapenem compound which has a potent antibacterial activity over a broad range of Gram positive bacteria and Gram negative bacteria, especially against penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*, and has excellent oral absorbability.

The present inventors have intensively studied to find that the carbapenem compound, wherein a substituted phenyl or a substituted thienyl is directly substituted at position 3 of 7-oxo-1-azabicyclo[3.2.0]hept-2-ene which is a basic nucleus of the carbapenem compound has a potent antibacterial activity over a broad range of Gram positive bacteria and Gram negative bacteria, especially against penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-resistant (BLNAR) *Haemophilus influenzae*. Further, they have also found that a compound having a group substituted onto the 2-carboxyl group, the said group being capable of regenerating a carboxyl group by hydrolyzing in the living body, shows a good absorbability from the digestive tract by oral administration, and shows a potent antibacterial activity after converted into a 2-de-esterified compound in the living body, and further shows an excellent resistance to renal dehydropeptidase, and finally have accomplished the present invention.

Namely, the present invention relates to:

1. The carbapenem compound represented by a following formula [1],

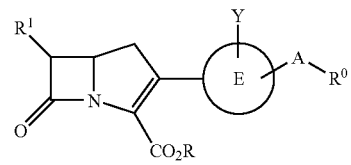

wherein ring E is benzene or thiophen.

$R^1$ is $C_1$ to $C_3$ alkyl or $C_1$ to $C_3$ alkyl substituted by hydroxy.

A is —$(CH_2)_r$—, wherein r is 1 to 3; —$(CH_2)_s$—O—$(CH_2)_t$—, wherein s and t are respectively independently 0 to 3; —$(CH_2)_s$—S—$(CH_2)_t$—, wherein s and t are the same as defined above; —$(CH_2)_s$—$NR^a$—$(CH_2)_t$—, wherein s and t are the same as defined above, and $R^a$ is hydrogen atom or optionally substituted $C_1$ to $C_6$ alkyl; —$(CH_2)_s$—$NR^a$—$CR^b$=N—$(CH_2)_t$—, wherein $R^a$, s and t are the same as defined above, and $R^b$ is hydrogen atom or optionally substituted $C_1$ to $C_6$ alkyl; —$(CH_2)_s$—

$NR^a$—$C(—NR^bR^c)$=$N$—$(CH_2)_t$—, wherein $R^a$, $R^b$, s and t are the same as defined above, and $R^c$ is hydrogen atom or optionally substituted $C_1$ to $C_6$ alkyl.

$R^0$ is hydrogen atom or a following formula [2],

[2]

wherein X is oxygen atom or sulfur atom, $R^2$ and $R^3$ are respectively independently (1) hydrogen atom, (2) optionally substituted $C_1$ to $C_6$ alkyl, (3) optionally substituted $C_3$ to $C_7$ cycloalkyl, (4) optionally substituted aryl which may optionally contain heteroatom(s) therein, (5) optionally substituted aralkyl in which ring may optionally contain heteroatom(s), or (6) optionally substituted 3 to 7 membered hetero ring; or $R^2$ and $R^3$ are combined together with the N atom to form a 3 to 7 hetero ring which may be optionally substituted, or $R^0$ is a following formula [3],

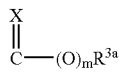
[3]

wherein X is oxygen atom or sulfur atom, m is 0 or 1, $R^{3a}$ is hydrogen atom, optionally substituted $C_1$ to $C_6$ alkyl, optionally substituted $C_3$ to $C_7$ cycloalkyl, optionally substituted aryl which may optionally contain heteroatom(s) therein, optionally substituted aralkyl in which ring may optionally contain heteroatom(s), or optionally substituted 3 to 7 membered hetero ring; but when X is oxygen atom and m is 1, $R^{3a}$ may be further a group which regenerates a carboxyl group by hydrolysis in vivo, but $R^{3a}$ is other group except hydrogen atom when t is 0, and m is 1, R is hydrogen atom or a group which regenerates a carboxyl group by hydrolysis in vivo.

Y is hydrogen atom, $C_1$ to $C_6$ alkyl, $C_3$ to $C_7$ cycloalkyl, optionally protected hydroxy group, $C_1$ to $C_6$ alkyloxy, $C_1$ to $C_6$ alkylthio, $C_2$ to $C_7$ alkylcarbonyl, $C_2$ to $C_7$ alkylcarbonyloxy, $C_2$ to $C_7$ alkyloxycarbonyl, optionally protected carboxyl, halogen atom, cyano, —$NR^4R^5$, —$OCONR^4R^5$, —$CONR^4SO_2R^5$, —$SO_2NR^4R^5$, —$NR^4SO_2NR^4R^5$ or —$NR^4CONR^4R^5$, or $C_1$ to $C_6$ alkyl substituted by a group selected from a group of optionally protected hydroxy group, $C_1$ to $C_6$ alkyloxy, $C_1$ to $C_6$ alkylthio, $C_2$ to $C_7$ alkylcarbonyl, $C_2$ to $C_7$ alkylcarbonyloxy, $C_2$ to $C_7$ alkyloxycarbonyl, optionally protected carboxyl, a halogen atom, cyano, —$NR^4R^5$, —$CONR^4R^5$, —$OCONR^4R^5$, —$CONR^4SO_2R^5$, —$SO_2NR^4R^5$, —$NR^4SO_2NR^4R^5$ and —$NR^4CONR^4R^5$. Amino group may be optionally protected and plural Ys may be substituted on ring E.

$R^4$ and $R^5$ are respectively independently (1) hydrogen atom, (2) optionally substituted $C_1$ to $C_6$ alkyl, (3) optionally substituted $C_3$ to $C_7$ cycloalkyl, (4) optionally substituted aryl which may optionally contain heteroatom(s) therein, (5) optionally substituted aralkyl in which ring may optionally contain heteroatom(s), or (6) optionally substituted 3 to 7 membered hetero ring; or $R^4$ and $R^5$ are combined together with the N atom to form pyrrolidine, piperidine or azepane, or its pharmaceutically acceptable salt.

2. The carbapenem compound or its pharmaceutically acceptable salt according to the above 1, wherein a group which regenerates a carboxyl group by hydrolysis in vivo is represented by a following formula [4],

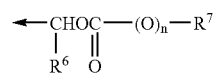
[4]

wherein $R^6$ is hydrogen atom or $C_1$ to $C_6$ alkyl, $R^7$ is optionally substituted $C_1$ to $C_6$ alkyl, optionally substituted $C_3$ to $C_7$ cycloalkyl and n is 0 or 1.

3. The carbapenem compound or its pharmaceutically acceptable salt according to the above 1, wherein R is represented by a following formula [4],

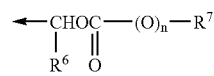
[4]

wherein $R^6$, $R^7$ and n are the same as defined in the above 2.

4. The carbapenem compound or its pharmaceutically acceptable salt according to the above 1, wherein R is pivaloyloxymethyl group.

5. The carbapenem compound or its pharmaceutically acceptable salt according to the above 1, wherein, R is hydrogen atom.

6. The carbapenem compound or its pharmaceutically acceptable salt according to any one of the above 1 to 5, wherein $R^1$ is 1-hydroxyethyl group.

7. The carbapenem compound or its pharmaceutically acceptable salt according to any one of the above 1 to 6, wherein $R^0$ is hydrogen atom.

8. The carbapenem compound or its pharmaceutically acceptable salt according to any one of the above 1 to 6, wherein $R^0$ is represented by a following formula [2],

[2]

wherein X, $R^2$ and $R^3$ are the same as defined in above 1.

9. The carbapenem compound or its pharmaceutically acceptable salt according to any one of the above 1 to 6, wherein $R^0$ is represented by a following formula [2a],

[2a]

wherein $R^2$ and $R^3$ are the same as defined in the above 1.

10. The carbapenem compound or its pharmaceutically acceptable salt according to any one of the above 1 to 6, wherein $R^0$ is represented by a following formula [3],

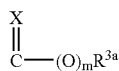

wherein X, m and $R^{3a}$ are the same as defined in the above 1.

11. The carbapenem compound or its pharmaceutically acceptable salt according to any one of the above 1 to 6, wherein $R^0$ is represented by a following formula [3a],

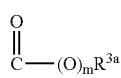

wherein m and $R^{3a}$ are the same as defined in the above 1.

12. The carbapenem compound or its pharmaceutically acceptable salt according to any one of the above 1 to 6, wherein $R^0$ is represented by a following formula [3b],

wherein R' is a group which regenerates a carboxyl group by hydrolysis in vivo.

13. The carbapenem compound represented by a following formula [1d],

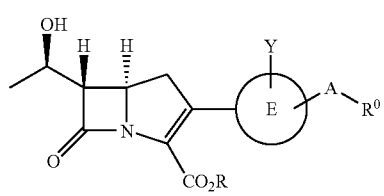

wherein ring E is benzene or thiophen.

A is $-(CH_2)_r-$, wherein r is 1 to 3; $-(CH_2)_s-O-(CH_2)_t-$, wherein s and t are respectively independently 0 to 3; $-(CH_2)_s-S-(CH_2)_t-$, wherein s and t are the same as defined above; $-(CH_2)_s-NR^a-(CH_2)_t-$, wherein s and t are the same as defined above, and $R^a$ is hydrogen atom or optionally substituted $C_1$ to $C_6$ alkyl; $-(CH_2)_s-NR^a-CR^b=N-(CH_2)_t-$, wherein $R^a$, s and t are the same as defined above, and $R^b$ is hydrogen atom or optionally substituted $C_1$ to $C_6$ alkyl; $-(CH_2)_s-NR^a-C(-NR^bR^c)=N-(CH_2)_t-$, wherein $R^a$, $R^b$, s and t are the same as defined above, and $R^c$ is hydrogen atom or optionally substituted $C_1$ to $C_6$ alky, $R^0$ is hydrogen atom or a following formula [2],

wherein X is oxygen atom or sulfur atom, $R^2$ and $R^3$ are respectively independently (1) hydrogen atom, (2) optionally substituted $C_1$ to $C_6$ alkyl, (3) optionally substituted $C_3$ to $C_7$ cycloalkyl, (4) optionally substituted aryl which may optionally contain heteroatom(s) therein, (5) optionally substituted aralkyl in which ring may optionally contain heteroatom(s), or (6) optionally substituted 3 to 7 membered hetero ring; or $R^2$ and $R^3$ are combined together with the N atom to form a 3 to 7 hetero ring which may be optionally substituted, or else $R^0$ is represented by a following formula [3],

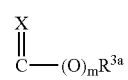

wherein X is oxygen atom or sulfur atom, m is 0 or 1, $R^{3a}$ is hydrogen atom, optionally substituted $C_1$ to $C_6$ alkyl, optionally substituted $C_3$ to $C_7$ cycloalkyl, optionally substituted aryl which may optionally contain heteroatom(s) therein, optionally substituted aralkyl in which ring may optionally contain heteroatom(s), or optionally substituted 3 to 7 membered hetero ring; but when X is oxygen atom and m is 1, $R^{3a}$ may be further a group which regenerates a carboxyl group by hydrolysis in vivo, but $R^{3a}$ is other group except hydrogen atom when t is 0, and m is 1, R is hydrogen atom or a group which regenerates a carboxyl group by hydrolysis in vivo.

Y is hydrogen atom, $C_1$ to $C_6$ alkyl, $C_3$ to $C_7$ cycloalkyl, optionally protected hydroxy group, $C_1$ to $C_6$ alkyloxy, $C_1$ to $C_6$ alkylthio, $C_2$ to $C_7$ alkylcarbonyl, $C_2$ to $C_7$ alkylcarbonyloxy, $C_2$ to $C_7$ alkyloxycarbonyl, optionally protected carboxyl, a halogen atom, cyano, $-NR^4R^5$, $-OCONR^4R^5$, $-CONR^4SO_2R^5$, $-SO_2NR^4R^5$, $-NR^4SO_2NR^4R^5$ or $-NR^4CONR^4R^5$, or, $C_1$ to $C_6$ alkyl substituted by a group selected from a group of optionally protected hydroxy group, $C_1$ to $C_6$ alkyloxy, $C_1$ to $C_6$ alkylthio, $C_2$ to $C_7$ alkylcarbonyl, $C_2$ to $C_7$ alkylcarbonyloxy, $C_2$ to $C_7$ alkyloxycarbonyl, optionally protected carboxyl, a halogen atom, cyano, $-NR^4R^5$, $-CONR^4R^5$, $-OCONR^4R^5$, $-CONR^4SO_2R^5$, $-SO_2NR^4R^5$, $-NR^4SO_2NR^4R^5$ and $-NR^4CONR^4R^5$. Amino group may be optionally protected and plural Ys may substitute on ring E.

$R^4$ and $R^5$ are respectively independently (1) hydrogen atom, (2) optionally substituted $C_1$ to $C_6$ alkyl, (3) optionally substituted $C_3$ to $C_7$ cycloalkyl, (4) optionally substituted aryl which may optionally contain heteroatom(s) therein, (5) optionally substituted aralkyl in which ring may contain heteroatom(s) or (6) optionally substituted 3 to 7 membered hetero ring; or $R^4$ and $R^5$ are combined together with the N atom to form pyrrolidine, piperidine or azepan, or its pharmaceutically acceptable salt.

14. The carbapenem compound or its pharmaceutically acceptable salt according to the above 13, wherein $R^0$ is hydrogen atom.

15. The carbapenem compound or its pharmaceutically acceptable salt according to the above 13, wherein $R^0$ is represented by a following formula [2],

(2)

wherein X, R² and R³ are the same as defined in the above 13.
16. The carbapenem compound or its pharmaceutically acceptable salt according to the above 13, wherein R⁰ is represented by a following formula [2a],

[2a]

wherein X, R² and R³ are the same as defined in the above 13.
17. The carbapenem compound or its pharmaceutically acceptable salt according to the above 13, wherein R⁰ is represented by a following formula [3],

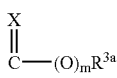
[3]

wherein X, m and $R^{3a}$ are the same as defined in the above 13.
18. The carbapenem compound or its pharmaceutically acceptable salt according to the above 13, wherein R⁰ is represented by a following formula [3a],

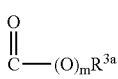
[3a]

wherein m and $R^{3a}$ are the same as defined in the above 13.
19. The carbapenem compound or its pharmaceutically acceptable salt according to the above 13, wherein R⁰ is represented by a following formula [3b],

[3b]

wherein R' is the same as defined in the above 12.
20. The carbapenem compound or its pharmaceutically acceptable salt according to any one of the above 13 to 19, wherein R is hydrogen atom.
21. The carbapenem compound or its pharmaceutically acceptable salt according to the above 13, wherein ring E is benzene and R⁰ is hydrogen atom.
22. The carbapenem compound or its pharmaceutically acceptable salt according to the above 13, wherein ring E is benzene and R⁰ is represented by a following formula [2],

[2]

wherein X, R² and R³ are the same as defined in the above 13.
23. The carbapenem compound or its pharmaceutically acceptable salt according to the above 13, wherein ring E is benzene and R⁰ is represented by a following formula [2a],

[2a]

wherein R² and R³ are the same as defined in the above 13.
24. The carbapenem compound or its pharmaceutically acceptable salt according to the above 13, wherein ring E is benzene and R⁰ is represented by a following formula [3],

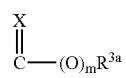
[3]

wherein X, m and $R^{3a}$ are the same as defined in the above 13.
25. The carbapenem compound or its pharmaceutically acceptable salt according to the above 13, wherein ring E is benzene and R⁰ is represented by a following formula [3a],

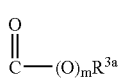
[3a]

wherein m and $R^{3a}$ are the same as defined in the above 13.
26. The carbapenem compound or its pharmaceutically acceptable salt according to the above 13, wherein E is benzene and R⁰ is represented by a following formula [3b],

[3b]

wherein R' is the same as defined in the above 12.
27. The carbapenem compound or its pharmaceutically acceptable salt according to any one of the above 21 to 26, wherein R is hydrogen atom.
28. The carbapenem compound or its pharmaceutically acceptable salt according to the above 13, wherein ring E is benzene, A is —(CH₂)$_v$—O—(CH₂)$_w$—, wherein one of v and w is 0 and the other is 0 to 3; —(CH₂)$_v$—S—(CH₂)$_w$—, wherein v and w are the same as defined above; —$(CH_2)_v$—$NR^a$—$(CH_2)_w$—, wherein v and w are the same as defined above, and $R^a$ is hydrogen atom or optionally substituted $C_1$ to $C_6$ alkyl; —$(CH_2)_v$—$NR^a$—$CR^b$=N—$(CH_2)_w$—, wherein $R^a$, v and w are the same as defined above, and $R^b$ is hydrogen atom or optionally substituted $C_1$ to $C_6$ alkyl; —$(CH_2)_v$—$NR^a$—C(=N $R^b R^c$)=N—$(CH_2)_w$—, wherein $R^a$, $R^b$, v and w are the same as defined above, and $R^c$ is hydrogen atom or optionally substituted $C_1$ to $C_6$ alkyl, and $R^0$ is hydrogen atom.

29. The carbapenem compound or its pharmaceutically acceptable salt according to the above 13, wherein ring E is benzene, A is —$(CH_2)_v$—O—$(CH_2)_w$—, wherein one of v and w is 0 and the other is 0 to 3; —$(CH_2)_v$—S—$(CH_2)_w$—, wherein v and w are the same as defined above; —$(CH_2)_v$—$NR^a$—$(CH_2)_w$—, wherein v and w are the same as defined above, and $R^a$ is hydrogen atom or optionally substituted $C_1$ to $C_6$ alkyl; —$(CH_2)_v$—$NR^a$—$CR^b$=N—$(CH_2)_w$—, wherein $R^a$, v and w are the same as defined above, and $R^b$ is hydrogen atom or optionally substituted $C_1$ to $C_6$ alkyl; —$(CH_2)_v$—$NR^a$—C(=N $R^b R^c$)=N—$(CH_2)_w$—, wherein $R^a$, $R^b$, v and w are the same as defined above, and $R^c$ is hydrogen atom or optionally substituted $C_1$ to $C_6$ alkyl, and $R^0$ is a group represented by a following formula[2],

[2]

wherein X, $R^2$ and $R^3$ are the same as defined in the above 13.

30. The carbapenem compound or its pharmaceutically acceptable salt according to the above 13, wherein ring E is benzene, A is —$(CH_2)_v$—O—$(CH_2)_w$—, wherein one of v and w is 0 and the other is 0 to 3; —$(CH_2)_v$—S—$(CH_2)_w$—, wherein v and w are the same as defined above; —$(CH_2)_v$—$NR^a$—$(CH_2)_w$—, wherein v and w are the same as defined above, and $R^a$ is hydrogen atom or optionally substituted $C_1$ to $C_6$ alkyl; —$(CH_2)_v$—$NR^a$—$CR^b$=N—$(CH_2)_w$—, wherein $R^a$, v and w are the same as defined above, and $R^b$ is hydrogen atom or optionally substituted $C_1$ to $C_6$ alkyl; —$(CH_2)_v$—$NR^a$—C(=N $R^b R^c$)=N—$(CH_2)_w$—, wherein $R^a$, $R^b$, v and w are the same as defined above, and $R^c$ is hydrogen atom or optionally substituted $C_1$ to $C_6$ alkyl, and $R^0$ is a group represented by a following formula [2a],

[2a]

wherein $R^2$ and $R^3$ are the same as defined in the above 13.

31. The carbapenem compound or its pharmaceutically acceptable salt according to the above 13, wherein ring E is benzene, A is —$(CH_2)_v$—O—$(CH_2)_w$—, wherein one of v and w is 0 and the other is 0 to 3; —$(CH_2)_v$—S—$(CH_2)_w$—, wherein v and w are the same as defined above; —$(CH_2)_v$—$NR^a$—$(CH_2)_w$—, wherein v and w are the same as defined above, and $R^a$ is hydrogen atom or optionally substituted $C_1$ to $C_6$ alkyl; —$(CH_2)_v$—$NR^a$—$CR^b$=N—$(CH_2)_w$—, wherein $R^a$, v and w are the same as defined above, and $R^b$ is hydrogen atom or optionally substituted $C_1$ to $C_6$ alkyl; —$(CH_2)_v$—$NR^a$—C(=N $R^b R^c$)=N—$(CH_2)_w$—, wherein $R^a$, $R^b$, v and w are the same as defined above, and $R^c$ is hydrogen atom or optionally substituted $C_1$ to $C_6$ alky, and $R^0$ is a group represented by a following formula [3],

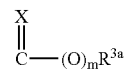

[3]

wherein X, m and $R^{3a}$ are the same as defined in the above 13.

32. The carbapenem compound or its pharmaceutically acceptable salt according to the above 13, wherein ring E is benzene, A is —$(CH_2)_v$—O—$(CH_2)_w$—, wherein one of v and w is 0 and the other is 0 to 3; —$(CH_2)_v$—S—$(CH_2)_w$—, wherein v and w are the same as defined above; —$(CH_2)_v$—$NR^a$—$(CH_2)_w$—, wherein v and w are the same as defined above, and $R^a$ is hydrogen atom or optionally substituted $C_1$ to $C_6$ alkyl; —$(CH_2)_v$—$NR^a$—$CR^b$=N—$(CH_2)_w$—, wherein $R^a$, v and w are the same as defined above, and $R^b$ is hydrogen atom or optionally substituted $C_1$ to $C_6$ alkyl; —$(CH_2)_v$—$NR^a$—C(=N $R^b R^c$)=N—$(CH_2)_w$—, wherein $R^a$, $R^b$, v and w are the same as defined above, and $R^c$ is hydrogen atom or optionally substituted $C_1$ to $C_6$ alky, and $R^0$ is a group represented by a following formula [3a],

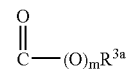

[3a]

wherein m and $R^{3a}$ are the same as defined in above 13.

33. The carbapenem compound or its pharmaceutically acceptable salt according to the above 13, wherein ring E is benzene, A is —$(CH_2)_v$—O—$(CH_2)_w$—, wherein one of v and w is 0 and the other is 0 to 3, —$(CH_2)_v$—S—$(CH_2)_w$—, wherein v and w are the same as defined above, —$(CH_2)_v$—$NR^a$—$(CH_2)_w$—, wherein v and w are the same as defined above, and $R^a$ is hydrogen atom or optionally substituted $C_1$ to $C_6$ alkyl, —$(CH_2)_v$—$NR^a$—$CR^b$=N—$(CH_2)_w$—, wherein $R^a$, v and w are the same as defined above, and $R^b$ is hydrogen atom or optionally substituted $C_1$ to $C_6$ alky, —$(CH_2)_v$—$NR^a$—C(=$NR^b R^c$)=N—$(CH_2)_w$—, wherein $R^a$, $R^b$, v and w are the same as defined above, and $R^c$ is hydrogen atom or optionally substituted $C_1$ to $C_6$ alkyl, and $R^0$ is a group represented by a following formula [3b],

[3b]

wherein R' is the same as defined in the above 12.

34. The carbapenem compound or its pharmaceutically acceptable salt according to any one of the above 28 to 33, wherein R is hydrogen atom. 35. The carbapenem compound or its pharmaceutically acceptable salt according to the above 13, wherein ring E is benzene, A is —$(CH_2)_2$—, —$CH_2$—, —$OCH_2$—, —$CH_2O$—, —O—, —$NHCH_2$—, —$CH_2NH$— or —NH—, and $R^0$ is hydrogen atom.

36. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, and R$^0$ is a group represented by a following formula [2],

[2]

wherein X, R$^2$ and R$^3$ are the same as defined in the above 13.

37. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, and R$^0$ is a group represented by a following formula [2a],

[2a]

wherein R$^2$ and R$^3$ are the same as defined in the above 13.

38. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, and R$^0$ is a group represented by a following formula [3],

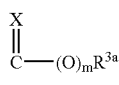
[3]

wherein X, m and R$^{3a}$ are the same as defined in the above 13.

39. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, and R$^0$ is a group represented by a following formula [3a],

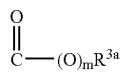
[3a]

wherein m and R$^{3a}$ are the same as defined in the above 13.

40. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, and a group R$^0$ is a group represented by a following formula [3b],

[3b]

wherein R' is the same as defined in the above 12.

41. The carbapenem compound or its pharmaceutically acceptable salt according to any one of the above 35 to 40, wherein R is hydrogen atom.

42. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl and R$^0$ is hydrogen atom.

43. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl and R$^0$ is a group represented by a following formula [2],

[2]

wherein X, R$^2$ and R$^3$ are the same as defined in the above 13.

44. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl and R$^0$ is a group represented by a following formula [2a],

[2a]

wherein R$^2$ and R$^3$ are the same as defined in the above 13.

45. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl and R$^0$ is a group represented by a following formula [3],

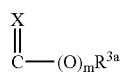
[3]

wherein X, m and R$^{3a}$ are the same as defined in the above 13.

46. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl and R$^0$ is a group represented by a following formula [3a],

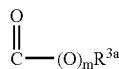

wherein m and $R^{3a}$ are the same as defined in the above 13.

47. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl and $R^o$ is a group represented by a following formula [3b],

wherein R' is the same as defined in the above 12.

48. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl, $R^o$ is hydrogen atom, Y is hydrogen atom and the the said A is bound to the benzene ring at meta or para position against the position where 7-oxo-1-azabicyclo[3.2.0]hept-2-ene is bound to the benzene.

49. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl, Y is hydrogen atom and $R^o$ is a group represented by a following formula [2],

wherein X, $R^2$ and $R^3$ are the same as defined in the above 13, and the said A is bound to the benzene ring at meta or para position against the position where 7-oxo-1-azabicyclo[3.2.0]hept-2-ene is bound to the benzene.

50. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl, Y is hydrogen atom and $R^o$ is a group represented by a following formula[2a],

wherein $R^2$ and $R^3$ are the same as defined in the above 13, and the said A is bound to the benzene ring at meta or para position against the position where 7-oxo-1-azabicyclo[3.2.0]hept-2-ene is bound to the benzene.

51. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl, Y is hydrogen atom and $R^o$ is a group represented by a following formula [3],

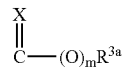

wherein X, m and $R^{3a}$ are the same as defined in the above 13, and the said A is bound to the benzene ring at meta or para position against the position where 7-oxo-1-azabicyclo[3.2.0]hept-2-ene is bound to the benzene.

52. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl, Y is hydrogen atom and a group $R^o$ is a group represented by a following formula [3a],

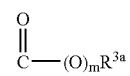

wherein m and $R^{3a}$ are the same as defined in the above 13, and the said A is bound to the benzene ring at meta or para position against the position where 7-oxo-1-azabicyclo[3.2.0]hept-2-ene is bound to the benzene.

53. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R is pivaloyloxymethyl, Y is hydrogen atom and $R^o$ is a group represented by a following formula [3b],

wherein R' is the same as defined in the above 12, and the said A is bound to the benzene ring at meta or para position against the position where 7-oxo-1-azabicyclo[3.2.0]hept-2-ene is bound to the benzene.

54. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH—or —NH—, $R^o$ is CONH$_2$, and the said A is bound to the benzene ring at meta or para position against the position where 7-oxo-1-azabicyclo[3.2.0]hept-2-ene is bound to the benzene.

55. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH—or —NH—, $R^o$ is CONHMe, and the said A is bound to the benzene ring at meta or para position against the position where 7-oxo-1-azabicyclo[3.2.0]hept-2-ene is bound to the benzene.

56. The carbapenem compound or its pharmaceutically acceptable salt according to the above 13, wherein ring E is benzene, A is —(CH$_2$)$_2$—, —CH$_2$—, —OCH$_2$—, —CH$_2$O—, —O—, —NHCH$_2$—, —CH$_2$NH— or —NH—, R$^0$ is CONMe$_2$, and the said A is bound to the benzene ring at meta or para position against the position where 7-oxo-1-azabicyclo[3.2.0]hept-2-ene is bound to the benzene.

57. The carbapenem compound or its pharmaceutically acceptable salt according to any one of the above 54 to 56, wherein Y is hydrogen atom.

58. The carbapenem compound or its pharmaceutically acceptable salt according to any one of the above 54 to 57, wherein R is hydrogen atom.

59. The carbapenem compound or its pharmaceutically acceptable salt according to the above 13, wherein ring E is benzene, R is pivaloyloxymethyl, A is —(CH$_2$)$_2$—, —CH$_2$—, —OCH$_2$—, —CH$_2$O—, —O—, —NHCH$_2$—, —CH$_2$NH— or —NH—, R$^0$ is CONH$_2$, and the said A is bound to the benzene ring at meta or para position against the position where 7-oxo-1-azabicyclo[3.2.0]hept-2-ene is bound to the benzene.

60. The carbapenem compound or its pharmaceutically acceptable salt according to the above 13, wherein ring E is benzene, R is pivaloyloxymethyl, A is —(CH$_2$)$_2$—, —CH$_2$—, —OCH$_2$—, —CH$_2$O—, —O—, —NHCH$_2$—, —CH$_2$NH— or —NH—, R$^0$ is CONHMe, and the said A is bound to the benzene ring at meta or para position against the position where 7-oxo-1-azabicyclo[3.2.0]hept-2-ene is bound to the benzene.

61. The carbapenem compound or its pharmaceutically acceptable salt according to the above 13, wherein ring E is benzene, R is pivaloyloxymethyl, A is —(CH$_2$)$_2$—, —CH$_2$—, —OCH$_2$—, —CH$_2$O—, —O—, —NHCH$_2$—, —CH$_2$NH— or —NH—, R$^0$ is CONMe$_2$, and the said A is bound to the benzene ring at meta or para position against the position where 7-oxo-1-azabicyclo[3.2.0]hept-2-ene is bound to the benzene.

62. The carbapenem compound or its pharmaceutically acceptable salt according to the above 13, wherein ring E is benzene, R is pivaloyloxymethyl, A is —(CH$_2$)$_2$—, —CH$_2$—, —OCH$_2$—, —CH$_2$O—, —O—, —NHCH$_2$—, —CH$_2$NH— or —NH—, R$^0$ is CONH$_2$, Y is hydrogen atom and the said A is bound to the benzene ring at meta or para position against the position where 7-oxo-1-azabicyclo[3.2.0]hept-2-ene is bound to the benzene.

63. The carbapenem compound or its pharmaceutically acceptable salt according to the above 13, wherein ring E is benzene, R is pivaloyloxymethyl, A is —(CH$_2$)$_2$—, or —CH$_2$—, R$^0$ is CONH$_2$, Y is hydrogen atom and the said A is bound to the benzene ring at meta or para position against the position where 7-oxo-1-azabicyclo[3.2.0]hept-2-ene is bound to the benzene.

64. The carbapenem compound or its pharmaceutically acceptable salt according to the above 13, wherein ring E is benzene, R is pivaloyloxymethyl, A is —OCH$_2$—, —CH$_2$O—, or —O—, R$^0$ is CONH$_2$, Y is hydrogen atom and the said A is bound to the benzene ring at meta or para position against the position where 7-oxo-1-azabicyclo[3.2.0]hept-2-ene is bound to the benzene.

65. The carbapenem compound or its pharmaceutically acceptable salt according to the above 13, wherein ring E is benzene, R is pivaloyloxymethyl, A is —NHCH$_2$—, —CH$_2$NH— or —NH—, R$^0$ is CONH$_2$, Y is hydrogen atom and the said A is bound to the benzene ring at meta or para position against the position where 7-oxo-1-azabicyclo[3.2.0]hept-2-ene is bound to the benzene.

66. The carbapenem compound or its pharmaceutically acceptable salt according to the above 13, wherein ring E is benzene, R is pivaloyloxymethyl, A is —(CH$_2$)$_2$—, —CH$_2$—, —OCH$_2$—, —CH$_2$O—, —O—, —NHCH$_2$—, —CH$_2$NH— or —NH—, R$^0$ is CONHMe, Y is hydrogen atom and the said A is bound to the benzene ring at meta or para position against the position where 7-oxo-1-azabicyclo[3.2.0]hept-2-ene is bound to the benzene.

67. The carbapenem compound or its pharmaceutically acceptable salt according to the above 13, wherein ring E is benzene, R is pivaloyloxymethyl, A is —(CH$_2$)$_2$—, or —CH$_2$—, R$^0$ is CONHMe, Y is hydrogen atom and the said A is bound to the benzene ring at meta or para position against the position where 7-oxo-1-azabicyclo[3.2.0]hept-2-ene is bound to the benzene.

68. The carbapenem compound or its pharmaceutically acceptable salt according to the above 13, wherein ring E is benzene, R is pivaloyloxymethyl, A is —OCH$_2$—, —CH$_2$O—, —O—, R$^0$ is CONHMe, Y is hydrogen atom and the said A is bound to the benzene ring at meta or para position against the position where 7-oxo-1-azabicyclo[3.2.0]hept-2-ene is bound to the benzene.

69. The carbapenem compound or its pharmaceutically acceptable salt according to the above 13, wherein ring E is benzene, R is pivaloyloxymethyl, A is —NHCH$_2$—, —CH$_2$NH— or —NH—, R$^0$ is CONHMe, Y is hydrogen atom and the said A is bound to the benzene ring at meta or para position against the position where 7-oxo-1-azabicyclo[3.2.0]hept-2-ene is bound to the benzene.

70. The carbapenem compound or its pharmaceutically acceptable salt according to the above 13, wherein ring E is benzene, R is pivaloyloxymethyl, A is —(CH$_2$)$_2$—, —CH$_2$—, —OCH$_2$—, —CH$_2$O—, —O—, —NHCH$_2$—, —CH$_2$NH— or —NH—, R$^0$ is CONMe$_2$, Y is hydrogen atom and the said A is bound to the benzene ring at meta or para position against the position where 7-oxo-1-azabicyclo[3.2.0]hept-2-ene is bound to the benzene.

71. The carbapenem compound or its pharmaceutically acceptable salt according to the above 13, wherein ring E is benzene, R is pivaloyloxymethyl, A is —(CH$_2$)$_2$—, or —CH$_2$—, R$^0$ is CONMe$_2$, Y is hydrogen atom and the said A is bound to the benzene ring at meta or para position against the position where 7-oxo-1-azabicyclo[3.2.0]hept-2-ene is bound to the benzene.

72. The carbapenem compound or its pharmaceutically acceptable salt according to the above 13, wherein ring E is benzene, R is pivaloyloxymethyl, A is —OCH$_2$—, —CH$_2$O—, —O—, R$^0$ is CONMe$_2$, Y is hydrogen atom and the said A is bound to the benzene ring at meta or para position against the position where 7-oxo-1-azabicyclo[3.2.0]hept-2-ene is bound to the benzene.

73. The carbapenem compound or its pharmaceutically acceptable salt according to the above 13, wherein ring E is benzene, R is pivaloyloxymethyl, A is —NHCH$_2$—, —CH$_2$NH— or —NH—, R$^0$ is CONMe$_2$, Y is hydrogen atom and the said A is bound to the benzene ring at meta or para position against the position where 7-oxo-1-azabicyclo[3.2.0]hept-2-ene is bound to the benzene.

74. A medicament, which comprises the carbapenem compound or its pharmaceutically acceptable salt according to any one of the above 1 to 73 as an active ingredient.

75. An antibacterial agent containing the carbapenem compound or its pharmaceutically acceptable salt according to any one of the above 1 to 73 as an active ingredient.

BEST MODE FOR CARRYING OUT THE INVENTION

The first aspect of the present invention relates to the above carbapenem compounds. Various terms and preferable examples referred to the present specification are explained as follows.

"$C_1$ to $C_3$ alkyl" in $R^1$ includes a straight or branched chain $C_1$ to $C_3$ alkyl, such as methyl, ethyl, n-propyl, isopropyl, etc., preferably ethyl or isopropyl.

"$C_1$ to $C_3$ alkyl substituted by hydroxy" in $R^1$ includes a group having $C_1$ to $C_3$, such as hydroxymethyl, 1-hydroxyethyl, 2-hydroxyethyl, 1-hydroxy-1-methylethyl, 1-hydroxypropyl, preferably 1-hydroxyethyl, 2-hydroxyethyl, 1-hydroxy-1-methylethyl, etc., and more preferably, 1-hydroxyethyl.

"$C_1$ to $C_6$ alkyl" includes a straight or branched chain $C_1$ to $C_6$ alkyl, such as methyl, ethyl, n-propyl, isopropyl, n-butyl, isobutyl, tert-butyl, n-pentyl, n-hexyl, etc., preferably a straight or branched chain $C_1$ to $C_3$ alkyl, such as methyl, ethyl, n-propyl, isopropyl, etc., and more preferably methyl or ethyl.

"Aryl which may optionally contain heteroatom(s) therein" includes a 5 to 10 membered mono cyclic or fused polycyclic aromatic ring containing 0 to 3 heteroatoms selected from nitrogen, oxygen and sulfur atoms, such as phenyl, pyridyl, pyrimidyl, pyridazinyl, thienyl, furyl, pyrrolyl, imidazolyl, oxazolyl, isoxazolyl, thiazolyl, isothiazolyl, triazolyl, indolyl, benzothiazolyl, naphthyl, quinazolyl, isoquinazolyl, etc., preferably pyridyl, pyrimidinyl, pyridazinyl, thienyl, furyl, pyrrolyl, imidazolyl, oxazolyl, isoxazolyl, thiazolyl, isothiazolyl or triazolyl, and more preferably pyridyl, thienyl, furyl, pyrrolyl, imidazolyl, oxazolyl, isoxazolyl or thiazolyl.

"Aralkyl in which ring may optionally contain heteroatom(s) therein" includes a combination of a 5 to 10 membered mono cyclic or fused polycyclic aromatic ring containing 0 to 3 heteroatoms selected from nitrogen, oxygen and sulfur atoms with $C_1$ to $C_3$ alkylene, such as benzyl, phenethyl, pyridylmethyl, pyrimidylmethyl, pyridazinylmethyl, thienylmethyl, furylmethyl, pyrrolylmethyl, imidazolylmethyl, oxazolylmethyl, isoxazolylmethyl, thiazolylmethyl, isothiazolylmethyl, triazolylmethyl, indolylmethyl, benzothiazolylmethyl, naphthylmethyl, quinazolylmethyl, isoquinazolylmethyl, etc., preferably pyridylmethyl, pyrimidylmethyl, pyridazinylmethyl, thienylmethyl, furylmethyl, pyrrolylmethyl, imidazolylmethyl, oxazolylmethyl, isoxazolylmethyl, thiazolylmethyl, isothiazolylmethyl, or triazolylmethyl, more preferably pyridylmethyl, thienylmethyl, furylmethyl, pyrrolylmethyl, imidazolylmethyl, oxazolylmethyl, isoxazolylmethyl, or thiazolylmethyl.

"$C_3$ to $C_7$ cycloalkyl" includes one having $C_3$ to $C_7$, such as cyclopropyl, cyclobutyl, cyclopentyl, cyclohexyl, cycloheptyl, etc.

The substituent of "optionally substituted $C_1$ to $C_6$ alkyl", "optionally substituted $C_3$ to $C_7$ cycloalkyl", "optionally substituted aryl which may optionally contain heteroatom(s) therein" and "optionally substituted aralkyl in which a ring may optionally contain heteroatom(s) therein" includes hydroxy group, $C_1$ to $C_6$ alkyloxy, $C_1$ to $C_6$ alkylthio, $C_2$ to $C_7$ alkylcarbonyl, $C_2$ to $C_7$ alkylcarbonyloxy, $C_2$ to $C_7$ alkyloxycarbonyl, $C_3$ to $C_7$ cycloalkyl, optionally protected carboxyl, a halogen atom, cyano, —$NR^4R^5$, —$CONR^4R^5$, —$OCONR^4R^5$, —$CONR^4SO_2R^5$, —$SO_2NR^4R^5$, —$R^4SO_2NR^4R^5$, —$NR^4CONR^4R^5$, (wherein $R^4$ and $R^5$ are the same as defined above.), —$COOCH_2OCOR^8$ (wherein $R^8$ is $C_1$ to $C_6$ alkyl), etc. These substituents may be optionally protected by an appropriate protecting group. The position and the number of the substituent(s) are not limited as long as they are chemically possible.

"$C_1$ to $C_6$ alkyloxy" includes a straight or branched chain $C_1$ to $C_6$ alkyloxy, such as methoxy, ethoxy, n-propoxy, isopropoxy, n-butoxy, isobutoxy, tert-butoxy, n-pentyloxy, n-hexyloxy, etc., preferably a straight or branched chain $C_1$ to $C_3$ alkyloxy, such as methoxy, ethoxy n-propoxy, isopropoxy, etc., more preferably methoxy or ethoxy.

"$C_1$ to $C_6$ alkylthio" includes a straight or branched chain $C_1$ to $C_6$ alkylthio, such as methylthio, ethylthio, n-propylthio, isopropylthio, n-butylthio, isobutylthio, tert-butylthio, n-pentylthio, n-hexylthio, etc., preferably a straight or branched chain $C_1$ to $C_3$ alkylthio, such as methylthio, ethylthio n-propylthio, isopropylthio, more preferably methylthio or ethylthio.

"$C_2$ to $C_7$ alkylcarbonyl" includes a straight or branched chain $C_2$ to $C_7$ alkylcarbonyl, such as acetyl, propionyl, n-propylcarbonyl, isopropylcarbonyl, n-butylcarbonyl, isobutylcarbonyl, tert-butylcarbonyl, n-pentylcarbonyl, n-hexylcarbonyl, etc., preferably a straight or branched chain $C_2$ to $C_4$ alkylcarbonyl, such as acetyl, propionyl, n-propylcarbonyl, isopropylcarbonyl, etc., more preferably acetyl or propionyl.

"$C_2$ to $C_7$ alkycarbonyloxy" includes a straight or branched chain $C_2$ to $C_7$ alkylcarbonyloxy, such as acetyloxy, propionyloxy, n-propylcarbonyloxy, isopropylcarbonyloxy, n-butylcarbonyloxy, isobutylcarbonyloxy, tert-butylcarbonyloxy, n-pentylcarbonyloxy, n-hexylcarbonyloxy, etc., preferably a straight or branched chain $C_2$ to $C_4$ alkylcarbonyloxy, such as acetyloxy, propionyloxy, n-propylcarbonyloxy, isopropylcarbonyloxy, etc., more preferably acetyloxy or propionyloxy.

"$C_2$ to $C_7$ alkyloxycarbonyl" includes a straight or branched chain $C_2$ to $C_7$ alkyloxycarbonyl, such as methoxycarbonyl, ethoxycarbonyl, n-propoxycarbonyl, isopropoxycarbonyl, n-butoxycarbonyl, isobutoxycarbonyl, tert-butoxycarbonyl, n-pentyloxycarbonyl, n-hexyloxycarbonyl, etc., preferably a straight or branched chain $C_2$ to $C_4$ alkyloxycarbonyl, such as methoxycarbonyl, ethoxycarbonyl n-propoxycarbonyl, isopropoxycarbonyl, etc., more preferably methoxycarbonyl or ethoxycarbonyl.

"A halogen atom" includes fluorine atom, chlorine atom, bromine atom or iodine atom, preferably fluorine atom, chlorine atom, or bromine atom.

Preferable one in $R^2$ and $R^3$ is hydrogen atom, optionally substituted $C_1$ to $C_6$ alkyl, optionally substituted aryl which may optionally contain heteroatom(s) therein, or optionally substituted aralkyl in which ring may optionally contain heteroatom(s) therein, more preferably hydrogen atom, optionally substituted methyl, optionally substituted ethyl, aryl which may optionally contain heteroatom(s) therein, or aralkyl in which ring may optionally contain heteroatom(s) therein.

"3 to 7 membered hetero ring" in $R^2$, $R^3$ and $R^{3a}$ and "3 to 7 membered hetero ring" in which $R^2$ and $R^3$ are combined together with the nitrogen atom to form, includes a 3 to 7 membered saturated or unsaturated hetero ring containing 1 to 2 nitrogen atoms, 0 to 1 sulfur atom or 0 to 1 oxygen atom, such as aziridine, azetidine, pyrrolidine, dihydropyrrole, piperidine, tetrahydropyridine, piperazine, thiazoline, thiazolidine, morpholine, thiomorpholine, azepan, tetrahydroazepine, tetrahydrodiazepine, hexahydrodiazepine, etc., preferably azetidine, pyrrolidine, tetrahydropyridine, piperazine, thiazoline, thiazolidine, morpholine, or thiomorpholine, more preferably azetidine, pyrrolidine, tetrahydropyridine, thiazoline, thiazolidine, or morpholine.

Preferable group of $R^{3a}$ is hydrogen atom, optionally substituted $C_1$ to $C_6$ alkyl, optionally substituted aryl which may optionally contain heteroatom(s) therein, or optionally substituted aralkyl in which ring may optionally contain heteroatom(s) therein, more preferably hydrogen atom, optionally substituted methyl, optionally substituted ethyl, aryl which may optionally contain heteroatom(s) therein, or aralkyl in which ring may optionally contain heteroatom(s) therein.

A substituent on "an optionally substituted $C_3$ to $C_7$ hetero ring" includes $C_1$ to $C_6$ alkyl, hydroxy, $C_1$ to $C_6$ alkyloxy, $C_2$ to $C_7$ alkylcarbonyl, $C_2$ to $C_7$ alkylcarbonyloxy, $C_2$ to $C_7$ alkyloxycarbonyl, carboxyl, a halogen atom, cyano, etc.

"A group which regenerates a carboxyl group by hydrolysis in vivo" includes any group as long as the group regenerates a carboxyl group by hydrolysis in vivo, and includes any group which is used for conversion into a compound called a prodrug, preferably is a group represented by a following formula [4],

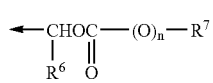

wherein $R^6$, $R^7$ and n are the same as defined above.

Examples thereof are pivaloyloxymethyl, acetyloxymethyl, cyclohexylacetyloxymethyl, 1-methylcyclohexylcarbonyloxymethyl, ethoxycarbonyloxy-1-ethyl, cyclohexyloxycarbonyloxy-1-ethyl, etc., preferably pivaloyloxymethyl. Other group which regenerates a carboxyl group by hydrolysis in vivo includes $C_1$ to $C_6$ alkyl such as methyl, ethyl etc., $C_2$ to $C_{12}$ alkyloxyalkyl, such as methoxymethyl, ethoxymethyl, 2-methoxyethyl, 2-methoxyethoxymethyl, etc., and (2-oxo-1,3-dioxol-4-yl)methyl, (5-methyl-2-oxo-1,3-dioxol-4-yl) methyl, (5-tert-butyl-2-oxo-1,3-dioxol-4-yl)methyl, (5-phenyl-2-oxo-1,3-dioxol-4-yl)methyl, etc., more preferably (5-methyl-2-oxo-1,3-dioxol-4-yl)methyl.

Various protecting groups used usually are used as the protecting group of carboxyl group and include preferably a straight or branched $C_1$ to $C_6$ alkyl, such as methyl, ethyl, isopropyl, tert-butyl, etc., $C_1$ to $C_6$ halogenoalkyl, such as 2-iodoethyl, 2,2,2-trichloroethyl, etc., $C_2$ to $C_7$ alkyloxymethyl, such as methoxymethyl, ethoxymethyl, isobutoxymethyl, etc, $C_2$ to $C_7$ alkylcarbonyloxymethyl, such as acetyloxymethyl, propionyloxymethyl, butyriloxymethyl, pivaloyloxymethyl, etc., $C_4$ to $C_{11}$ 1-alkyloxycarbonyloxyethyl, such as 1-ethoxycarbonyloxyethyl, etc., aralkyl, such as benzyl, p-methoxybenzyl, o-nitrobenzyl, p-nitrobenzyl, etc., $C_3$ to $C_7$ alkenyl, such as allyl, 3-methylallyl, etc., benzhydryl, phthalidyl, (2-oxo-1,3-dioxol-4-yl)methyl, (5-methyl-2-oxo-1,3-dioxol-4-yl)methyl, (5-t-butyl-2-oxo-1,3-dioxol-4-yl)methyl, (5-phenyl-2-oxo-1,3-dioxol-4-yl) methyl, etc.

Various protecting groups used usually can be used as the protecting group of hydroxy, amino, amidino or guanidino group and include preferably $C_2$ to $C_7$ alkyloxycarbonyl, such as tert-butoxycarbonyl, etc, $C_1$ to $C_5$ halogenoalkyloxycarbonyl, such as 2-iodoethoxycarbonyl, 2,2,2-trichloroethoxycarbonyl, etc., optionally substituted $C_2$ to $C_7$ alkenyloxycarbonyl, such as allyloxycarbonyl, etc., aralkyloxycarbonyl, such as benzyloxycarbonyl, p-methoxybenzyloxycarbonyl, o-nitrobenzyloxycarbonyl, p-nitrobenzyloxycarbonyl, etc., trialkylsilyl, such as trimethylsilyl, triethylsilyl, tert-butyldimethylsilyl, etc. Furthermore, various protecting groups which regenerates a hydroxy and/or amino, amidino or guanidino group by hydrolysis in vivo, can be used, such as (5-methyl-1,3-dioxolen-2-on-4-yl)methoxycarbonyl.

Preferable ring E is benzene.

About A, wherein r is 1 to 2, or s and/or t are 0 is preferable. More preferable A is $—(CH_2)_2—$, $—CH_2—$, $—OCH_2—$, $—CH_2O—$, $—O—$, $—NHCH_2—$, $—CH_2NH—$ or $—NH—$.

Preferable X is an oxygen atom.

Preferable Y is a hydrogen atom, an optionally protected hydroxy, a $C_1$ to $C_6$ alkyloxy, a halogen atom, or a cyano group, more preferably a hydrogen atom.

The pharmaceutically acceptable salt of the carbapenem of the present invention includes a conventional non-toxic salt. Such salts include, as a salt with an intramolecular carboxylic acid, a salt with an inorganic base, such as sodium, potassium, calcium, magnesium, ammonium salt, etc., a salt with an organic base, such as triethylammonium, pyridinium, diisopropylammonium salt, etc., or as a salt with an intramolecular basic group, a salt with an inorganic acid such as hydrochloric acid, sulfuric acid, phosphoric acid, or a salt with an organic acid, such as formic acid, acetic acid, oxalic acid, methanesulfuric acid, benzenesulfonic acid, etc.

The carbapenem of the present invention or the pharmaceutically acceptable salt thereof may be in the form of an anhydride thereof, a hydrate thereof, or a solvate thereof.

The second aspect of the present invention relates to a pharmaceutical composition containing a carbapenem compound as an active ingredient.

Since the carbapenem compound of the present invention has a potent antibacterial activity, excellent oral absorbability and furthermore, has stability to DHP-1, the compound is expected as a potent antibacterial agent which is clinically applicable, especially an orally antibacterial agent.

The carbapenem compound of the present invention exhibits broad antibacterial spectrum including gram positive bacteria, such as *Staphylococcus aureus, Staphylococcus epidermidis, Streptococcus pyogenes, Streptococcus pneumoniae, Enterococcus faecalis*, etc., and gram negative bacteria, such as *Escherichia coli*, the genus *Proteus, Klebsiella pneumoniae, Haemophilus influenzae, Neisseria gonorrhoe*, the genus *Branhamella*, etc. The carbapenem compound of the present invention has been found to have a potent antibacterial activity especially against *Haemophilus influenzae* (which widely gain resistance to the inhibitory effect of known β-lactam agents together with mutation of a penicillin binding protein (PBP), which have been recently increasingly isolated and provide a clinical trouble, such as penicillin resistant *Streptococcus pneumoniae* (PRSP) and β-lactamase non-producing ampicillin resistant *Haemophilus influenzae* (BLNAR)).

It is well known that dehydropeptidase-I (DHP-I), a renal enzyme can easily hydrolyze a carbapenem derived from natural sources. Some of the present carbapenem compounds show resistance to DHP-I and it is possible to use them solely. However, it is possible to use the compound of the present invention together with a DHP-I inhibitor, if necessary.

When used as an antibacterial agent in the treatment of infectious diseases caused by bacteria, the carbapenem compounds of the present invention are administered, for example, orally in the form of a tablet, a capsule, powders, syrup, etc., or parenterally such as intravenous injection, intramuscular injection, or intrarectal administration.

The suitable administration forms as mentioned above may be prepared in a conventional manner by mixing an active ingredient with a pharmaceutically acceptable carrier, excipient, binder, stabilizer, etc. When administered in the form of injection, a pharmaceutically acceptable buffering agent, a solubilizer, an isotonic agent, etc. may be added thereto.

The dosage of the compound varies according to the symptoms, ages, body weights, the administration form, the frequency of the administration, etc., but it is usually in the range of 100 to 3000 mg per day for an adult, which is administered once or divided into several dosage units. Besides, the dosage of the compound may be increased or decreased, if necessary.

The carbapenem compound of the present invention is prepared by various known methods (Tetrahedron, 39, 2531–2549 (1983), Tetrahedron Letters, 31, 2853–2856 (1990), ibid. 34, 3211–3214 (1993), ibid. 36, 4563–4566 (1995), Japanese patent publication B 4-40357, etc.). One of these methods, for example is illustrated as follows:

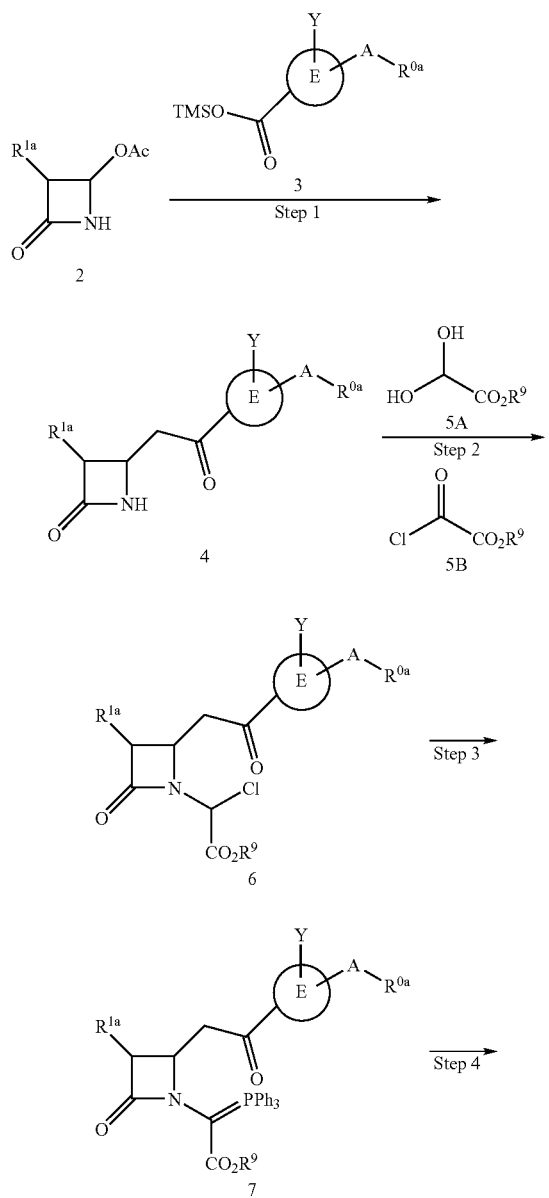

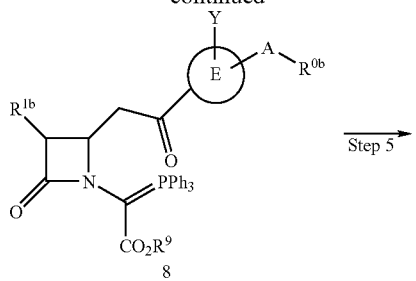

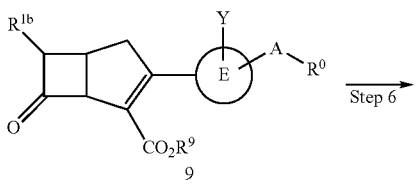

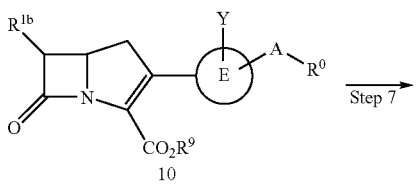

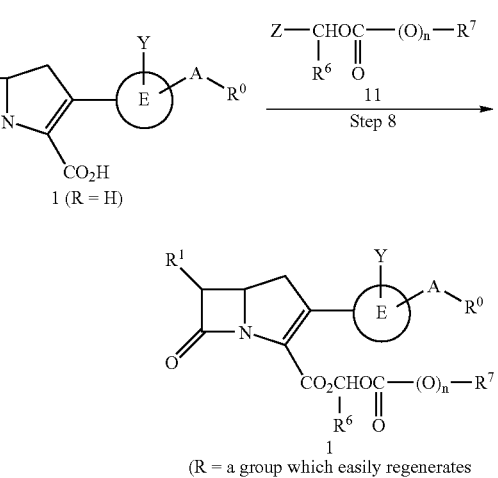

(R = a group which easily regenerates carboxyl group by hydrolysis in vivo)

wherein, ring E, $R^1$, A, $R^6$, $R^7$ and Y are the same as defined above, $R^9$ is a protecting group of carboxyl group, $R^{1a}$ and $R^{1b}$ are $C_1$ to $C_3$ alkyl or $C_1$ to $C_3$ alkyl substituted by a protected hydroxy group, respectively, and $R^{0a}$ and $R^{0b}$ are respectively, hydroxy group, amino group, amidino group, guanidino group, a protecting group of mercapto group, a group represented by a following formula [2], $$\overset{X}{\underset{CN}{\parallel}}\diagdown_{R^3}^{R^2}\quad[2]$$

wherein X, $R^2$ and $R^3$ are the same as defined above, or a group represented by a following formula [3],

[3]

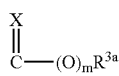

wherein X, m and $R^{3a}$ are the same as defined above, and Z is chlorine atom, bromine atom or iodine atom.

Step 1: Process for Preparation of Compound 4

Compound 4 is prepared by the reaction of compound 2 and compound 3 in the presence of acid catalyst in an inactive solvent. The catalyst includes zinc chloride, zinc bromide, zinc iodide, tin(IV) chloride, trifluoromethanesulfonic acid trimethylsilyl ester, boron trifluoride•diethyl ether complex, etc.

The inactive solvent includes dichloromethane, 1,2-dichloroethane, acetonitrile, monochlorobenzene, dioxane, tetrahydrofuran, benzene, toluene, etc.

The reaction is carried out at −78 to +60° C., preferably −30 to +40° C.

The starting material 3 is prepared by enol-etherifying various acetophenone derivatives or acetylthiophene derivatives prepared in accordance with known methods (e.g. Synthesis and reaction of organic compound [II] page 751–875 (1977), Sin Jikken Kagaku Kouza edited by The Chemical Society of Japan, Vol. 14 (Maruzen), or Organic Synthesis [III], Aldehyde•Ketone•Quinone, page 149–353 (1991), Sin Jikken Kagaku Kouza edited by The Chemical Society of Japan, 4th Edition (Maruzen)).

Step 2: Process for Preparation of Compound 6

A corresponding hemiacetal compound is prepared by heating compound 4 and compound 5A under dehydrated condition in an inactive solvent. The inactive solvent includes dichloromethane, 1,2-dichloroethane, monochlorobenzene, benzene, toluene, xylene, etc.

The reaction is carried out at +50 to +200° C., preferably +80 to +150 ° C. According to a known method (e.g., Journal of Organic Chemistry, 61, 7889–7894 (1996)), compound 4 and compound 5B are reacted in the presence of a base in an inactive solvent to give an imido compound and then the imido compound can be reduced to give a corresponding hemiacetal compound. The base includes triethylamine, diisopropylethylamine, N-methylmorpholine, etc. The inactive solvent used in imidation includes dichloromethane, 1,2-dichloroethane, monochlorobenzene, etc. The reaction temperature used in imidation is at −50 to +50 ° C., preferably −30 to +30 ° C. The reduction agent is preferably zinc, and the reduction is carried out preferably in a solvent such as a mixture of acetic acid and dichloromethane, a mixture of acetic acid and 1,2-dichloroethane, a mixture of acetic acid and monochlorobenzene, etc. The reaction temperature in reduction is at −50 to +50° C., preferably −30 to +30° C.

Thus obtained hemiacetal compound is reacted with a chlorination agent, such as thionyl chloride, oxalyl chloride, phosphorous oxychloride, etc., to give compound 6. The chlorination reaction is carried out in the presence of a base, such as lutidine, pyridine, quinoline, diisopropylethylamine, triethylamine, etc., in an inactive solvent, such as ether, tetrahydrofuran, dichloromethane, etc. The reaction temperature is at −78 to +60° C., preferably −30 to +40° C.

Step 3: Process for Preparation of Compound 7

Compound 6 is reacted with triphenylphosphine in the presence of a base, such as lutidine, pyridine, quinoline, diisopropylethylamine, triethylamine, etc., in an inactive solvent, such as tetrahydrofuran, dioxane, dimethoxyethane, etc., to give compound 7. The reaction temperature is at 0 to +100° C., preferably +10 to +70° C.

Step 4: Process for Preparation of Compound 8

If necessary, the removal of the protecting groups of hydroxy group in $R^{1a}$ and a protecting group in $R^{0a}$ is carried out, followed by re-protection of them to give compound 8. The removal of the protecting group and the introduction of the protecting group are carried out by conventional methods (See e.g., T. W. Greene: Protecting groups in Organic Synthesis, J. Wiley & Sons Inc., 1981).

Step 5: Process for Preparation of Compound 9

The cyclization reaction of compound 8 is carried out in an inactive solvent, such as benzene, toluene, xylene, etc., at +80 to +200° C. to give compound 9.

Step 6: Process for Preparation of Compound 10

The protecting group in $R^{0b}$ of compound 9 is removed, if necessary followed by subjecting to a known chemical reaction (acylation, carbamate-formation, urea-formation, etc.) to give compound 10. The removal of the protecting group is carried out by conventional methods (See e.g., T. W. Greene: Protecting groups in Organic Synthesis, J. Wiley & Sons Inc., 1981).

Step 7: Process for Preparation of Carbapenem 1 (R=hydrogen Atom)

Carbapenem 1 can be prepared by removing a protecting group of carboxyl group in $R^9$ of compound 9 and when hydroxy group in $R^{1b}$ is protected, by removing the protecting group. The removal of the protecting group is carried out by conventional methods, namely by treating with an acid, a base, a reduction agent, etc. (See e.g., T. W. Greene: Protecting groups in Organic Synthesis, J. Wiley & Sons Inc., 1981). Furthermore, when $R^{0b}$ is a protecting group of hydroxy group, amino group, amidino group, guanidino group or mercapto group, a subsequent known chemical reaction (acylation, carbamate-formation, urea-formation) may be carried out, if necessary.

Step 8: Process for Preparation of Carbapenem Compound 1 (R=a Protecting Group which Regenerates a Carboxyl Group by Hydrolysis in vivo.)

By introducing a protecting group which regenerates a carboxyl group by hydrolysis in vivo into carbapenem compound 1 (R=hydrogen atom) in accordance with a conventional method, carbapenem compound 1 (R=a protecting group which regenerates a carboxyl group by hydrolysis in vivo.) is obtainable. For example, a cabapenem compound (R=hydrogen atom) or its carboxylic acid salt is reacted and esterified with a halide 11, if necessary in the presence of a base, such as diisopropylethylamine, triethylamine, 4-dimethylaminopyridine, potassium carbonate or sodium hydrogencarbonate to give a carbapenem compound (R=a protecting group which regenerates a hydroxy group by hydrolysis in vivo).

The reaction solvent is not limited as long as it is an inactive solvent, and preferably dimethyl formamide, dimethyl sulfoxide, hexamethylphosphoramide, acetonitrile, dioxane, tetrahydrofuran, acetone, etc. The carboxylic acid salt includes preferably sodium salt and potassium salt. The reaction temperature is at −78 to +100° C., preferably −20 to +60° C. Furthermore, when $R^{0b}$ is a protecting group of hydroxy group, amino group, amidino group, or mercapto group, a subsequent known chemical reaction (acylation, carbamate-formation, urea-formation) may be carried out, if necessary.

In the above step, when compound 5A or compound 5B, wherein $R^9$ is a protecting group which regenerates a carboxyl group by hydrolysis in vivo, is used, and the remaining steps are carried out, carbapenem compound 1 (R=a protecting group which regenerates carboxyl group by hydrolysis in vivo.) can be directly prepared.

When the above reaction is completed, a reaction product is isolated by a conventional organic procedure, but when a water soluble product is obtained, a solution of the reaction mixture is neutralized, and the solution is subjected to a column chromatography using absorption resin, etc. and parts which an object compound is eluted are separated and lyophilized to give a reaction product.

The process for preparation of the carbapenem compound is not limited by the above preparation methods.

The optical isomers based on asymmetric carbon atoms on the present carbapenem compound at the 5- and 6-positions of 7-oxo-1-azabicyclo[3.2.0]hept-2-ene, a basic nuclear, present as shown in a following formula [1],

[1]

These isomers are all conveniently expressed by only one formula, but the scope of the present invention should not be construed to be limited thereto, and includes all isomers and a mixture of isomers based on each asymmetric carbon atom. The preferable isomers are ones wherein the 5-carbon atom has an R-configuration such as (5R,6R)-compounds or (5R,6S)-compounds. More preferable compounds are ones represented by a following formula [1b],

[1b]

Furthermore, when $R^1$ is 1-hydroxyethyl group, there are isomers having an R-configuration and an S-configuration at the position 8 as shown in a following formula [1c], and an isomer having the R-configuration is preferable.

[1c]

In regard to the substitution position of $-A-R^0$ on benzene ring or thiophene ring, a side chain at the position 3, the said position is not limited, and meta or para position is preferable in case of the benzene ring.

The carbapenem compound of the present inventions can be illustrated by following examples 1 to 72.

TABLE 1

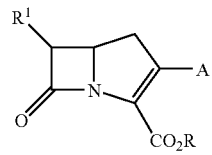

| Compound No. | $R^1$ | R | A |
|---|---|---|---|
| 1 | $CH(OH)CH_3$ | $-CH_2OCOt$-Bu | 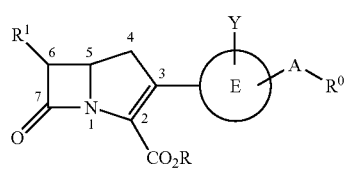 3-$OCONH_2$-phenyl |
| 2 | $CH(OH)CH_3$ | $-CH_2OAc$ | 3-$OCONHMe$-phenyl |
| 3 | $CH(OH)CH_3$ | $-CH_2OC(O)CH_2-$cyclohexyl- | 3-$OCONH_2$-phenyl |
| 4 | $CH(OH)CH_3$ | $-CH_2OC(O)-$C(Me)-cyclohexyl- | 3-$OCONH_2$-phenyl |
| 5 | $CH(OH)CH_3$ | $-CH(Me)OC(O)OEt$ | 3-$OCONH_2$-phenyl |
| 6 | $CH(OH)CH_3$ | $-CH(Me)OC(O)O-$cyclohexyl- | 3-$OCONH_2$-phenyl |
| 7 | $CH(OH)CH_3$ | H | 3-$OCONHMe$-phenyl |
| 8 | $CH(OH)CH_3$ | $-CH_2OCOt$-Bu | 3-$OCONHPh$-phenyl |

TABLE 2
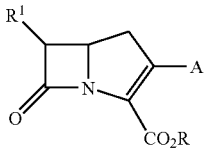
| Compound No. | R¹ | R | A |
|---|---|---|---|
| 9 | CH(OH)CH₃ | —CH₂OCOt-Bu | 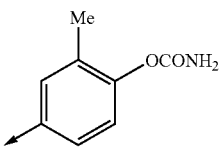 |
| 10 | CH(OH)CH₃ | —CH₂OAc |  |
| 11 | CH(OH)CH₃ | —CH₂OCCH₂-cyclohexyl | 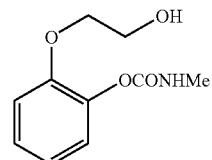 |
| 12 | CH(OH)CH₃ | —CH₂OC(Me)(cyclohexyl) | 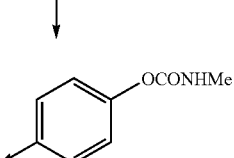 |
| 13 | CH(OH)CH₃ | —CH(Me)OCOEt | 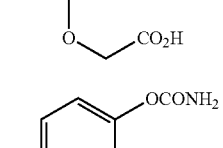 |
| 14 | CH(OH)CH₃ | —CH(Me)OCO-cyclohexyl | 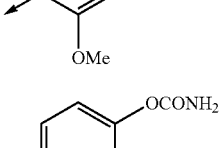 |
| 15 | CH(OH)CH | —CH₂OCOt-Bu | 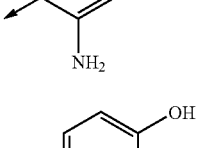 |
| 16 | CH(OH)CH₃ | H | 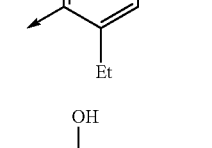 |

TABLE 3
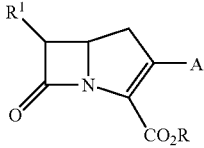
| Compound No. | R¹ | R | A |
|---|---|---|---|
| 17 | CH(OH)CH₃ | —CH₂OCOt-Bu | 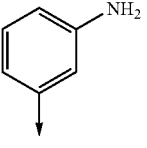 |
| 18 | CH(OH)CH₃ | —CH₂OAc | 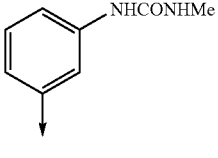 |
| 19 | CH(OH)CH₃ | 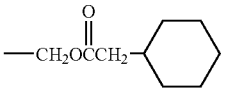 | 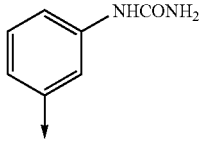 |
| 20 | CH(OH)CH₃ | 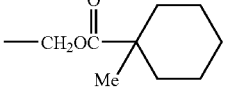 | 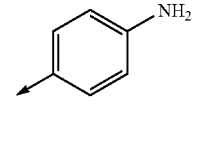 |
| 21 | CH(OH)CH₃ |  | 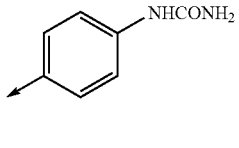 |
| 22 | CH(OH)CH₃ | 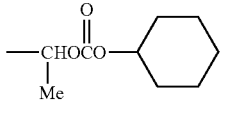 | 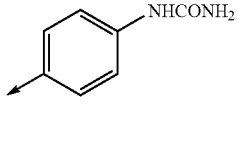 |
| 23 | CH(OH)CH₃ | H | 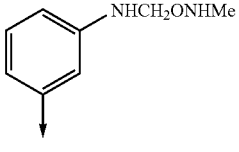 |
| 24 | CH(OH)CH₃ | —CH₂OCOt-Bu | 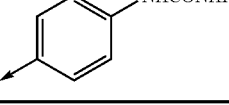 |

TABLE 4

| Compound No. | R¹ | R | A |
|---|---|---|---|
| 25 | CH(OH)CH3 | —CH₂OCOt-Bu | 3-(CH₂CONH₂)phenyl |
| 26 | CH(OH)CH₃ | —CH₂OCOt-Bu | 3-[CH₂C(O)-(azetidin-1-yl)]phenyl |
| 27 | CH(OH)CH₃ | —CH₂OCOt-Bu | 3-[CH₂C(O)-(pyrrolidin-1-yl)]phenyl |
| 28 | CH(OH)CH₃ | —CH₂OCOt-Bu | 3-[CH₂C(O)-(piperidin-1-yl)]phenyl |
| 29 | CH(OH)CH₃ | —CH₂OCOt-Bu | 4-[CH₂C(O)-(4-hydroxypiperidin-1-yl)]phenyl |
| 30 | CH(OH)CH₃ | —CH₂OCOt-Bu | 4-[CH₂C(O)-(morpholin-4-yl)]phenyl |
| 31 | CH(OH)CH₃ | —CH₂OCOt-Bu | 4-{CH₂C(O)NH-[3-(CO₂H)phenyl]}phenyl |

TABLE 4-continued

[Structure: bicyclic β-lactam core with R¹, A, and CO₂R substituents]

| Compound No. | R¹ | R | A |
|---|---|---|---|
| 32 | CH(OH)CH₃ | —CH₂OCOt-Bu | 4-CH₂C(O)NH-(pyridin-3-yl)-phenyl |

TABLE 5

[Structure: bicyclic β-lactam core with R¹, A, and CO₂R substituents]

| Compound No. | R¹ | R | A |
|---|---|---|---|
| 33 | CH(OH)CH₃ | —CH₂OCOt-Bu | 4-(CH₂OH)phenyl |
| 34 | CH(OH)CH₃ | —CH₂OCOt-Bu | 4-(CH₂OCONH₂)phenyl |
| 35 | CH(OH)CH₃ | —CH₂OCOt-Bu | 4-(CH₂OCONHMe)phenyl |
| 36 | CH(OH)CH₃ | —CH₂OCOt-Bu | 3-(CH₂OH)phenyl |
| 37 | CH(OH)CH₃ | —CH₂OCOt-Bu | 3-(CH₂OCONH₂)phenyl |
| 38 | CH(OH)CH₃ | —CH₂OCOt-Bu | 3-(CH₂OCONHMe)phenyl |
| 39 | CH(OH)CH₃ | —CH₂OCOt-Bu | 4-(CH₂OCONH-thien-2-yl)phenyl |

TABLE 5-continued

[Structure: bicyclic β-lactam core with R¹, A, and CO₂R substituents]

| Compound No. | R¹ | R | A |
|---|---|---|---|
| 40 | CH(OH)CH₃ | —CH₂OCOt-Bu | 4-(CH₂SCONMe₂)phenyl |

TABLE 6

[Structure: bicyclic β-lactam core with R¹, A, and CO₂R substituents]

| Compound No. | R¹ | R | A |
|---|---|---|---|
| 41 | CH(OH)CH₃ | —CH₂OCOt-Bu | 4-(CH₂NH₂)phenyl |
| 42 | CH(OH)CH₃ | —CH₂OCOt-Bu | 4-(CH₂NHCONH₂)phenyl |
| 43 | CH(OH)CH₃ | —CH₂OCOt-Bu | 4-(CH₂NHCONHMe)phenyl |

TABLE 6-continued
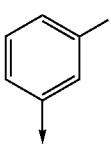
| Compound No. | R¹ | R | A |
|---|---|---|---|
| 44 | CH(OH)CH$_3$ | —CH$_2$OCOt-Bu | 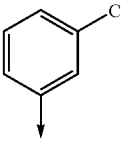 |
| 45 | CH(OH)CH$_3$ | —CH$_2$OCOt-Bu | 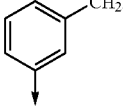 |
| 46 | CH(OH)CH$_3$ | —CH$_2$OCOt-Bu | 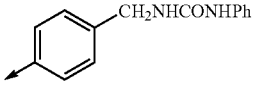 |
| 47 | CH(OH)CH$_3$ | —CH$_2$OCOt-Bu | 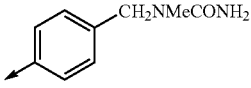 |
| 48 | CH(OH)CH$_3$ | —CH$_2$OCOt-Bu | 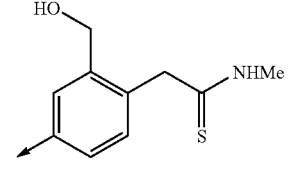 |
TABLE 7
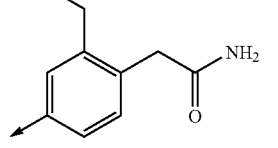
| Compound No. | R¹ | R | A |
|---|---|---|---|
| 49 | CH(OH)CH$_3$ | —CH$_2$OCOt-Bu | |
| 50 | CH(OH)CH$_3$ | —CH$_2$OCOt-Bu | |

TABLE 7-continued
| Compound No. | R¹ | R | A |
|---|---|---|---|
| 51 | CH(OH)CH₃ | —CH₂OCOt-Bu | 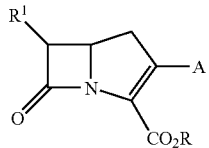 3-(PhCH₂C(=S)NHEt) |
| 52 | CH(OH)CH₃ | —CH₂OCOt-Bu | 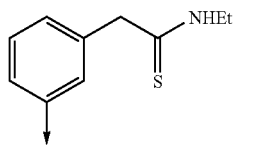 3-(PhCH₂C(=S)NHCH₂CH₂OH) |
| 53 | CH(OH)CH₃ | —CH₂OCOt-Bu | 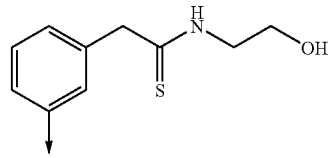 5-(CH₂CONH₂)thien-2-yl |
| 54 | CH(OH)CH₃ | —CH₂OCOt-Bu | 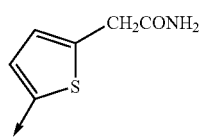 4-(CH₂CONH₂)thien-2-yl |
| 55 | CH(OH)CH₃ | —CH₂OCOt-Bu | 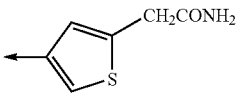 5-(CH₂CONH₂)thien-3-yl |
| 56 | CH(OH)CH₃ | —CH₂OCOt-Bu | 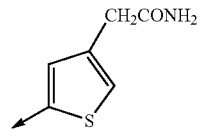 4-(CH₂CONH₂)thien-3-yl |
TABLE 8
| Compound No. | R¹ | R | A |
|---|---|---|---|
| 57 | CH(OH)CH₃ | —CH₂OCOt-Bu | 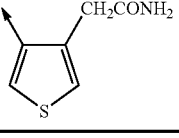 5-(CH₂OH)thien-2-yl |
| 58 | CH(OH)CH₃ | —CH₂OCOt-Bu | 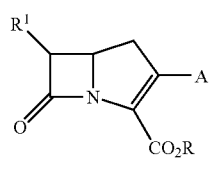 4-(CH₂OCONH₂)thien-2-yl |

TABLE 8-continued

![Structure: carbapenem core with R¹, CO₂R, and A substituents]

| Compound No. | R¹ | R | A |
|---|---|---|---|
| 59 | CH(OH)CH₃ | —CH₂OCOt-Bu | 5-(CH₂OCONH₂)-thiophen-2-yl (attached at 2-position) |
| 60 | CH(OH)CH₃ | —CH₂OCOt-Bu | 4-(CH₂OCONHPh)-thiophen-3-yl |
| 61 | CH(OH)CH₃ | —CH₂OCOt-Bu | 5-(CH₂NH₂)-thiophen-2-yl |
| 62 | CH(OH)CH₃ | —CH₂OCOt-Bu | 5-(CH₂NHCONH₂)-thiophen-3-yl |
| 63 | CH(OH)CH₃ | —CH₂OCOt-Bu | 5-(CH₂NHCONHMe)-thiophen-3-yl |
| 64 | CH(OH)CH₃ | —CH₂OCOt-Bu | 3-(H₂N)-thiophen-2-yl |

TABLE 9

![Structure: carbapenem core with R¹, CO₂R, and A substituents]

| Compound No. | R¹ | R | A |
|---|---|---|---|
| 65 | CH(OH)CH₃ | —CH₂OCOt-Bu | 3-(H₂NOCO)-thiophen-2-yl |

TABLE 9-continued

| Compound No. | R¹ | R | A |
|---|---|---|---|
| 66 | CH(OH)CH₃ | —CH₂OCOt-Bu | 5-(CH₂CSNH₂)-thiophen-2-yl |
| 67 | CH(OH)CH₃ | —CH₂OCOt-Bu | 4-(CH₂CSNH₂)-thiophen-2-yl |
| 68 | CH(OH)CH₃ | —CH₂OCOt-Bu | 5-(CH₂OCSNH₂)-thiophen-3-yl |
| 69 | CH(OH)CH₃ | —CH₂OCOt-Bu | 4-(CH₂OCSNH₂)-thiophen-3-yl |
| 70 | CH₂CH₃ | —CH₂OCOt-Bu | 5-(CH₂NHCSNH₂)-thiophen-2-yl |
| 71 | C(OH)(CH₃)₂ | —CH₂OCOt-Bu | 5-(CH₂NHCSNH₂)-thiophen-3-yl |
| 72 | CH(CH₃)₂ | —CH₂OCOt-Bu | 5-(CH₂NHCSNH₂)-thiophen-3-yl |

The compounds illustrated above have stereoisomers as described above or else stereoisomers based on asymmetric carbon atoms, and the compounds include all these isomers.

EXAMPLE

The present invention is illustrated by following examples, but the present invention is not limited by these examples.

The following abbreviations are used in Examples.

Me: methyl
t-Bu: tert-butyl
Ph: phenyl
Ac: acetyl
Boc: tert-butoxycarbonyl
ALOC: allyloxycarbonyl
TMS: trimethylsilyl
TES: triethylsilyl TBDMS: tert-butyl(dimethyl)silyl
PNB: p-nitrobenzyl
THF: tetrahydrofuran
ATR: all radiation absorption method
Example 1
According to the present invention, carbapenem compounds selected from the following compounds can be prepared.
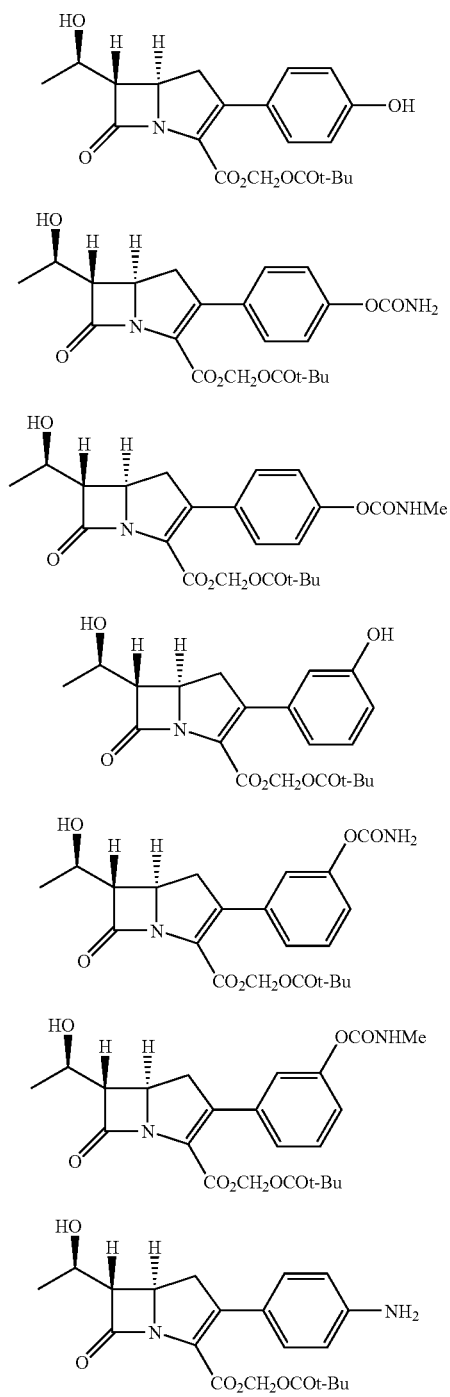
-continued
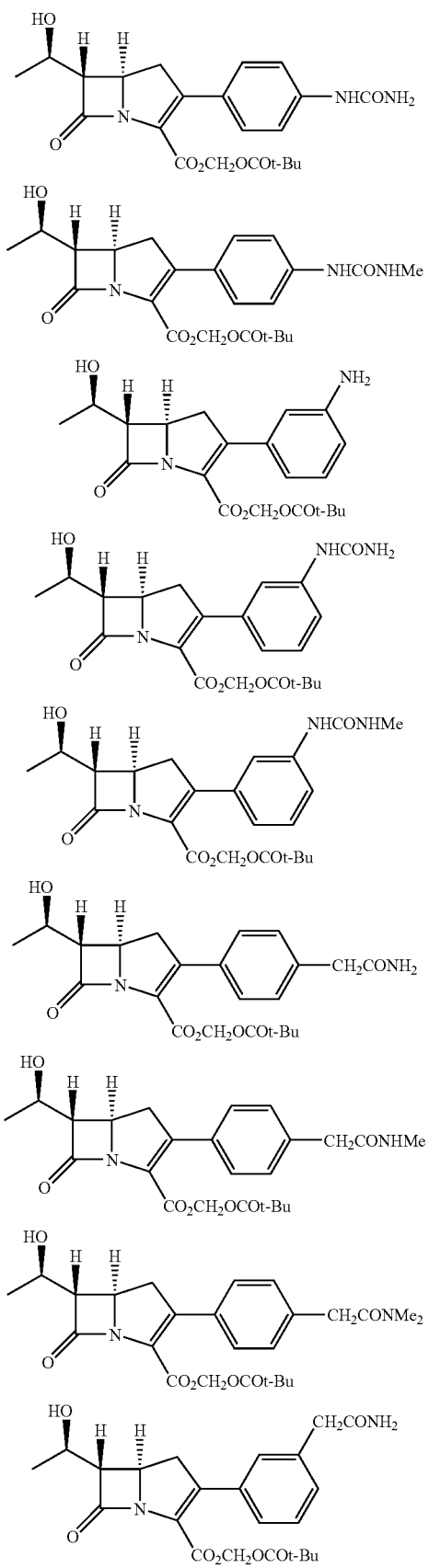

-continued
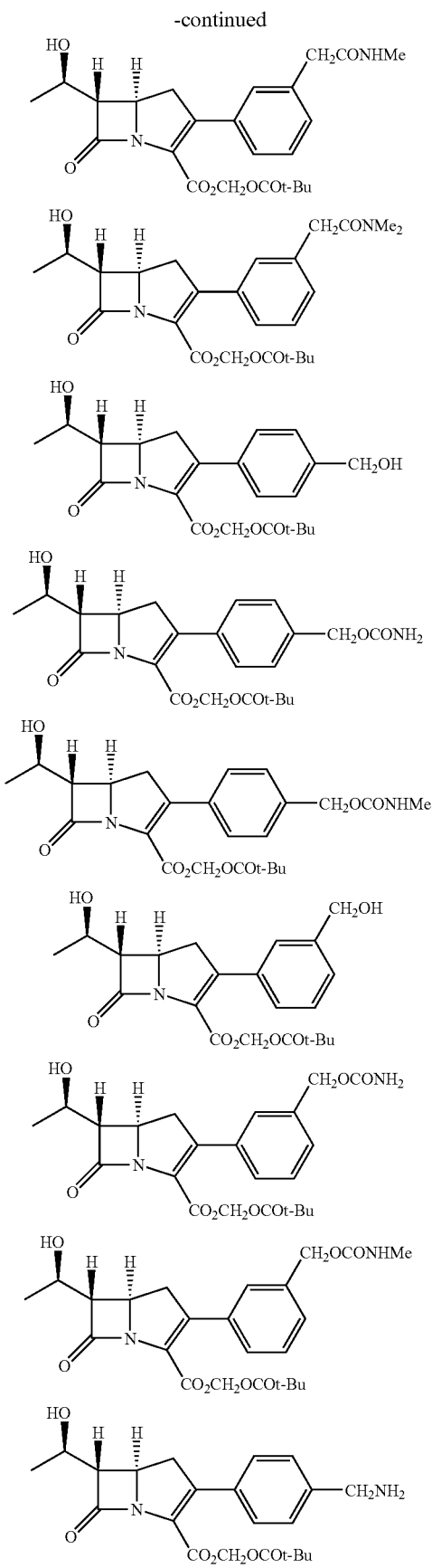
-continued
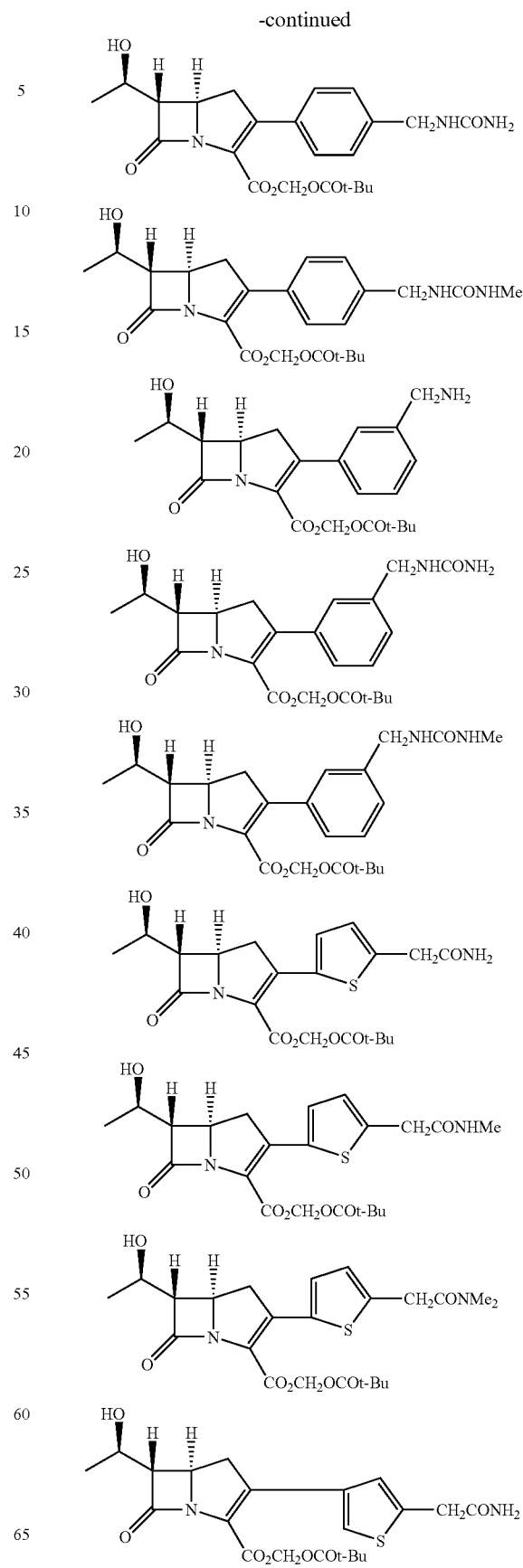

-continued
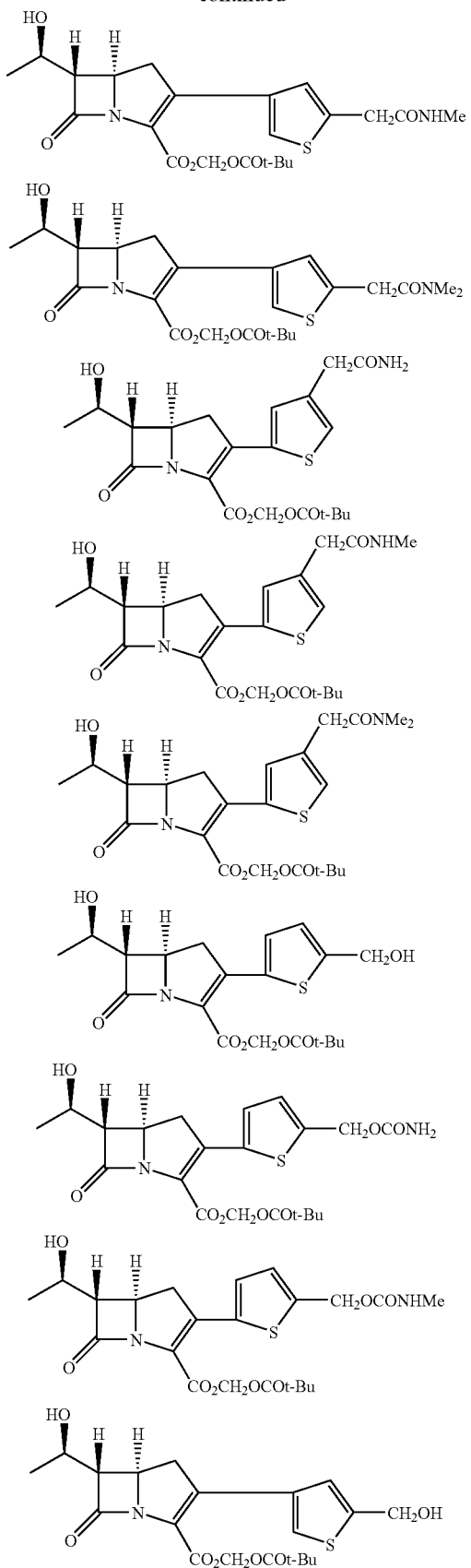
-continued
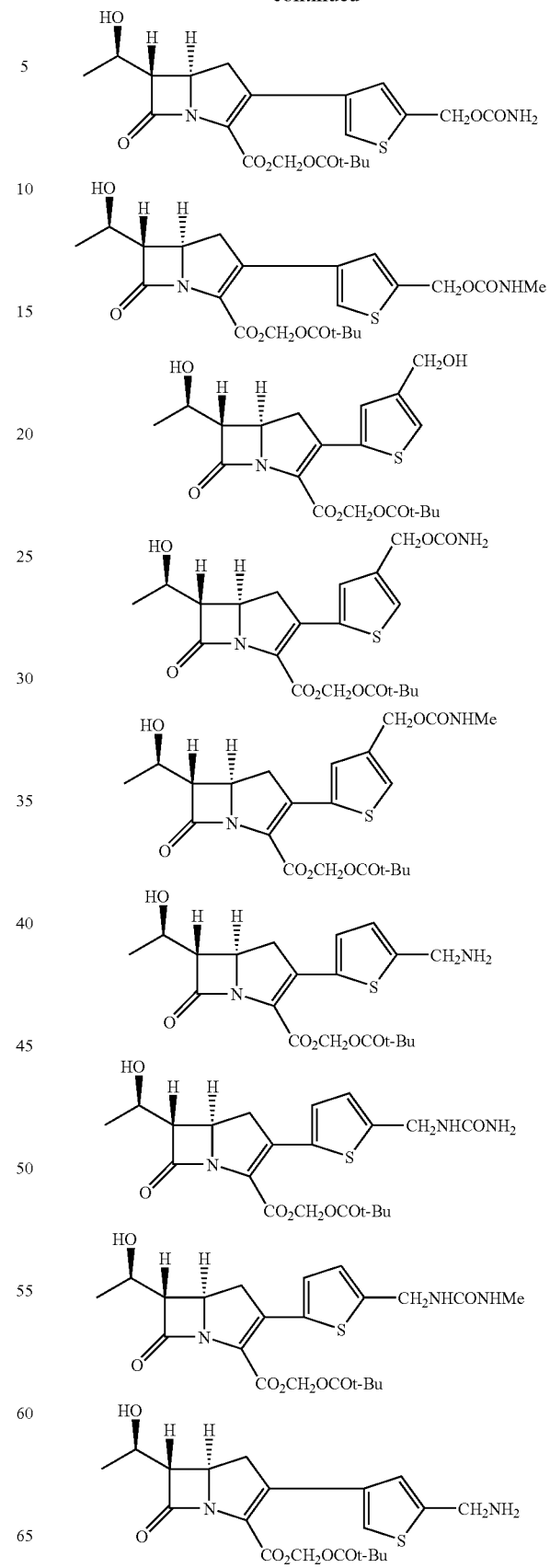

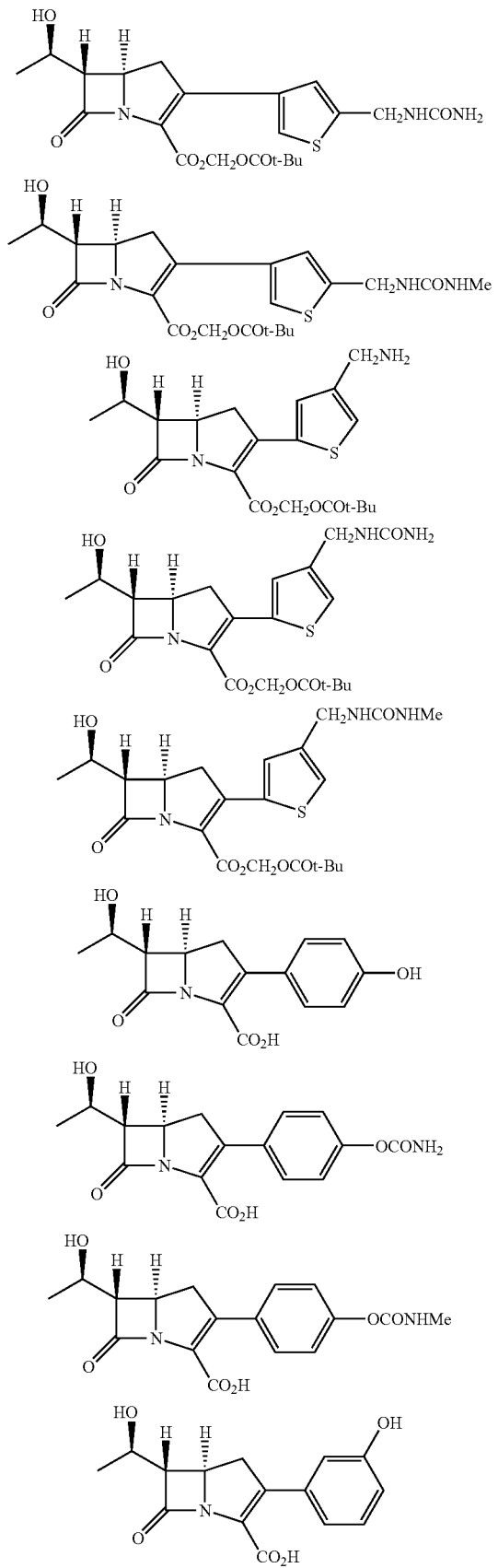
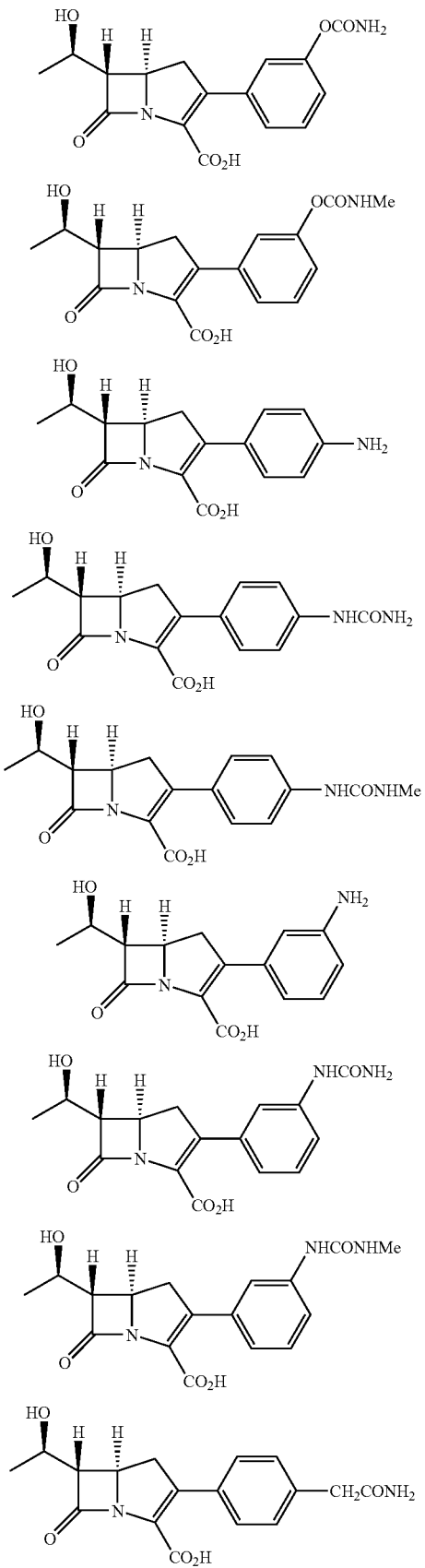

-continued
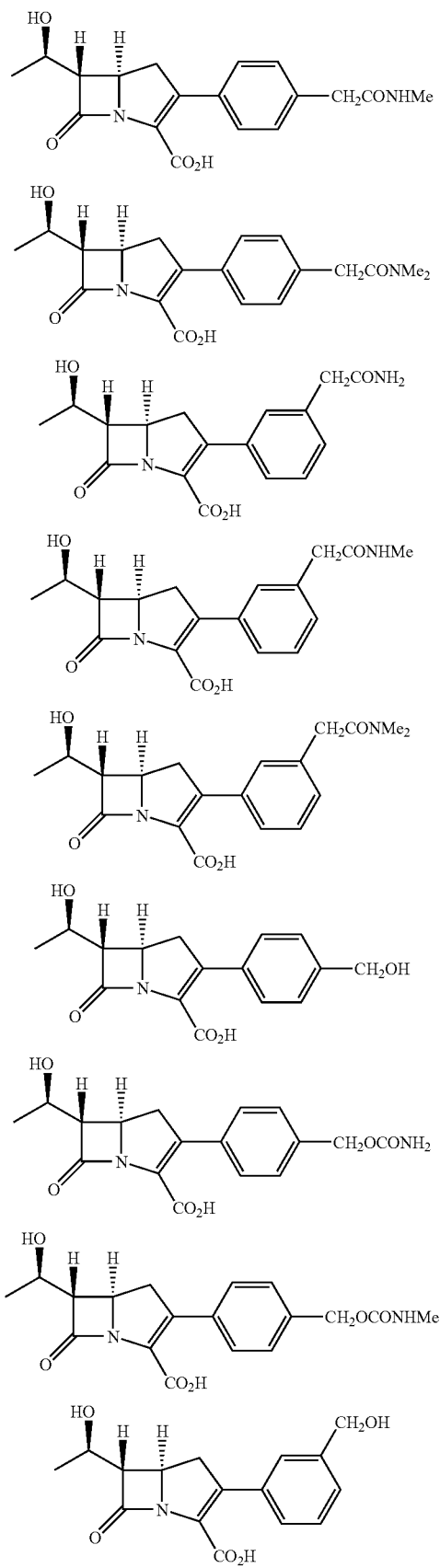
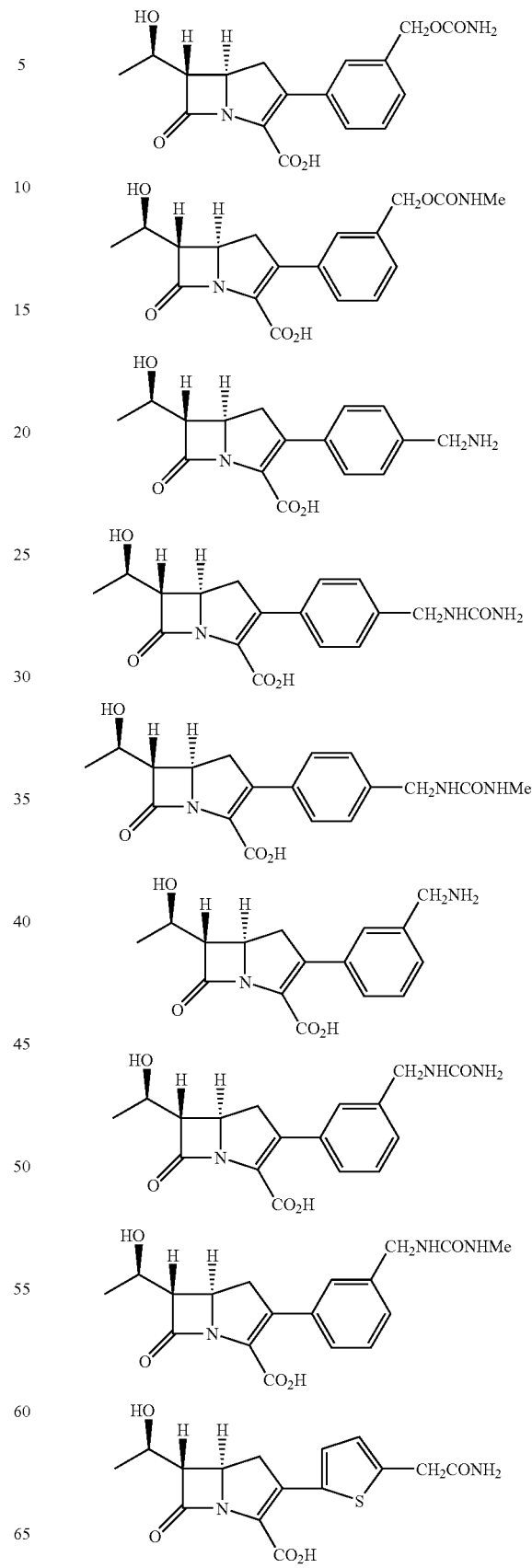

-continued
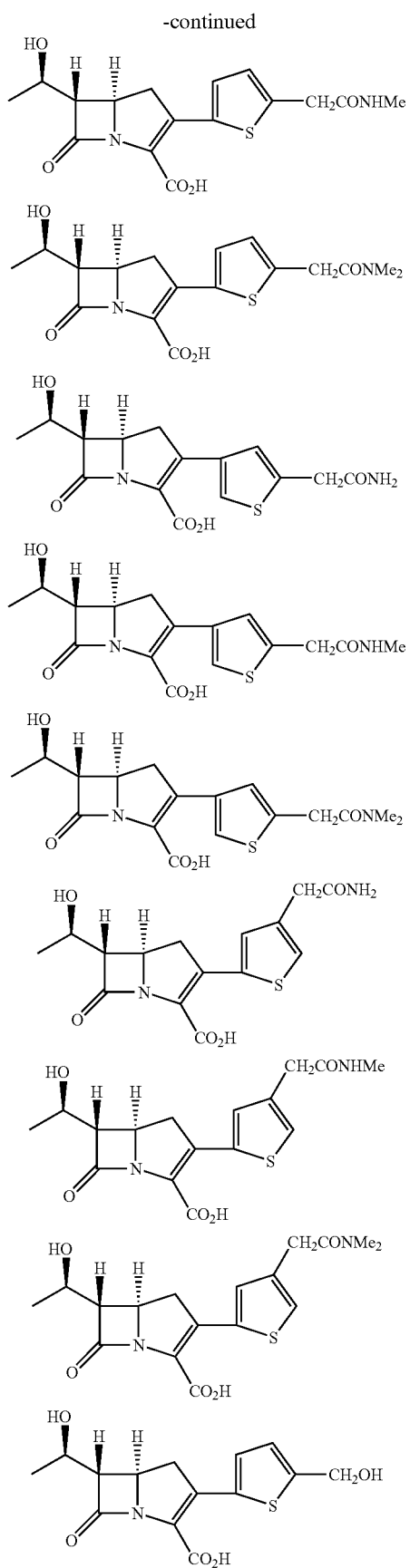
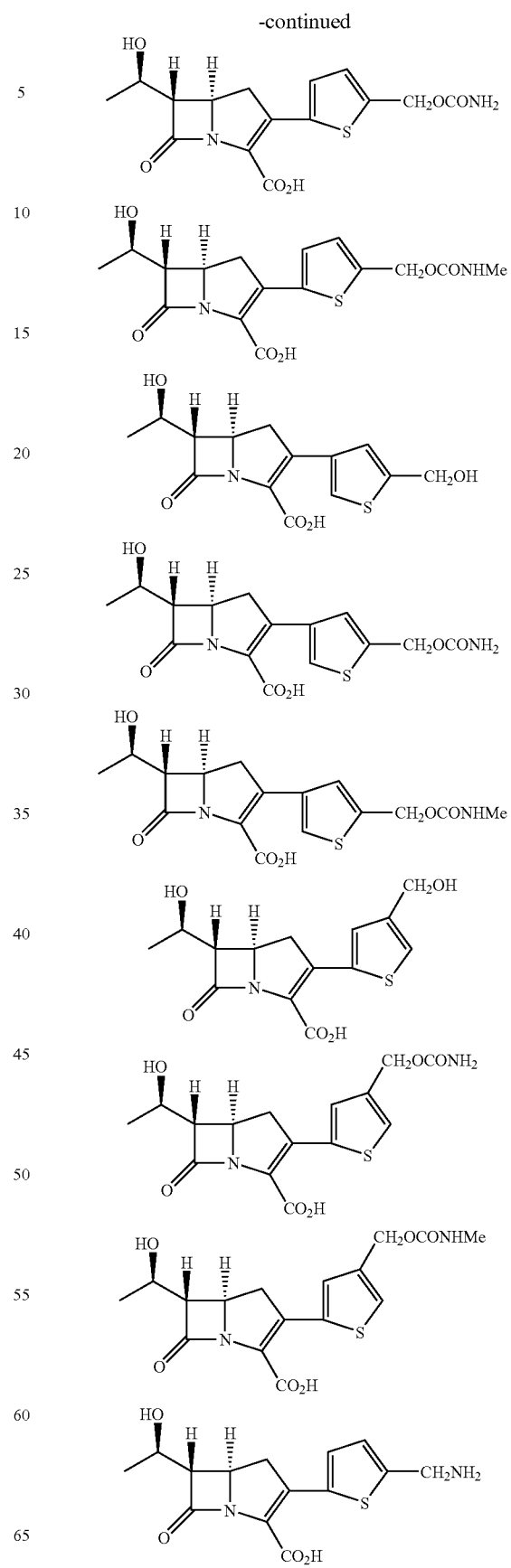

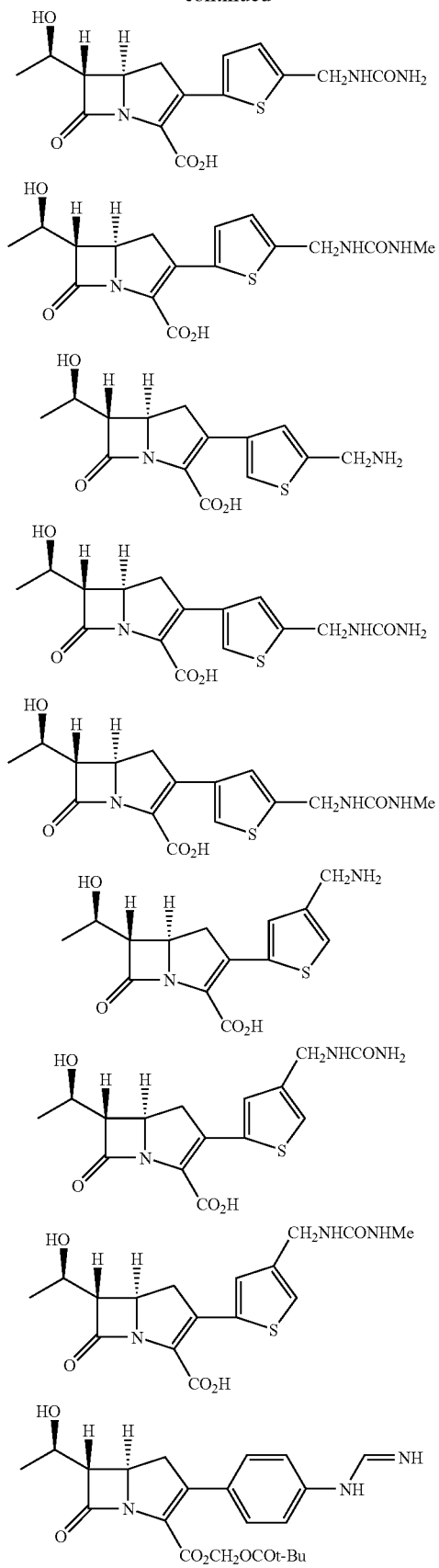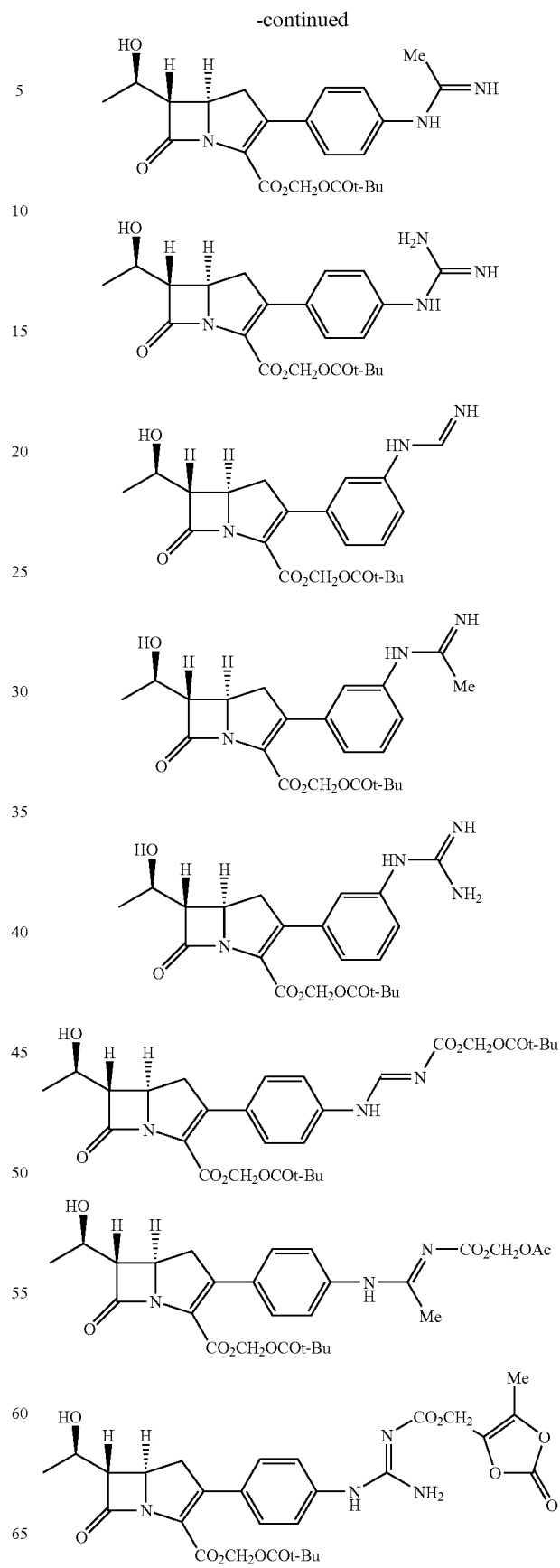

-continued
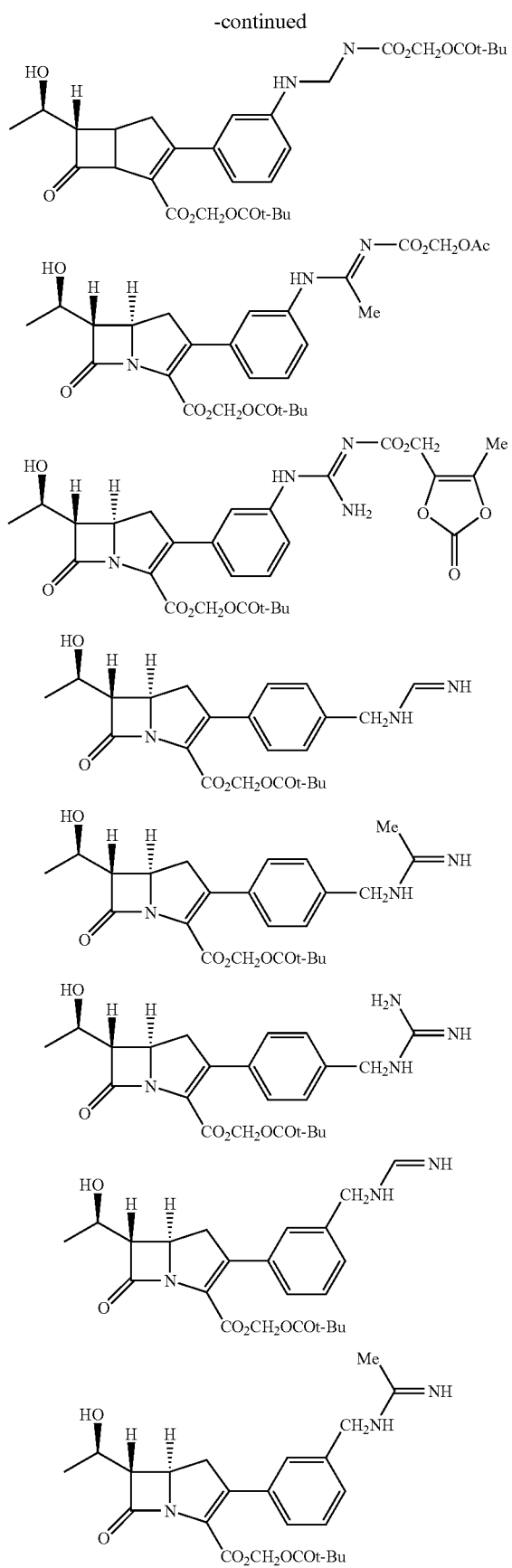
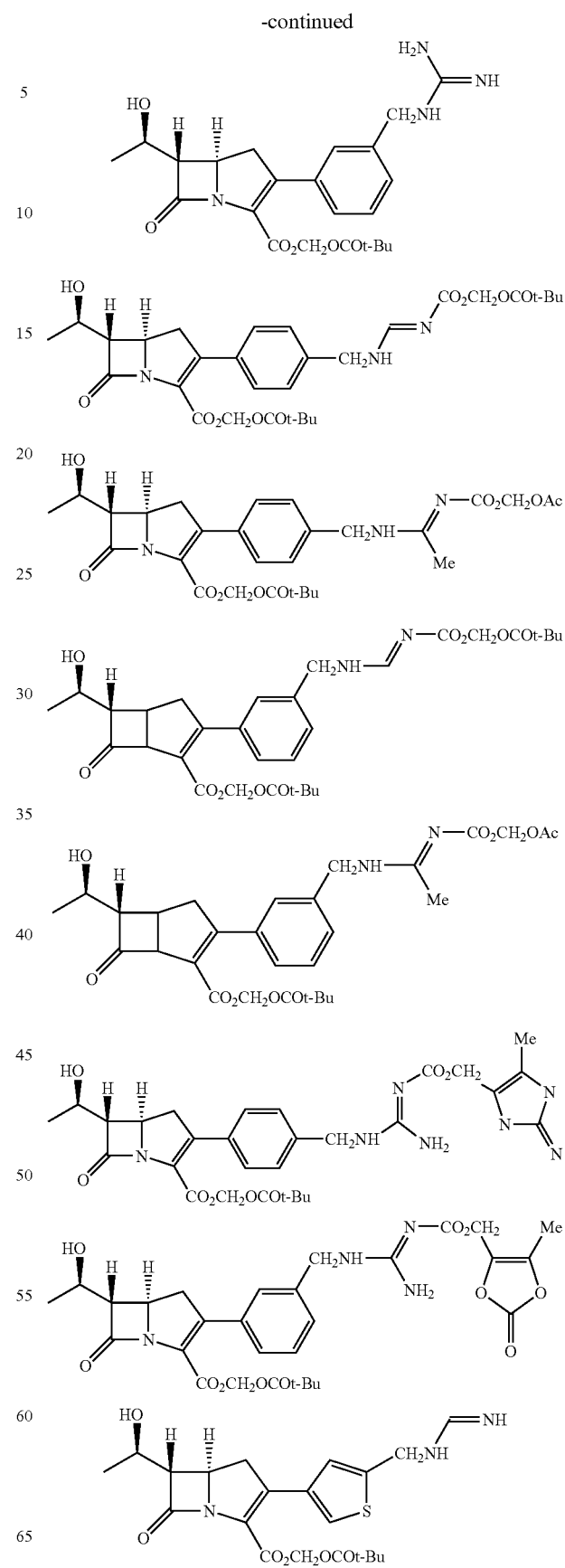

-continued
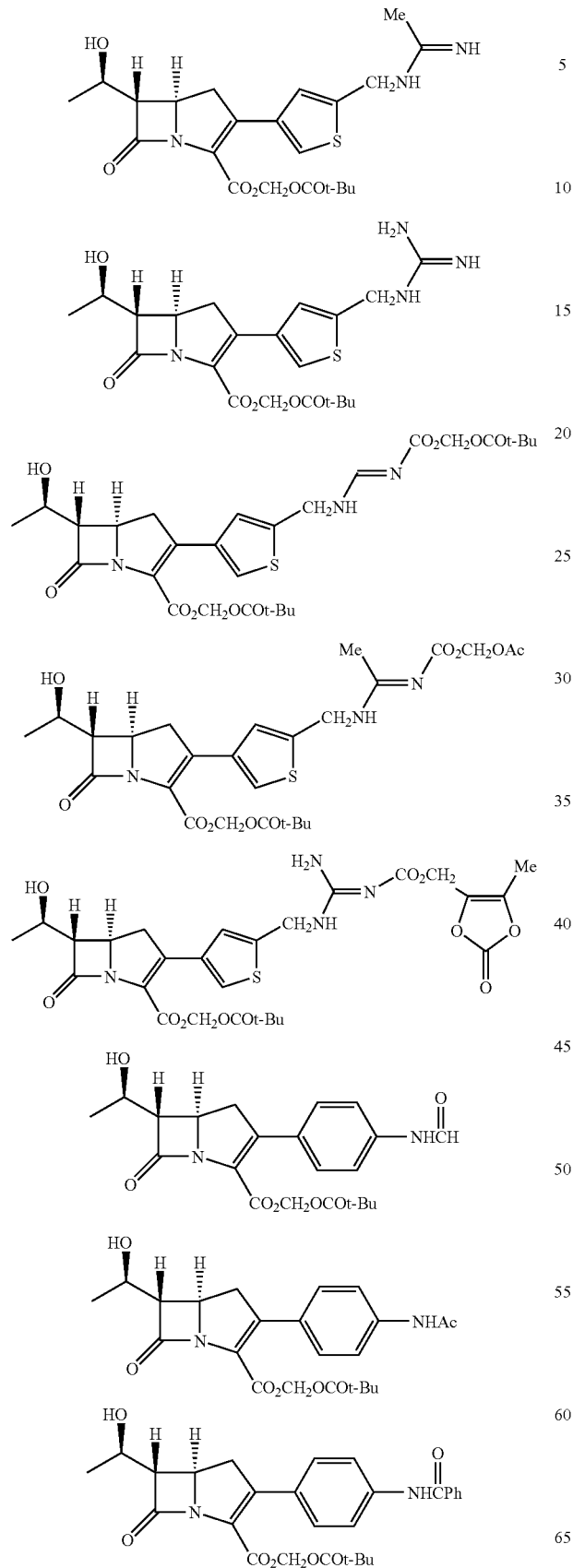
-continued
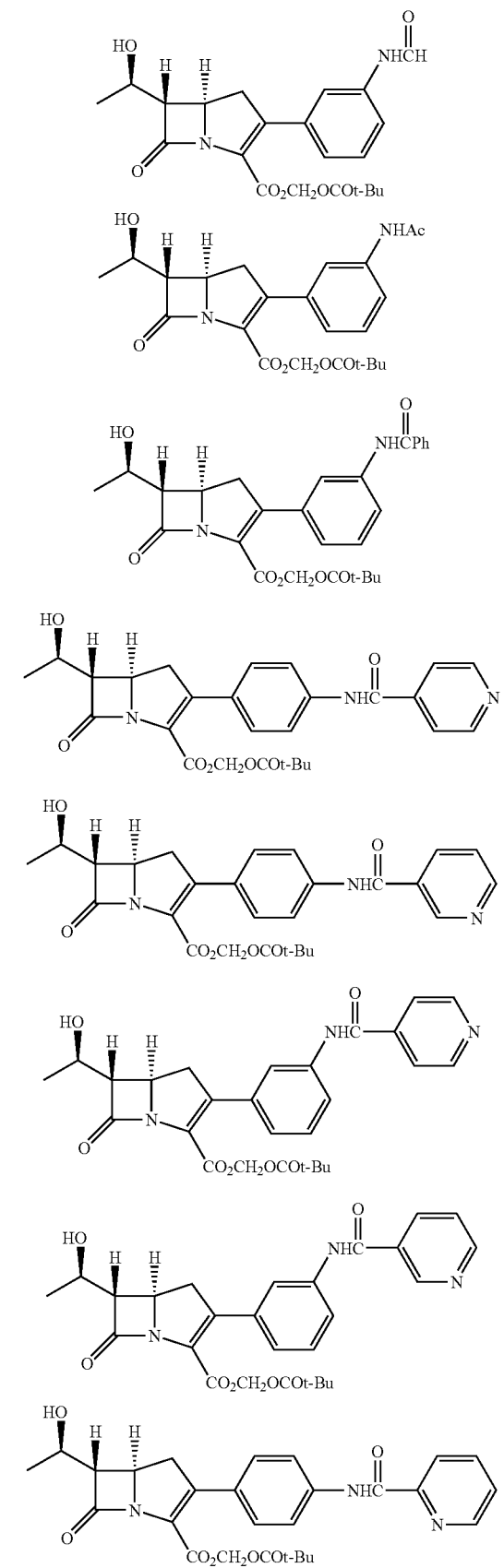

-continued
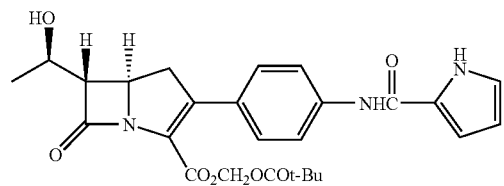
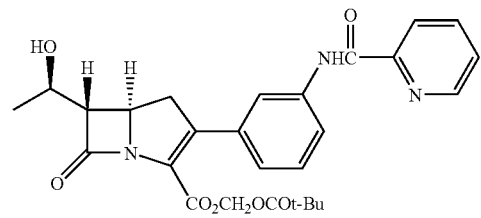
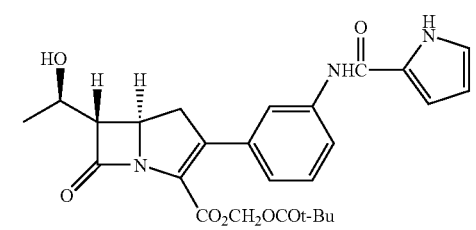
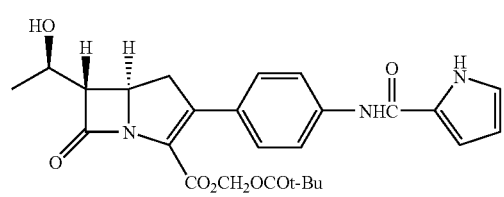
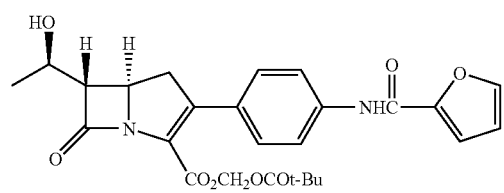
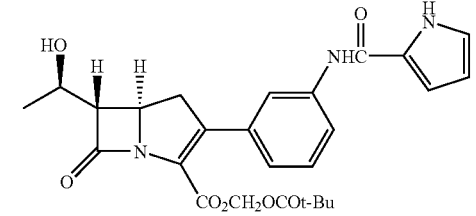
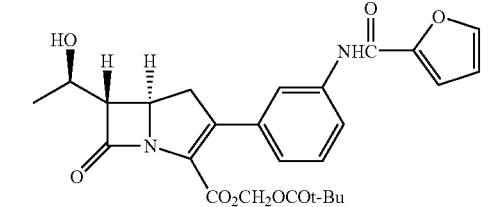
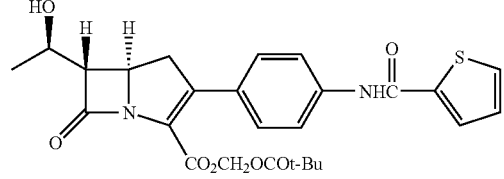
-continued
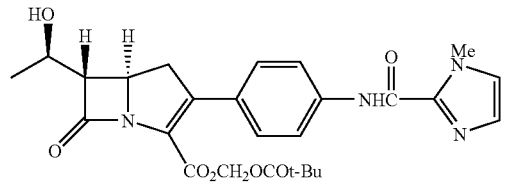
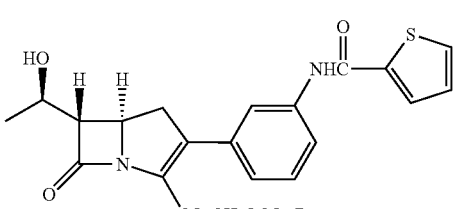
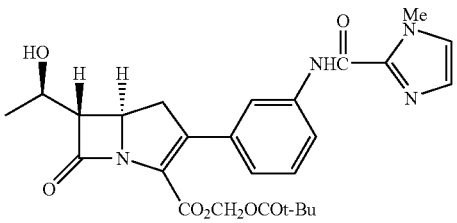
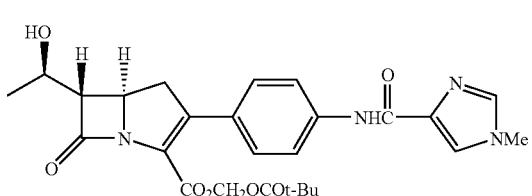
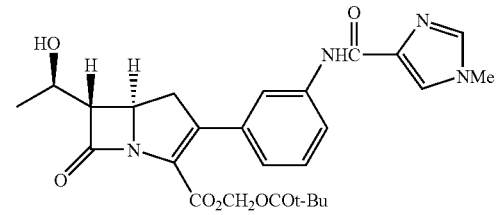
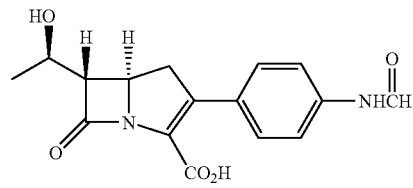
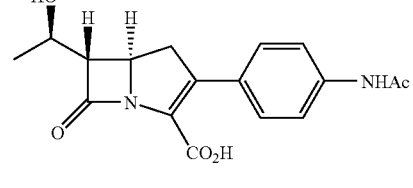
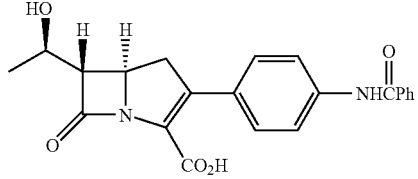

-continued
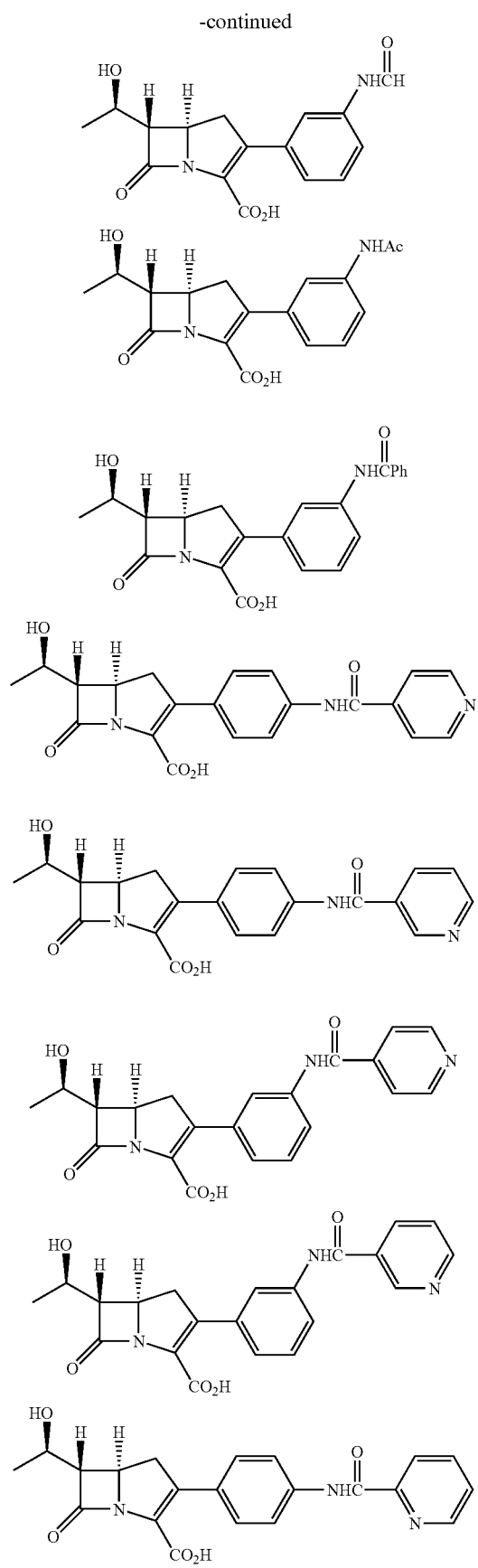
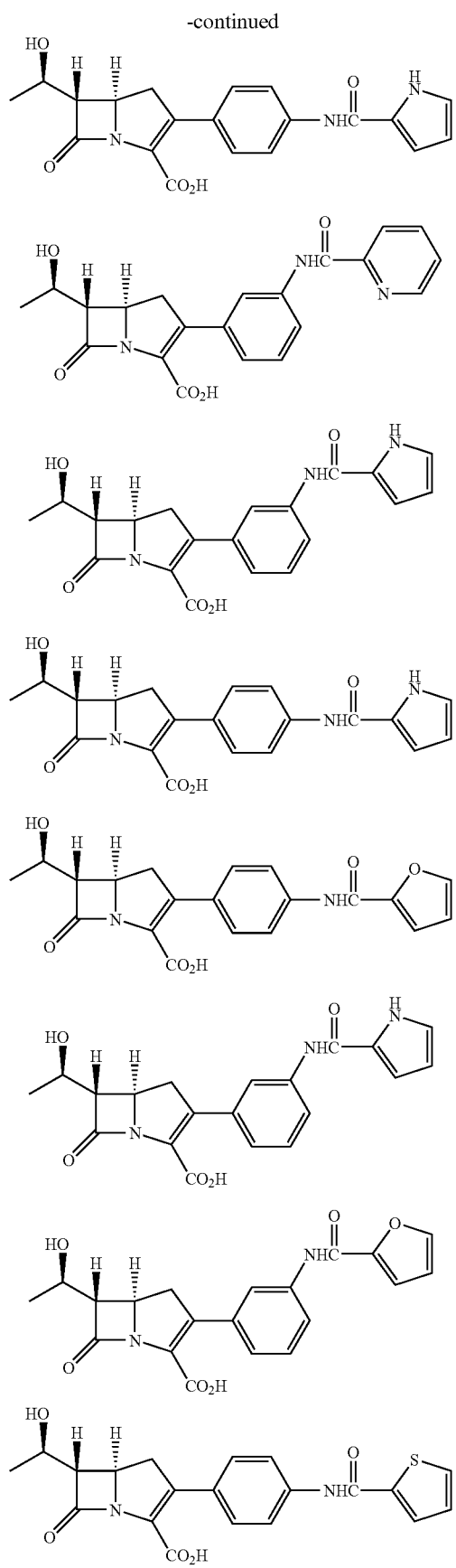

-continued
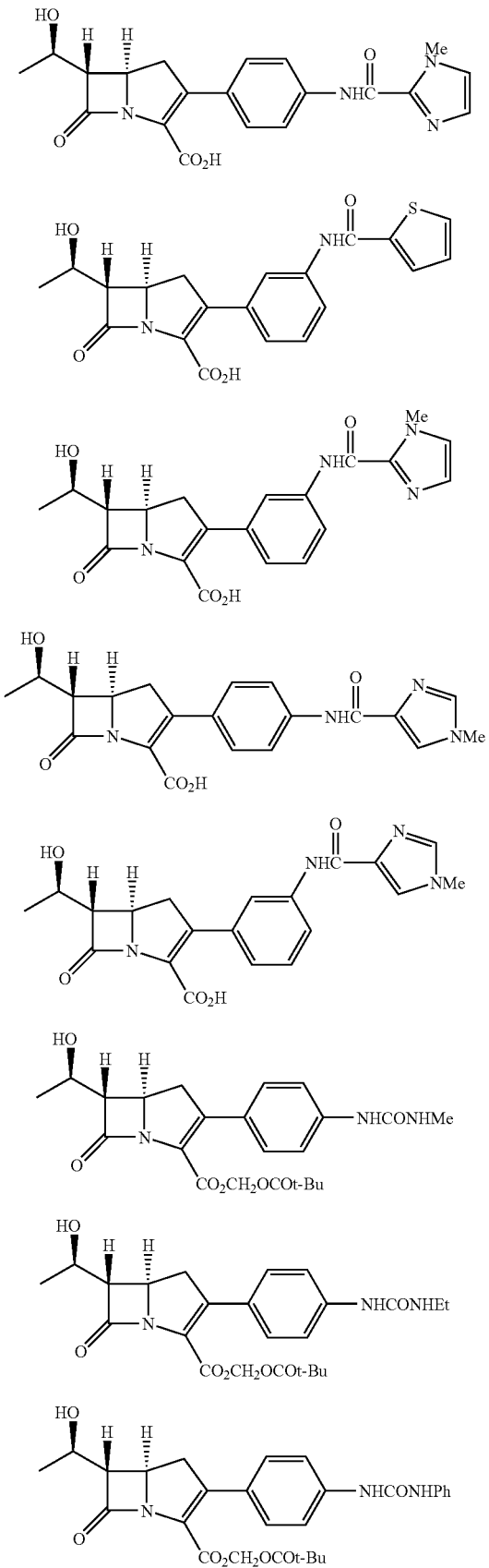
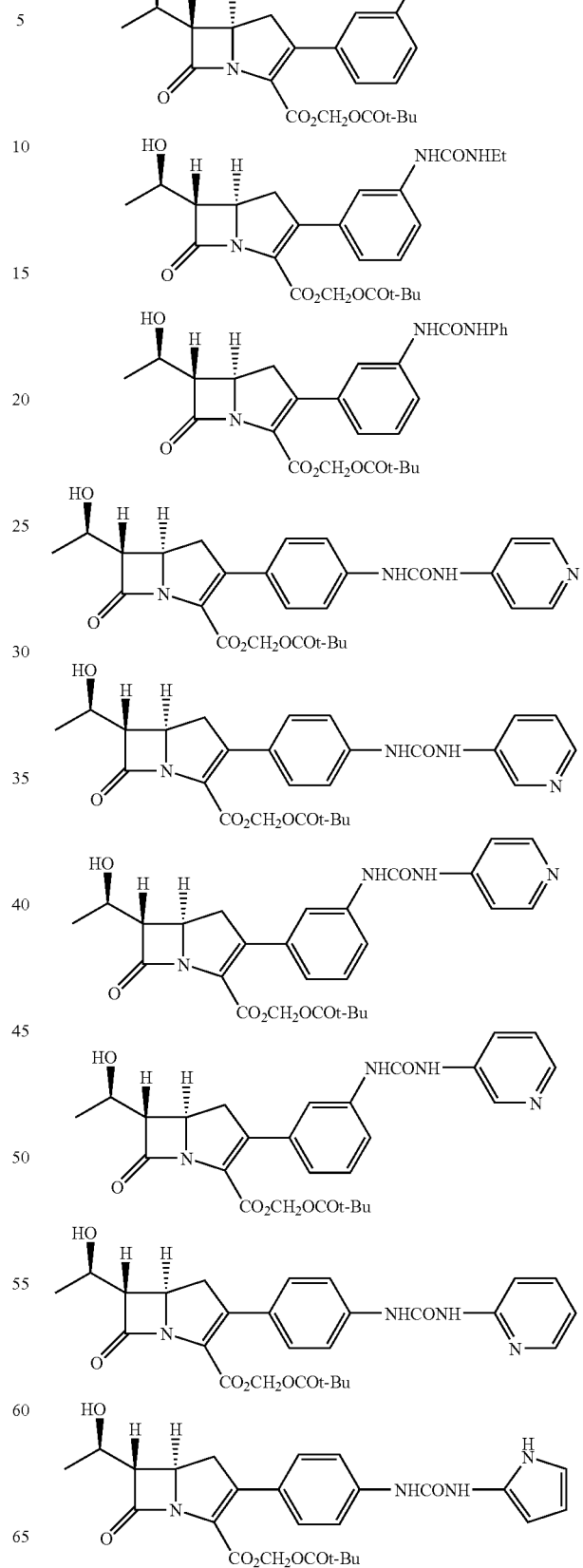

-continued

-continued
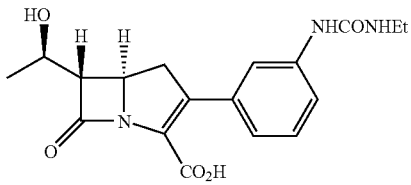
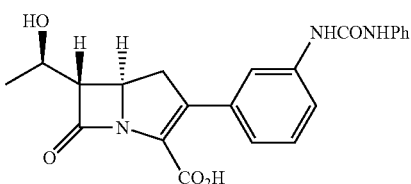
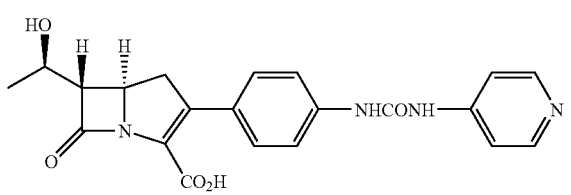
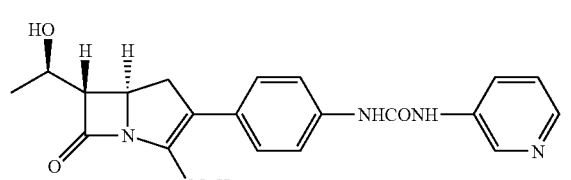
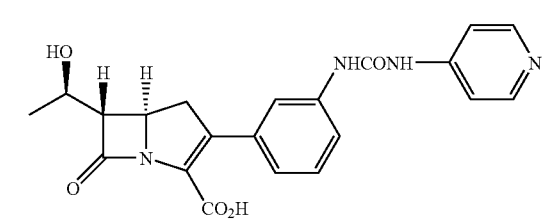
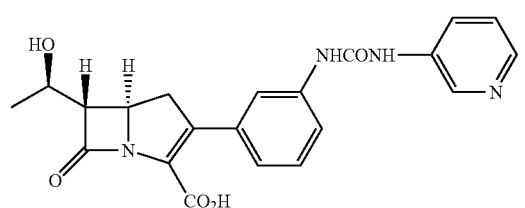
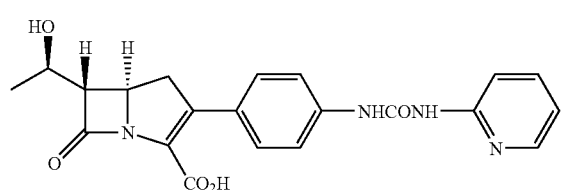
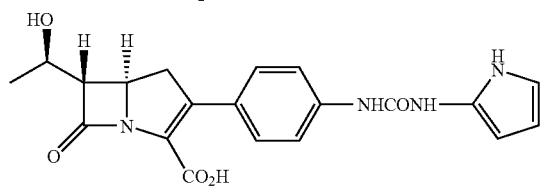
-continued
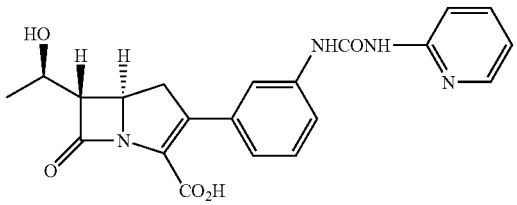
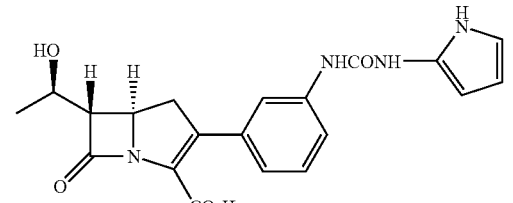
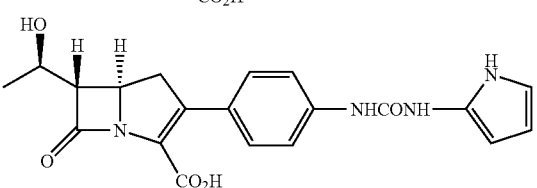
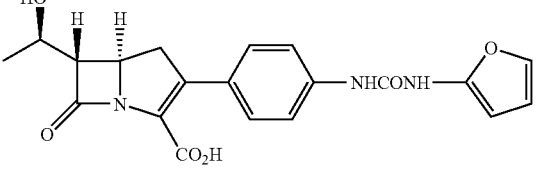
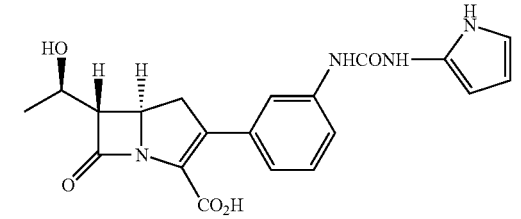
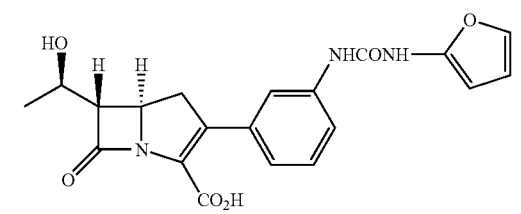
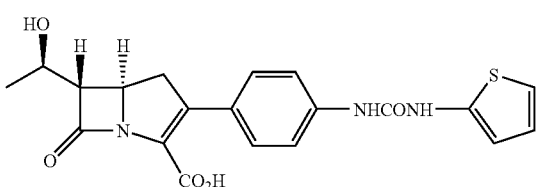
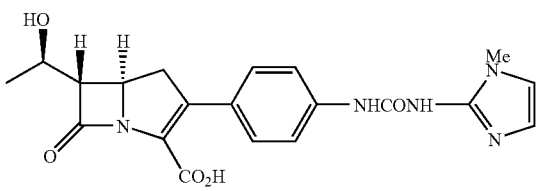

-continued
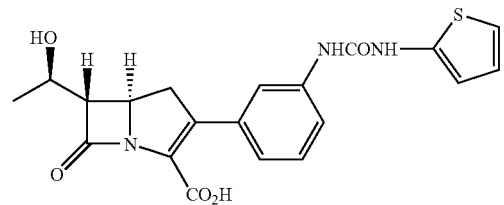
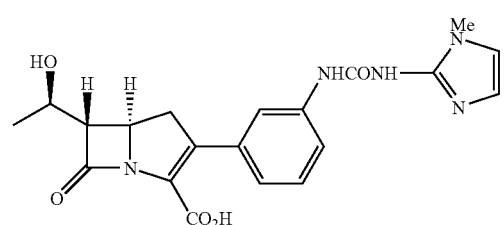
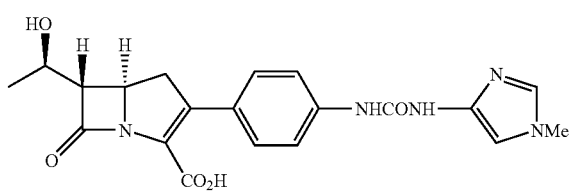
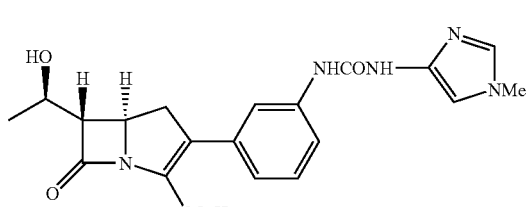
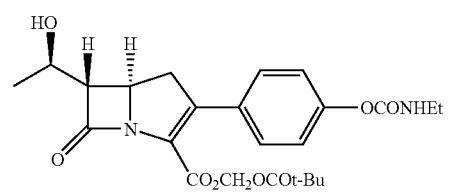
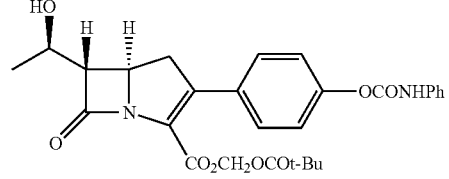
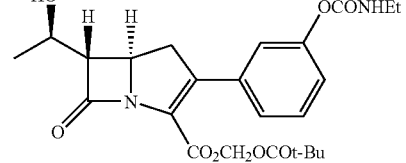
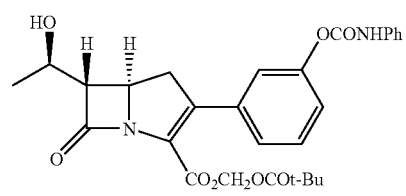
-continued
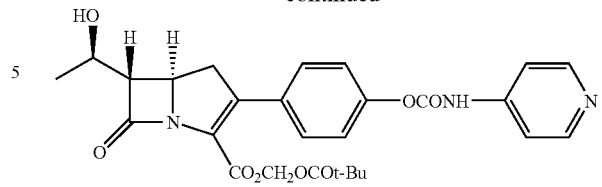
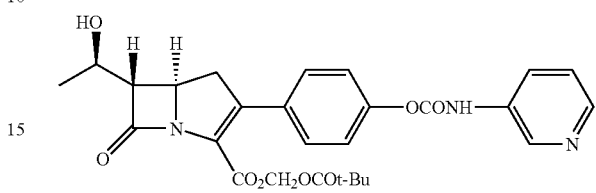
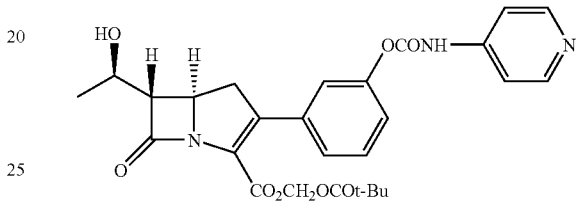
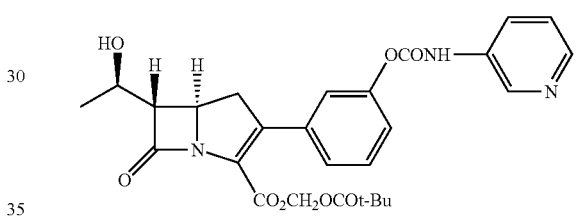
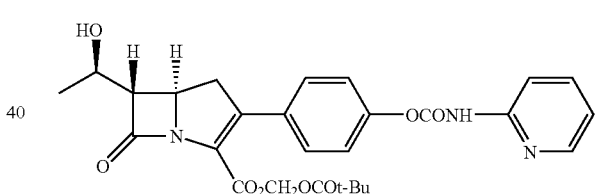
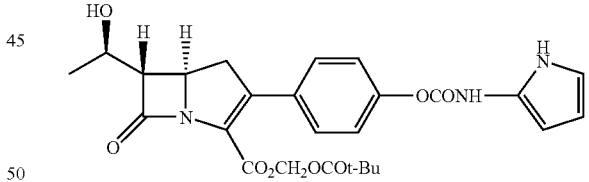
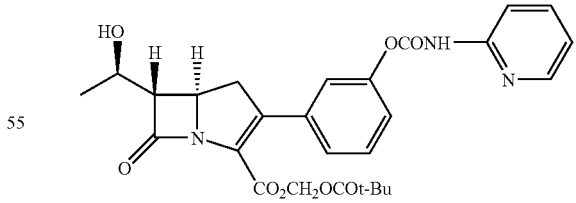
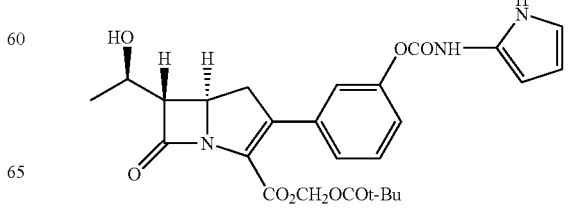

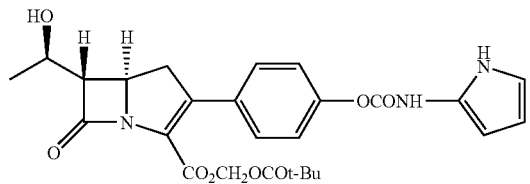
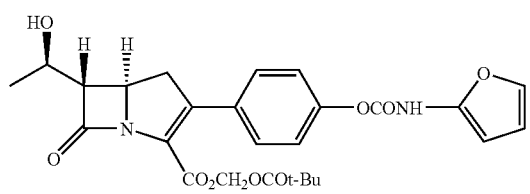
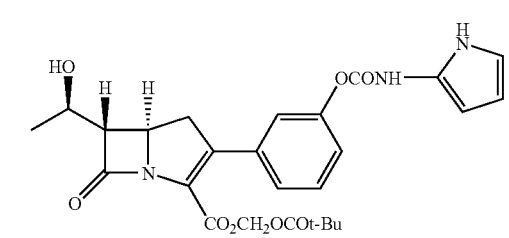
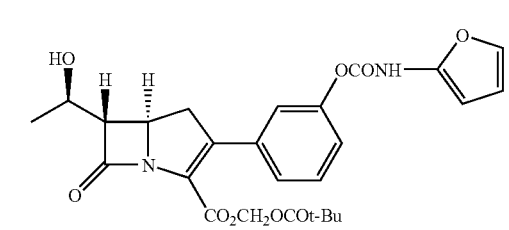
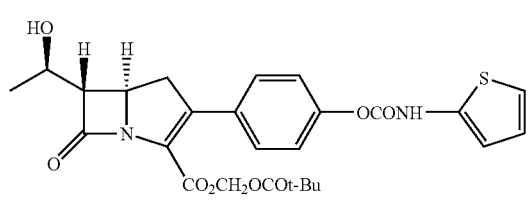
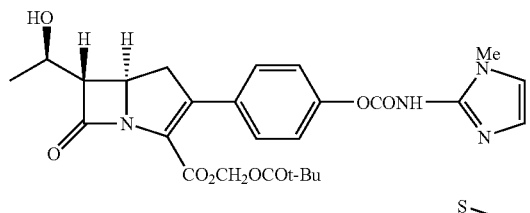
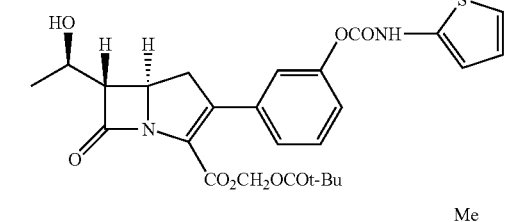
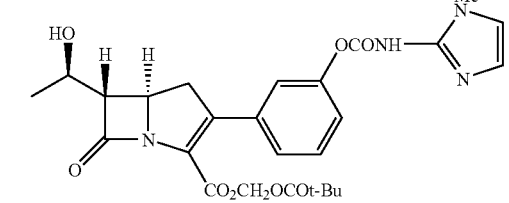
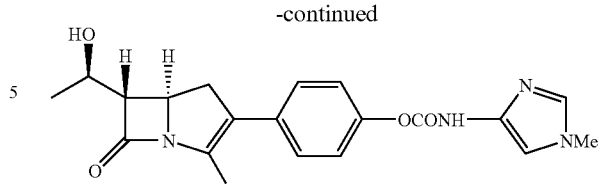
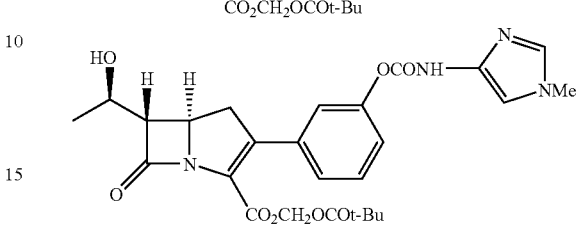
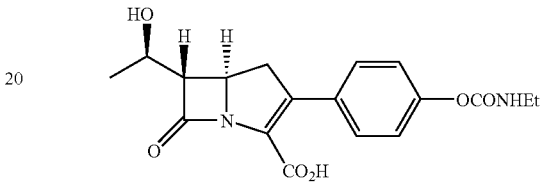
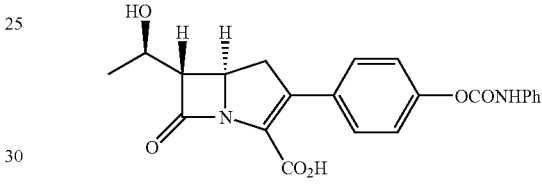
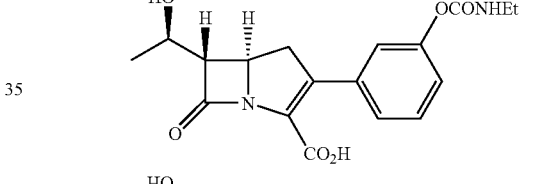
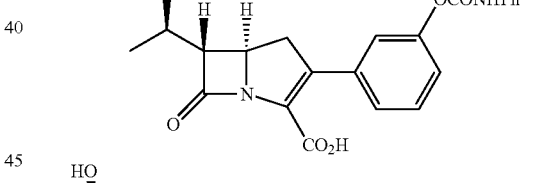
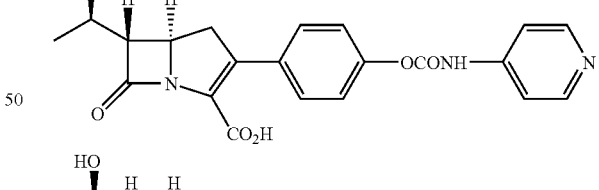
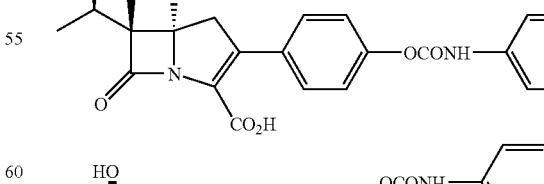
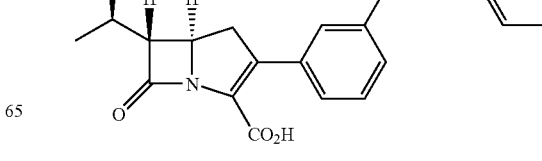

-continued
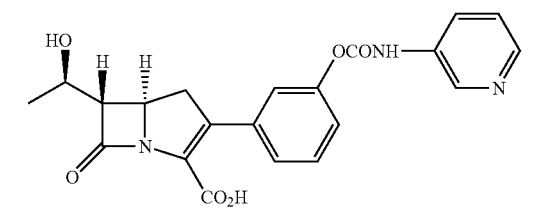
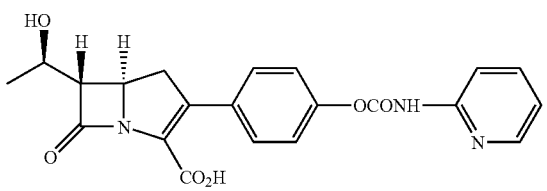
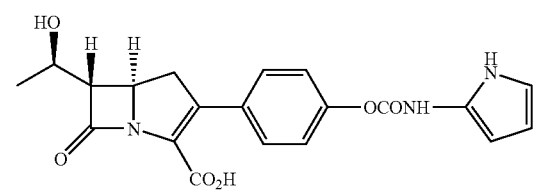
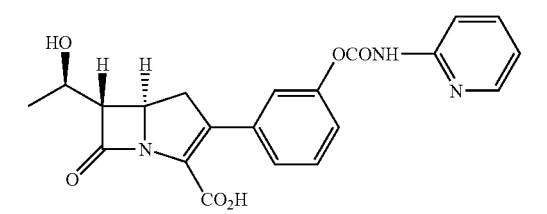
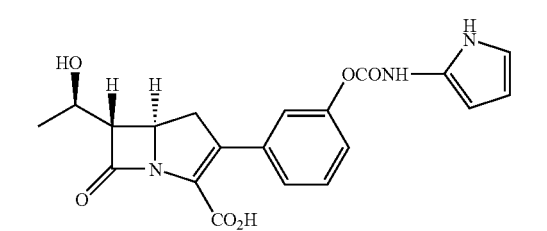
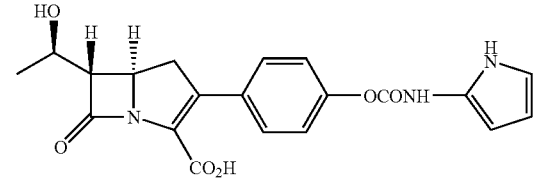
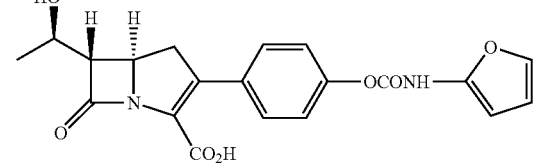
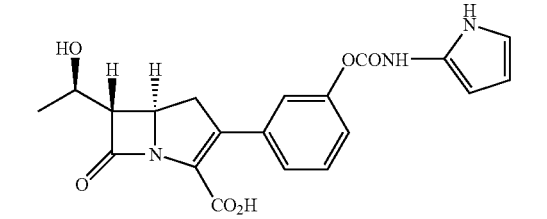
-continued
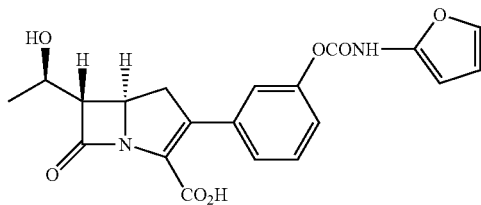
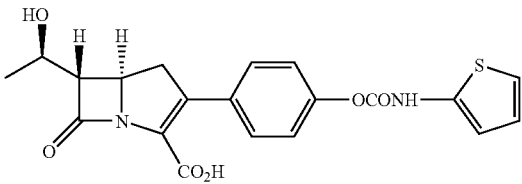
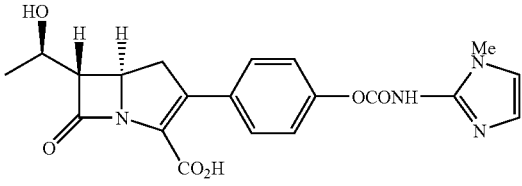
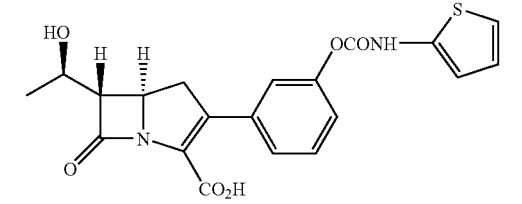
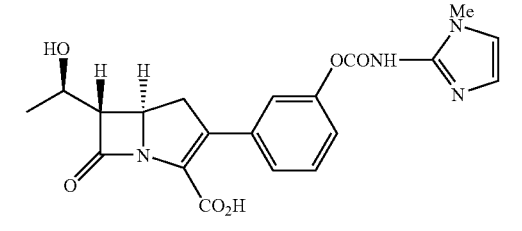
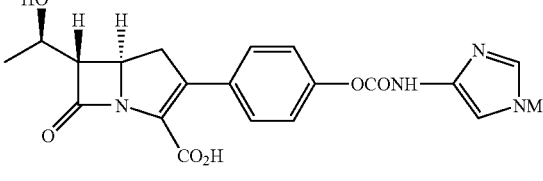
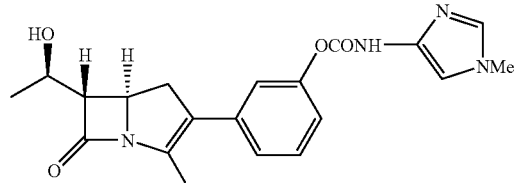
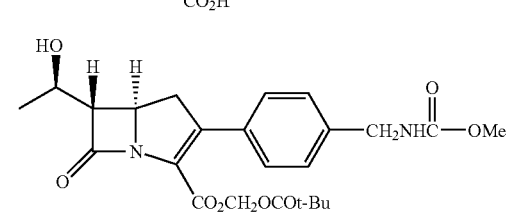

75
-continued
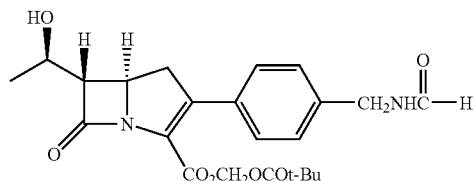
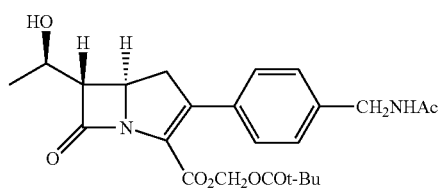
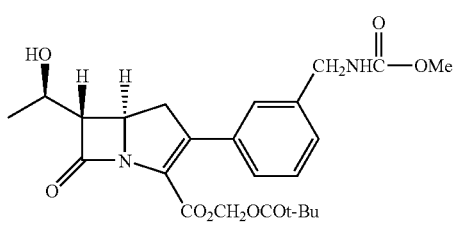
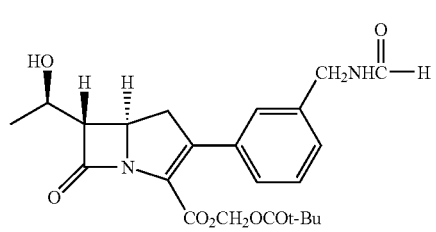
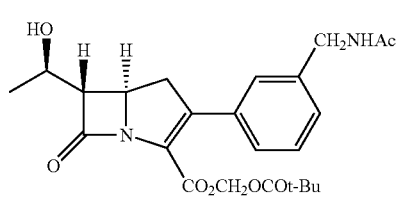
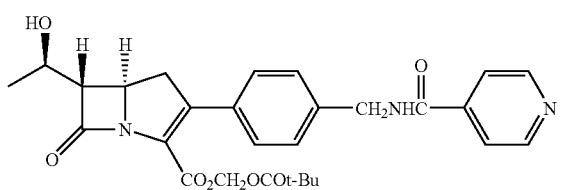
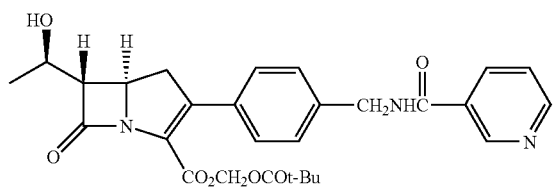
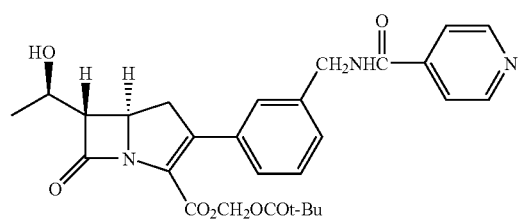
76
-continued
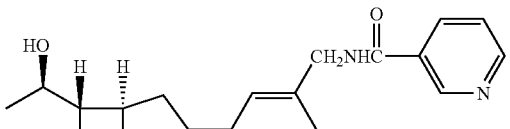
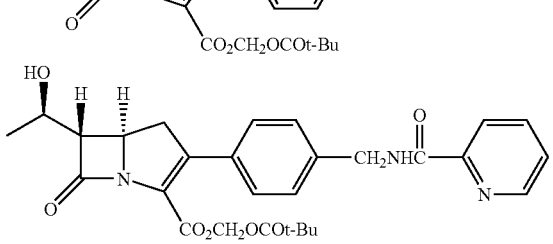
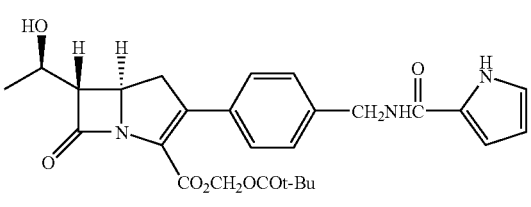
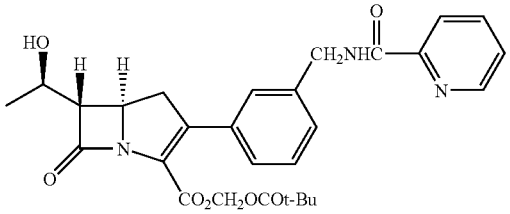
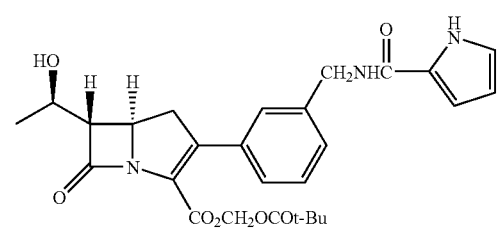
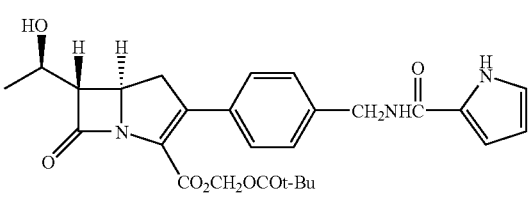
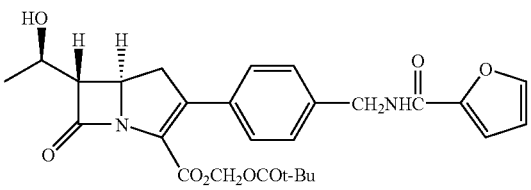
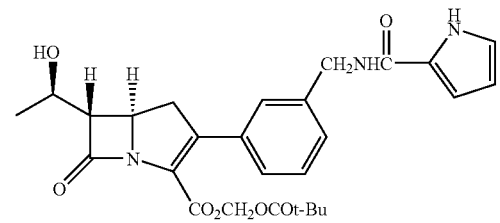

-continued
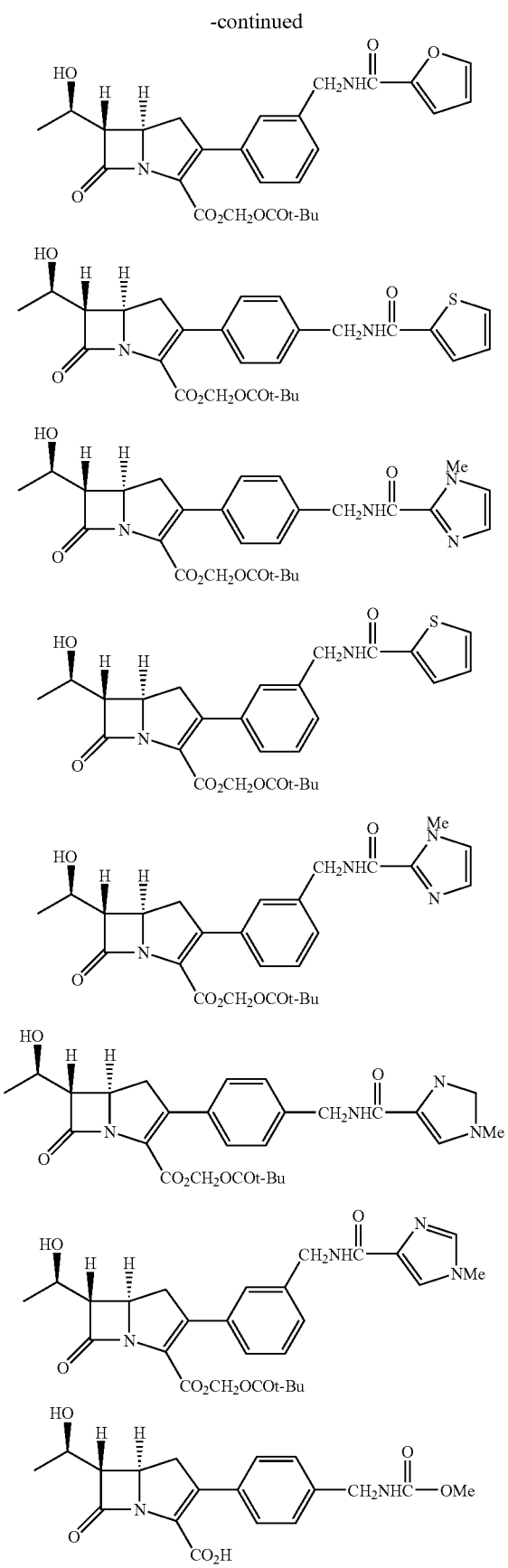
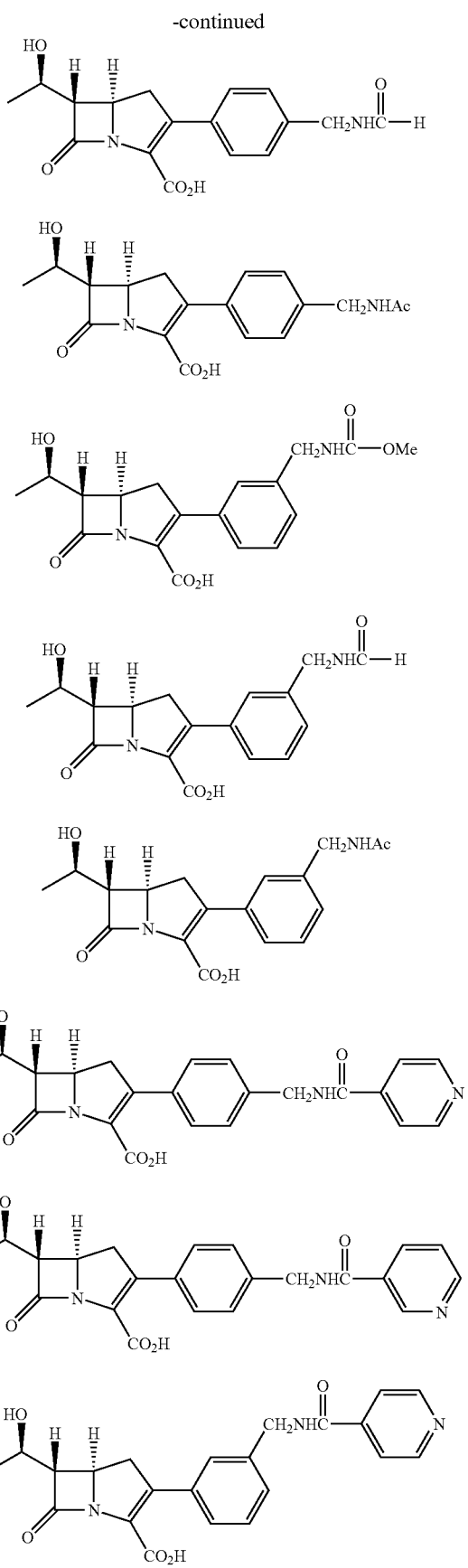

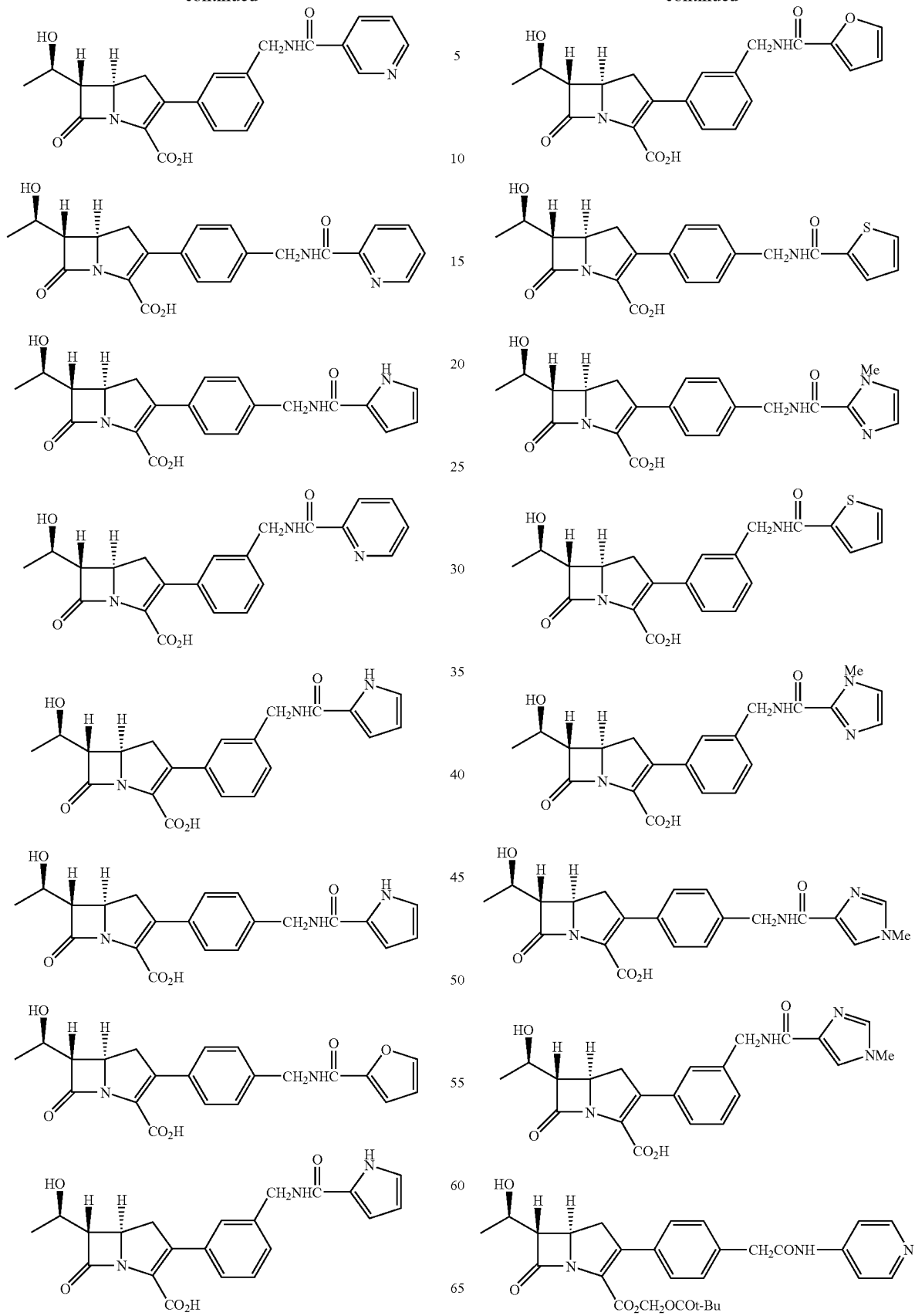

-continued
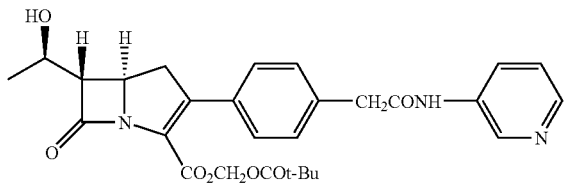
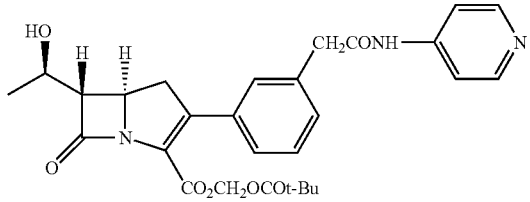
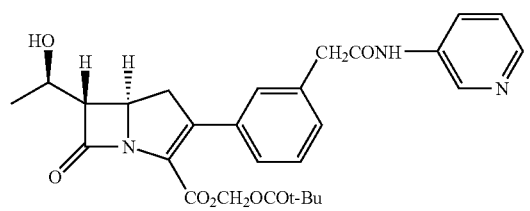
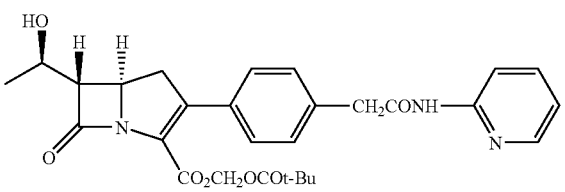
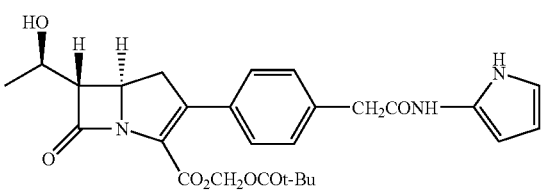
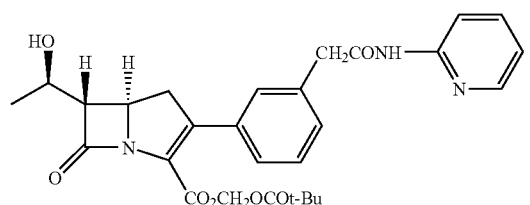
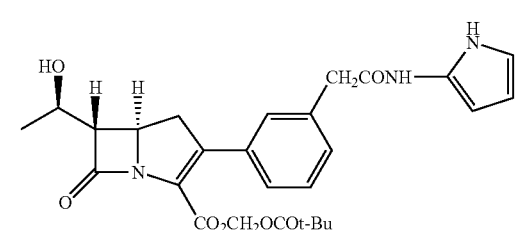
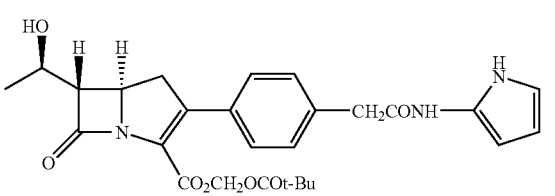
-continued
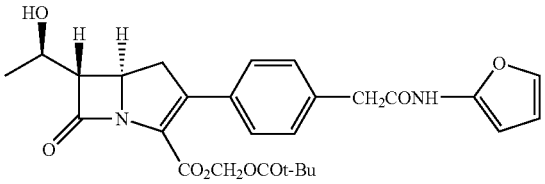
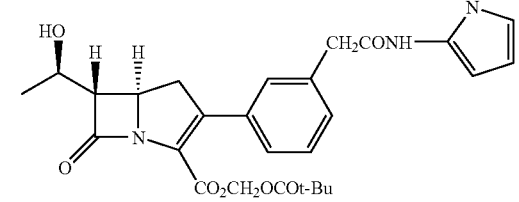
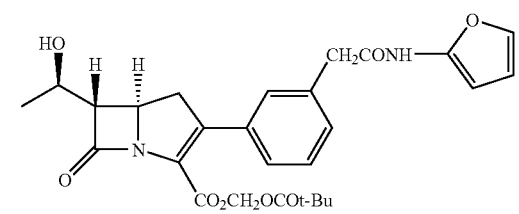
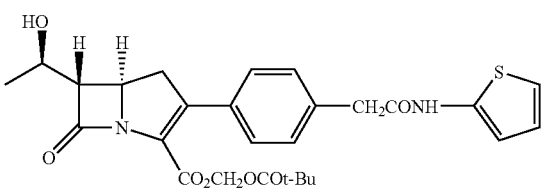
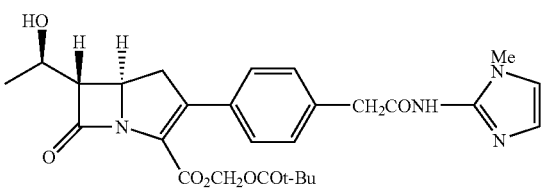
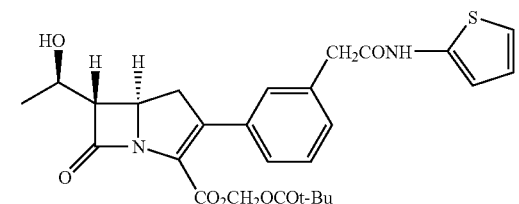
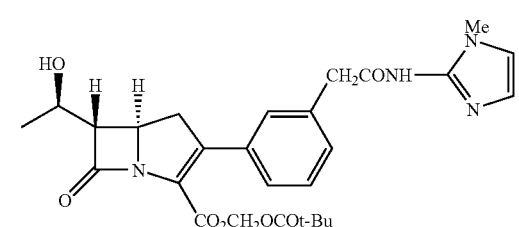
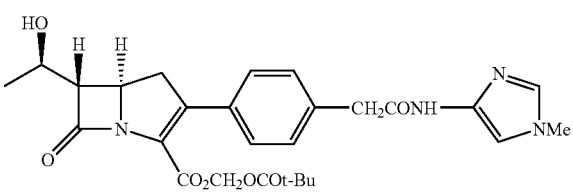

-continued
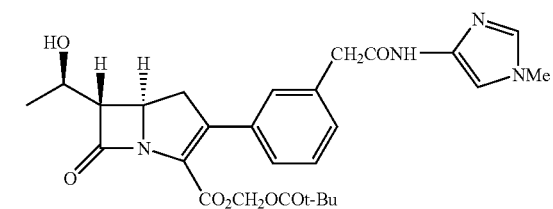
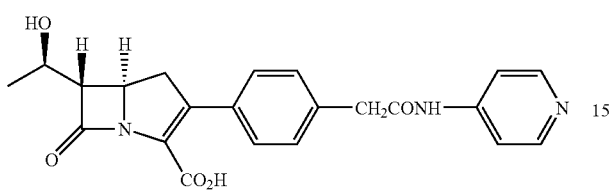
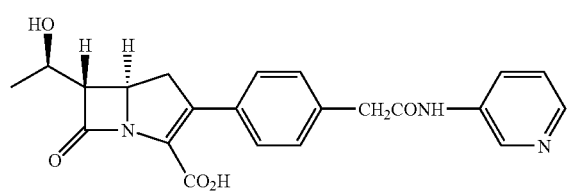
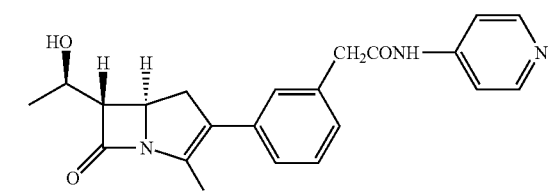
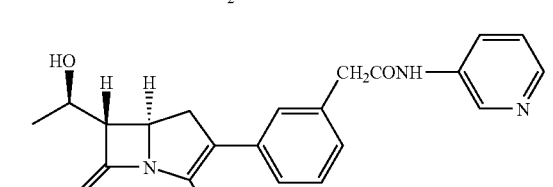
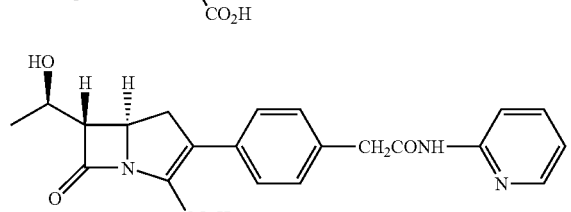
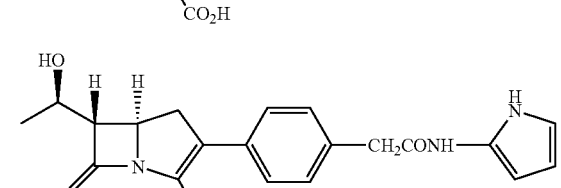
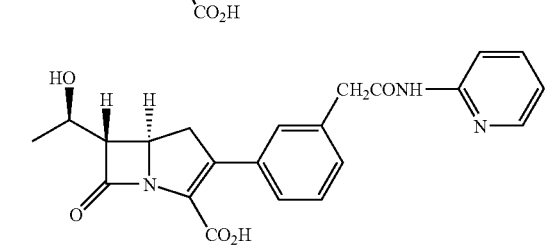
-continued
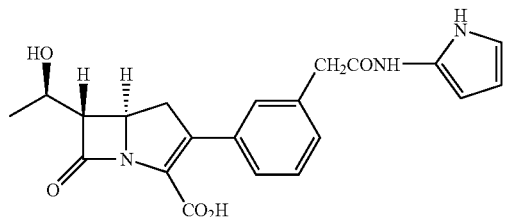
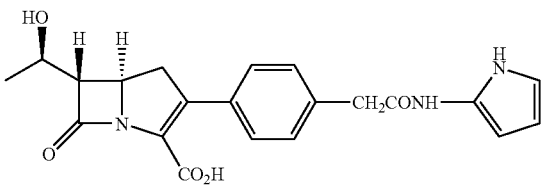
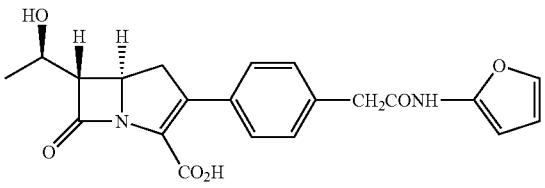
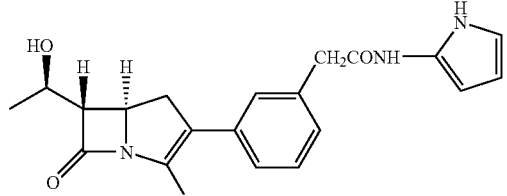
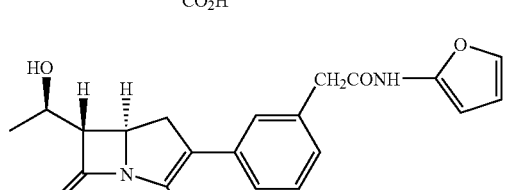
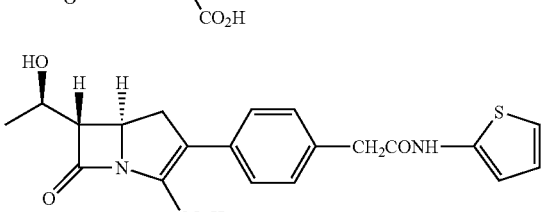
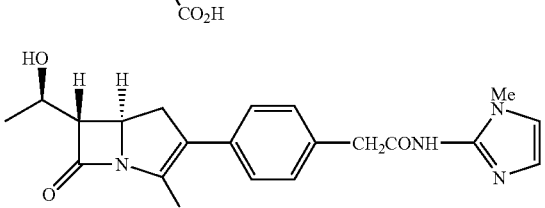
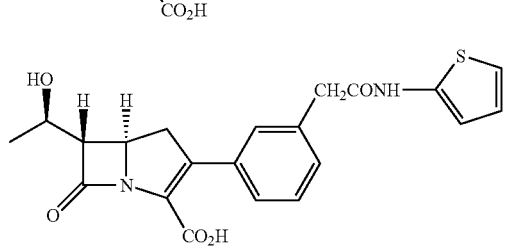

-continued
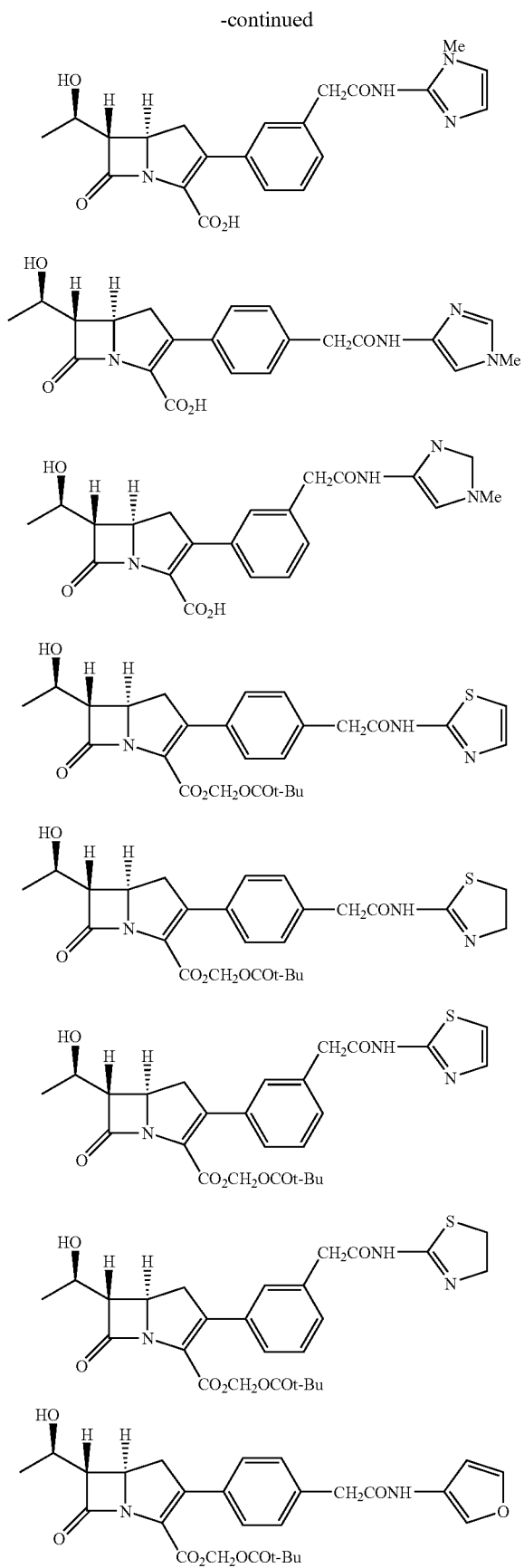
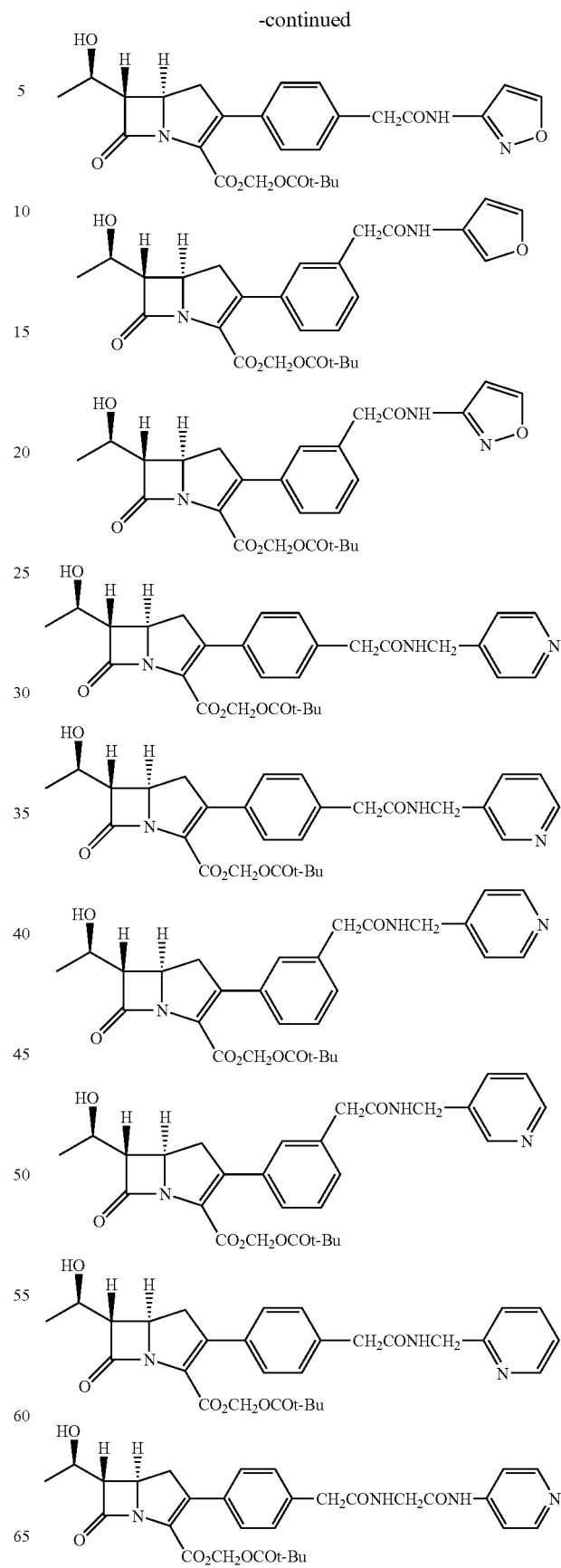

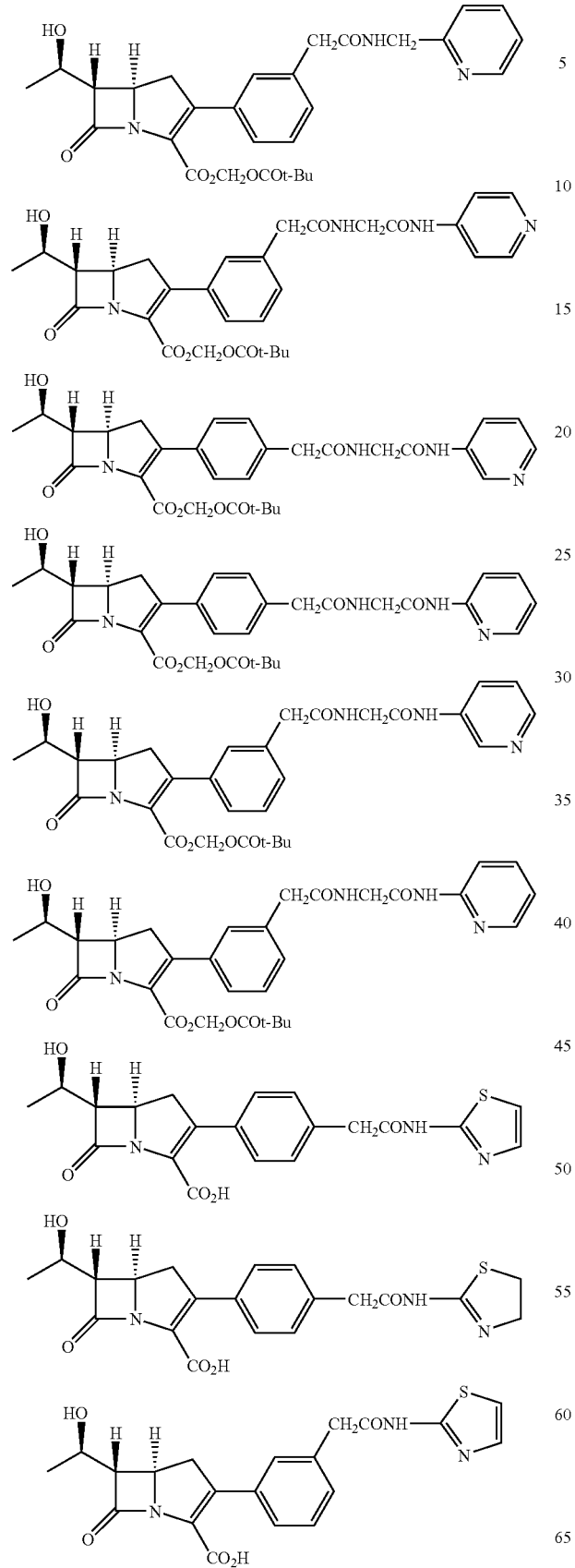

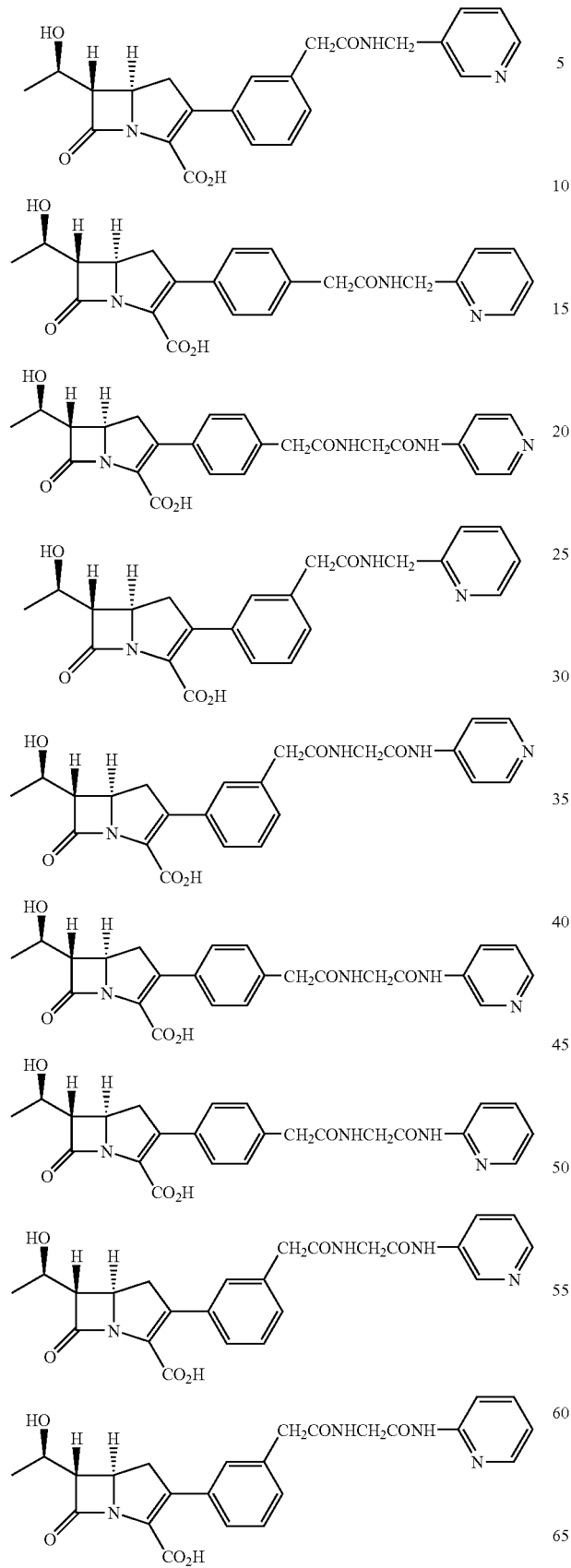
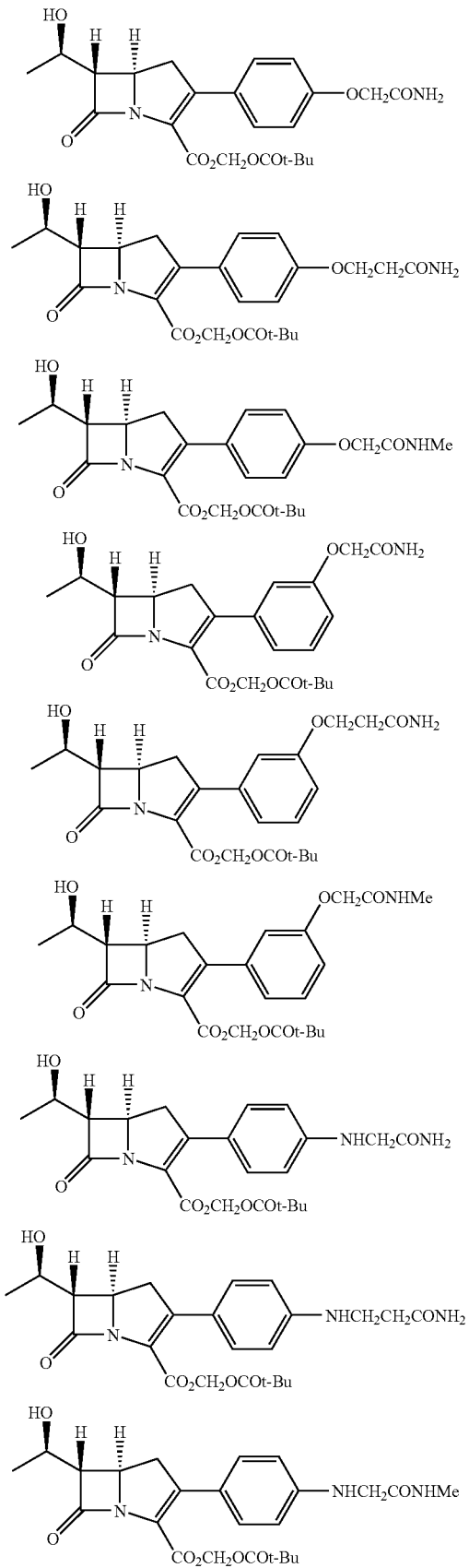

-continued
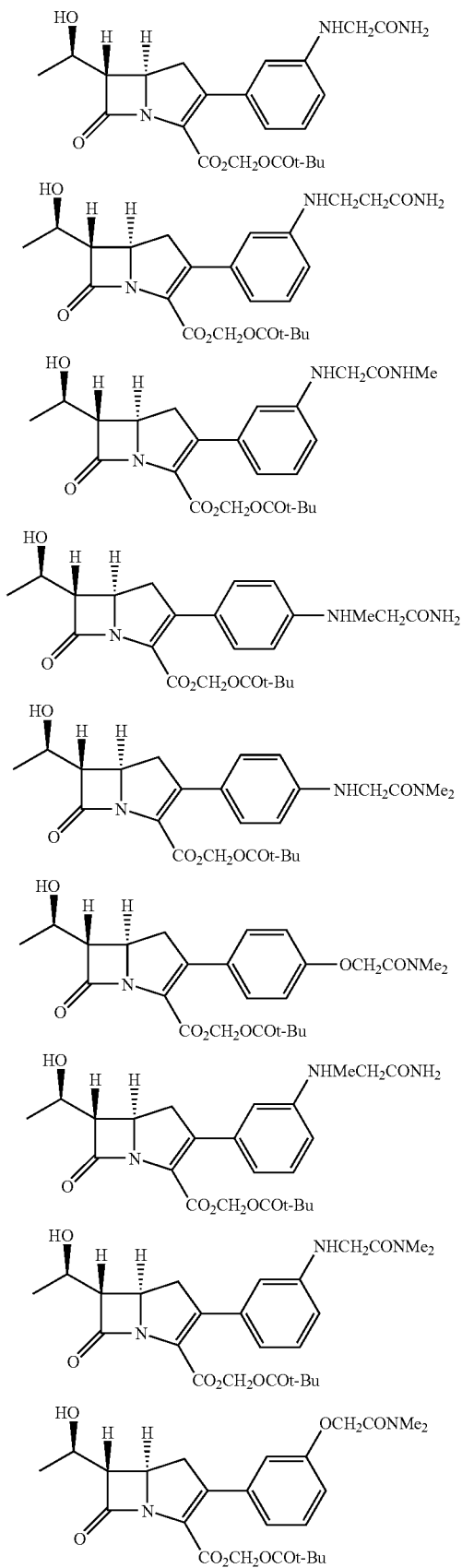
-continued
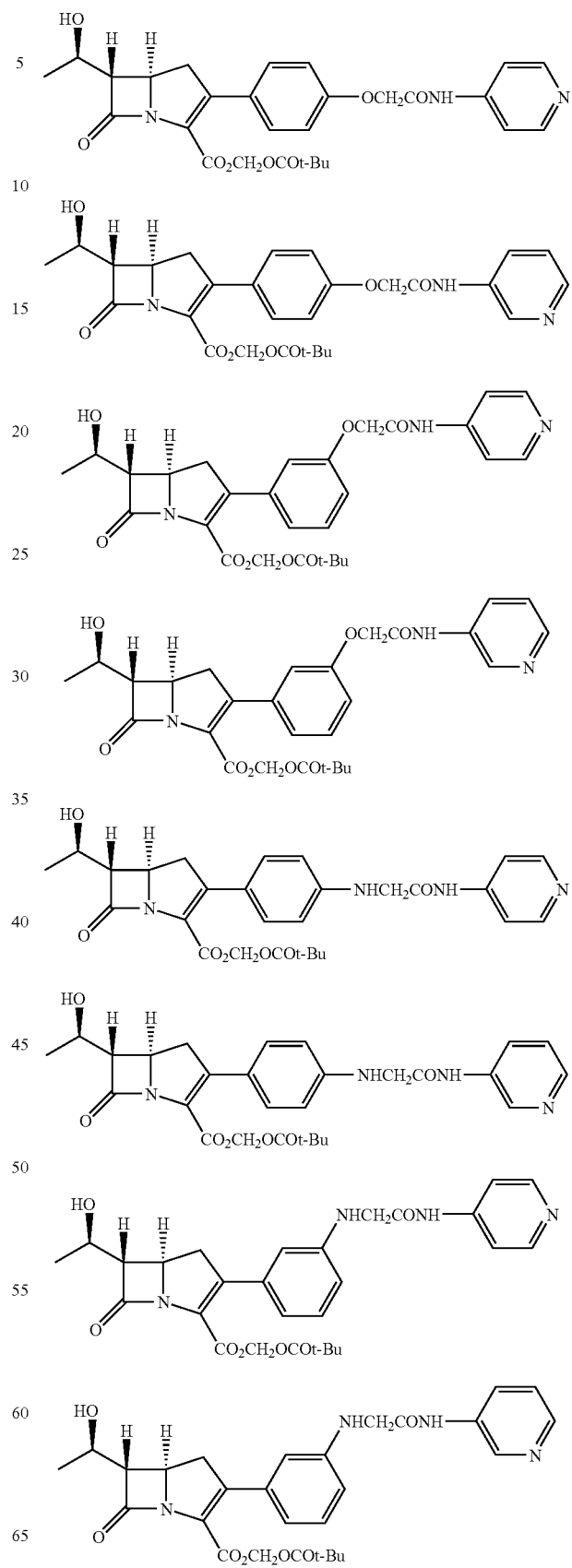

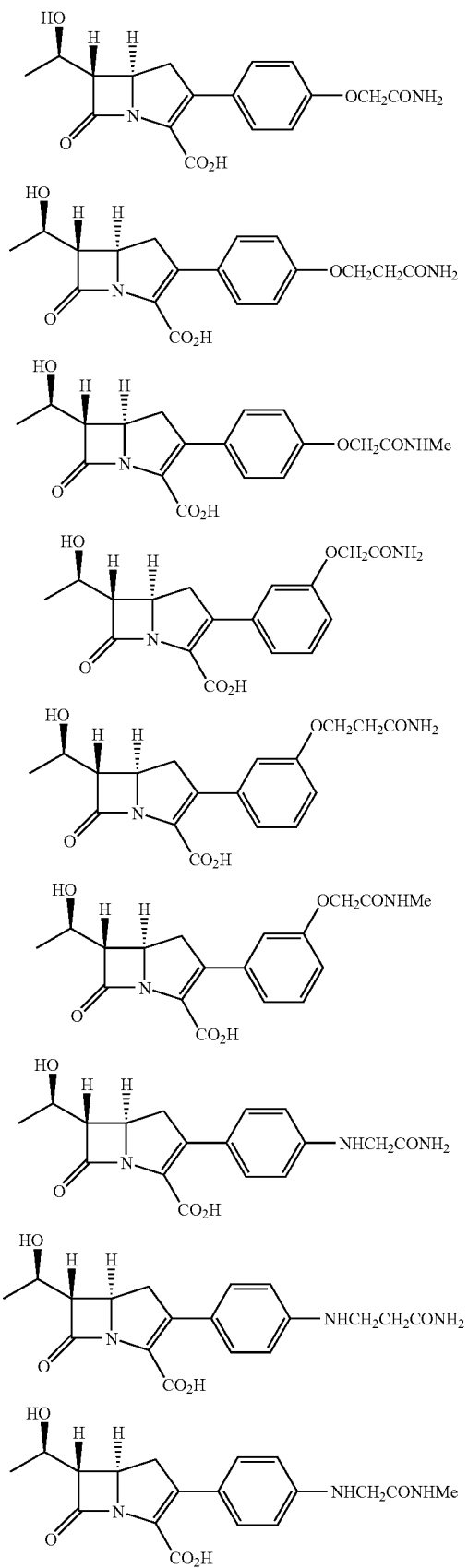
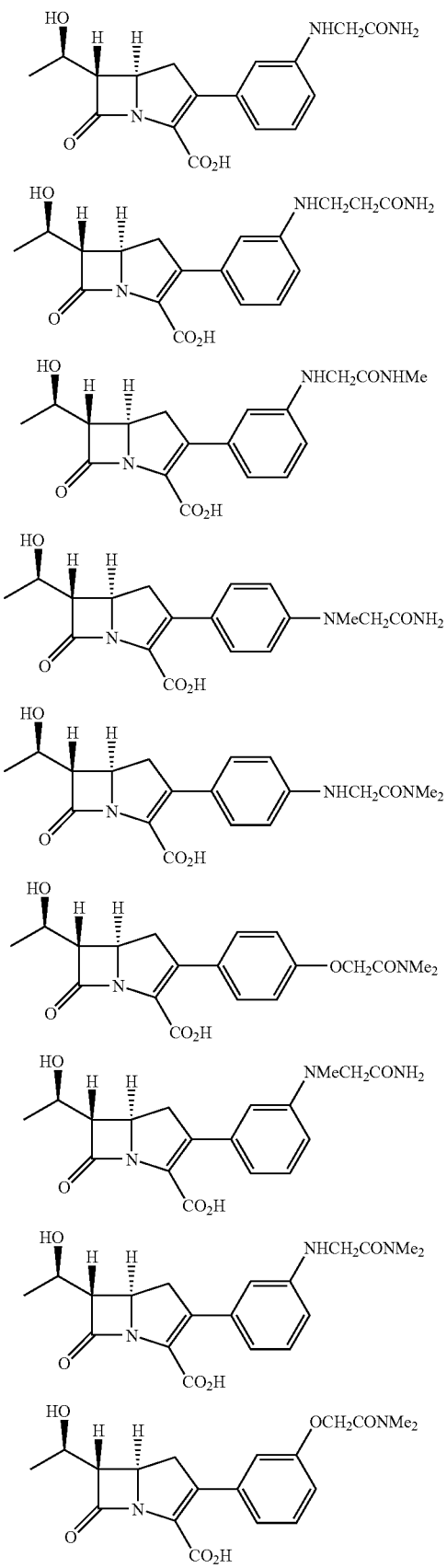

-continued
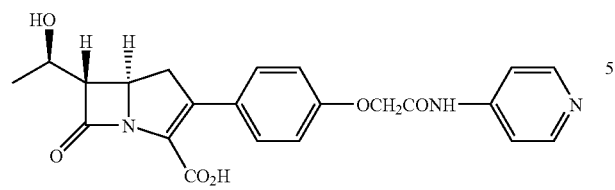
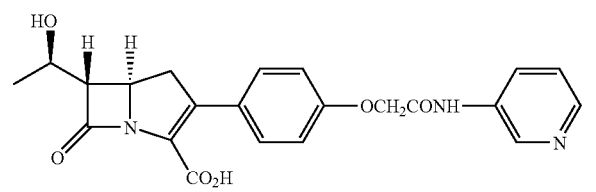
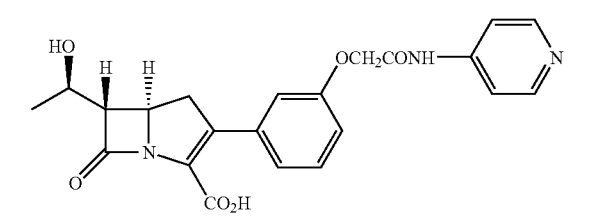
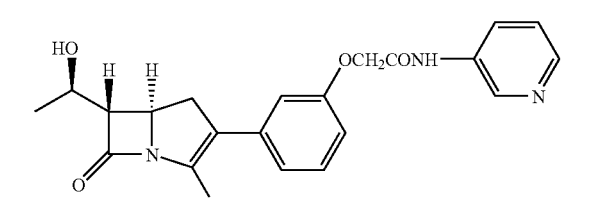
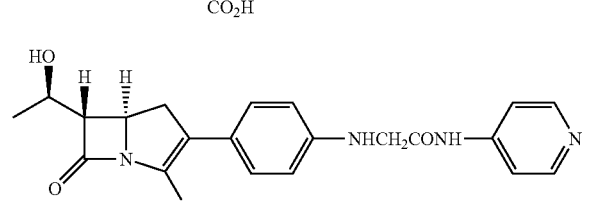
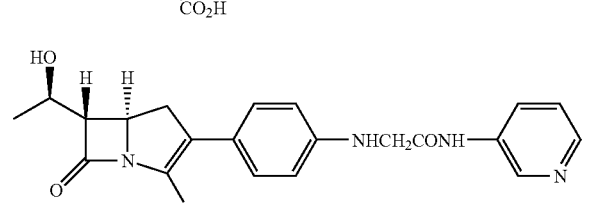
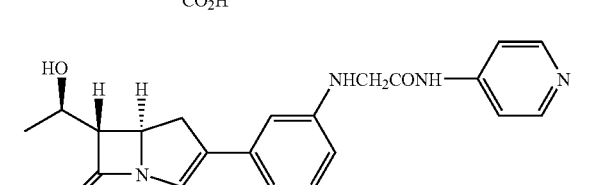
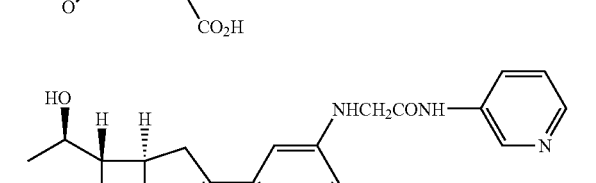
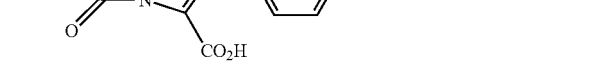
-continued
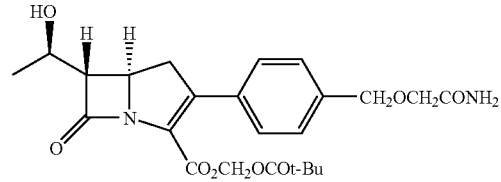
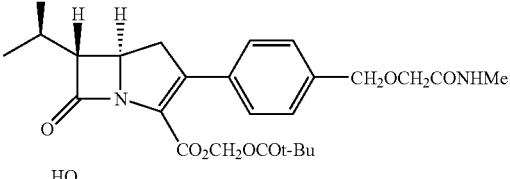
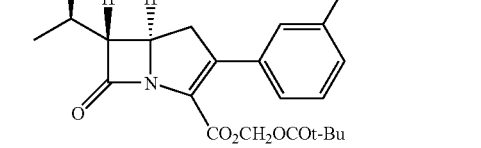
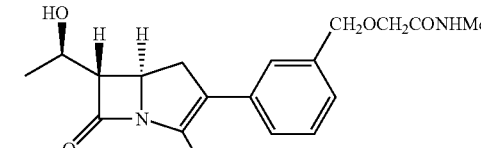
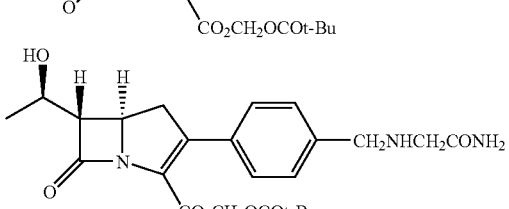
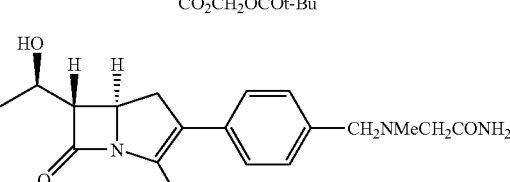
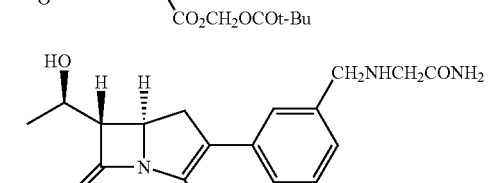
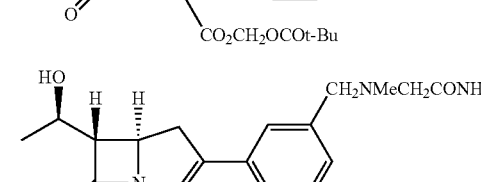
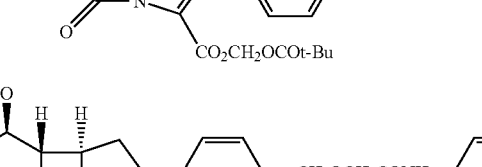
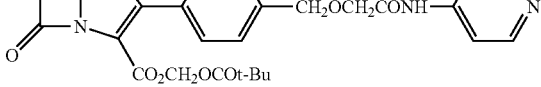

-continued
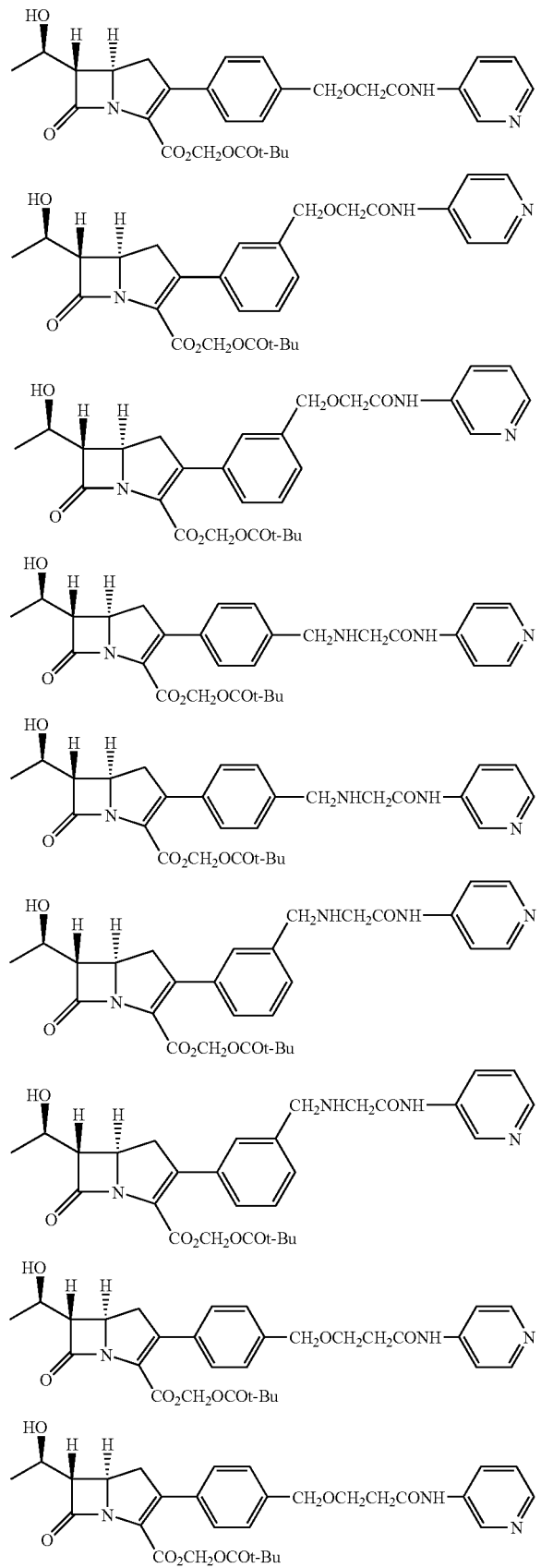
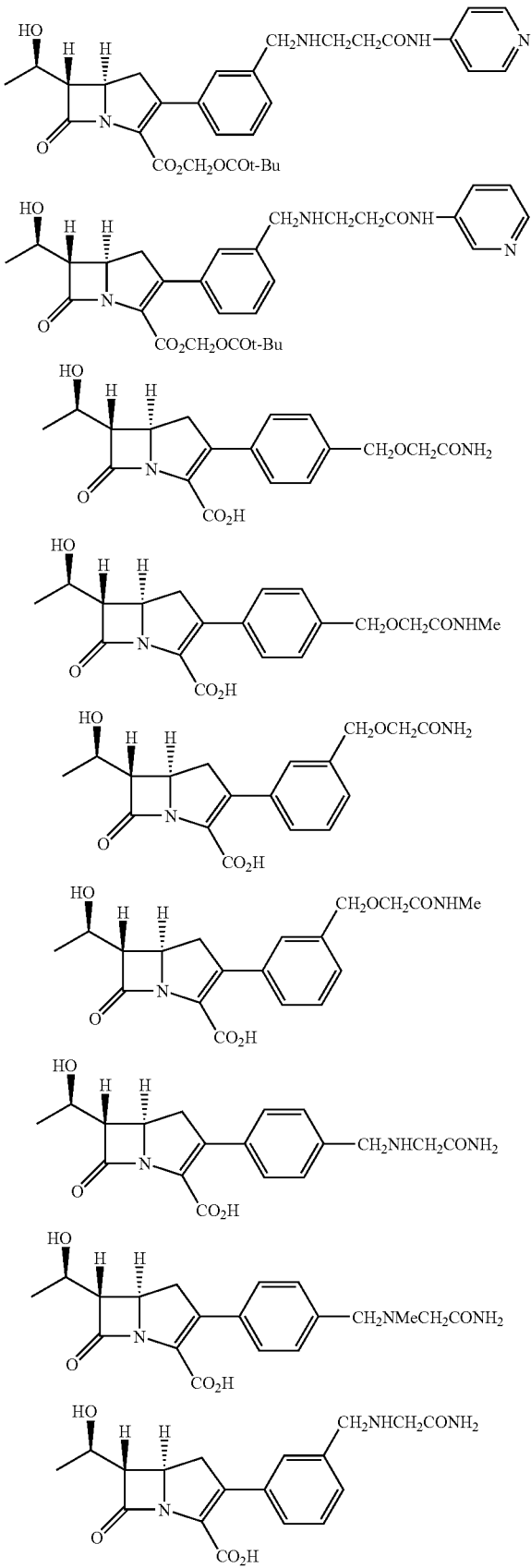

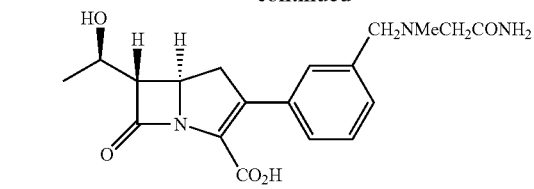
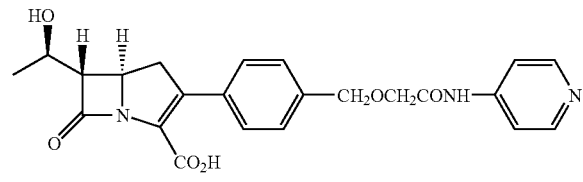
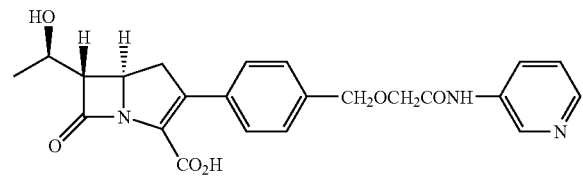
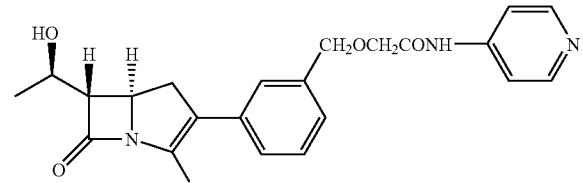
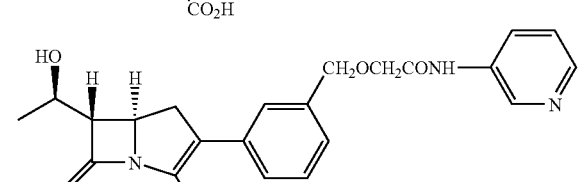
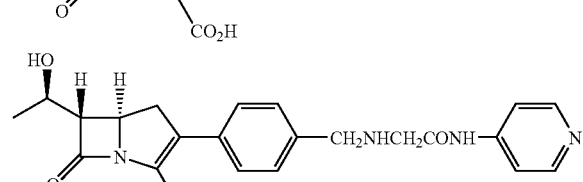
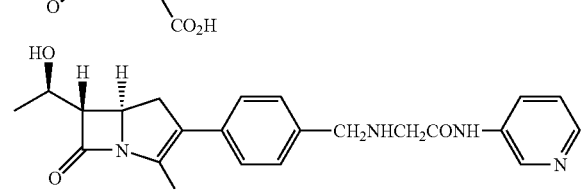
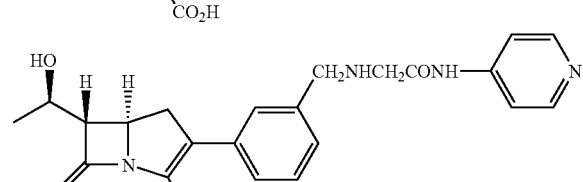
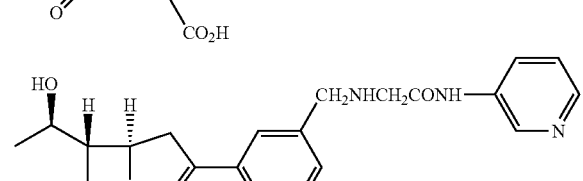
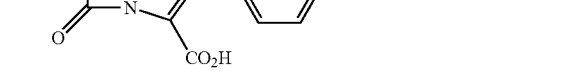
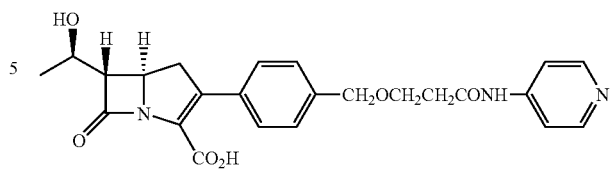
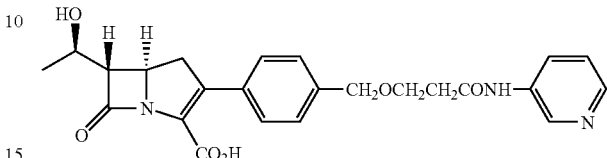
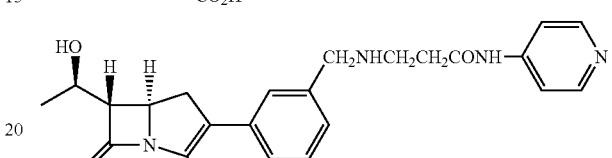
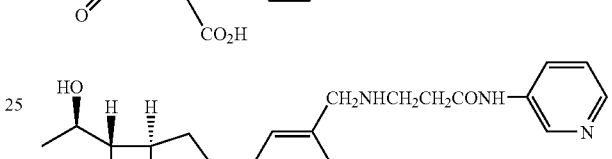
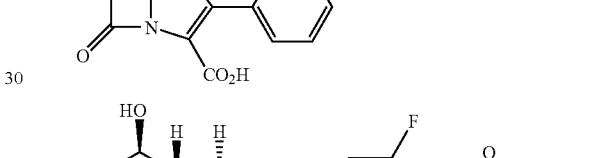
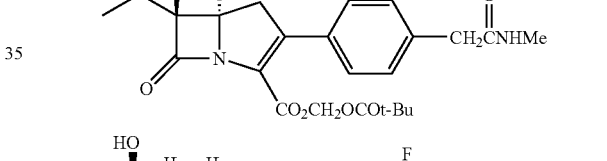
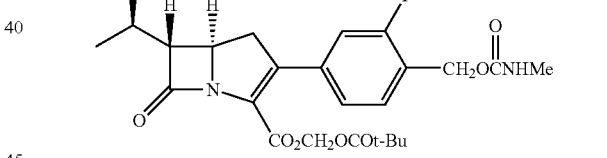
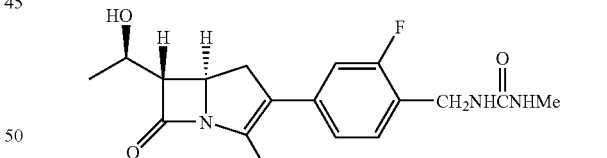
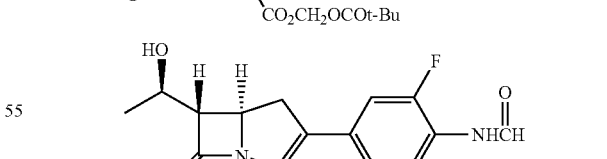
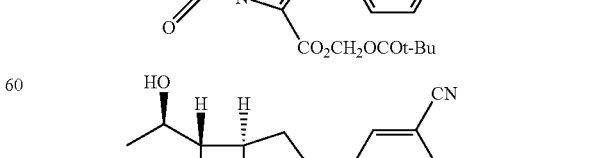
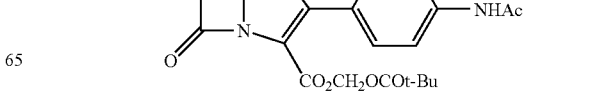

-continued
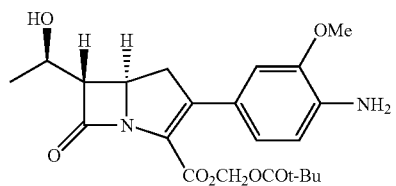
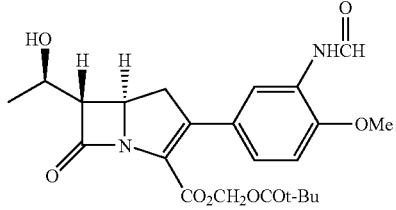
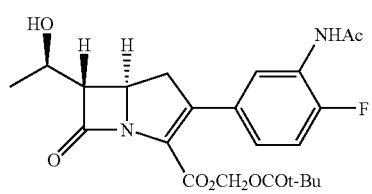
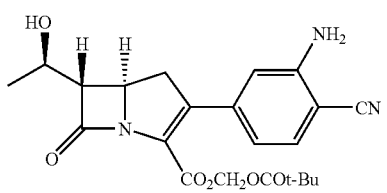
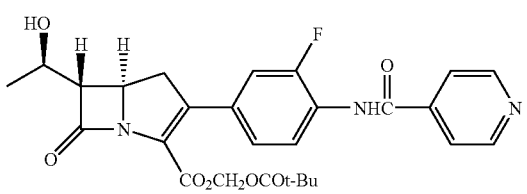
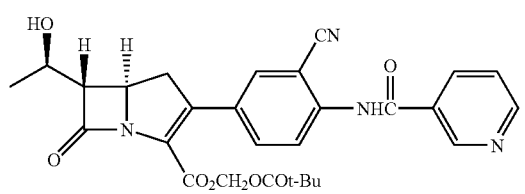
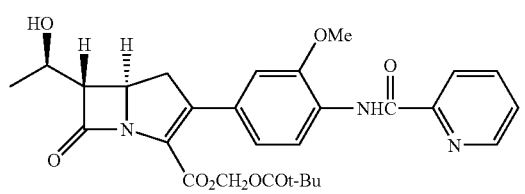
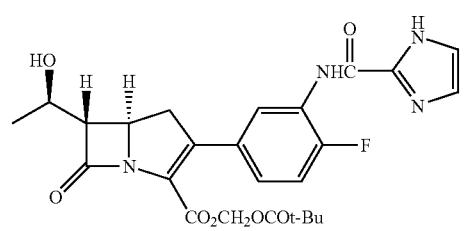
-continued
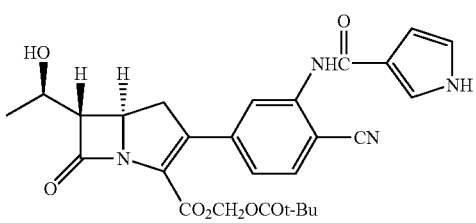
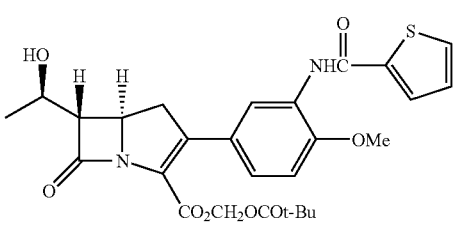
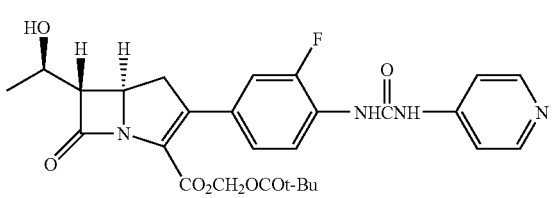
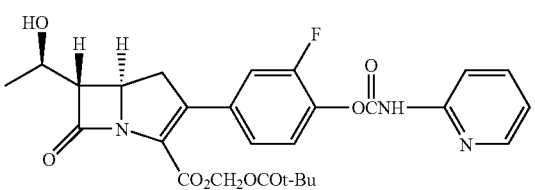
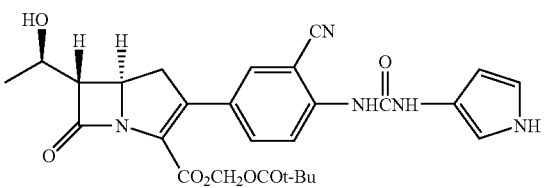
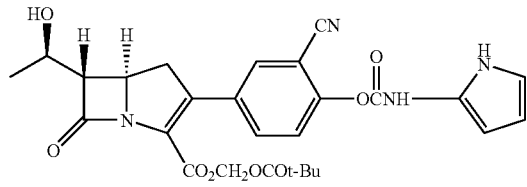
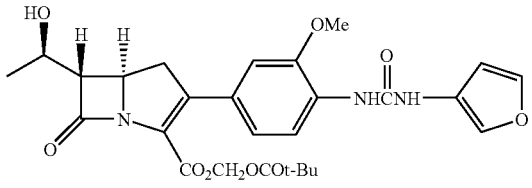
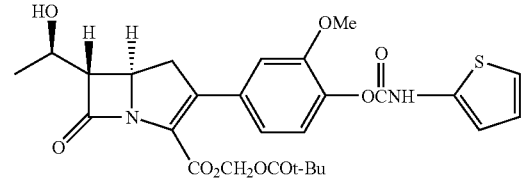

-continued
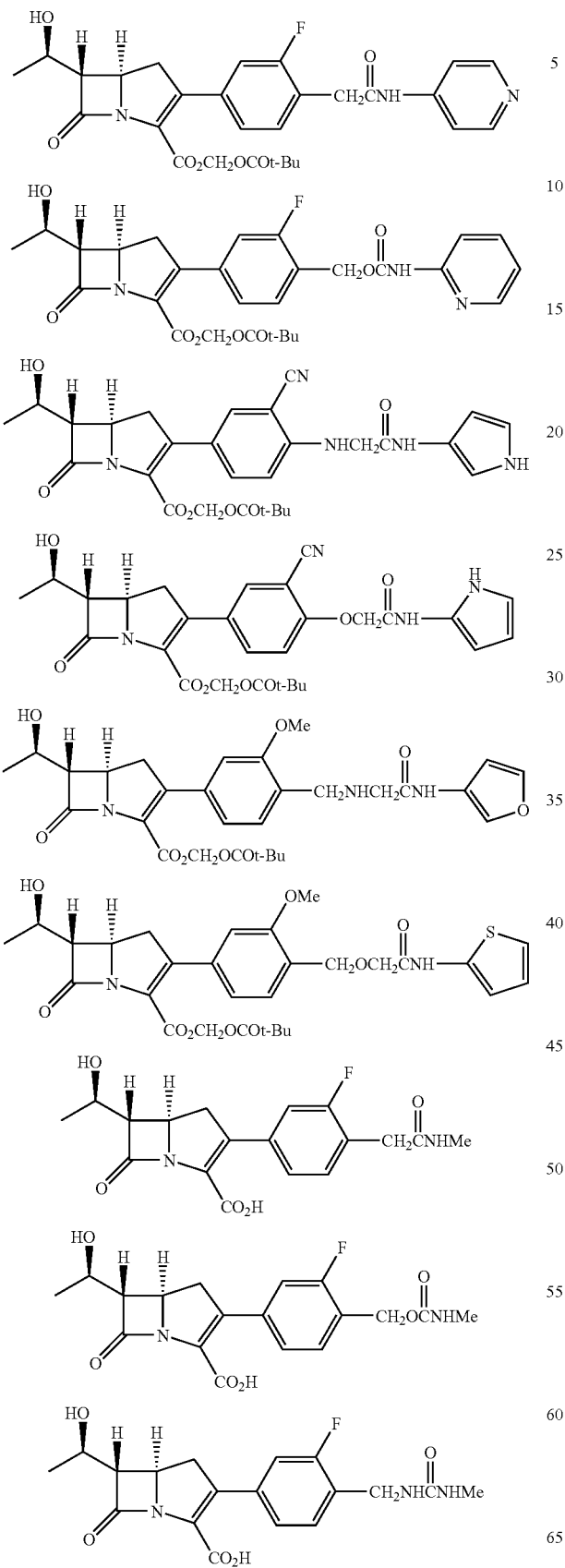
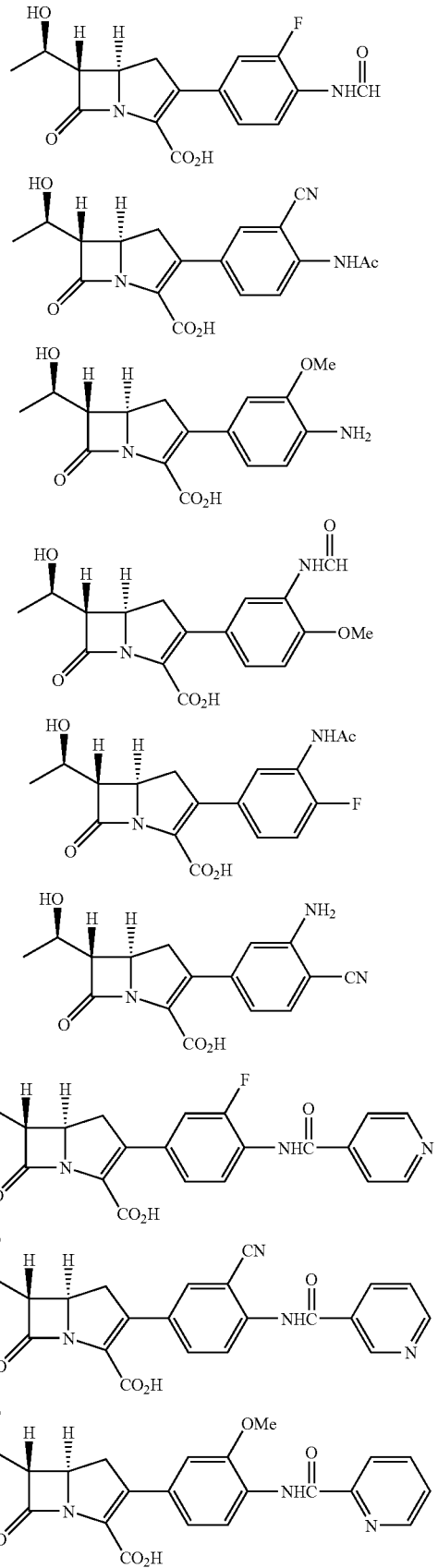

105
-continued
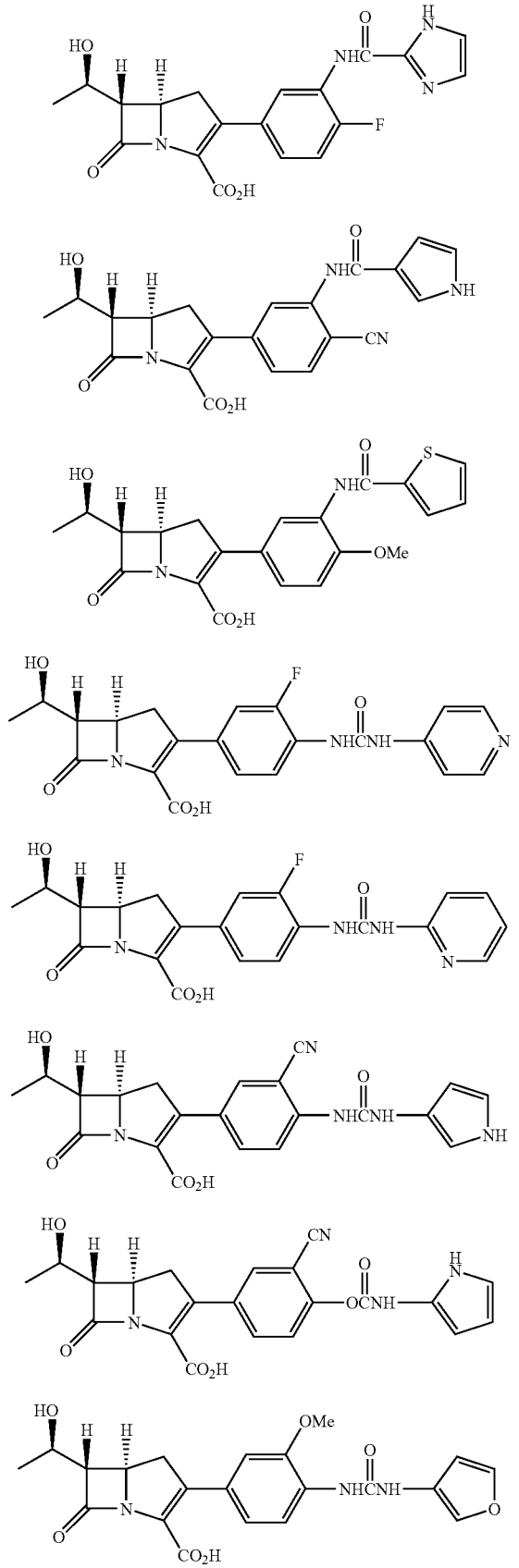
106
-continued
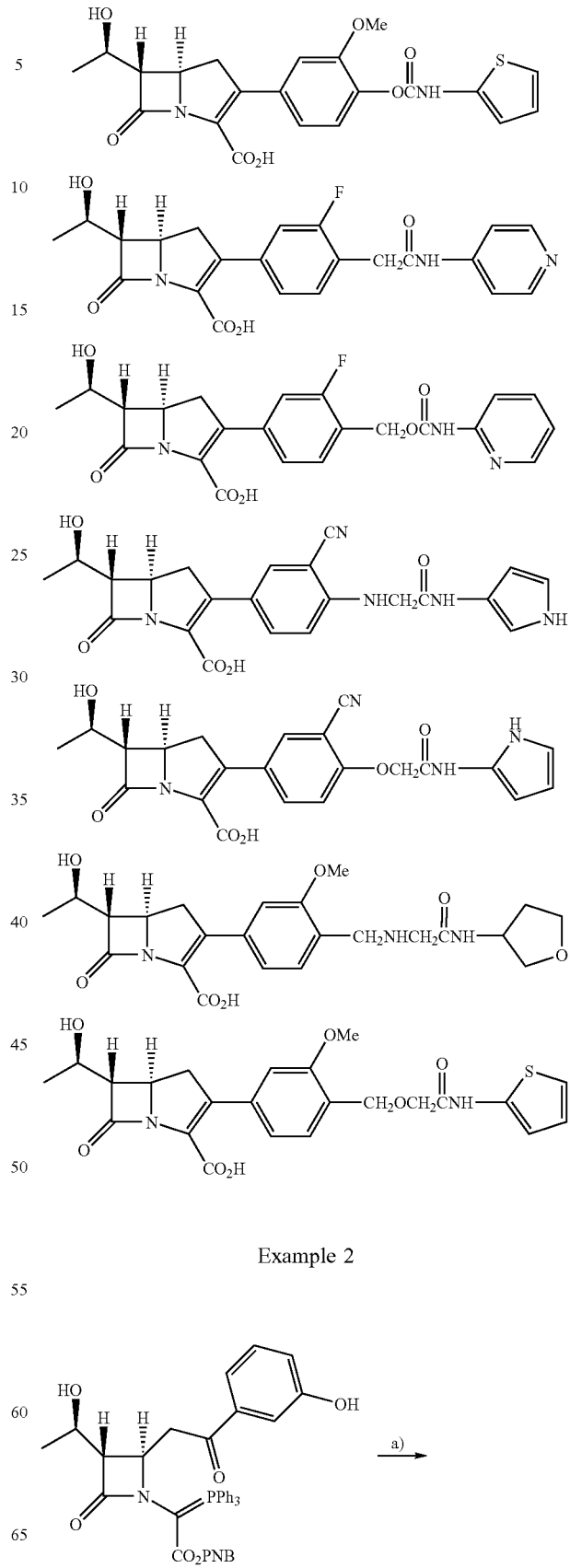
Example 2

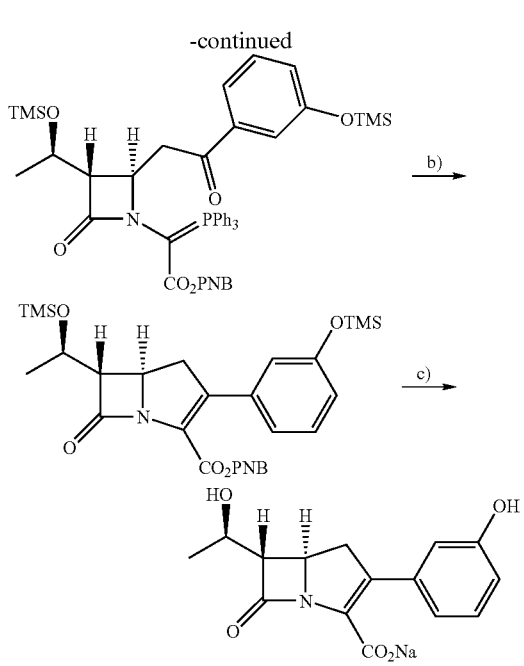

Step a)

To a solution of 4-nitrobenzyl {(2R,3S)-3-[(1R)-1-hydroxyethyl]-2-[2-(3-hydroxyphenyl)-2-oxoethyl]-4-oxoazetidin-1-yl}(triphenylphosphoranilidene)acetate (358 mg) in THF (6 ml) were added at room temperature triethylamine (405 mg) and chlorotrimethylsilane (435 mg), and the solution was stirred for 1 hour. The reaction solution was poured into ice water. The solution was diluted, extracted with ethyl acetate and separated by a separating funnel. The organic layer was washed with a cold saturated aqueous sodium chloride solution, and dried over anhydrous sodium sulfate. The solvent was removed under reduced pressure to give 4-nitrobenzyl ((3S,4R)-2-oxo-4-(2-oxo-2-{3-[(trimethylsilyl)oxy]phenyl}ethyl)-3-{(1R)-1-[(trimethylsilyl)oxy]ethyl}azetidin-1-yl)(triphenylphosphoranilidene)acetate. This compound was used in the next step without further purification.

Step b)

Toluene (50 ml) was added to 4-nitrobenzyl ((3 S,4 R)-2-oxo-4-(2-oxo-2-{3-[(trimethylsilyl)oxy]phenyl}ethyl)-3-{(1R)-1-[(trimethylsilyl)oxy]ethyl}azetidin-1-yl)(triphenylphosphoranilidene)acetate prepared in the above step and 2,6-di-tert-butyl-p-cresol (catalytic amount), and the mixture was stirred for 2.5 hours in an oil bath at 100° C. Then the temperature was raised to 130° C. and the mixture was stirred for 6.5 hours. The solvent was removed under reduced pressure and the residue was crystallized from hexane/ethyl acetate, filtered, washed and dried under reduced pressure to give 4-nitrobenzyl (5R,6S)-7-oxo-6-{(1R)-1-[(trimethylsilyl)oxy]ethyl}-3-{3-[(trimethylsilyl)oxy]phenyl}-1-azabicyclo[3.2.0]hept-2-ene-2-carboxylate (218 mg).

$^1$H NMR (400 MHz, CDCl$_3$) δ 0.15 (9H, s), 0.25 (9H, s), 1.30 (3H, d, J=6.2 Hz), 3.11–3.35 (3H, m), 4.18–4.32 (2H, m), 5.15–5.41 (2H, m), 6.77–6.88 (2H, m), 6.90–6.99 (1H, m), 7.12–7.23 (1H, m), 7.44 (2H, d, J=8.9 Hz), 8.15 (2H, d, J=8.8 Hz).

Step c)

To a solution of 4-nitrobenzyl (5R,6S)-7-oxo-6-{(1R)-1-[(trimethylsilyl)oxy]ethyl}-3-{3-[(trimethylsilyl)oxy]phenyl}-1-azabicyclo[3.2.0]hept-2-ene-2-carboxylate (207 mg) in acetonitrile (3 ml) was added under ice cooling 0.1N hydrochloric acid (0.3 ml), and the mixture was stirred for 15 minutes. After the solution was neutralized with a 0.1N aqueous sodium hydrogencarbonate solution (0.3 ml), further thereto 0.25M phosphate buffer (10 ml, pH6) and acetonitrile (7 ml) were added. Zinc dust (1.49 g) was added thereto and the mixture was vigorously stirred for an hour under ice cooling and for additional an hour at room temperature. The insoluble materials were removed with celite and washed with water and chloroform. Then, the filtrate and the washed solvent were combined to separate by a separating funnel. The aqueous layer was washed with chloroform, twice separated with a separating funnel and an organic solvent in the aqueous layer was removed under reduced pressure. The aqueous solution was purified by polymer chromatography (CHP-20P), and the fractions eluted with water were collected to be subjected to freeze-drying to give sodium (5R,6S)-6-[(1R)-1-hydroxyethyl]-3-(hydroxyphenyl)-7-oxo-1-azabicyclo[3.2.0]hept-2-ene-2-carboxylate (14 mg).

$^1$H NMR (400 MHz, D$_2$O) δ 1.23 (3H, d, J=6.4 Hz), 2.90–3.04 (1H, m), 3.25–3.38 (1H, m), 3.43 (1H, dd, J=2.8 Hz, 5.9 Hz), 4.09–4.27 (2H, m), 6.71–6.81 (2H, m), 6.81–6.89 (1H, m), 7.18 (1H, t, J=7.9 Hz).

Example 3

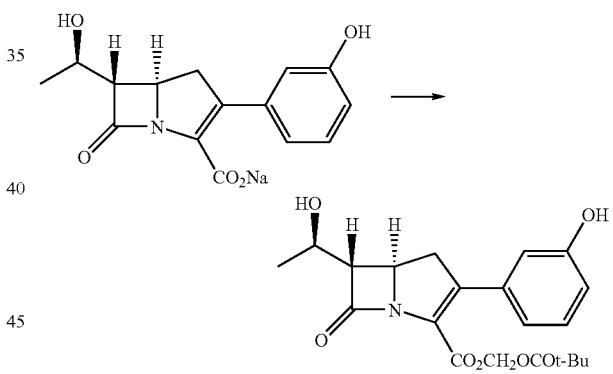

A solution of sodium (5R,6S)-6-[(1R)-1-hydroxyethyl]-3-(hydroxyphenyl)-7-oxo-1-azabicyclo[3.2.0]hept-2-ene-2-carboxylate (106 mg) in dry dimethylformamide (4.5 ml) was cooled with ice, and thereto pivaloyloxymethyl iodide (123 mg) was added. The mixture was stirred for 1 hour at the same temperature. Ethyl acetate and ice water were added to the reaction solution, and the mixture was separated with a separating funnel. After the organic layer was washed with a cold saturated aqueous sodium chloride solution (4 times), it was dried over anhydrous magnesium sulfate. The solvent was removed under reduced pressure, and then the residue was purified by silica gel column chromatography (chloroform/methanol) to give [(2,2-dimethylpropanoyl)oxy]methyl(5R,6S)-6-[(1R)-1-hydroxyethyl]-3-(hydroxyphenyl)-7-oxo-1-azabicyclo[3.2.0]hept-2-ene-2-carboxylate (36 mg).

$^1$H NMR (400 MHz, CDCl$_3$) δ 1.20 (9H, s), 1.37 (3H, d, J=6.3 Hz), 3.17–3.40 (3H, m), 4.21–4.34 (2H, m), 5.72–5.90 (2H, m), 6.80–6.95 (3H, m), 7.17–7.25 (1H, m).

Example 4

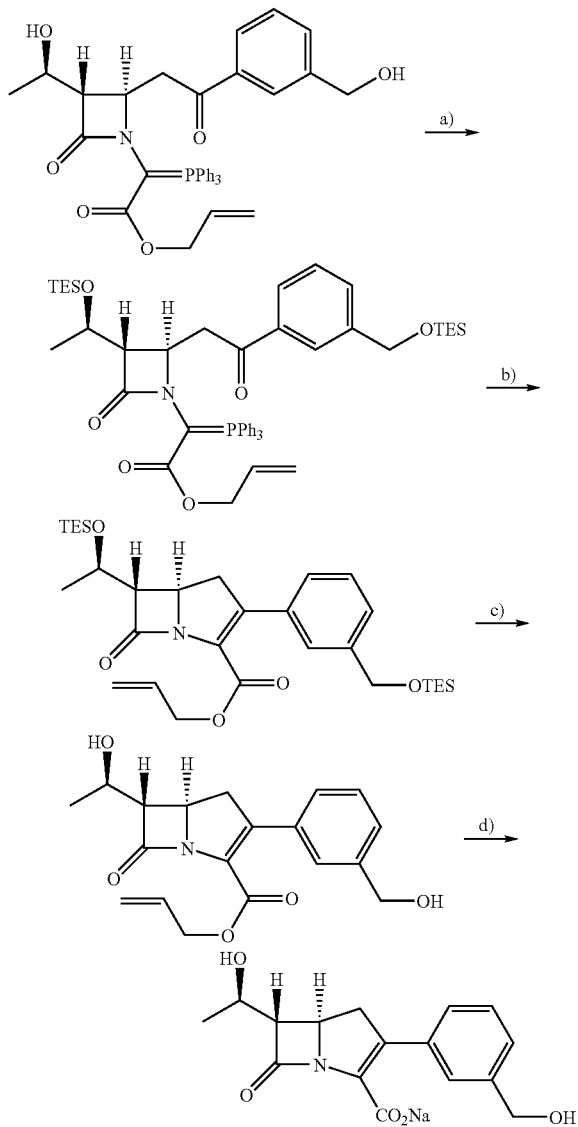

Step a)

In the same manner as Example 1, to a solution of allyl ((2R,3S)-3-[(1R)-1-hydroxyethyl]-2-{2-[3-(hydroxymethyl)phenyl]-2-oxoethyl}-4-oxoazetidin-1-yl) (triphenylphosphoranilidene) acetate (2.30 g) in dichloromethane (46 ml) were added at room temperature 4-(dimethylamino) pyridine (60 mg) and triethylamine (2.25 g), and thereto. triethylsilyl chloride(1.67 g) was dropped at 0° C. The solution was stirred at room temperature for 1 hour and then, methanol (3 ml) was added thereto. The solvent was removed under reduced pressure. To the residue were added water and ethyl acetate, and the mixture was separated with a separating funnel. The organic layer was washed with a saturated aqueous sodium chloride solution, dried over anhydrous sodium sulfate, and the solvent was removed under reduced pressure to give allyl ((3S,4R)-2-oxo-4-[2-oxo-2-(3-{[(triethylsilyl)oxy]methyl}phenyl)ethyl]-3-{(1R)-1-[(triethylsilyl)oxy]ethyl}azetidin-1-yl)(triphenylphosphoranilidene)acetate. This product was used in the next step without further purification.

Step b)

To allyl ((3S,4R)-2-oxo-4-[2-oxo-2-(3-{[(triethylsilyl)oxy]methyl}phenyl)ethyl]-3-{(1R)-1-[(triethylsilyl)oxy]ethyl}azetidin-1-yl)(triphenylphosphoranilidene)acetate prepared by the above step was added toluene (100 ml), and the solution was stirred in a bath at 130° C. for 2.5 hours. The solvent was removed under reduced pressure and the residue was purified by silica gel column chromatography (hexane/ethyl acetate) to give allyl (5R,6S)-7-oxo-6-{(1R)-1-[(triethylsilyl)oxy]ethyl}-3-(3-{[(triethylsilyl)oxy]methyl}phenyl)-1-azabicyclo[3.2.0]hept-2-ene-2-carboxylate (1.44 g).

$^1$H NMR (400 MHz, CDCl$_3$) δ 0.59–0.68 (m, 12H), 0.95–0.99 (m, 18H), 1.31 (d, 3H, J=6.2 Hz), 3.12–3.32 (m, 3H), 4.22–4.27 (m, 2H), 4.59–4.69 (m, 2H), 3.71 (s, 2H), 5.15–5.27 (m, 2H), 5.79–5.87 (m, 1H), 7.23–7.31 (m, 4H).

Step c)

Anhydrous trifluoromethanesulfonic acid was added to THF (7 ml) and water (4 ml), and the solution was adjusted to pH2.2. To the solution was added at 0° C. allyl (5R,6S)-7-oxo-6-{(1R)-1-[(triethylsilyl)oxy]ethyl}-3-(3-{[(triethylsilyl)oxy]methyl}phenyl)-1-azabicyclo[3.2.0]hept-2-ene-2-carboxylate (520 mg). After stirring for 1 hour, thereto was added a saturated aqueous sodium hydrogencarbonate solution, and the solution was extracted with ethyl acetate. The organic layer was washed with a saturated aqueous sodium chloride solution, dried over anhydrous sodium sulfate, and the solvent was removed under reduced pressure to give allyl (5R,6S)-6-[(1R)-1-hydroxyethyl]-3-[3-(hydroxymethyl)phenyl]-7-oxo-1-azabicyclo[3.2.0]hept-2-ene-2-carboxylate. This product was used in the next step without further purification.

Step d)

Allyl (5R,6S)-6-[(1R)-1-hydroxyethyl]-3-[3-(hydroxymethyl)phenyl]-7-oxo-1-azabicyclo[3.2.0]hept-2-ene-2-carboxylate prepared in the above step, sodium 2-ethylhexanoate (242 mg) and triphenylphosphine (32 mg) were dissolved in THF (10 ml), and the solution was cooled to 0° C. Thereto tetrakis(triphenylphosphine) palladium(0) (70 mg) was added. Thirty minutes later, thereto hexane (3 ml) was added and then the solution was stirred for additional 30 minutes. The resulting crystals were filtered under nitrogen atmosphere, and dried under reduced pressure to give sodium (5R,6S)-6-[(1R)-1-hydroxyethyl]-3-[3-(hydroxymethyl)phenyl]-7-oxo-1-azabicyclo[3.2.0]hept-2-ene-2-carboxylate (217 mg).

$^1$H NMR (400 MHz, D$_2$O) δ 1.23 (d, 3H, J=6.4 Hz), 2.98–3.04 (m, 1H), 3.34–3.40 (m, 1H), 3.43–3.45 (m, 1H), 4.16–4.20 (m, 2H), 4.54 (s, 2H), 7.22–7.33 (m, 4H).

Example 5

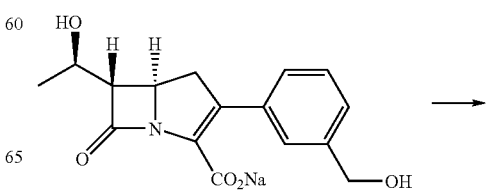

-continued

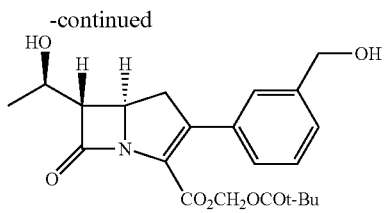

In the same manner as Example 3, starting from sodium (5R,6S)-6-[(1R)-1-hydroxyethyl]-3-[4-(hydroxymethyl)phenyl]-7-oxo-1-azabicyclo[3.2.0]hept-2-ene-2-carboxylate, there was obtained [(2,2-dimethylpropanoyl)oxy]methyl (5R,6S)-6-[(1R)-1-hydroxyethyl]-3-[4-(hydroxymethyl)phenyl]-7-oxo-1-azabicyclo[3.2.0]hept-2-ene-2-carboxylate.

$^1$H NMR (300 MHz, CDCl$_3$) δ 1.18 (s, 9H), 1.34 (d, 3H, J=6.2 Hz), 3.09–3.34 (m, 3H), 4.17–4.30 (m, 2H), 4.68 (s, 2H), 5.73 (d, 1H, J=5.5 Hz), 5.83 (d, 1H, J=5.5 Hz), 7.29–7.36 (m, 4H).

Example 6

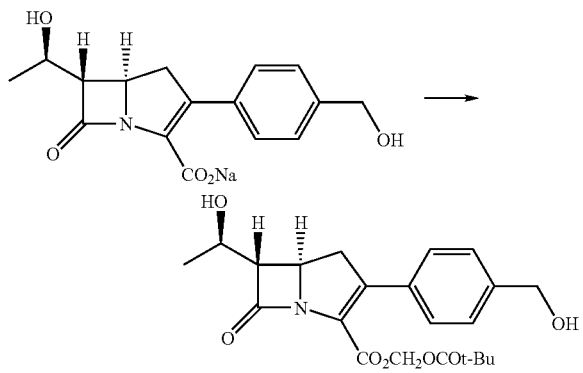

In the same manner as Example 3, starting from sodium (5R,6S)-6-[(1R)-1-hydroxyethyl]-3-[4-(hydroxymethyl)phenyl]-7-oxo-1-azabicyclo[3.2.0]hept-2-ene-2-carboxylate, there was obtained [(2,2-dimethylpropanoyl)oxy]methyl (5R,6S)-6-[(1R)-1-hydroxyethyl]-3-[4-(hydroxymethyl)phenyl]-7-oxo-1-azabicyclo[3.2.0]hept-2-ene-2-carboxylate.

$^1$H NMR (300 MHz, CDCl$_3$) δ 1.18 (s, 9H), 1.34 (d, 3H, J=6.2 Hz), 3.09–3.34 (m, 3H), 4.17–4.30 (m, 2H), 4.68 (s, 2H), 5.73 (d, 1H, J=5.5 Hz), 5.83 (d, 1H, J=5.5 Hz), 7.29–7.36 (m, 4H).

Example 7

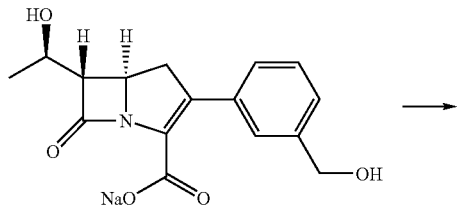

-continued

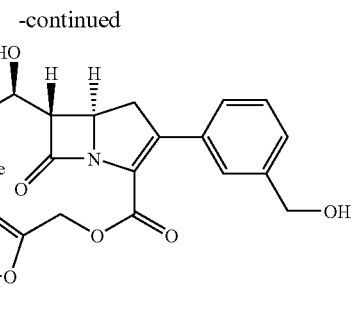

Sodium (5R,6S)-6-[(1R)-1-hydroxyethyl]-3-[3-(hydroxymethyl)phenyl]-7-oxo-1-azabicyclo[3.2.0]hept-2-ene-2-carboxylate (160 mg) prepared by example 4 was dissolved in DMF (2.0 ml), and thereto 4-(bromomethyl)-5-methyl-1,3-dioxol-2-one (143 mg) was added at 0° C. The mixture was stirred at 0° C. for 1 hour and then thereto ice water was added. The mixture was extracted with ethyl acetate. The organic layer was washed three times with a cold saturated aqueous sodium chloride solution, followed by a cold saturated aqueous sodium hydrogencarbonate solution and a saturated aqueous sodium chloride solution, and dried over anhydrous sodium sulfate. The solvent was removed under reduced pressure and the residue was purified by preparative thin-layer chromatography (ethyl acetate/acetone) to give (5-methyl-2-oxo-1,3-dioxol-4-yl)methyl (5R,6S)-6-[(1R)-1-hydroxyethyl]-3-[3-(hydroxymethyl)phenyl]-7-oxo-1-azabicyclo[3.2.0]hept-2-ene-2-carboxylate (62 mg).

$^1$H NMR (400 MHz, CDCl$_3$) δ 1.38 (d, 3H, J=6.3 Hz), 1.76 (broad d, 1H, J=3.9 Hz), 2.13 (s, 3H), 3.19–3.37 (m, 3H), 4.28–4.34 (m, 2H), 4.72–4.73 (m, 2H), 4.79 (d, 1H, J=13.9 Hz), 4.93 (d, 1H, J=13.9 Hz), 7.18–7.20 (m, 1H), 7.32 (s, 1H), 7.35–7.36 (m, 2H). IR(ATR) 3421(broad), 2968, 2927, 2877, 1817, 1770, 1732, 1718, 1437, 1387, 1338, 1267, 1228, 1190, 1030, 1009, 768, 696 cm$^{-1}$ Example 8

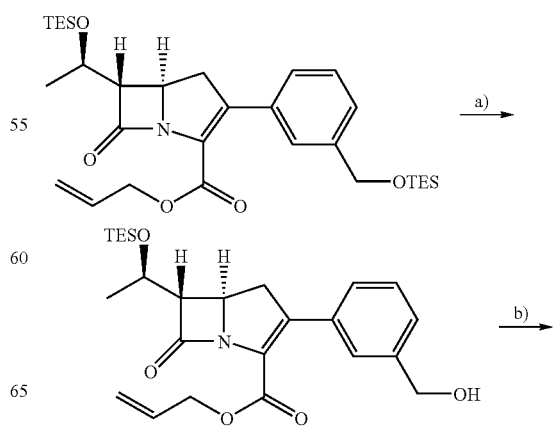

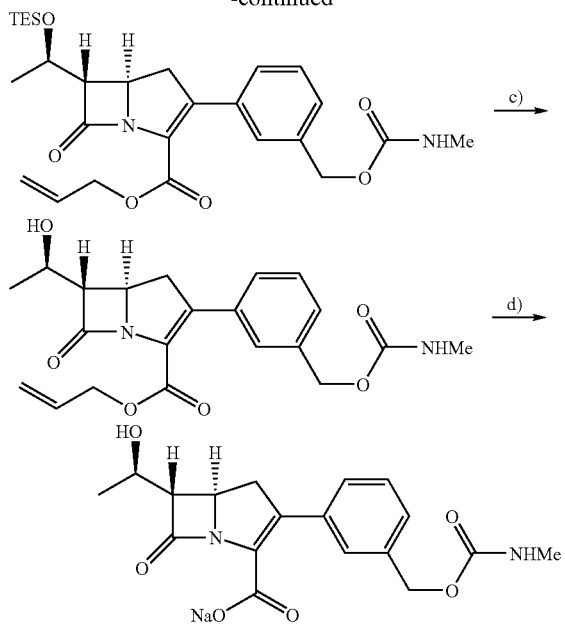

Step a)

Allyl (5R,6S)-7-oxo-6-{(1R)-1-[(triethylsilyl)oxy]ethyl}-3-(3-{[(triethylsilyl)oxy]methyl}phenyl)-1-azabicyclo[3.2.0]hept-2-ene-2-carboxylate (911 mg) prepared by step b) of example 4 was dissolved in THF (13 ml), and thereto water (6 ml) and acetic acid (3 ml) were added at 0° C. After stirring for 30 minutes, a saturated aqueous sodium hydrogencarbonate solution was added thereto and the solution was extracted with ethyl acetate. The organic layer was washed with a saturated aqueous sodium chloride solution, and dried over anhydrous sodium sulfate. The solvent was removed under reduced pressure and the residue was purified by silica gel column chromatography (hexane/ethyl acetate) to give allyl (5R,6S)-3-[3-(hydroxymethyl)phenyl]-7-oxo-6-{(1R)-1-[(triethylsilyl)oxy]ethyl}-1-azabicyclo[3.2.0]hept-2-ene-2-carboxylate (535 mg).

$^1$H NMR (400 MHz, CDCl$_3$) δ 0.57–0.67 (m, 6H), 0.95–0.99 (m, 9H), 1.30 (d, 3H, J=6.2 Hz), 1.76 (broad s, 1H), 3.13–3.33 (m, 3H), 4.23–4.28 (m, 2H), 4.59–4.73 (m, 4H), 5.16–5.29 (m, 2H), 5.81–5.90 (m, 1H), 7.26–7.37 (m, 4H). IR (KBr) 3522(broad), 2956, 2877, 1779, 1723, 1272, 1203, 1005, 746 cm$^{-1}$ Step b)

Allyl (5R,6S)-3-[3-(hydroxymethyl)phenyl]-7-oxo-6-{(1R)-1-[(triethylsilyl)oxy]ethyl}-1-azabicyclo[3.2.0]hept-2-ene-2-carboxylate (250 mg) prepared in the above step, was dissolved in dichloromethane (10 ml), and thereto were added N,N-diisopropylethylamine (14 mg) and methyl isocyanate (276 mg). The mixture was stirred for 1 day, concentrated under reduced pressure, and the residue was purified by silica gel column chromatography (chloroform) to give allyl (5R,6S)-3-[3-({[(methylamino)carbonyl]oxy}methyl)phenyl]-7-oxo-6-{(1R)-1-[(triethylsilyl)oxy]ethyl}-1-azabicyclo[3.2.0]hept-2-ene-2-carboxylate (122 mg).

$^1$H NMR (400 MHz, CDCl$_3$) δ 0.62 (q, 2H×3, J=7.8 Hz), 0.97 (t, 3H×3, J=7.8 Hz), 1.30 (d, 3H, J=6.2 Hz), 2.82 (d, 3H, J=4.9 Hz), 3.13–3.33 (m, 3H), 4.22–4.28 (m, 2H), 4.59–4.72 (m, 3H), 5.09 (s, 2H), 5.16–5.28 (m, 2H), 5.81–5.88 (m, 1H), 7.29–7.52 (m, 4H).

Step c)

To a solution of allyl (5R,6S)-3-[3-({[(methylamino)carbonyl]oxy}methyl)phenyl]-7-oxo-6-{(1R)-1-[(triethylsilyl)oxy]ethyl}-1-azabicyclo[3.2.0]hept-2-ene-2-carboxylate (284 mg) in THF (4 ml) was added a solution of anhydrous trifluoromethanesulfonic acid (0.6 ml) in water (2 ml) at 0° C., and the solution was stirred for 25 minutes. Thereto was added a cold aqueous saturated sodium hydrogencarbonate solution and the mixture was extracted with ethyl acetate. The organic layer was washed with a saturated aqueous sodium chloride solution, and dried over anhydrous sodium sulfate. The solvent was removed under reduced pressure and the residue was purified by silica gel column chromatography (chloroform/methanol) to give allyl (5R,6S)-6-[(1R)-1-hydroxyethyl]-3-[3-({[(methylamino)carbonyl]oxy}methyl)phenyl]-7-oxo-1-azabicyclo[3.2.0]hept-2-ene-2-carboxylate (139 mg).

$^1$H NMR (400 MHz, CDCl$_3$) δ 1.38 (d, 3H, J=6.3 Hz), 1.77 (d, 1H, J=4.9 Hz), 2.82 (d, 3H, J=4.9 Hz), 3.18–3.34 (m, 3H), 4.25–4.33 (m, 2H), 4.59–4.74 (m, 3H), 5.09 (s, 2H), 5.16–5.28 (m, 2H), 5.79–5.88 (m, 1H), 7.30–7.36 (m, 4H).

Step d)

In the same manner as step d) of example 4, starting from allyl (5R,6S)-6-[(1R)-1-hydroxyethyl]-3-[3-({[(methylamino)carbonyl]oxy}methyl)phenyl]-7-oxo-1-azabicyclo[3.2.0]hept-2-ene-2-carboxylate, there was obtained sodium (5R,6S)-6-[(1R)-1-hydroxyethyl]-3-[3-({[(methylamino)carbonyl]oxy}methyl)phenyl]-7-oxo-1-azabicyclo[3.2.0]hept-2-ene-2-carboxylate $^1$H NMR (400 MHz, D$_2$O) δ 1.22 (d, 3H, J=6.4 Hz), 2.61 (s, 3H), 2.99 (dd, 1H, J=17.0 Hz, 9.8 Hz), 3.34 (dd, 1H, J=17.0 Hz, 8.5 Hz), 3.42 (dd, 1H, J=6.0 Hz, 2.8 Hz), 4.13–4.24 (m, 2H), 4.99 (s, 2H), 7.21–7.33 (m, 4H).

Example 9

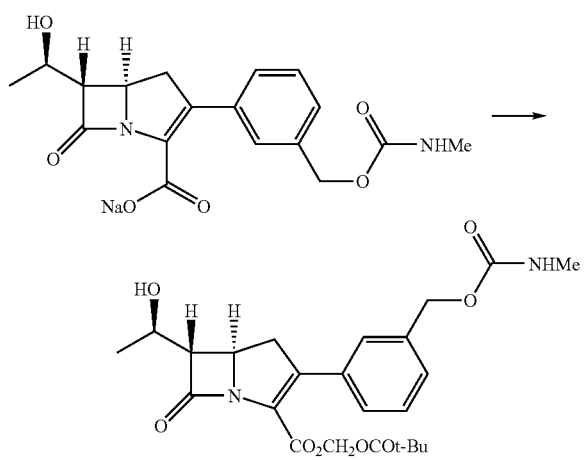

In the same manner as example 3, starting from sodium (5R,6S)-6-[(1R)-1-hydroxyethyl]-3-[3-({[(methylamino)carbonyl]oxy}methyl)phenyl]-7-oxo-1-azabicyclo[3.2.0]hept-2-ene-2-carboxylate prepared by example 8, there was obtained [(2,2-dimethylpropanoyl)oxy]methyl (5R,6S)-6-

[(1R)-1-hydroxyethyl]-3-[3-({[(methylamino)carbonyl]oxy}methyl)phenyl]-7-oxo-1-azabicyclo[3.2.0]hept-2-ene-2-carboxylate.

$^1$H NMR (400 MHz, CDCl$_3$) δ 1.18 (s, 9H), 1.37 (d, 3H, J=6.3 Hz), 1.86 (broad s, 1H), 2.82 (d, 3H, J=4.9 Hz), 3.18–3.36 (m, 3H), 4.25–4.33 (m, 2H), 4.78 (broad s, 1H), 5.10 (s, 2H), 5.77 (d, 1H, J=5.5 Hz), 5.84 (d, 1H, J=5.5 Hz), 7.26–7.34 (m, 4H). IR(ATR) 3396(broad), 2972, 1701, 1527, 1259, 1187, 1120, 1095, 1022, 980, 775, 698 cm$^{-1}$ Example 10

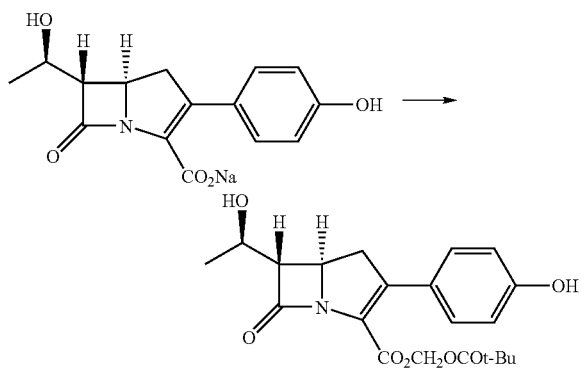

In the same manner as example 2, starting from sodium (5R,6S)-6-[(1R)-1-hydroxyethyl]-4-(hydroxyphenyl)-7-oxo-1-azabicyclo[3.2.0]hept-2-ene-2-carboxylate (43 mg) prepared, there was obtained [(2,2-dimethylpropanoyl)oxy]methyl (5R,6S)-6-[(1R)-1-hydroxyethyl]-4-(hydroxyphenyl)-7-oxo-1-azabicyclo[3.2.0]hept-2-ene-2-carboxylate (28.7 mg).

$^1$H NMR (400 MHz, CDCl$_3$) δ 1.20 (9H, s), 1.37 (3H, d, J=6.3 Hz), 3.16–3.33 (3H, m), 4.21–4.31 (2H, m), 5.74–5.91 (2H, m), 6.81 (2H, d, J=8.7 Hz), 7.31 (2H, d, J=8.7 Hz).

Example 11

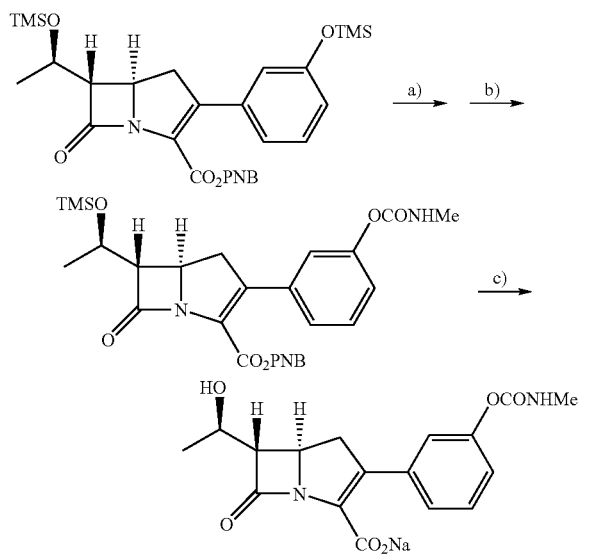

Step a)

To a solution of 4-nitrobenzyl (5R,6S)-7-oxo-6-{(1R)-1-[(trimethylsilyl)oxy]ethyl}-3-{3-[(trimethylsilyl)oxy]phenyl}-1-azabicyclo[3.2.0]hept-2-ene-2-carboxylate (500 mg) in THF (8.6 ml) was added at −78° C. acetic acid (51 mg). Thereto was dropped 1M tetrabutylammonium fluoride/THF solution (0.86 ml), and the mixture was stirred at the same temperature for 15 minutes. The reaction mixture was poured into a mixture of a cold aqueous sodium hydrogencarbonate (72 mg) and ethyl acetate. The mixture was extracted and separated by a separating funnel. The organic layer was washed with a cold saturated aqueous sodium chloride solution (three times) and cold water in the order, and dried over anhydrous sodium sulfate. The solvent was removed under reduced pressure to give 4-nitrobenzyl (5R,6S)-3-(3-hydroxyphenyl)-7-oxo-6-{(1R)-1-[(trimethylsilyl)oxy]ethyl}-1-azabicyclo[3.2.0]hept-2-ene-2-carboxylate. This product was used in the next step without further purification.

Step b)

To a solution of 4-nitrobenzyl (5R,6S)-3-(3-hydroxyphenyl)-7-oxo-6-{(1R)-1-[(trimethylsilyl)oxy]ethyl}-1-azabicyclo[3.2.0]hept-2-ene-2-carboxylate prepared in the above step in dichloromethane (10 ml) was added N,N-diisopropylethylamine (catalytic amount), and thereto was added under ice cooling a solution of methyl isocyanate (57 mg) in dichloromethane (5 ml). After stirring under ice cooling for 2 hours, the temperature was raised to room temperature and the reaction mixture was poured into a mixture of ice water and ethyl acetate. The mixture was extracted and separated with a separating funnel. The organic layer was washed with cold water (twice) and a cold saturated aqueous sodium chloride solution in the order, and dried over anhydrous sodium sulfate. The solvent was removed under reduced pressure. The residue was purified by silica gel column chromatography (hexane/ethyl acetate) to give 4-nitrobenzyl (5R,6S)-3-(3-{[(methylamino)carbonyl]oxy}phenyl)-7-oxo-6-{(1R)-1-[(trimethylsilyl)oxy]ethyl}-1-azabicyclo[3.2.0]hept-2-ene-2-carboxylate (276 mg).

$^1$H NMR (400 MHz, CDCl$_3$) δ 0.15 (9H, s), 1.30 (3H, d, J=6.2 Hz), 2.89, 2.91 (total 3H, each s), 3.14–3.36 (3H, m), 4.18–4.31 (2H, m), 4.97 (1H, broad d, J=4.4 Hz), 5.16–5.40 (2H, m), 7.04–7.22 (3H, m), 7.31 (1H, t, J=7.9 Hz), 7.43 (2H, d, J=8.7 Hz), 8.15 (2H, d, J=8.8 Hz).

Step c)

In the same manner as step c) of example 2, starting from 4-nitrobenzyl (5R,6S)-3-(3-{[(methylamino)carbonyl]oxy}phenyl)-7-oxo-6-{(1R)-1-[(trimethylsilyl)oxy]ethyl}-1-azabicyclo[3.2.0]hept-2-ene-2-carboxylate (270 mg), there was obtained sodium (5R,6S)-6-[(1R)-1-hydroxyethyl]-3-(3-{[(methylamino)carbonyl]oxy}phenyl)-7-oxo-1-azabicyclo[3.2.0]hept-2-ene-2-carboxylate (66 mg).

$^1$H NMR (400 MHz, D$_2$O) δ 1.20 (3H, d, J=6.4 Hz), 2.69 (3H, s), 2.94–3.05 (1H, m), 3.26–3.37 (1H, m), 3.42 (1H, dd, J=2.8 Hz, 5.9 Hz), 4.10–4.26 (2H, m), 6.92–7.04 (2H, m), 7.17 (1H, d, J=7.8 Hz), 7.29 (1H, t, J=7.9 Hz).

Example 12

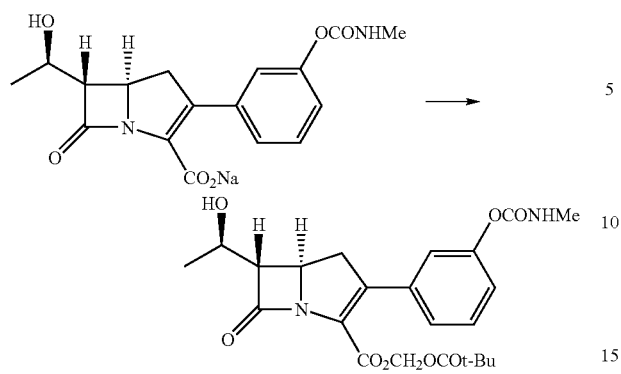

In the same manner as example 3, starting from sodium (5R,6S)-6-[(1R)-1-hydroxyethyl]-3-(3-{[(methylamino)carbonyl]oxy}phenyl)-7-oxo-1-azabicyclo[3.2.0]hept-2-ene-2-carboxylate (53 mg), there was obtained [(2,2-dimethylpropanoyl)oxy]methyl (5R, S)-6-[(1R)-1-hydroxyethyl]-3-(3-{[(methylamino)carbonyl]oxy}phenyl)-7-oxo-1-azabicyclo[3.2.0]hept-2-ene-2-carboxylate (28 mg).

$^1$H NMR (400 MHz, CDCl$_3$) δ 1.19 (9H, s), 1.37 (3H, d, J=6.3 Hz), 2.89, 2.91 (total 3H, each s), 3.17–3.37 (3H, m), 4.21–4.35 (2H, m), 4.99 (1H, broad d, J=3.4 Hz), 5.74–5.90 (2H, m), 7.06–7.23 (3H, m), 7.33 (1H, t, J=7.9 Hz).

Example 13

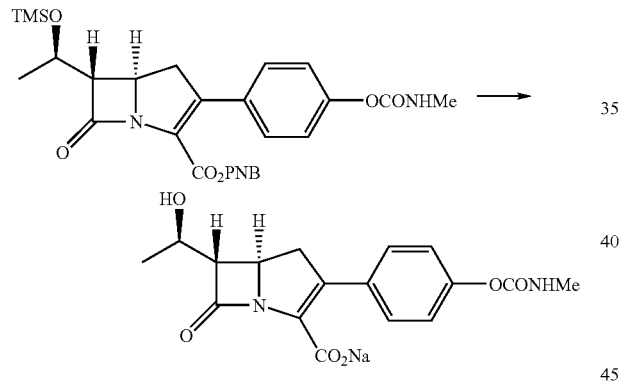

In the same manner as step c) of example 2, starting from 4-nitrobenzyl (5R,6S)-3-(4-{[(methylamino)carbonyl]oxy}phenyl)-7-oxo-6-{(1R)-1-[(trimethylsilyl)oxy]ethyl}-1-azabicyclo[3.2.0]hept-2-ene-2-carboxylate (340 mg), there was obtained sodium (5R,6S)-6-[(1R)-1-hydroxyethyl]-3-(4-{[(methylamino)carbonyl]oxy}phenyl)-7-oxo-1-azabicyclo[3.2.0]hept-2-ene-2-carboxylate (112 mg).

$^1$H NMR (400 MHz, D$_2$O) δ 1.22 (3H, d, J=6.4 Hz), 2.70 (3H, s), 2.95–3.07 (1H, m), 3.29–3.40 (1H, m), 3.42 (1H, dd, J=2.8 Hz, 5.9 Hz), 4.11–4.27 (2H, m), 7.02 (2H, d, J=8.7 Hz), 7.30 (2H, d, J=8.7 Hz).

Example 14

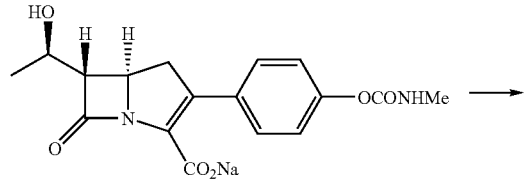

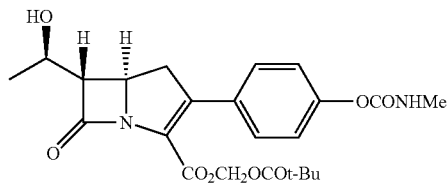

In the same manner as example 3, starting from sodium (5R,6S)-6-[(1R)-1-hydroxyethyl]-3-(4-{[(methylamino)carbonyl]oxy}phenyl)-7-oxo-1-azabicyclo[3.2.0]hept-2-ene-2-carboxylate (78 mg), there was obtained [(2,2-dimethylpropanoyl)oxy]methyl (5R,6S)-6-[(1R)-1-hydroxyethyl]-3-(4-{[(methylamino)carbonyl]oxy}phenyl)-7-oxo-1-azabicyclo[3.2.0]hept-2-ene-2-carboxylate (40.2 mg).

$^1$H NMR (400 MHz, CDCl$_3$) δ 1.19 (9H, s), 1.37 (3H, d, J=6.3 Hz), 2.90, 2.91 (total 3H, each s), 3.14–3.36 (3H, m), 4.20–4.35 (2H, m), 5.00 (1H, broad d, J=4.9 Hz), 5.71–5.91 (2H, m), 7.12 (2H, d, J=8.6 Hz), 7.36 (2H, d, J=8.6 Hz).

Example 15

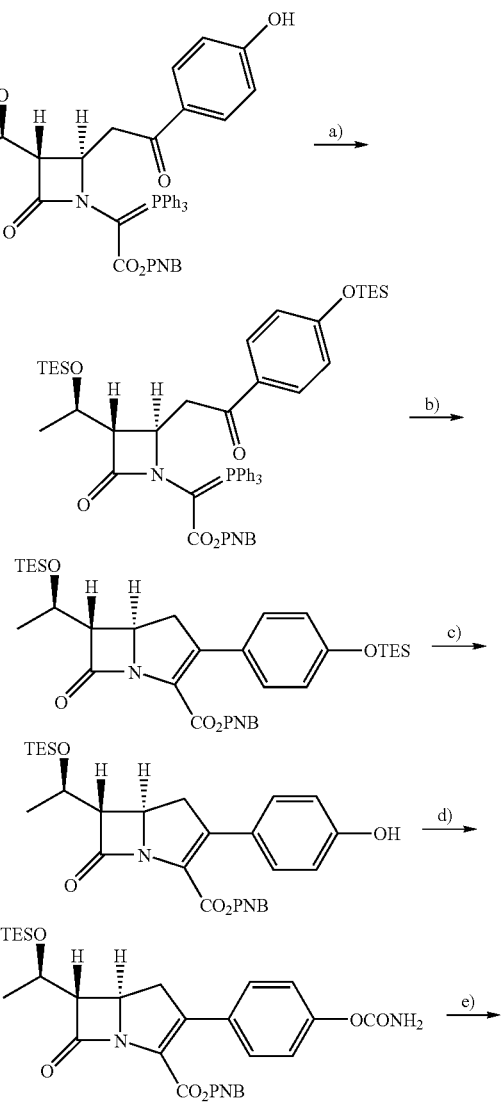

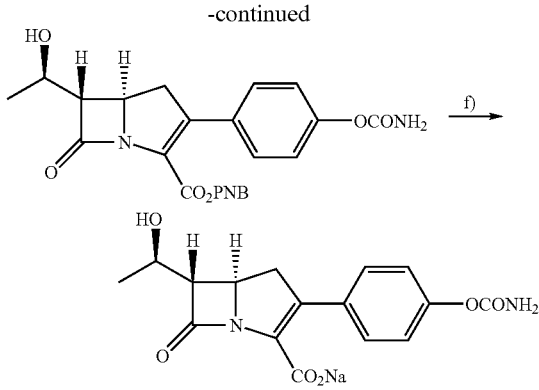

Step a)
In the same manner as step a) of example 2, by using chlorotriethylsilane (3.20 g) instead of chlorotrimethylsilane and starting from 4-nitrobenzyl {(2R,3S)-3-[(1R)-1-hydroxyethyl]-2-[2-(4-hydroxyphenyl)-2-oxoethyl]-4-oxoazetidin-1-yl}(triphenylphosphoranilidene)acetate (1.90 g), there was obtained 4-nitrobenzyl ((3S,4R)-2-oxo-4-(2-oxo-2-{4-[(triethylsilyl)oxy]phenyl}ethyl)-3-{(1R)-1-[(triethylsilyl)oxy]ethyl}azetidin-1-yl)(triphenylphosphoranilidene)acetate. This product was used in the next step without further purification.

Step b)
The residue prepared in the same manner as step b) of example 2 by using 4-nitrobenzyl ((3S,4R)-2-oxo-4-(2-oxo-2-{4-[(triethylsilyl)oxy]phenyl}ethyl)-3-{(1R)-1-[(triethylsilyl)oxy]ethyl}azetidin-1-yl)(triphenylphosphoranilidene)acetate prepared in the above step, was purified by silica gel column chromatography (chloroform/acetone after hexane/ethyl acetate) to give 4-nitrobenzyl (5R,6S)-7-oxo-6-{(1R)-1-[(triethylsilyl)oxy]ethyl}-3-{4-[(triethylsilyl)oxy]phenyl}-1-azabicyclo[3.2.0]hept-2-ene-2-carboxylate (395 mg, a mixture with about equimolar triethylsilanol). This product was used in the next step without further purification.

Step c)
The residue prepared in the same manner as step a) of example 11 by using 4-nitrobenzyl (5R,6S)-7-oxo-6-{(1R)-1-[(triethylsilyl)oxy]ethyl}-3-{4-[(triethylsilyl)oxy]phenyl}-1-azabicyclo[3.2.0]hept-2-ene-2-carboxylate (367 mg, a mixture with about equimolar triethylsilanol), was purified by silica gel thin-layer chromatography (hexane/ethyl acetate=2/1) to give 4-nitrobenzyl (5R,6S)-3-(4-hydroxyphenyl)-7-oxo-6-{(1R)-1-[(triethylsilyl)oxy]ethyl}-1-azabicyclo[3.2.0]hept-2-ene-2-carboxylate (210 mg).

$^1$H NMR (400 MHz, CDCl$_3$) δ 0.55–0.68 (6H, m), 0.96 (9H, t, J=7.9 Hz), 1.31 (3H, d, J=6.2 Hz), 3.13–3.31 (3H, m), 4.21–4.31 (2H, m), 5.16–5.43 (3H, m), 6.78 (2H, d, J=8.7 Hz), 7.31 (2H, d, J=8.7 Hz), 7.53 (2H, d, J=8.7 Hz), 8.18 (2H, d, J=8.8 Hz).

Step d)
4-Nitrobenzyl (5R,6S)-3-(4-hydroxyphenyl)-7-oxo-6-{(1R)-1-[(triethylsilyl)oxy]ethyl}-1-azabicyclo[3.2.0]hept-2-ene-2-carboxylate (200 mg) prepared in the above step was dissolved in dichloromethane (4.5 ml). Thereto were added under ice cooling pyridine in a catalytic amount and trichloroacetyl isocyanate (106 mg), and the mixture was stirred for 1 hour. The reaction mixture was poured into a mixture of ice water and ethyl acetate. The mixture was extracted and separated with a separating funnel. The organic layer was washed with cold water (twice) and a cold saturated aqueous sodium chloride solution in the order, and dried over anhydrous sodium sulfate. The solvent was removed under reduced pressure. The residue was dissolved in methanol (13.5 ml) and thereto silica gel (2.7 g) was added. The mixture was stirred for 1.5 hours and then, kept in a refrigerator overnight. After the reaction mixture was diluted with chloroform, silica gel was removed by filtration. The solution was washed with chloroform/methanol (=4/1) and the solvent was removed under reduced pressure. The residue was purified by silica gel thin layer chromatography (chloroform/acetone=9/1) to give 4-nitrobenzyl (5R,6S)-3-{4-[(aminocarbonyl)oxy]phenyl}-6-{(1R)-1-[(triethylsilyl)oxy]ethyl}-7-oxo-1-azabicyclo[3.2.0]hept-2-ene-2-carboxylate (113 mg).

$^1$H NMR (400 MHz, CDCl$_3$) δ 0.53–0.69 (6H, m), 0.96 (9H, t, J=7.9 Hz), 1.31 (3H, d, J=6.2 Hz), 3.11–3.35 (3H, m), 4.22–4.35 (2H, m), 5.14–5.43 (2H, m), 7.10 (2H, d, J=8.7 Hz), 7.35 (2H, d, J=8.7 Hz), 7.44 (2H, d, J=8.8 Hz), 8.17 (2H, d, J=8.8 Hz).

Step e)
To a solution of 4-nitrobenzyl (5R,6S)-3-{4-[(aminocarbonyl)oxy]phenyl}-6-{(1R)-1-[(triethylsilyl)oxy]ethyl}-7-oxo-1-azabicyclo[3.2.0]hept-2-ene-2-carboxylate (110 mg) prepared in the above step in THF (1.9 ml) was added under ice cooling acetic acid (11 mg). Then 1M tetrabutylammonium fluoride/THF solution (0.19 ml) was dropped thereto and the mixture was stirred at the same temperature for 45 minutes. The residue prepared by the same manner as step a) of example 11 was purified by silica gel thin-layer chromatography (chloroform/acetone=2/1) to give 4-nitrobenzyl (5R,6S)-3-{4-[(aminocarbonyl)oxy]phenyl}-6-[(1R)-1-hydroxyethyl]-7-oxo-1-azabicyclo[3.2.0]hept-2-ene-2-carboxylate (11 mg).

$^1$H NMR (400 MHz, CD$_3$OD) δ 1.31 (3H, d, J=6.3 Hz), 3.15–3.50 (2H, m), 3.36 (1H, dd, J=2.8 Hz, 6.8 Hz), 4.07–4.19 (1H, m), 4.25–4.35 (1H, m), 5.18–5.40 (2H, m), 7.07 (2H, d, J=8.7 Hz), 7.40 (2H, d, J=8.7 Hz), 7.46 (2H, d, J=8.8 Hz), 8.16 (2H, d, J=8.8 Hz).

Step f)
In the same manner as step c) of example 2, starting from 4-nitrobenzyl (5R,6S)-3-{4-[(aminocarbonyl)oxy]phenyl}-6-[(1R)-1-hydroxyethyl]-7-oxo-1-azabicyclo[3.2.0]hept-2-ene-2-carboxylate (11 mg), there was obtained sodium (5R,6S)-3-{4-[(aminocarbonyl)oxy]phenyl}-6-[(1R)-1-hydroxyethyl]-7-oxo-1-azabicyclo[3.2.0]hept-2-ene-2-carboxylate (4 mg).

$^1$H NMR (400 MHz, D$_2$O) δ 1.22 (3H, d, J=6.4 Hz), 2.93–3.08 (1H, m), 3.25–3.40 (1H, m), 3.42 (1H, dd, J=2.8 Hz, 6.0 Hz), 4.10–4.28 (2H, m), 7.04 (2H, d, J=8.7 Hz), 7.30 (2H, d, J=8.7 Hz).

Example 16

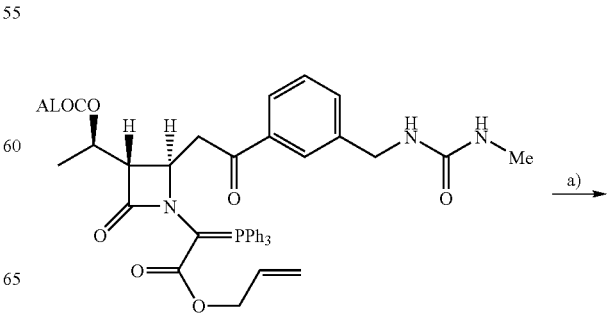

-continued

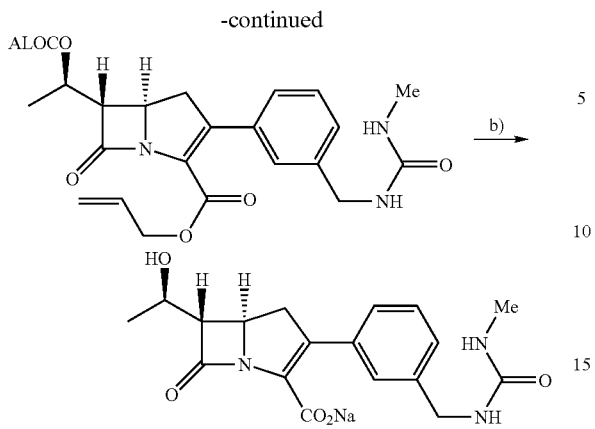

Step a)

In the same manner as step b of example 1, by using allyl ((2R, 3S)-3-((1R)-1-{[(allyloxy)carbonyl]oxy}ethyl)-2-{2-[3-({[(methylamino)carbonyl]amino}methyl)phenyl]-2-oxoethyl}-4-oxoazetidin-1-yl)(triphenylphosphoranilidene)acetate (94 mg) prepared by reference example 7, there was obtained allyl (5R,6S)-6-((1R)-1-{[(allyloxy)carbonyl oxy}ethyl)-3-[3-({[(methylamino)carbonyl]amino}methyl)phenyl]-7-oxo-1-azabicyclo[3.2.0]hept-2-ene-2-carboxylate (25 mg).

Step b)

To the compound (25 mg) prepared in the above step a), acetic acid (8 μl) and a solution of tributyltin hydride (140 μl) in dichloromethane (2 ml) was added at room temperature bis(triphenylphosphine) palladium chloride (II) (3.6 mg), and the mixture was stirred at room temperature for 30 minutes. To the reaction mixture was added a 0.1N aqueous sodium hydrogencarbonate solution (10 ml) and the aqueous layer was separated. The organic layer was extracted with water (2×5 ml). The aqueous layers were combined and washed with dichloromethane. The organic solvent in the aqueous layer was removed under reduced pressure. The aqueous solution was purified by polymer chromatography (CHP-20P) and fractions eluted with water alone were collected and subjected to freeze-drying to give sodium (5R,6S)-6-[(1R)-1-hydroxyethyl]-3-[3-({[(methylamino)carbonyl]amino}methyl)phenyl]-7-oxo-1-azabicyclo[3.2.0]hept-2-ene-2-carboxylate (1.4 mg).

$^1$H NMR (300 MHz, D$_2$O) δ 1.15 (d, 3H, J=6.2 Hz), 2.53 (s, 3H), 2.91 (dd, 1H, J=10.6 Hz, 17.0 Hz), 3.28 (dd, 1H, J=8.8 Hz, 17.0 Hz), 3.35 (dd, 1H, J=2.9 Hz, 5.8 Hz), 4.07–4.14 (m, 4H), 7.06–7.21 (m, 4H). IR (ATR) 3315 (broad), 2954, 2924, 1749, 1576, 1456, 1396, 1375, 1259, 1134, 1068, 881, 833, 785 cm$^{-1}$.

Example 17

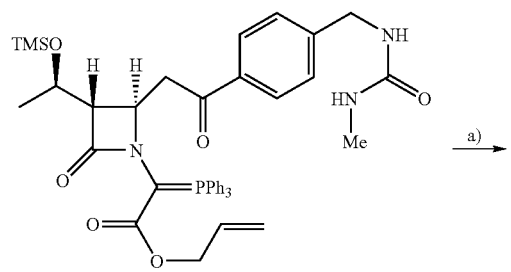

-continued

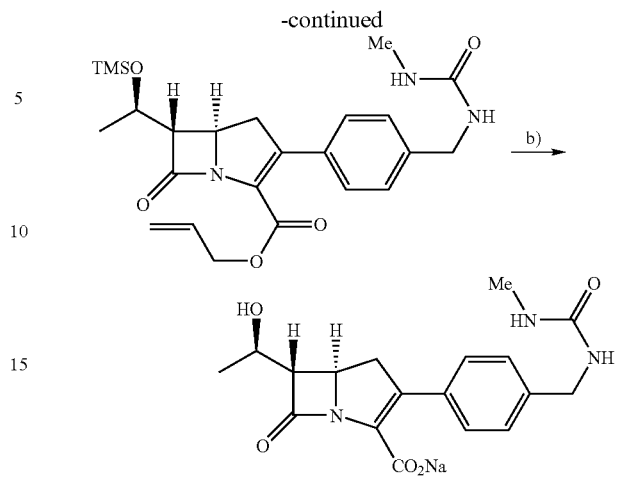

Step a)

Allyl ((2R,3S)-2-{2-[4-({[(methylamino)carbonyl]amino}methyl)phenyl]-2-oxoethyl}-4-oxo-3-{(1R)-1-[(trimethylsilyl)oxy]ethyl}azetidin-1-yl)(triphenylphosphoranilidene)acetate (0.61 g) prepared by reference example 10 and bistrimethylsilylamide (0.34 ml) were dissolved in toluene/dioxane (10 ml/5 ml), and the solution was refluxed for 6 hours. After being cooled, the solvent was removed under reduced pressure and the residue was purified by silica gel column chromatography (chloroform/methanol=10:1) to give allyl (5R,6S)-3-[4-({[(methylamino)carbonyl]amino}methyl)phenyl]-7-oxo-6-{(1R)-1-[(trimethylsilyl)oxy]ethyl}-1-azabicyclo[3.2.0]hept-2-ene-2-carboxylate (0.24 g) as a pale yellow oil.

$^1$H NMR (400 MHz, CDCl$_3$) δ 0.10 (s, 9H), 1.24 (d, 3H, J=6.2 Hz), 2.64 (d, 3H, J=4.8 Hz), 3.07 (dd, 1H, J=9.9 Hz, 18.1 Hz), 3.16 (dd, 1H, J=2.7 Hz, 6.6 Hz), 3.20 (dd, 1H, J=18.1 Hz), 4.14–4.20 (m, 2H), 4.23 (d, 2H, J=5.8 Hz), 4.43–4.58 (m, 1H), 4.61–4.70 (m, 1H), 5.07 (q, 1H, J=4.8 Hz), 5.12–5.16 (m, 1H), 5.22–5.28 (m, 1H), 5.42 (t, 1H, J=5.8 Hz), 5.76–5.86 (m, 1H), 7.15–7.17 (m, 2H), 7.21–7.24 (m, 2H).

Step b)

The compound (0.24 g) prepared in step a) was dissolved in THF/water (12 ml/3 ml), and thereto was added under ice cooling 1N hydrochloric acid to adjust pH 2.5. The solution was stirred for 1 hour. Thereto were added pH 6.86 phosphate buffer (15 ml) and a saturated aqueous sodium chloride solution (15 ml), and the mixture was extracted with ethyl acetate (3×20 ml). The organic layer were combined, dried over magnesium sulfate, and filtered. The solvent was removed under reduced pressure to give a yellow oil (0.24 g). This oil, triphenylphosphine. (13 mg) and sodium 2-ethylhexanoate (93 mg) were dissolved in THF (6 mL), and thereto was added under ice cooling tetrakis(triphenylphosphine) palladium(0) (29 mg). The mixture was stirred for 1 hour. The resulting solid was collected by filtration, washed with a small amount of THF, and dried under reduced pressure to give sodium (5R,6S)-6-[(1R)-1-hydroxyethyl]-3-[4-({[(methylamino)carbonyl]amino}methyl)phenyl]-7-oxo-1-azabicyclo[3.2.0]hept-2-ene-2-carboxylate (183 mg) as a pale yellow solid.

$^1$H NMR (400 MHz, DMSO-d6) δ 1.15 (d, 3H, J=6.3 Hz), 2.54 (d, 3H, J=4.6 Hz), 2.85 (dd, 1H, J=9.9 Hz, 15.7 Hz), 3.07 (dd, 1H, J=8.5 Hz, 15.7 Hz), 3.12 (dd, 1 H, J=2.8 Hz, 6.6 Hz), 3.88–3.93 (m, 1H), 3.97–4.02 (m, 1H), 4.12 (d, 2 H, J=5.8 Hz), 4.99 (d, 1 H, J=5.0 Hz), 6.01 (q, 1 H, J=4.6 Hz), 6.56 (t, 1 H, J=6.1 Hz), 7.07–7.09 (m, 2H), 7.38–7.40 (m, 2 H). IR (ATR) 3309, 2931, 1749, 1578, 1560, 1508, 1396, 1254, 1221, 1157, 1130, 1072, 808, 789, 669 cm$^{-1}$.

Example 18

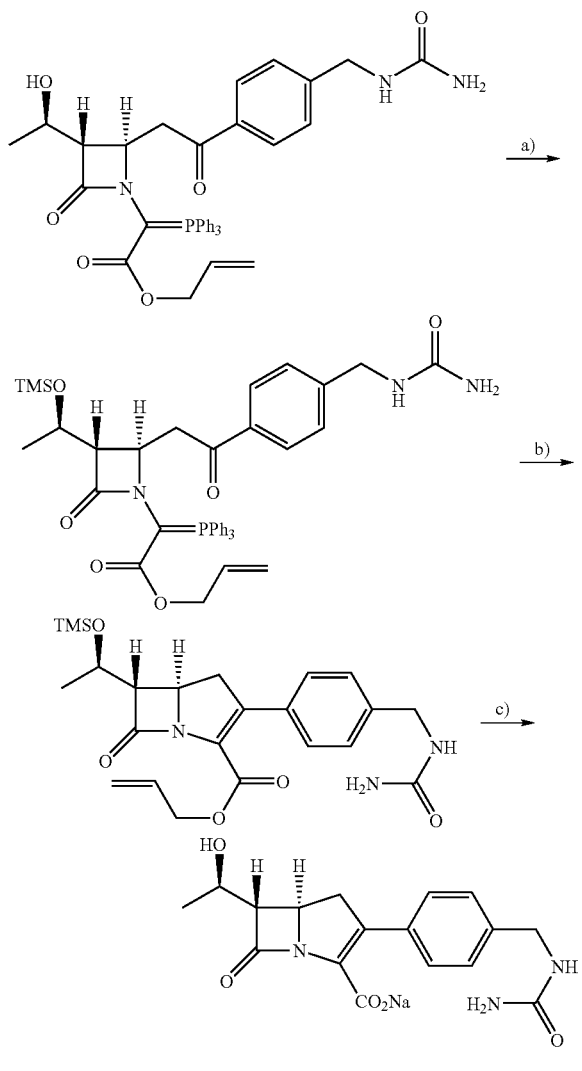

Step a)

In the same manner as step a) of Example 2, by using allyl {(2R,3S)-2-[2-(4-{[(aminocarbonyl)amino]methyl}phenyl)-2-oxoethyl]-3-[(1R)-1-hydroxyethyl]-4-oxoazetidin-1-yl}(triphenylphosphoranilidene)acetate (0.83 g) prepared by reference example 11, there was obtained allyl {(2R,3S)-2-[2-(4-{[(aminocarbonyl)amino]methyl}phenyl)-2-oxoethyl]-3-[(1R)-1-({trimethylsilyl}oxy)ethyl]-4-oxoazetidin-1-yl}(triphenylphosphoranilidene)acetate. This product was used in the next step without further purification.

Step b)

In the same manner as step b) of example 2, by using the compound prepared in step a), there was obtained allyl (5R,6S)-3-(4-{[(aminocarbonyl)amino]methyl}phenyl)-7-oxo-6-{(1R)-1-[(trimethylsilyl)oxy]ethyl}-1-azabicyclo[3.2.0]hept-2-ene-2-carboxylate (0.14 g)

$^{1}$H NMR (400 MHz, CDCl$_3$) δ 0.15 (s, 9H), 1.29 (d, 3H, J=6.2 Hz), 3.13 (dd, 1H, J=9.9 Hz, 18.1 Hz), 3.21 (dd, 1H, J=2.8 Hz, 6.7 Hz), 3.26 (dd, 1H, J=8.9 Hz, 18.1 Hz), 4.19–4.25 (m, 2H), 4.29 (d, 2H, J=5.8 Hz), 4.55 (broad s, 2H), 4.58–4.63 (m, 1H), 4.66–4.71 (m, 1H), 5.17–5.21 (m, 1H), 5.29–5.34 (m, 1H), 5.38 (t, 1H, J=5.8 Hz), 5.81–5.91 (m, 1H), 7.23–7.25 (m, 2H), 7.28–7.30 (m, 2H).

Step c)

In the same manner as in step b) of example 17, by using the compound (0.14 g) prepared in step b), there was obtained crude sodium (5R,6S)-3-(4-{[(aminocarbonyl)amino]methyl}phenyl)-6-[(1R)-1-hydroxyethyl]-7-oxo-1-azabicyclo[3.2.0]hept-2-ene-2-carboxylate (0.16 g). The product was purified by polymer chromatography (CHP-20P) and fractions eluted with water alone were collected and subjected to freeze-drying to give the object compound (0.02 g).

$^{1}$H NMR (400 MHz, DMSO-d6) δ 1.21 (d, 3H, J=6.3 Hz), 2.91 (dd, 1H, J=9.8 Hz, 15.6 Hz), 3.13 (dd, 1H, J=8.5 Hz, 15.6 Hz), 3.19 (dd, 1 H, J=2.8 Hz, 6.6 Hz), 3.95–3.98 (m, 1H), 4.03–4.08 (m, 1H), 4.17 (d, 2H, J=5.9 Hz), 5.05 (broad s, 1H), 5.60 (broad s, 2H), 6.56 (t, 1H, J=5.9 Hz), 7.13–7.16 (m, 2H), 7.45–7.47 (m, 2H). IR (ATR 3323, 1743, 1655, 1581, 1560, 1394, 1340, 1304, 1252, 1221, 1132, 806, 789 cm$^{-1}$.

Example 19

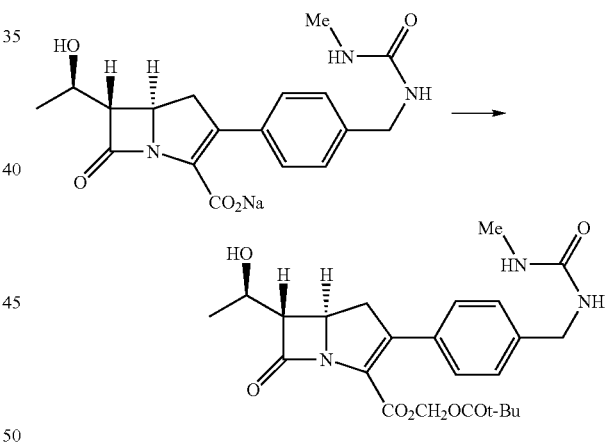

In the same manner as example 3, from sodium (5R,6S)-6-[(1R)-1-hydroxyethyl]-3-[4-({[(methylamino)carbonyl]amino}methyl)phenyl]-7-oxo-1-azabicyclo[3.2.0]hept-2-ene-2-carboxylate prepared by example 17, there was obtained [(2,2-dimethylpropanoyl)oxy]methyl (5R,6S)-6-[(1R)-1-hydroxyethyl]-3-[4-({[(methylamino)carbonyl]amino}methyl)phenyl]-7-oxo-1-azabicyclo[3.2.0]hept-2-ene-2-carboxylate.

$^{1}$H NMR (400 MHz, CDCl$_3$) δ 1.19 (s, 9H), 1.34 (d, 3H, J=6.3 Hz), 2.74 (d, 3H, J=4.8 Hz), 3.08 (dd, 1H, J=9.9 Hz, 18.3 Hz), 3.20–3.27 (m, 2H), 4.16–4.26 (m, 2H), 4.31 (d, 2H, J=5.7 Hz), 4.86 (q, 1H, J=4.8 Hz), 5.22 (t, 1H, J=5.7 Hz), 5.73 (d, 1H, J=5.5 Hz), 5.82 (d, 1H, J=5.5 Hz), 7.21 (broad s, 4H). IR (ATR) 3356, 2970, 1774, 1751, 1637, 1558, 1481, 1458, 1414, 1338, 1265, 1192, 1153, 1122, 1095, 1022, 991, 978, 943, 816, 752, 665 cm$^{-1}$.

Example 20

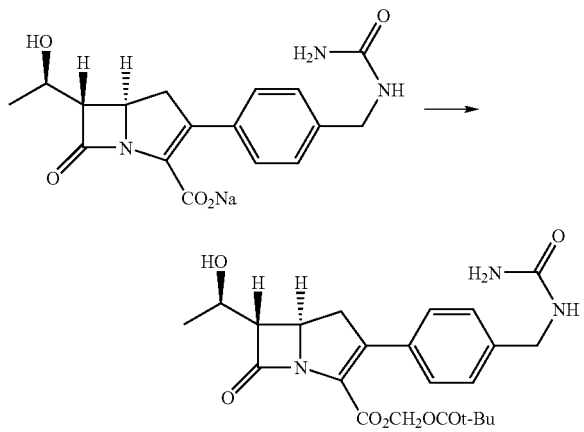

In the same manner as example 3, from sodium (5R,6S)-3-(4-{[(aminocarbonyl)amino]methyl}phenyl)-6-[(1R)-1-hydroxyethyl]-7-oxo-1-azabicyclo[3.2.0]hept-2-ene-2-carboxylate prepared by example 18, there was obtained [(2,2-dimethylpropanoyl)oxy]methyl(5R,6S)-3-(4-{[(aminocarbonyl)amino]methyl}phenyl)-6-[(1R)-1-hydroxyethyl]-7-oxo-1-azabicyclo[3.2.0]hept-2-ene-2-carboxylate.

$^1$H NMR (400 MHz, CD$_3$CN) δ 1.05 (s, 9H), 1.10 (d, 3H, J=6.3 Hz), 2.99 (dd, 1H, J=10.0 Hz, 18.3 Hz), 3.19 (dd, 1H, J=2.9 Hz, 6.1 Hz), 3.27 (dd, 1H, J=8.8 Hz, 18.3 Hz), 3.34 (d, 1H, J=4.8 Hz), 3.92–4.01 (m, 1H), 4.08–4.13 (m, 3H), 4.74 (broad s, 2H), 5.58 (d, 1H, J=5.8 Hz), 5.61 (t, 1H, J=6.0 Hz), 5.66 (d, 1H, J=5.8 Hz), 7.10–7.12 (m, 2H), 7.17–7.19 (m, 2H). IR (ATR) 3369, 2972, 1768, 1751, 1728, 1655, 1602, 1541, 1481, 1458, 1336, 1269, 1194, 1122, 1094, 1022, 991, 978, 750, 667 cm$^{-1}$.

Example 21

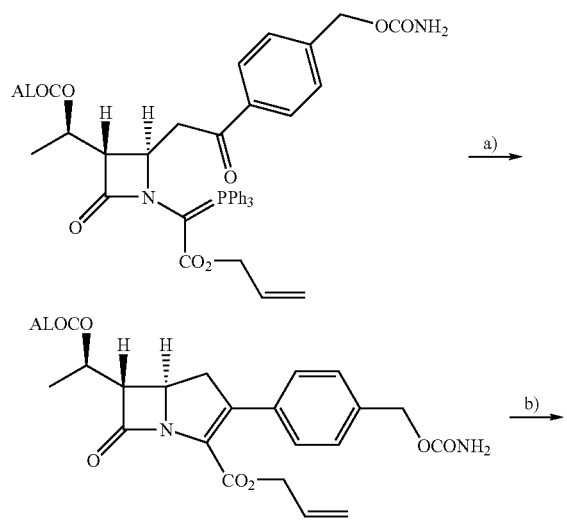

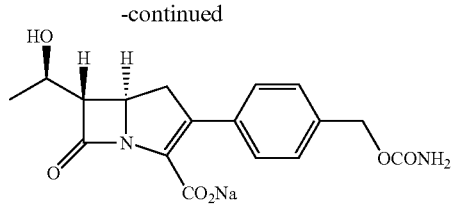

Allyl (5R,6S)-6-{(1R)-1-[(allyloxycarbonyl)oxy]ethyl}-3-(4-{[(aminocarbonyl)oxy]methyl}phenyl)-7-oxo-1-azabicyclo[3.2.0]hept-2-ene-2-carboxylate was prepared in the same manner as example 16 starting from allyl {(2R,3S)-3-((1R)-1-{[(allyloxy)carbonyl]oxy}ethyl)-2-[2-(4-{[(aminocarbonyl)oxy]methyl}phenyl)-2-oxoethyl]-4-oxoazetidin-1-yl}(triphenylphosphoranilidene)acetate prepared by reference example 12, followed by deprotection reaction to give sodium (5R,6S)-3-(4-{[(aminocarbonyl)oxy]methyl}phenyl)-6-[(1R)-1-hydroxyethyl]-7-oxo-1-azabicyclo[3.2.0]hept-2-ene-2-carboxylate.

Allyl (5R,6S)-6-{(1R)-1-[(allyloxycarbonyl)oxy]ethyl}-3-(4-{[(aminocarbonyl)oxy]methyl}phenyl)-7-oxo-1-azabicyclo[3.2.0]hept-2-ene-2-carboxylate.

$^1$H NMR (400 MHz, CD$_3$OD) δ 1.49 (3H, d, J=6.3 Hz), 3.13–3.33 (2H, m), 3.42 (1H, dd, J=2.8 Hz, 8.5 Hz), 4.28 (1H, dt, J=2.8 Hz, 9.4 Hz), 4.55–4.78 (5H, m), 5.11 (2H, s), 5.12–5.42 (5H, m), 5.80–6.00 (2H, m), 7.35 (4H, s).

Sodium (5R,6S)-3-(4-{[(aminocarbonyl)oxy]methyl}phenyl)-6-[(1R)-1-hydroxyethyl]-7-oxo-1-azabicyclo[3.2.0]hept-2-ene-2-carboxylate $^1$H NMR (400 MHz, D$_2$O) δ 1.22 (3H, d, J=6.4 Hz), 2.93–3.05 (1H, m), 3.28–3.40 (1H, m), 3.42 (1H, dd, J=2.8 Hz, 6.0 Hz), 4.10–4.27 (2H, m), 5.00 (2H, s), 7.29 (4H, s).

Example 22

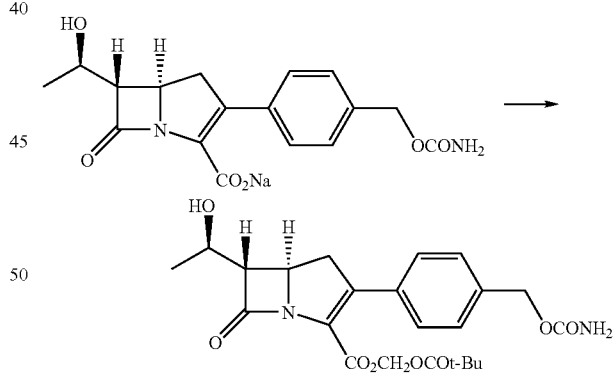

A solution of sodium (5R,6S)-3-(4-{[(aminocarbonyl)oxy]methyl}phenyl)-6-[(1R)-1-hydroxyethyl]-7-oxo-1-azabicyclo[3.2.0]hept-2-ene-2-carboxylate (13 mg) in dry dimethylformamide (0.5 ml) was cooled with ice, and thereto were added N,N-diisopropylethylamine (5 mg), benzyltriethylammonium chloride (5 mg) and pivaloyloxymethyl chloride (11 mg). The mixture was gradually warmed to room temperature and stirred for overnight. To the reaction mixture were added ethyl acetate and ice water to separate by a separating funnel. The organic layer was washed with cold water (three times) and a cold saturated aqueous sodium chloride solution (twice), and dried over anhydrous magnesium sulfate. The solvent was removed under reduced pressure and the residue was purified by silica gel thin-layer chromatography (ethyl acetate) to give [(2,2-dimethylpropanoyl)oxy]methyl (5R,6S)-3-(4-{[(aminocarbonyl)oxy]methyl}phenyl)-6-[(1R)-1-hydroxyethyl]-7-oxo-1-azabicyclo[3.2.0]hept-2-ene-2-carboxylate (9.2 mg).

$^1$H NMR (400 MHz, CDCl$_3$) δ 1.19 (9H, s), 1.37 (3H, d, J=6.3 Hz), 3.15–3.38 (3H, m), 4.20–4.35 (2H, m), 4.73 (2H, broad s), 5.11 (2H, s), 5.74–5.90 (2H, m), 7.35 (4H, s).

Example 23

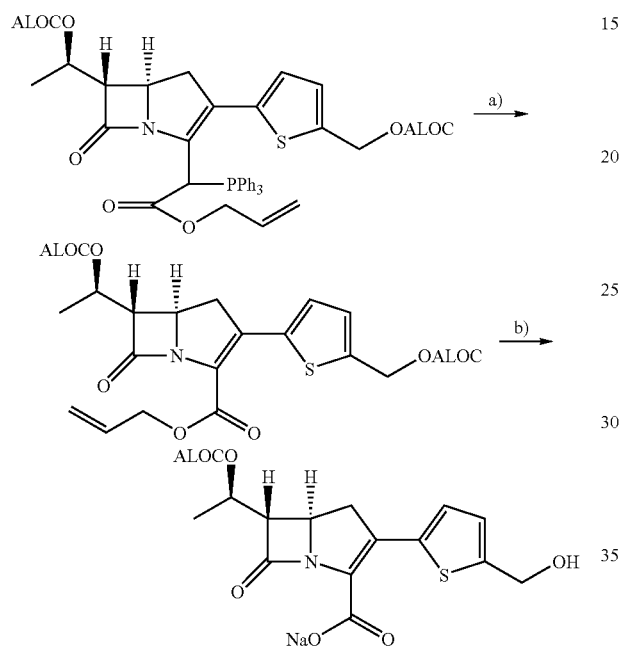

Allyl (5R,6S)-6-((1R)-1-{[(allyloxy)carbonyl]oxy}ethyl)-3-[5-({[(allyloxy)carbonyl]oxy}methyl)thien-2-yl]-7-oxo-1-azabicyclo[3.2.0]hept-2-ene-2-carboxylate was prepared in the same manner as example 16, starting from allyl ((2R,3S)-3-((1R)-1-{[(allyloxy)carbonyl]oxy}ethyl)-2-{2-[5-({[(allyloxy)carbonyl]oxy}methyl)thien-2-yl]-2-oxoethyl}-4-oxoazetidin-1-yl)(triphenylphosphoranilidene)acetate prepared by reference example 14, followed by deprotection reaction to give sodium (5R,6S)-6-[(1R)-1-hydroxyethyl]-3-[5-(hydroxymethyl)thien-2-yl]-7-oxo-1-azabicyclo[3.2.0]hept-2-ene-2-carboxylate.

Allyl (5R,6S)-6-((1R)-1-{[(allyloxy)carbonyl]oxy}ethyl)-3-[5-({[(allyloxy)carbonyl]oxy}methyl)thien-2-yl]-7-oxo-1-azabicyclo[3.2.0]hept-2-ene-2-carboxylate.

$^1$H NMR (400 MHz, CDCl$_3$) δ 1.48 (d, 3H, J=6.3 Hz), 3.28–3.46(m, 3H), 4.22 (td, 1H, J=9.4, 2.8 Hz), 4.63–4.65 (m, 4H), 4.72–4.78 (m, 1H), 4.83–4.89 (m, 1H), 5.14–5.18 (m, 1H), 5.25–5.49 (m, 8H), 5.87–6.03 (m, 3H), 7.09 (d, 1H, J=3.9 Hz), 7.43 (d, 1H, J=3.9 Hz).

Sodium (5R,6S)-6-[(1R)-1-hydroxyethyl]-3-[5-(hydroxymethyl)thien-2-yl]-7-oxo-1-azabicyclo[3.2.0]hept-2-ene-2-carboxylate $^1$H NMR (400 MHz, D$_2$O) δ 1.21 (d, 3H, J=6.4 Hz), 3.17–3.29 (m, 2H), 3.38 (dd, 1H, J=5.9 Hz, 2.7 Hz), 4.13–4.18 (m, 2H), 4.66 (s, 2H), 6.89 (d, 1H, J=3.6 Hz), 7.02 (d, 1H, J=3.6 Hz). IR(ATR) 3267(broad), 2968, 1734, 1593, 1387, 1300, 1254, 1227, 1132, 1007, 802 cm$^{-1}$ Example 24

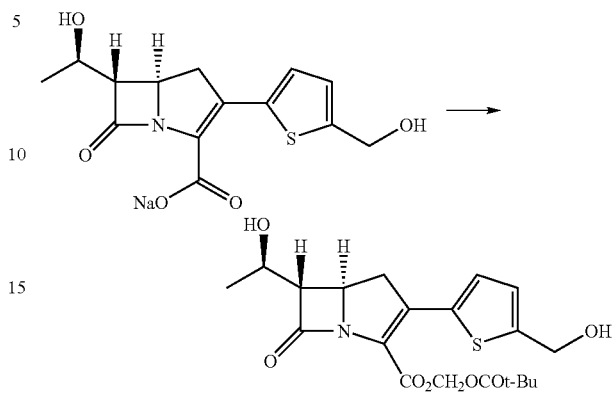

In the same manner as example 3, from sodium (5R,6S)-6-[(1R)-1-hydroxyethyl]-3-[5-(hydroxymethyl)thien-2-yl]-7-oxo-1-azabicyclo[3.2.0]hept-2-ene-2-carboxylate (108 mg), there was obtained [(2,2-dimethylpropanoyl)oxy]methyl (5R,6S)-6-[(1R)-1-hydroxyethyl]-3-[5-(hydroxymethyl)thien-2-yl]-7-oxo-1-azabicyclo[3.2.0]hept-2-ene-2-carboxylate (114 mg).

$^1$H NMR (400 MHz, CDCl$_3$) δ 1.23 (s, 9H), 1.37 (d, 3H, J=6.3 Hz), 1.80 (d, 1H, J=4.7 Hz), 1.92 (t, 1H, J=6.1 Hz), 3.20 (dd, 1H, J=6.8 Hz, 2.8 Hz), 3.31–3.49 (m, 2H), 4.21–4.29 (m, 2H), 4.84 (d, 2H, J=5.9 Hz), 5.91 (d, 1H, J=5.5 Hz), 5.99 (d, 1H, J=5.5 Hz), 7.00 (d, 1H, J=3.9 Hz), 7.47 (d, 1H, J=3.9 Hz). IR(ATR) 3408(broad), 2972, 1751, 1271, 1189, 1093, 1022, 985, 802 cm$^{-1}$ Example 25

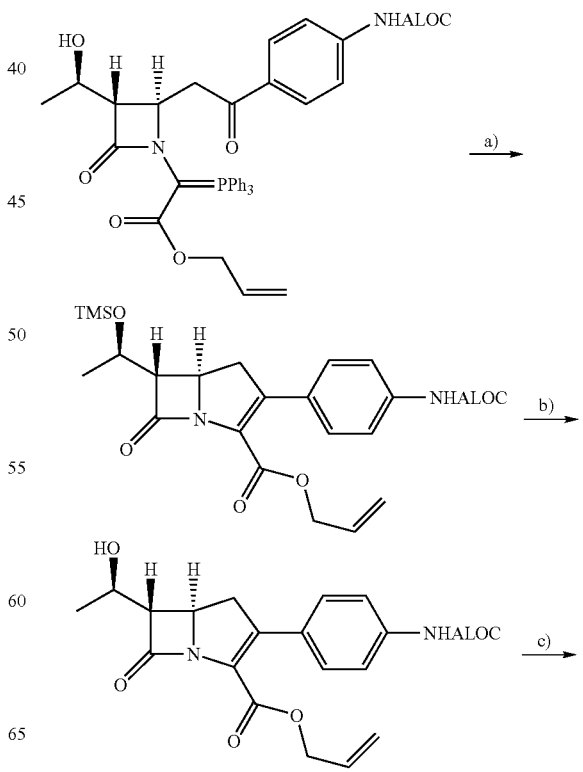

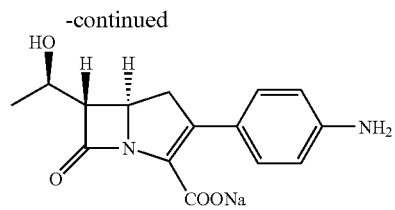

Step a)

In the same manner as step a) and step b) of example 2, from allyl [(2R,3S)-2-[2-(4-{[(allyloxy)carbonyl]amino}phenyl)-2-oxoethyl]-3-[(1R)-1-hydroxyethyl]-4-oxoazetidin-1-yl](triphenylphosphoranilidene)acetate, there was obtained allyl (5R,6S)-3-(4-{[(allyloxy)carbonyl]amino}phenyl)-7-oxo-6-{(1R)-1-[(trimethylsilyl)oxy]ethyl}-1-azabicyclo[3.2.0]hept-2-ene-2-carboxylate.

$^1$H NMR (400 MHz, CDCl$_3$) δ 0.15 (s, 9H), 1.30 (d, 3H, J=6.1 Hz), 3.15–3.30 (m, 3H), 4.17–4.24 (m, 2H), 4.64–4.73 (m, 4H), 5.17–5.40 (m, 4H), 5.86–6.00 (m, 2H), 6.76 (s, 1H), 7.32–7.40 (m, 4H).

Step b), Step c)

Allyl (5R,6S)-3-(4-{[(allyloxy)carbonyl]amino}phenyl)-6-[(1R)-1-hydroxyethyl]-7-oxo-1-azabicyclo[3.2.0]hept-2-ene-2-carboxylate was prepared in the same manner as step b) of example 17 by detrimethylsilyletherification of allyl (5R,6S)-3-(4-{[(allyloxy)carbonyl]amino}phenyl)-7-oxo-6-{(1R)-1-[(trimethylsilyl)oxy]ethyl}-1-azabicyclo[3.2.0]hept-2-ene-2-carboxylate and then, the product was treated in the same manner as step b) of example 16 to give sodium (5R,6S)-3-(4-aminophenyl)-6-[(1R)-1-hydroxyethyl]-7-oxo-1-azabicyclo[3.2.0]hept-2-ene-2-carboxylate.

Allyl (5R,6S)-3-(4-{[(allyloxy)carbonyl]amino}phenyl)-6-[(1R)-1-hydroxyethyl]-7-oxo-1-azabicyclo[3.2.0]hept-2-ene-2-carboxylate.

$^1$H NMR (400 MHz, CDCl$_3$) δ 1.38 (d, 3H, J=6.3 Hz), 3.17–3.30 (m, 3H), 4.22–4.30 (m, 2H), 4.64–4.74 (m, 4H), 5.17–5.40 (m, 4H), 5.84–5.98 (m, 2H), 6.73 (s, 1H), 7.34–7.38 (m, 4H).

Sodium (5R,6S)-3-(4-aminophenyl)-6-[(1R)-1-hydroxyethyl]-7-oxo-1-azabicyclo[3.2.0]hept-2-ene-2-carboxylate $^1$H NMR (400 MHz, D$_2$O) δ 1.40 (d, 3H, J=6.4 Hz), 3.13 (dd, 1H, J=16.9 Hz, 9.7 Hz), 3.48 (dd, 1H, J=16.9 Hz and 8.6 Hz), 3.53–3.58 (m, 1H), 4.30–4.39 (m, 2H), 6.85–6.93 (m, 2H), 7.28–7.33 (m, 2H).

Example 26

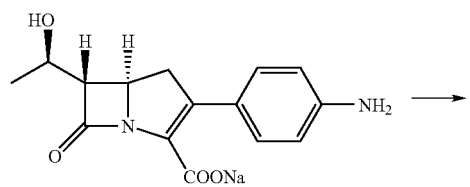

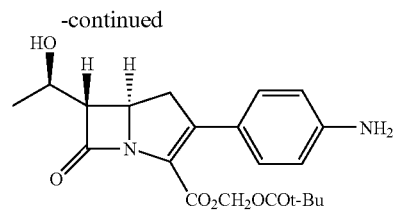

In the same manner as example 3, by using sodium (5R,6S)-3-(4-aminophenyl)-6-[(1R)-1-hydroxyethyl]-7-oxo-1-azabicyclo[3.2.0]hept-2-ene-2-carboxylate, there was obtained [(2,2-dimethylpropanoyl)oxy]methyl (5R,6S)-3-(4-aminophenyl)-6-[(1R)-1-hydroxyethyl]-7-oxo-1-azabicyclo[3.2.0]hept-2-ene-2-carboxylate.

$^1$H NMR (400 MHz, CDCl$_3$) δ 1.21 (s, 9H), 1.36 (d, 3H, J=6.3 Hz), 3.16–3.26 (m, 3H), 3.89 (broads, 2H), 4.18–4.30 (m, 2H), 5.81 (d, 1H, J=5.5 Hz), 5.90 (d, 1H, J=5.5 Hz), 6.62 (d, 2H, J=8.6 Hz), 7.28 (d, 2H, J=8.6 Hz).

Example 27

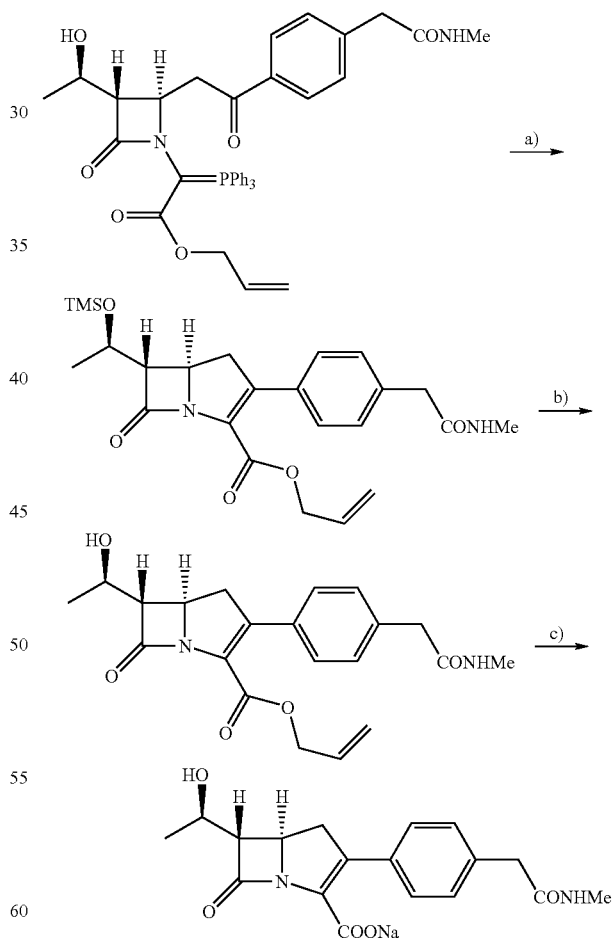

Step a)

In the same manner as step a) and step b) of example 2, from allyl [(2R,3S)-3-[(1R)-1-hydroxyethyl]-2-(2-{4-[2-(methylamino)-2-oxoethyl]phenyl}-2-oxoethyl)-4-oxoazetidin-1-yl](triphenylphosphoranilidene)acetate, there was obtained allyl (5R,6S)-3-{4-[2-(methylamino)-2-oxoethyl]phenyl}-7-oxo-6-{(1R)-1-[(trimethylsilyl)oxy]ethyl}-1-azabicyclo[3.2.0]hept-2-ene-2-carboxylate.

$^{1}$H NMR (400 MHz, CDCl$_3$) δ 0.14 (s, 9H), 1.30 (d, 3H, J=6.2 Hz), 2.76 (d, 3H, J=4.8 Hz), 3.15–3.28 (m, 3H), 3.57 (s, 2H), 4.21–4.26 (m, 2H), 4.64–4.67 (m, 1H), 4.70–4.74 (m, 1H), 5.17–5.22 (m, 1H), 5.28–5.35 (m, 1H), 5.46 (broads, 1H), 5.82–5.90 (m, 1H), 7.26 (d, 2H, J=8.1 Hz), 7.36 (d, 2H, J=8.1 Hz).

Step b), Step c)

Allyl (5R,6S)-6-[(1R)-1-hydroxyethyl]-3-{4-[2-(methylamino)-2-oxoethyl]phenyl}-7-oxo-1-azabicyclo[3.2.0]hept-2-ene-2-carboxylate was prepared in the same manner as step b) of example 17 by detrimethylsilyletherification of allyl (5R,6S)-3-{4-[2-(methylamino)-2-oxoethyl]phenyl}-7-oxo-6-{(1R)-1-[(trimethylsilyl)oxy]ethyl}-1-azabicyclo[3.2.0]hept-2-ene-2-carboxylate and then, the product was treated in the same manner as step d) of example 4 to give sodium (5R,6S)-6-[(1R)-1-hydroxyethyl]-3-{,4-[2-(methylamino)-2-oxoethyl]phenyl}-7-oxo-1-azabicyclo[3.2.0]hept-2-ene-2-carboxylate.

Allyl (5R,6S)-6-[(1R)-1-hydroxyethyl]-3-{4-[2-(methylamino)-2-oxoethyl]phenyl}-7-oxo-1-azabicyclo[3.2.0]hept-2-ene-2-carboxylate $^{1}$H NMR (400 MHz, CDCl$_3$) δ 1.38 (d, 3H, J=6.3 Hz), 2.11 (brs, 1H), 2.77 (d, 3H, J=4.8 Hz), 3.18–3.30 (m, 3H), 3.57 (s, 2H), 4.26–4.32 (m, 2H), 4.64–4.67 (m, 1H), 4.70–4.74 (m, 1H), 5.17–5.22 (m, 1H), 5.26–5.34 (m, 1H), 5.46 (broads, 1H), 5.83–5.93 (m, 1H), 7.24 (d, 2H, J=8.2 Hz), 7.36 (d, 2H, J=8.2 Hz).

Sodium (5R,6S)-6-[(1R)-1-hydroxyethyl]-3-{4-[2-(methylamino)-2-oxoethyl]phenyl}-7-oxo-1-azabicyclo[3.2.0]hept-2-ene-2-carboxylate $^{1}$H NMR (400 MHz, D$_2$O) δ 1.14 (d, 3H, J=6.5 Hz), 2.58 (s, 3H), 2.95 (dd, 1H, J=17.0 Hz, 9.8 Hz), 3.31 (dd, 1H, J=17 Hz, 8.5 Hz), 3.36–3.40 (m, 1H), 3.46 (s, 2H), 4.10–4.22 (m, 2H), 7.13 (d, 2H, J=8.2 Hz), 7.21 (d, 2H, J=8.2 Hz).

Example 28

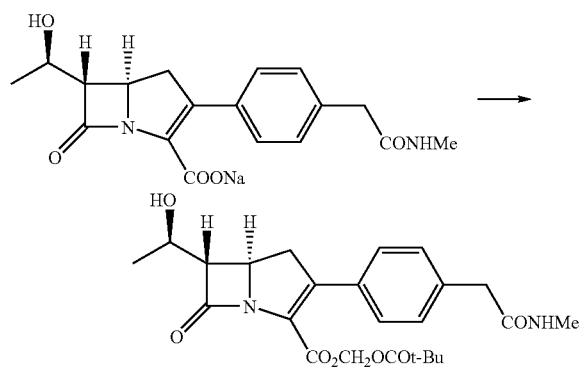

In the same manner as example 3, by using sodium (5R,6S)-6-[(1R)-1-hydroxyethyl]-3-{4-[2-(methylamino)-2-oxoethyl]phenyl}-7-oxo-1-azabicyclo[3.2.0]hept-2-ene-2-carboxylate, there was obtained [(2,2-dimethylpropanoyl)oxy]methyl(5R,6S)-6-[(1R)-1-hydroxyethyl]-3-{4-[2-(methylamino)-2-oxoethyl]phenyl}-7-oxo-1-azabicyclo[3.2.0]hept-2-ene-2-carboxylate.

$^{1}$H NMR (400 MHz, CDCl$_3$) δ 1.18 (s, 9H), 1.38 (d, 3H, J=6.3 Hz), 2.48 (d, 3H, J=4.8 Hz), 3.15–3.35 (m, 3H), 3.60 (s, 2H), 4.24–4.34 (m, 2H), 5.65 (broads, 1H), 5.73 (d, 1H, J=5.5 Hz), 5.82 (d, 1H, J=5.5 Hz), 7.24 (d, 2H, J=8.2 Hz), 7.29 (d, 2H, J=8.2 Hz).

Example 29

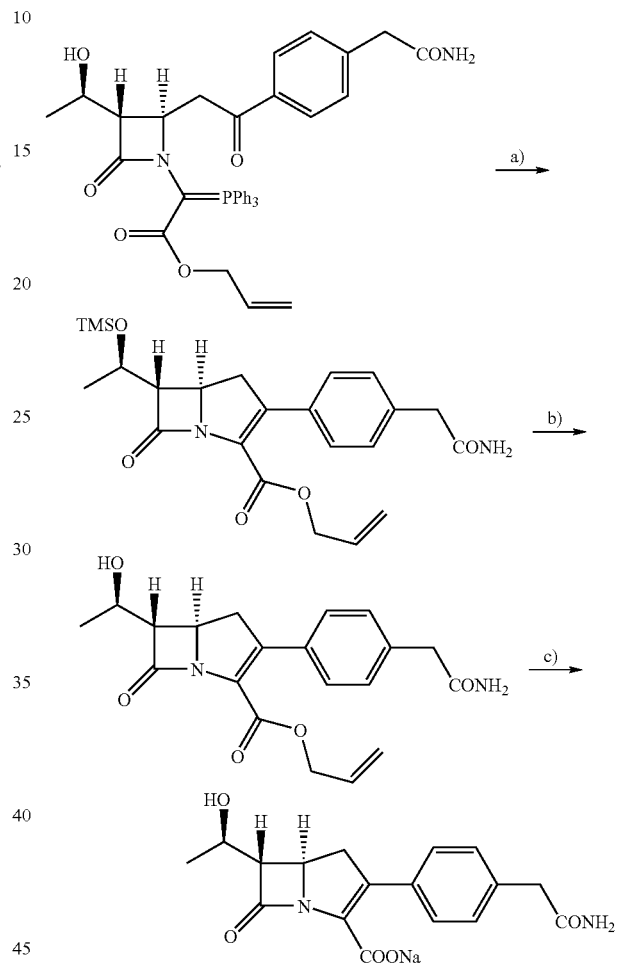

Step a)

In the same manner as step a) and step b) of example 2, from allyl [(2R,3S)-2-{2-[4-(2-amino-2-oxoethyl)phenyl]-2-oxoethyl}-3-[(1R)-1-hydroxyethyl]-4-oxoazetidin-1-yl](triphenylphosphoranilidene) acetate, there was obtained allyl (5R,6S)-3-[4-(2-amino-2-oxoethyl)phenyl]-7-oxo-6-{(1R)-1-[(trimethylsilyl)oxy]ethyl}-1-azabicyclo[3.2.0]hept-2-ene-2-carboxylate.

$^{1}$H NMR (400 MHz, ODCl$_3$) δ 0.15 (s, 9H), 1.30 (d, 3H, J=6.2 Hz), 3.15–3.28 (m, 3H), 3.58 (s, 2H), 4.20–4.25 (m, 2H), 4.63–4.67 (m, 1H), 4.68–4.72 (m, 1H), 5.17–5.22 (m, 1H), 5.27–5.33 (m, 1H), 5.52 (broads, 1H), 5.82–5.90 (m, 1H), 7.25–7.28 (m, 2H), 7.36 (d, 2H, J=8.2 Hz).

Step b), Step c)

Allyl (5R,6S)-3-[4-(2-amino-2-oxoethyl)phenyl]-6-[(1R)-1-hydroxyethyl]-7-oxo-1-azabicyclo[3.2.0]hept-2-ene-2-carboxylate was prepared in the same manner as step b) of example 17 by detrimethylsilyletherification of allyl (5R,6S)-3-[4-(2-amino-2-oxoethyl)phenyl]-7-oxo-6-{(1R)-

[(trimethylsilyl)oxy]ethyl}-1-azabicyclo[3.2.0]hept-2-ene-2-carboxylate and then, the product was treated in the same manner as step d) of example 4 to give sodium (5R,6S)-3-[4-(2-amino-2-oxoethyl)phenyl]-6-[(1R)-1-hydroxyethyl]-7-oxo-1-azabicyclo[3.2.0]hept-2-ene-2-carboxylate.

allyl (5R,6S)-3-[4-(2-amino-2-oxoethyl)phenyl]-6-[(1R)-1-hydroxyethyl]-7-oxo-1-azabicyclo[3.2.0]hept-2-ene-2-carboxylate.

$^1$H NMR (300 MHz, CDCl$_3$) δ 1.38 (d, 3H, J=6.2 Hz), 3.14–3.35 (m, 3H), 3.59 (s, 2H), 4.22–4.35 (m, 2H), 4.60–4.68 (m, 1H), 4.69–4.77 (m, 1H), 5.17–5.22 (m, 1H), 5.25–5.34 (m, 1H), 5.44 (broads, 1H), 5.80–5.94 (m, 1H), 7.25–7.28 (m, 2H), 7.37 (d, 2H, J=8.2 Hz).

Sodium (5R,6S)-3-[4-(2-amino-2-oxoethyl)phenyl]-6-[(1R)-1-hydroxyethyl]-7-oxo-1-azabicyclo[3.2.0]hept-2-ene-2-carboxylate $^1$H NMR (400 MHz, D$_2$O) δ 1.12 (d, 3H, J=6.4 Hz), 2.89 (dd, 1H, J=17.0 Hz, 9.8 Hz), 3.25 (dd, 1H, J=17 Hz, 8.5 Hz), 3.28–3.34 (m, 1H), 3.43 (s, 2H), 4.04–4.16 (m, 2H), 7.09 (d, 2H, J=8.2 Hz), 7.16 (d, 2H, J=8.2 Hz).

Example 30

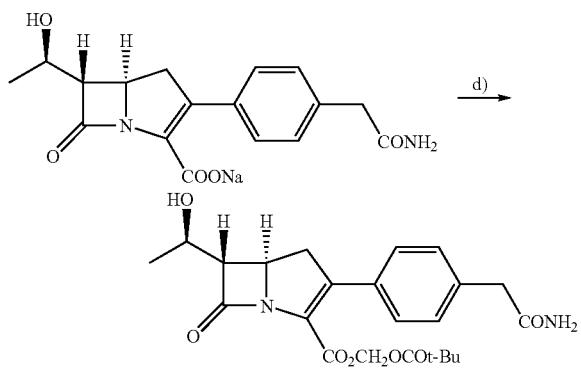

In the same manner as example 3, by using sodium (5R,6S)-3-[4-(2-amino-2-oxoethyl)phenyl]-6-[(1R)-1-hydroxyethyl]-7-oxo-1-azabicyclo[3.2.0]hept-2-ene-2-carboxylate, there was obtained [(2,2-dimethylpropanoyl)oxy]methyl (5R,6S)-3-[4-(2-amino-2-oxoethyl)phenyl]-6-[(1R)-1-hydroxyethyl]-7-oxo-1-azabicyclo[3.2.0]hept-2-ene-2-carboxylate.

$^1$H NMR (400 MHz, CDCl$_3$) δ 1.18 (s, 9H), 1.37 (d, 3H, J=6.3 Hz), 3.16–3.35 (m, 3H), 3.60 (s, 2H), 4.26–4.35 (m, 2H), 5.32 (broads, 1H), 5.41 (broads, 1H), 5.73(d, 1H, J=5.5 Hz), 5.82 (d, 1H, J=5.5 Hz), 7.25–7.34 (m, 4H).

Example 31

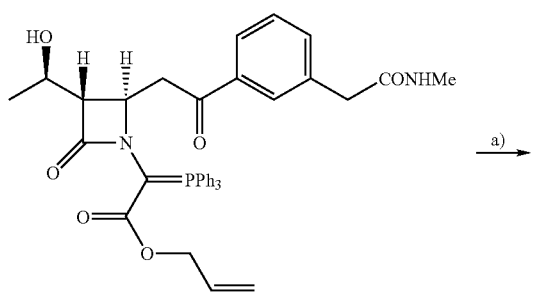

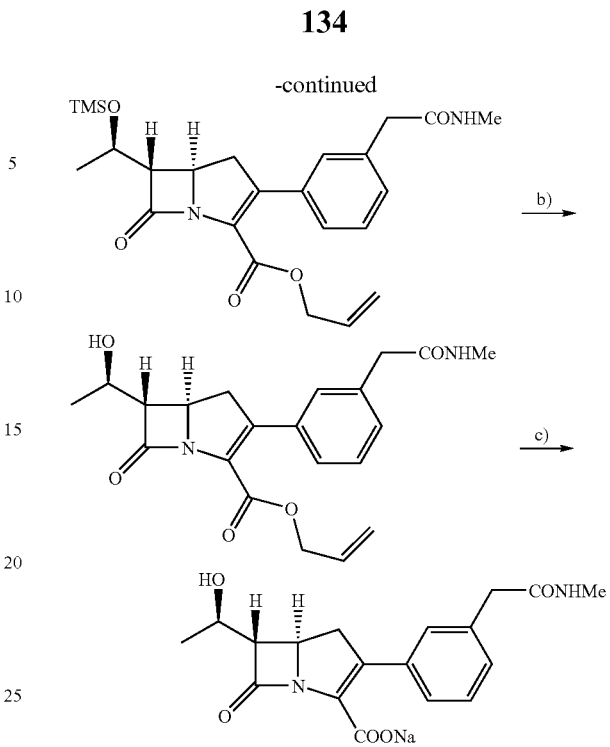

Step a)

In the same manner as step a) and step b) of example 2, by using allyl [(2R,3S)-3-[(1R)-1-hydroxyethyl]-2-(2-{3-[2-(methylamino)-2-oxoethyl]phenyl}-2-oxoethyl)-4-oxoazetidin-1-yl](triphenylphosphoranilidene)acetate, there was obtained allyl (5R,6S)-3-{3-[2-(methylamino)-2-oxoethyl]phenyl}-7-oxo-6-{(1R)-1-[(trimethylsilyl)oxy]ethyl}-1-azabicyclo[3.2.0]hept-2-ene-2-carboxylate.

$^1$H NMR (400 MHz, CDCl$_3$) δ 0.15 (s, 9H), 1.30 (d, 3H, J=6.1 Hz), 2.76 (d, 3H, J=4.8 Hz), 3.18–3.28 (m, 3H), 3.57 (s, 2H), 4.19–4.25 (m, 2H), 4.62–4.67 (m, 1H), 4.67–4.72 (m, 1H), 5.17–5.23 (m, 1H), 5.29–5.36 (m, 1H), 5.72 (broads, 1H), 5.80–5.95 (m, 1H), 7.24–7.30 (m, 3H), 7.32–7.39 (m, 1H).

Step b), Step c)

Allyl (5R,6S)-6-[(1R)-1-hydroxyethyl]-3-{3-[2-(methylamino)-2-oxoethyl]phenyl}-7-oxo-1-azabicyclo[3.2.0]hept-2-ene-2-carboxylate was prepared in the same manner as step b) of example 17 by detrimethylsilyletherification of allyl (5R,6S)-3-{3-[2-(methylamino)-2-oxoethyl]phenyl}-7-oxo-6-{(1R)-1-[(trimethylsilyl)oxy]ethyl}-1-azabicyclo[3.2.0]hept-2-ene-2-carboxylate and then, the product was treated in the same manner as step of d) of example 4 to give sodium (5R,6S)-6-[(1R)-1-hydroxyethyl]-3-{3-[2-(methylamino)-2-oxoethyl]phenyl}-7-oxo-1-azabicyclo[3.2.0]hept-2-ene-2-carboxylate.

Allyl (5R,6S)-6-[(1R)-1-hydroxyethyl]-3-{3-[2-(methylamino)-2-oxoethyl]phenyl}-7-oxo-1-azabicyclo[3.2.0]hept-2-ene-2-carboxylate $^1$H NMR (400 MHz, CDCl$_3$) δ 1.30 (d, 3H, J=6.1 Hz), 2.77 (d, 3H, J=4.8 Hz), 3.22–3.32 (m, 3H), 3.58 (s, 2H), 4.25–4.34 (m, 2H), 4.62–4.67 (m, 1H), 4.67–4.74 (m, 1H), 5.18–5.25 (m, 1H), 5.29–5.36 (m, 1H), 5.72 (broads, 1H), 5.85–5.95 (m, 1H), 7.20–7.30 (m, 3H), 7.32–7.39 (m, 1H).

Sodium (5R,6S)-6-[(1R)-1-hydroxyethyl]-3-{3-[2-(methylamino)-2-oxoethyl]phenyl}-7-oxo-1-azabicyclo[3.2.0]hept-2-ene-2-carboxylate $^1$H NMR (400 MHz, D$_2$O) δ 1.18 (d, 3H, J=6.4 Hz), 2.93 (s, 3H), 2.92–3.01 (m, 1H), 3.28–3.36 (m, 1H), 3.38–3.42

(m, 1H), 3.47 (s, 2H), 4.12–4.24 (m, 2H), 7.08–7.15 (m, 2H), 7.16–7.20 (m, 1H), 7.22–7.28 (m, 1H).

Example 32

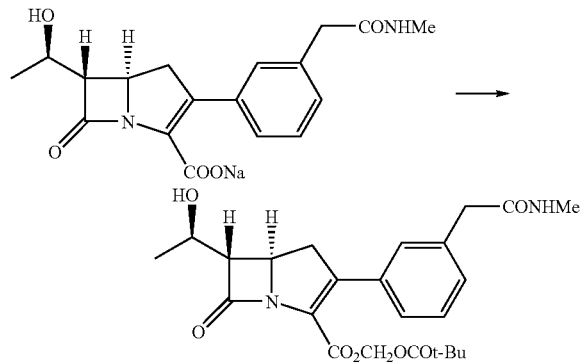

In the same manner as example 3, by using sodium (5R,6S)-6-[(1R)-1-hydroxyethyl]-3-{3-[2-(methylamino)-2-oxoethyl]phenyl}-7-oxo-1-azabicyclo[3.2.0]hept-2-ene-2-carboxylate, there was obtained [(2,2-dimethylpropanoyl)oxy]methyl (5R,6S)-6-[(1R)-1-hydroxyethyl]-3-{3-[2-(methylamino)-2-oxoethyl]phenyl}-7-oxo-1-azabicyclo[3.2.0]hept-2-ene-2-carboxylate.

$^1$H NMR (400 MHz, CDCl$_3$) δ 1.18 (s, 9H), 1.38 (d, 3H, J=6.3 Hz), 2.78 (d, 3H, J=4.8 Hz), 3.21–3.57 (m, 3H), 3.59 (s, 2H), 4.25–4.34 (m, 2H), 5.77 (d, 1H, J=5.5 Hz), 5.81 (broads, 1H), 5.84 (d, 1H, J=5.5 Hz), 7.15–7.27 (m, 3H), 7.30–7.37 (m, 1H).

Example 33

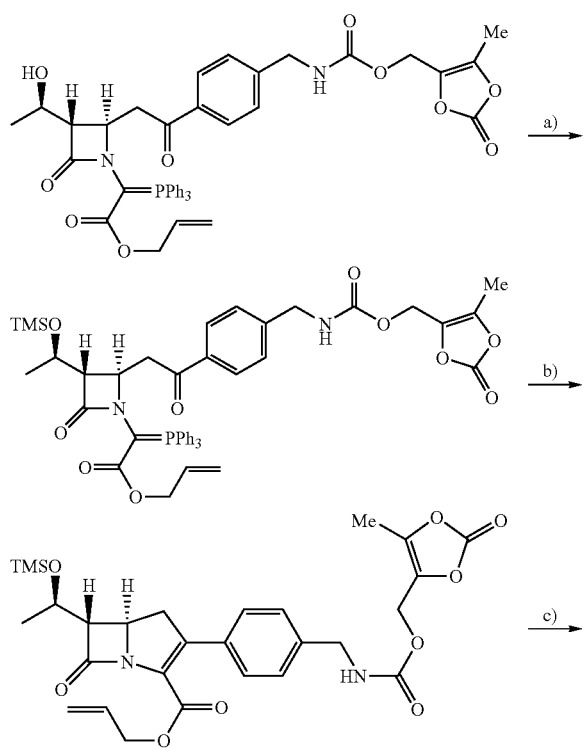

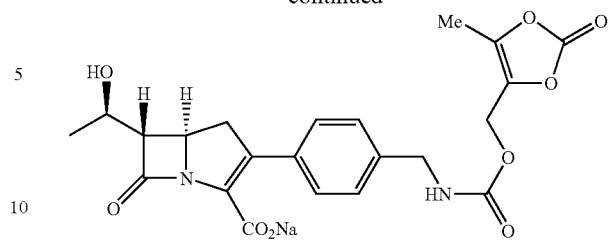

Step a)

In the same manner as step a) of example 2, by using allyl [(2R,3S)-3-[(1R)-1-hydroxyethyl]-2-(2-{4-[({[(5-methyl-2-oxo-1,3-dioxo-4-yl)methoxy]carbonyl}amino)methyl]phenyl}-2-oxoethyl)-4-oxoazetidin-1-yl](triphenylphosphoranilidene)acetate (0.52 g) prepared by reference example 26, there was obtained allyl [(2R,3S)-3-[(1R)-1-({trimethylsilyl}oxy)ethyl]-2-(2-{4-[({[(5-methyl-2-oxo-1,3-dioxo-4-yl)methoxy]carbonyl}amino)methyl]phenyl}-2-oxoethyl)-4-oxoazetidin-1-yl](triphenylphosphoranilidene)acetate. This product was used in the next step without further purification.

Step b)

In the same manner as step b) of example 2, by using a compound prepared in the above step, there was obtained allyl (5R,6S)-3-{4-[({[(5-methyl-2-oxo-1,3-dioxo-4-yl)methoxy]carbonyl}amino)methyl]phenyl}-7-oxo-6-{(1R)-1-[(trimethylsilyl)oxy]ethyl}-1-azabicyclo[3.2.0]hept-2-ene-2-carboxylate (0.21 g).

$^1$H NMR (400 MHz, CDCl$_3$) δ 1.30 (d, 3H, J=6.2 Hz), 2.19 (s, 3H), 3.16 (dd, 1H, J=9.9 Hz, 18.1 Hz), 3.22 (dd, 1H, J=2.8 Hz, 6.9 Hz), 3.28 (dd, 1H, J=8.9 Hz, 18.1 Hz), 4.19–4.25 (m, 2H), 4.36 (d, 2H, J=6.0 Hz), 4.60–4.65 (m, 1H), 4.69–4.74 (m, 1H), 4.84 (s, 2H), 5.17–5.21 (m, 1H), 5.28–5.33 (m, 1H), 5.30 (broad s, 1H), 5.82–5.92 (m, 1H), 7.25–7.27 (m, 2H), 7.33–7.36 (m, 2H).

Step c)

In the same manner as step b) of example 17, by using the compound (0.05 g) prepared in the above step b), there was obtained crude sodium (5R,6S)-6-[(1R)-1-hydroxyethyl]-3-{4-[({[(5-methyl-2-oxo-1,3-dioxo-4-yl)methoxy]carbonyl}amino)methyl]phenyl}-7-oxo-1-azabicyclo[3.2.0]hept-2-ene-2-carboxylate (0.01 g), and the crude product was purified by polymer chromatography (CHP-20P) and fractions eluted with THF 2~8% were collected and subjected to freeze-drying to give the object compound (0.01 g).

LC/MS (EI) 459 (M+1)+. $^1$H NMR (400 MHz, DMSO-d6) δ 1.09 (d, 3H, J=6.2 Hz), 2.08 (s, 3H), 2.78 (dd, 1H, J=10.0 Hz, 15.6 Hz), 3.00 (dd, 1H, J=8.6 and 15.6 Hz), 3.06 (dd, 1H, J=2.7 Hz, 6.5 Hz), 3.81–3.83 (m, 1H), 3.85–3.88 (m, 1H), 4.07 (d, 2H, J=5.9 Hz), 4.82 (s, 2H), 4.92 (br, 1H), 7.01–7.03 (m, 2H), 7.32–7.34 (m, 2H), 7.84 (t, 1H, J=5.9 Hz). IR (ATR) 3348 (broad), 1817, 1736, 1718, 1591, 1518, 1394, 1308, 1252, 1227, 1196, 1132, 1038, 1011, 984, 769 cm$^{-1}$.

Example 34

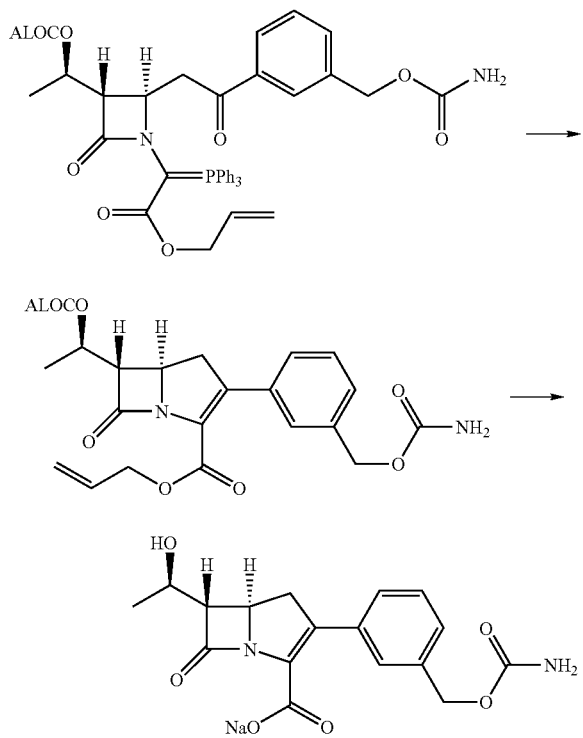

Allyl (5R,6S)-6-((1R)-1-{[(allyloxy)carbonyl]oxy}ethyl)-3-(3-{[(aminocarbonyl)oxy]methyl}phenyl)-7-oxo-1-azabicyclo[3.2.0]hept-2-ene-2-carboxylate was prepared in the same manner as example 16 starting from allyl {(2R,3S)-3-((1R)-1-{[(allyloxy)carbonyl]oxy}ethyl)-2-[2-(3-{[(aminocarbonyl)oxy]methyl}phenyl)-2-oxoethyl]-4-oxoazetidin-1-yl}(triphenylphosphoranilidene)acetate prepared by reference example 27 and then, the product was subjected to deprotection reaction to give sodium (5R,6S)-3-(3-{[(aminocarbonyl)oxy]methyl}phenyl)-6-[(1R)-1-hydroxyethyl]-7-oxo-1-azabicyclo[3.2.0]hept-2-ene-2-carboxylate.

Allyl (5R,6S)-6-((1R)-1-{[(allyloxy)carbonyl]oxy}ethyl)-3-(3-{{[(aminocarbonyl)oxy]methyl}phenyl)-7-oxo-1-azabicyclo[3.2.0]hept-2-ene-2-carboxylate $^1$H NMR (400 MHz, CDCl$_3$) δ 1.49 (d, 3H, J=6.3 Hz), 3.17–3.33 (m, 2H), 3.42 (dd, 1H, J=8.4, 2.8 Hz), 4.26–4.31 (m, 1H), 4.59–4.73 (m, 6H), 5.09 (s, 2H), 5.15–5.40 (m, 5H), 5.80–5.98 (m, 2H), 7.30–7.37 (m, 4H). IR(ATR) 3178 (broad), 2981(broad), 1778, 1720, 1331, 1257, 1180, 748, 721 cm$^{-1}$. LC/MS (EI) 471 (M+1)+.

Sodium (5R,6S)-3-(3-{f[(aminocarbonyl)oxy]methyl}phenyl)-6-[(1R)-1-hydroxyethyl]-7-oxo-1-azabicyclo[3.2.0]hept-2-ene-2-carboxylate $^1$H NMR (400 MHz, D$_2$O) δ 1.23 (d, 3H, J=6.4 Hz), 3.00 (dd, 1H, J=17.0, 9.8 Hz), 3.36 (dd, 1H, J=17.0, 8.5 Hz), 3.44 (dd, 1H, J=6.0, 2.8 Hz), 4.16–4.26 (m, 2H), 4.72 (s, 2H), 7.23–7.33 (m, 4H). IR(ATR) 3336(broad), 2966, 1709, 1589, 1392, 1335, 1049, 787, 698 cm$^{-1}$.

Example 35

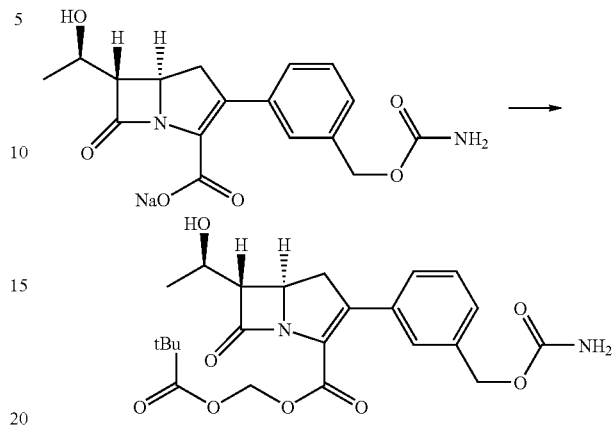

In the same manner as example 3, from sodium (5R,6S)-3-(3-{[(aminocarbonyl)oxy]methyl}phenyl)-6-[(1R)-1-hydroxyethyl]-7-oxo-1-azabicyclo[3.2.0]hept-2-ene-2-carboxylate prepared by example 34, there was obtained [(2,2-dimethylpropanoyl)oxy]methyl (5R,6S)-3-(3-{[(aminocarbonyl)oxy]methyl}phenyl)-6-[(1R)-1-hydroxyethyl]-7-oxo-1-azabicyclo[3.2.0]hept-2-ene-2-carboxylate $^1$H NMR (400 MHz, CDCl$_3$) δ 1.17 (s, 9H), 1.36 (d, 3H, J=6.3 Hz), 1.97 (br-s, 1H), 3.19–3.36 (m, 3H), 4.25–4.33 (m, 2H), 4.74 (br-s, 2H), 5.10 (s, 2H), 5.77 (d, 1H, J=5.5 Hz), 5.84 (d, 1H, J=5.5 Hz), 7.28–7.37 (m, 4H). IR(ATR) 3460 (broad), 3367(broad), 2974, 1713, 1331, 1265, 1122, 1095, 1049, 1022, 980, 787, 698 cm$^{-1}$. LC/MS (EI) 461 (M+1)+.

Example 36

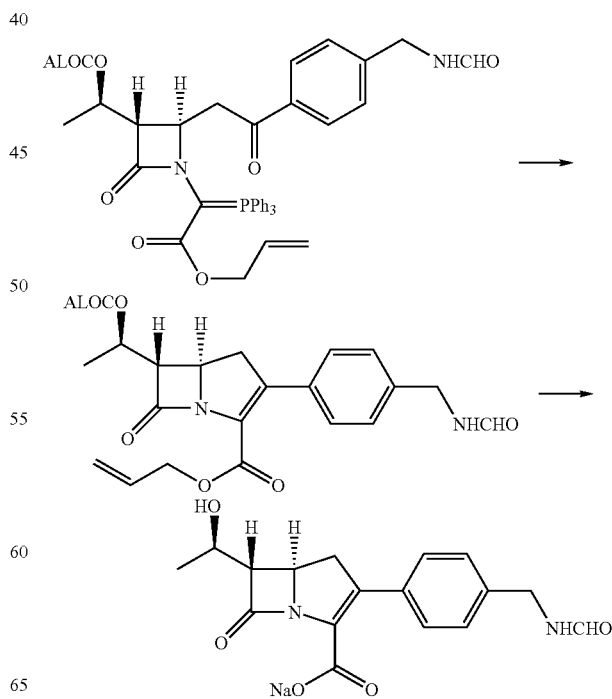

Allyl (5R,6S)-6-((1R)-1-{[(allyloxy)carbonyl]oxy}ethyl)-3-{4-[(formylamino) methyl]phenyl}-7-oxo-1-azabicyclo[3.2.0]hept-2-ene-2-carboxylate was prepared in the same manner as example 16 starting from allyl [(2R,3S)-3-((1R)-1-{[(allyloxy)carbonyl]oxy}ethyl)-2-(2-{4-[(formylamino)methyl]phenyl}-2-oxoethyl)-4-oxoazetidin-1-yl](triphenylphosphoranilidene)acetate prepared by reference example 28 and then, the product was subjected to deprotection reaction to give sodium (5R,6S)-3-{4-[(formylamino)methyl]phenyl}-6-[(1R)-1-hydroxyethyl]-7-oxo-1-azabicyclo[3.2.0]hept-2-ene-2-carboxylate.

Allyl (5R,6S)-6-((1R)-1-{[(allyloxy)carbonyl]oxy}ethyl)-3-{4-[(formylamino)methyl]phenyl}-7-oxo-1-azabicyclo[3.2.0]hept-2-ene-2-carboxylate $^1$H NMR (400 MHz, CDCl$_3$) δ 1.42 (d, 3H, J=6.3 Hz), 3.21–3.29 (m, 1H), 3.56 (dd, 1H, J=18.1, 8.6 Hz), 3.71 (dd, 1H, J=6.5, 3.0 Hz), 4.33–4.38 (m, 1H), 4.44 (d, 2H, J=6.3 Hz), 4.57–4.70 (m, 4H), 5.11–5.18 (m, 2H), 5.23–5.39 (m, 3H), 5.83–6.02 (m, 2H), 7.29–7.31 (m, 2H), 7.39–7.41 (m, 2H), 7.62 (br-s, 1H), 8.26 (d, 1H, J=0.5 Hz). IR(ATR) 3375(broad), 2939, 1774, 1743, 1720, 1670, 1373, 1335, 1254, 1192, 1138, 1107, 945, 752 cm$^{-1}$. LC/MS (EI) 455 (M+1)+.

Sodium (5R,6S)-3-{4-[(formylamino)methyl]phenyl}-6-[(1R)-1-hydroxyethyl]-7-oxo-1-azabicyclo[3.2.0]hept-2-ene-2-carboxylate $^1$H NMR (400 MHz, D$_2$O) δ 1.22 (d, 3H, J=6.4 Hz), 2.99 (dd, 1H, J=16.9, 7.8 Hz), 3.35 (dd, 1H, J=17.0, 8.5 Hz), 3.42 (dd, 1H, J=6.0, 2.8 Hz), 4.16–4.35 (m, 2H), 4.72 (s, 1.76H), 4.77 (s, 0.24H), 7.21 (d, 2H, J=8.4 Hz), 7.26–7.28 (m, 2H), 8.06 (s, 0.12H), 8.08 (s, 0.88H). IR(ATR) 3248(broad), 2974, 1743, 1659, 1585, 1385, 1308, 1242, 1223, 1130, 671 cm$^{-1}$.

Example 37

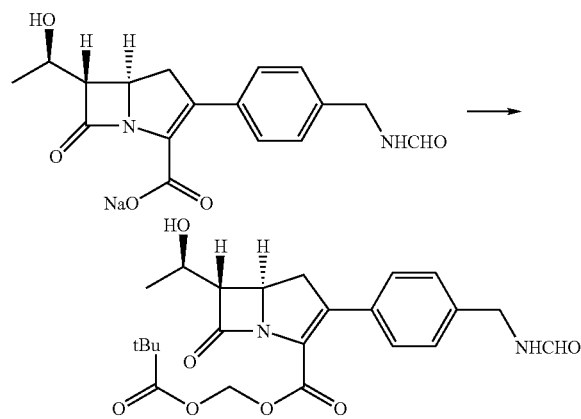

In the same manner as example 3, from sodium (5R,6S)-3-{4-[(formylamino)methyl]phenyl}-6-[(1R)-1-hydroxyethyl]-7-oxo-1-azabicyclo[3.2.0]hept-2-ene-2-carboxylate prepared by example 36, there was obtained [(2,2-dimethylpropanoyl)oxy]methyl (5R,6S)-3-{4-[(formylamino)methyl]phenyl}-6-[(1R)-1-hydroxyethyl]-7-oxo-1-azabicyclo[3.2.0]hept-2-ene-2-carboxylate.

$^1$H NMR (400 MHz, CDCl$_3$) δ 1.18 (s, 9H), 1.37 (d, 3H, J=5.6 Hz), 1.88 (br-s, 1H), 3.17–3.34 (m, 3H), 4.24–4.33 (m, 2H), 4.44 (d, 0.3H, J=6.6 Hz), 4.50 (d, 1.7H, J=5.8 Hz), 5.74–5.77 (m, 1H), 5.83–5.86 (m, 1H), 5.95 (br-s, 1H), 7.29–7.36 (m, 4H), 8.19–8.28 (m, 1H). IR(ATR) 3367 (broad), 2974, 2935, 2873, 1774, 1747, 1662, 1269, 1122, 1095, 1022, 991, 980 cm$^{-1}$. LC/MS (EI) 445 (M+1)+.

Example 38

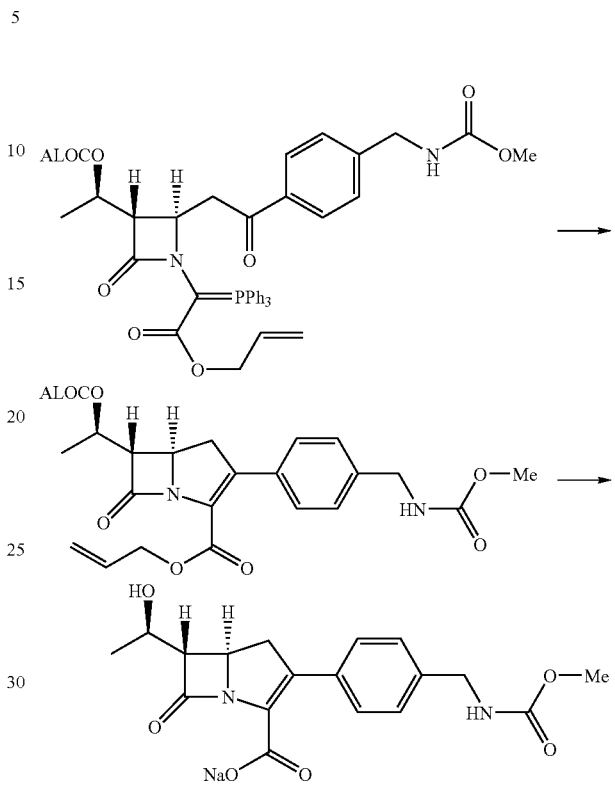

Allyl (5R,6S)-6-((1R)-1-{[(allyloxy)carbonyl]oxy}ethyl)-3-(4-{[(methoxycarbonyl)amino]methyl}phenyl)-7-oxo-1-azabicyclo[3.2.0]hept-2-ene-2-carboxylate was prepared in the same manner as example 16 from allyl {(2R,3S)-3-((1R)-1-{[(allyloxy)carbonyl]oxy}ethyl)-2-[2-(4-{[(methoxycarbonyl)amino]methyl}phenyl)-2-oxoethyl]-4-oxoazetidin-1-yl}(triphenylphosphoranilidene)acetate prepared by reference example 29 and then, the product was subjected to deprotection reaction to give sodium (5R,6S)-6-[(1R)-1-hydroxyethyl]-3-(4-{[(methoxycarbonyl)amino]methyl}phenyl)-7-oxo-1-azabicyclo[3.2.0]hept-2-ene-2-carboxylate.

Allyl (5R,6S)-6-((1R)-1-{[(allyloxy)carbonyl]oxy}ethyl)-3-(4-{[(methoxycarbonyl)amino]methyl}phenyl)-7-oxo-1-azabicyclo[3.2.0]hept-2-ene-2-carboxylate $^1$H NMR (400 MHz, CDCl$_3$) δ 1.48 (d, 3H, J=6.3 Hz), 3.15–3.30 (m, 2H), 3.40–3.42 (m, 1H), 3.71 (s, 3H), 4.25–4.30 (m, 1H), 4.37 (d, 2H, J=6.0 Hz), 4.60–4.66 (m, 3H), 4.69–4.75 (m, 1H), 5.02 (br-s, 1H), 5.13–5.22 (m, 2H), 5.26–5.28 (m, 1H), 5.30–5.31 (m, 1H), 5.34–5.40 (m, 1H), 5.82–5.99 (m, 2H), 7.27 (d, 2H, J=8.3 Hz), 7.33 (d, 2H, J=8.3 Hz). IR(ATR) 3251(broad), 2947, 1778, 1743, 1716, 1254, 748, 721 cm$^{-1}$. LC/MS (EI) 485 (M+1)+.

Sodium (5R,6S)-6-[(1R)-1-hydroxyethyl]-3-(4-{[(methoxycarbonyl)amino]methyl}phenyl)-7-oxo-1-azabicyclo[3.2.0]hept-2-ene-2-carboxylate $^1$H NMR (400 MHz, D$_2$O) δ 1.22 (d, 3H, J=6.4 Hz), 2.96–3.03 (m, 1H), 3.32–3.38 (m, 1H), 3.41–3.43 (m, 1H), 3.58 (s, 3H), 4.14–4.24 (m, 4H), 7.20 (d, 2H, J=8.4 Hz), 7.25–7.27 (m, 2H). IR(ATR) 3302(broad), 2966, 1747, 1693, 1589, 1551, 1389, 1261 cm$^{-1}$.

Example 39

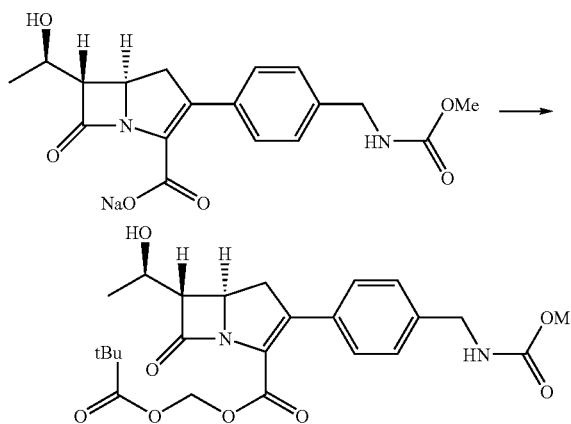

In the same manner as example 3, from sodium (5R,6S)-6-[(1R)-1-hydroxyethyl]-3-(4-{[(methoxycarbonyl)amino]methyl}phenyl)-7-oxo-1-azabicyclo[3.2.0]hept-2-ene-2-carboxylate prepared by example 38, there was obtained [(2,2-dimethylpropanoyl)oxy]methyl (5R,6S)-6-[(1R)-1-hydroxyethyl]-3-(4-{[(methoxycarbonyl)amino]methyl}phenyl)-7-oxo-1-azabicyclo[3.2.0]hept-2-ene-2-carboxylate.

$^1$H NMR (400 MHz, CDCl$_3$) δ 1.18 (s, 9H), 1.37 (d, 3H, J=6.3 Hz), 1.85 (br-s, 1H), 3.16–3.34 (m, 3H), 3.71 (s, 3H), 4.25–4.32 (m, 2H), 4.38 (d, 2H, J=5.9 Hz), 5.06 (br-s, 1H), 5.76 (d, 1H, J=5.5 Hz), 5.85 (d, 1H, J=5.5 Hz), 7.26–7.33 (m, 4H). IR(ATR) 3390(broad), 2974, 1701, 1527, 1261, 1192, 1122, 1095, 1022, 991, 980, 775 cm$^{-1}$. LC/MS (EI) 475 (M+1)+.

Example 40

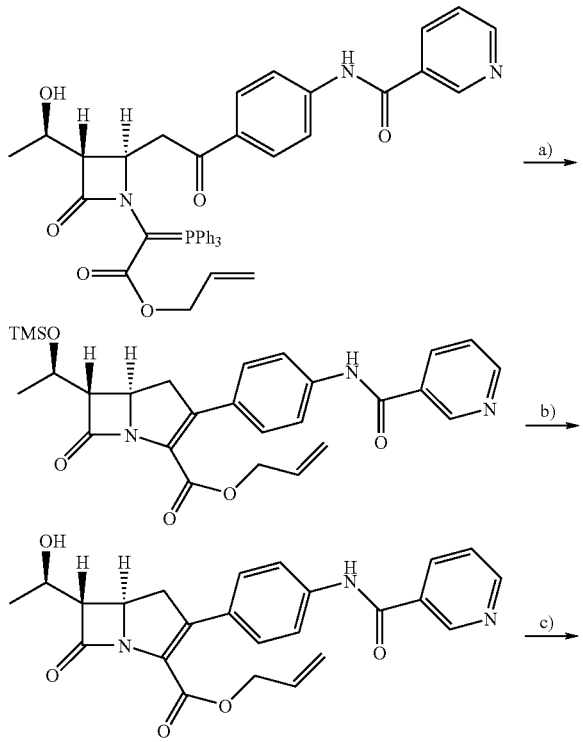

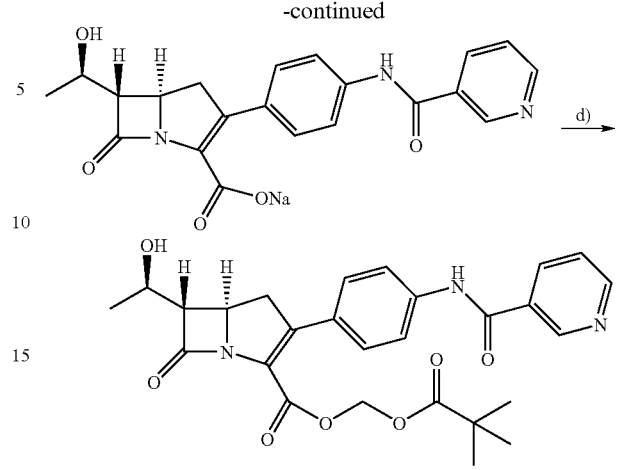

Step a)

In the same manner as step b) of example 2, from allyl [(3S,4R)-3-[(1R)-1-hydroxyethyl]-2-oxo-4-(2-oxo-2-{4-[(pyridin-3-ylcarbonyl)amino]phenyl}ethyl)azetidin-1-yl](triphenylphosphoranilidene)acetate (3.32 g) prepared by reference example 32, there was obtained allyl ((3S,4R)-2-oxo-4-(2-oxo-2-{4-[(pyridin-3-ylcarbonyl)amino]phenyl}ethyl)-3-{(1R)-1-[(trimethylsilyl)oxy]ethyl}azetidin-1-yl)(triphenylphosphoranilidene)acetate (2.80 g). The product without purification was treated in the same manner as step b) of example 2 to give allyl (5R,6S)-7-oxo-3-{4-[(pyridin-3-ylcarbonyl)amino]phenyl}-6-{(1R)-1-[(-[(trimethylsilyl)oxy]ethyl)-1-azabicyclo[3.2.0]hept-2-ene-2-carboxylate (2.86 g).

$^1$H NMR (400 MHz, CDCl$_3$) δ 0.15 (s, 9H), 1.30 (d, 3H, J=6.0 Hz), 3.15–3.28 (m, 3H), 4.19–4.23 (m, 2H), 4.65–4.73 (m, 2H), 5.19–5.35 (m, 2H), 5.85–5.95 (m, 1H), 7.50–7.56 (m, 2H), 8.18(s, 1H), 8.22(d, 1H, J=8.0 Hz), 9.10 (s, 1H).

Step b)

In the same manner as step b) of example 17, from the compound (1.43 g) prepared in the above step, there was obtained allyl (5R,6S)-6-[(1R)-1-hydroxyethyl]-7-oxo-3-{4-[(pyridin-3-ylcarbonyl)amino]phenyl}-1-azabicyclo[3.2.0]hept-2-ene-2-carboxylate (0.49 g).

$^1$H NMR (400 MHz, CDCl$_3$) δ 1.38 (d, 3H, J=6.0 Hz), 3.24–3.30 (m, 3H), 4.26–4.31 (m, 2H), 4.66–4.74 (m, 2H), 5.20–5.35 (m, 2H), 5.86–6.00 (m, 1H), 7.44 (d, 2H, J=8.4 Hz), 7.67 (d, 2H, J=8.4 Hz), 7.99 (s, 1H), 8.25 (d, 1H, J=7.6 Hz), 8.80 (d, 1H, J=6.4 Hz), 9.14 (s, 1H).

Step c)

In the same manner as step b) of example 17, from the compound (0.49 g) prepared in the above step, there was obtained sodium (5R,6S)-6-[(1R)-1-hydroxyethyl]-7-oxo-3-{4-[(pyridin-3-ylcarbonyl)amino]phenyl}-1-azabicyclo[3.2.0]hept-2-ene-2-carboxylate (0.28 g).

$^1$H NMR (400 MHz, D$_2$O) δ1.12 (d, 3H, J=6.4 Hz), 2.92 (dd, 1H, J=16.8 Hz, 9.8 Hz), 3.26 (dd, 1H, J=16.8 Hz, 8.4 Hz), 3.31–3.33 (m, 1H), 4.05–4.14 (m, 2H), 7.23 (d, 2H, J=8.4 Hz), 7.35 (d, 2H, J=8.4 Hz), 7.40–7.43 (m, 1H), 8.10 (d, 1H, J=8.0 Hz), 8.53(d, 1H, J=2.0 Hz), 8.79 (d, 1H, J=8.0 Hz).

Step d)

In the same manner as example 3, from the compound (0.22 g) prepared in the above step, there was obtained

[(2,2-dimethylpropanoyl)oxymethyl (5R,6S)-6-[(1R)-1-hydroxyethyl]-7-oxo-3-{4-[(pyridin-3-ylcarbonyl)amino]phenyl}-1-azabicyclo[3.2.0]hept-2-ene-2-carboxylate (0.17 g).

¹H NMR (400 MHz, CDCl₃) δ 1.19 (s, 9H), 1.37 (d, 3H, J=6.0 Hz), 3.20–3.37 (m, 3H), 4.25–4.33 (m, 2H), 5.78 (d, 1H, J=5.6 Hz), 5.87 (d, 1H, J=5.6 Hz), 7.42 (d, 2H, J=8.8 Hz), 7.47–7.51 (m, 1H), 7.67 (d, 2H, J=8.8 Hz), 8.80 (s, 1H), 8.24 (d, 1H, J=6.8 Hz), 8.79 (d, 1H, J=3.6 Hz), 9.13 (s, 1H).

Example 41

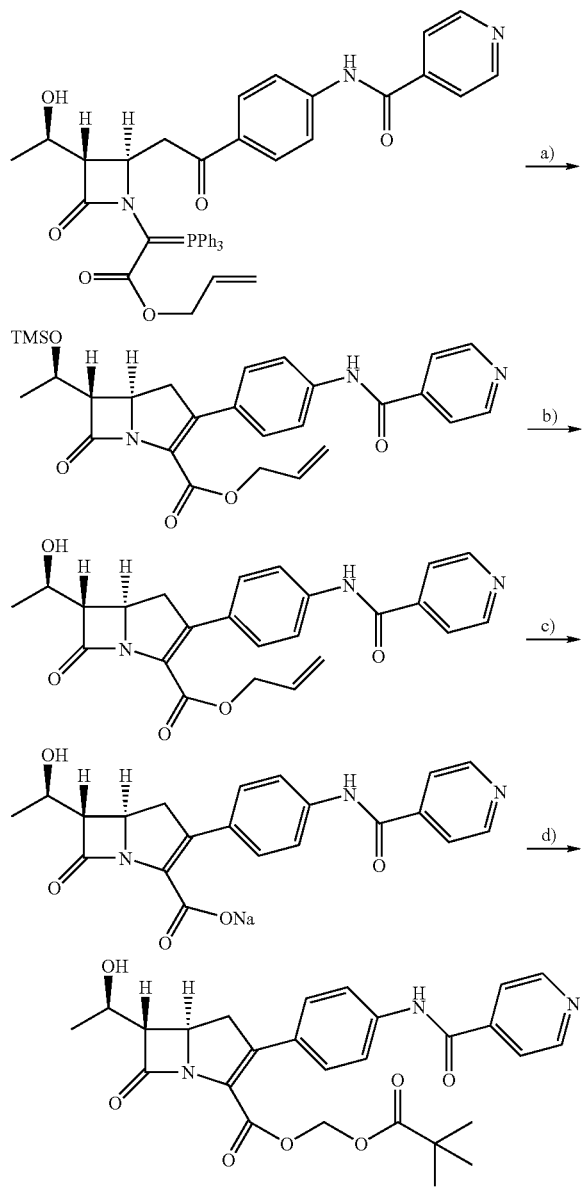

Step a)

In the same manner as step b) of example 2, from allyl ((2R,3S)-3-[(1R)-1-hydroxyethyl]-2-{2-[4-(isonicotinoylamino)phenyl]-2-oxoethyl}-4-oxoazetidin-1-yl)(triphenylphosphoranilidene)acetate (2.15 g) prepared by reference example 33, there was obtained allyl ((3S,4R)-2-oxo-4-(2-oxo-2-{4-(isonicotinoylmino)phenyl}ethyl)-3-{(1R)-1-[(trimethylsilyl)oxy]ethyl}azetidin-1-yl)(triphenylphosphoranilidene)acetate (2.16 g). The product without purification was treated in the same manner as step b) of example 2 to give allyl (5R,6S)-3-[4-(isonicotinoylamino)phenyl]-7-oxo-6-{(1R)-1-[(trimethylsilyl)oxy]ethyl}-1-azabicyclo[3.2.0]hept-2-ene-2-carboxylate (2.35 g).

¹H NMR (400 MHz, CDCl₃) δ 0.15 (s, 9H), 1.30 (d, 3H, J=6.0 Hz), 3.15–3.30 (m, 3H), 4.17–4.25 (m, 2H), 5.19–5.35 (m, 2H), 5.83–5.95 (m, 1H), 7.13–7.15 (m, 2H), 7.75–7.77 (m, 2H), 7.99–8.01 (m, 2H), 8.18 (s, 1H), 8.78–8.80 (m, 2H).

Step b)

In the same manner as step b) of example 17, from the compound (1.18 g) prepared in the above step, there was obtained allyl (5R,6S)-6-[(1R)-1-hydroxyethyl]-3-[4-(isonicotinoylamino)phenyl]-7-oxo-1-azabicyclo[3.2.0]hept-2-ene-2-carboxylate (0.25 g).

¹H NMR (400 MHz, CDCl₃) δ 1.38 (d, 3H, J=6.4 Hz), 3.20–3.12 (m, 3H), 4.20–4.33 (m, 2H), 4.61–4.80 (m, 2H), 5.20–5.35 (m, 2H), 5.85–5.93 (m, 1H), 7.45 (d, 2H, J=8.8 Hz), 7.65 (d, 2H, J=8.8 Hz), 7.72–7.73 (d, 2H, J=8.8 Hz), 7.90 (s, 1H), 8.89–8.90 (m, 2H).

Step c)

In the same manner as step b) of example 17, from the compound (0.25 g) prepared in the above step, there was obtained sodium (5R,6S)-6-[(1R)-1-hydroxyethyl]-7-oxo-3-[4-(isonicotinoylamino)phenyl]-7-oxo-1-azabicyclo[3.2.0]hept-2-ene-2-carboxylate (0.19 g).

¹H NMR (400 MHz, D₂O) δ 1.23 (d, 3H, J=6.4 Hz), 2.96–3.03 (m, 1H), 3.31–3.37 (m, 3H), 3.40–3.43 (m, 1H), 4.16–4.22 (m, 2H), 7.27 (s, 4H).

Step d)

In the same manner as example 3, from the compound (0.12 g) prepared in the above step, there was obtained [(2,2-dimethylpropanoyl)oxymethyl (5R,6S)-6-[(1R)-1-hydroxyethyl]-3-[4-(isonicotinoylamino)phenyl]-7-oxo-1-azabicyclo[3.2.0]hept-2-ene-2-carboxylate (0.08 g).

¹H NMR (400 MHz, CDCl₃) δ 1.20 (s, 9H), 1.37 (d, 3H, J=6.0 Hz), 3.23–3.35 (m, 3H), 4.26–4.30 (m, 2H), 5.79 (d, 1H, J=5.6 Hz), 5.88 (d, 1H, J=5.6 Hz), 7.42 (d, 2H, J=8.8 Hz), 7.66 (d, 2H, J=8.8 Hz), 7.72 (d, 2H, J=6.0 Hz), 7.95 (s, 1H), 8.83 (d, 2H, J=6.0 Hz).

Example 42

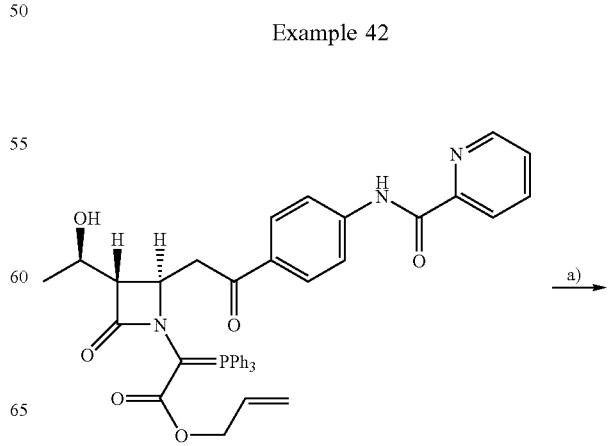

-continued

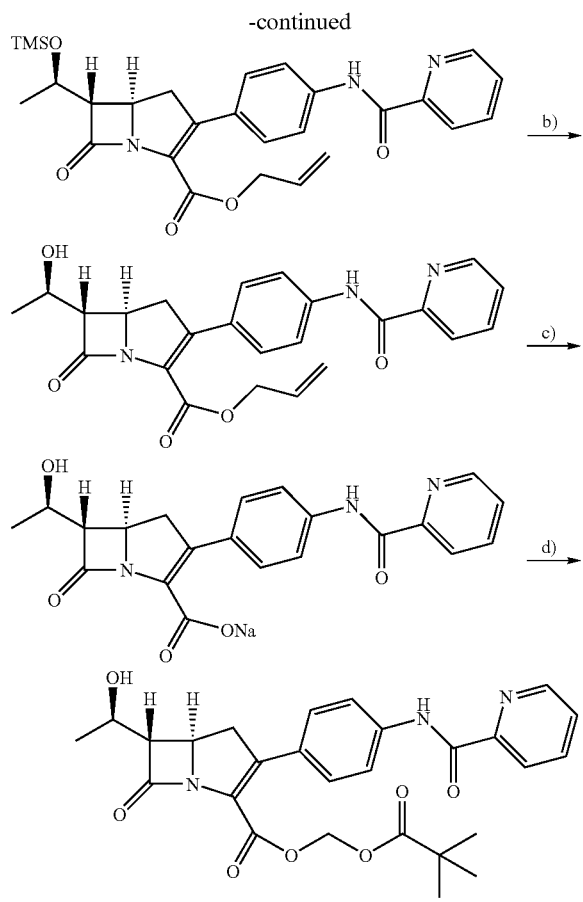

Step a)

In the same manner as step b) of example 2, from allyl [(3S,4R)-3-[(1R)-1-hydroxyethyl]-2-oxo-4-(2-oxo-2-{4-[(pyridin-2-ylcarbonyl)amino]phenyl}ethyl)azetidin-1-yl](triphenylphosphoranilidene)acetate prepared by reference example 34, there was obtained allyl ((3S,4R)-2-oxo-4-(2-oxo-2-{4-[(pyridin-2-ylcarbonyl)amino]phenyl}ethyl)-3-{(1R)-1-[(trimethylsilyl)oxy]ethyl}azetidin-1-yl)(triphenylphosphoranilidene)acetate. The product without purification was treated in the same manner as step b) of example 2 to give allyl (5R,6S)-7-oxo-3-{4-[(pyridin-2-ylcarbonyl)amino)phenyl}-6-{(1R)-1-[(-[(trimethylsilyl)oxy]ethyl)-1-azabicyclo[3.2.0]hept-2-ene-2-carboxylate.

$^1$H NMR (400 MHz, CDCl$_3$) δ 0.15 (s, 9H), 1.31 (d, 3H, J=6.0 Hz), 3.12–3.35 (m, 3H), 4.15–4.25 (m, 2H), 4.60–4.67 (m, 2H), 5.19–5.34 (m, 2H), 5.85–5.95 (m, 1H), 7.44 (d, 2H, J=8.4 Hz), 7.48–7.51 (m, 1H), 7.78 (d, 2H, J=8.4 Hz), 7.80–7.94 (m, 1H), 8.30 (d, 1H, J=7.6 Hz), 8.63 (d, 1H, J=4.4 Hz).

Step b)

In the same manner as step b) of example 17, from the compound prepared in the above step, there was obtained allyl (5R,6S)-6-[(1R)-1-hydroxyethyl]-7-oxo-3-{4-[(pyridin-2-ylcarbonyl)amino]phenyl}-1-azabicyclo[3.2.0]hept-2-ene-2-carboxylate.

$^1$H NMR (400 MHz, CDCl$_3$) δ 1.38 (d, 3H, J=6.0 Hz), 3.24–3.31 (m, 3H), 4.21–4.34 (m, 2H), 4.60–4.83 (m, 2H), 5.18–5.36 (m, 2H), 5.80–5.91 (m, 1H), 7.41–7.52 (m, 2H), 7.77–7.82 (m, 2H), 7.92–7.94 (m, 1H), 8.30 (d, 1H, J=4.0 Hz), 8.63 (d, 1H, J=4.4 Hz), 10.09–10.13 (m, 1H).

Step c)

In the same manner as step b) of example 17, from the compound prepared in the above step, there was obtained sodium (5R,6S)-6-[(1R)-1-hydroxyethyl]-7-oxo-3-{4-[(pyridin-2-ylcarbonyl) amino]phenyl}-1-azabicyclo[3.2.0]hept-2-ene-2-carboxylate.

$^1$H NMR (400 MHz, D$_2$O) δ 1.12 (d, 3H, J=6.4 Hz), 2.91 (dd, 1H, J=16.8 Hz, 9.6 Hz), 3.22–3.33 (m, 2H), 4.03–4.14 (m, 2H), 7.23 (d, 2H, J=8.8 Hz), 7.42–7.47 (m, 3H), 7.85–7.87 (m, 1H), 7.93 d, 1H, J=8.0 Hz), 8.48 (d, 1H, J=4.4 Hz).

Step d)

In the same manner as example 3, from the compound prepared in the above step, there was obtained [(2,2-dimethylpropanoyl)oxymethyl (5R,6S)-6-[(1R)-1-hydroxyethyl]-7-oxo-3-{4-[(pyridin-2-ylcarbonyl)amino]phenyl}-1-azabicyclo[3.2.0]hept-2-ene-2-carboxylate.

$^1$H NMR (400 MHz, CDCl$_3$) δ 1.20 (s, 9H), 1.37 (d, 3H, J=6.0 Hz), 3.22–3.48 (m, 3H), 4.27–4.33 (m, 2H), 5.80 (d, 1H, J=5.6 Hz), 5.89 (d, 1H, J=5.6 Hz), 7.44 (d, 2H, J=8.8 Hz), 7.49–7.52 (m, 1H), 7.79 (d, 2H, J=8.8 Hz), 7.90–7.95 (m, 1H), 8.30 (d, 1H, J=8.0 Hz), 8.63 (d, 1H, J=4.0 Hz), 10.13 (s, 1H).

Example 43

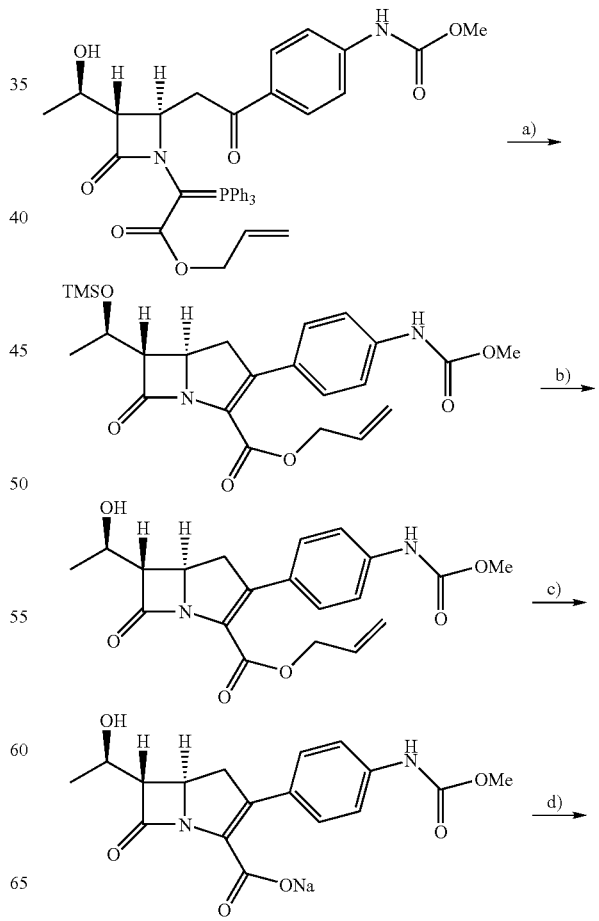

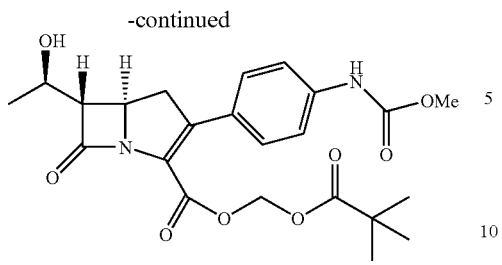

Step a)
In the same manner as step b) of example 2, from allyl [(2R,3S)-3-[(1R)-1-hydroxyethyl]-2-(2-{4-[(methoxycarbonyl) amino]phenyl}-2-hydroxyethyl)-4-oxoazetidin-1-yl] (triphenylphosphoranilidene) acetate (2.64 g) prepared by reference example 35, there was obtained allyl ((2R,3S)-2-(2-{4-[(methoxycarbonyl)amino]phenyl}-2-oxoethyl)-4-oxo-3-{(1R)-1-[(trimethylsilyl) oxy]ethyl}azetidin-1-yl) (triphenylphosphoranilidene)acetate (2.59 g). The product without purification is treated in the same manner as step b) of example 2 to give allyl (5R,6S)-3-{4-[(methoxycarbonyl) amino]phenyl}-7-oxo-6-{(1R)-1-[(trimethylsilyl)oxy] ethyl}-1-azabicyclo[3.2.0]hept-2-ene-2-carboxylate (2.66 g).
LC/MS (EI) 459 (M+1)

Step b)
In the same manner as step b) of example 17 from the compound (1.33 g) prepared in the above step, there was obtained allyl (5R,6S)-6-[(1R)-1-hydroxyethyl]-3-{4-[(methoxycarbonyl)amino]phenyl}-7-oxo-1-azabicyclo [3.2.0]hept-2-ene-2-carboxylate (0.29 g).
$^1$H NMR (400 MHz, CDCl$_3$) δ 1.26 (d, 3H, J=6.4 Hz), 3.05–3.20 (m, 3H), 3.67 (s, 3H), 4.14–4.22 (m, 2H), 4.50–4.68 (m, 2H), 5.08–5.22 (m, 2H), 5.74–5.81 (m, 1H), 6.55 (s, 1H), 7.20–7.28 (m, 4H).

Step c)
In the same manner as step b) of example 17, from the compound (0.29 g) prepared in the above step, there was obtained sodium (5R,6S)-6-[(1R)-1-hydroxyethyl]-3-{4-[(methoxycarbonyl)amino]phenyl}-7-oxo-1-azabicyclo [3.2.0]hept-2-ene-2-carboxylate (0.11 g).
$^1$H NMR (400 MHz, D$_2$O) δ 1.11 (d, 3H, J=6.4 Hz), 2.87–2.94 (m, 1H), 3.21–3.32 (m, 3H), 4.04–4.12 (m, 2H), 7.22 (d, 2H, J=8.4 Hz), 7.34 (d, 2H, J=8.4 Hz), 7.49 (s, 1H), 7.72 (d, 2H, J=6.0 Hz), 8.52 (d, 2H, J=6.0 Hz).

Step d)
In the same manner as example 3, from the compound (0.15 g) prepared in the above step, there was obtained [(2,2-dimethylpropanoyl)oxymethyl (5R,6S)-6-[(1R)-1-hydroxyethyl]-3-{4-[(methoxycarbonyl)amino]phenyl}-7-oxo-1-azabicyclo[3.2.0]hept-2-ene-2-carboxylate (0.11 g).
$^1$H NMR (400 MHz, CDCl$_3$) δ 1.19 (s, 9H), 1.36 (d, 3H, J=6.4 Hz), 3.18–3.33 (m, 3H), 3.78 (s, 3H), 4.24–4.32 (m, 2H), 5.78 (d, 1H, J=5.6 Hz), 5.87 (d, 1H, J=5.6 Hz), 6.68 (s, 1H), 7.30–7.38 (m, 4H).

Example 44

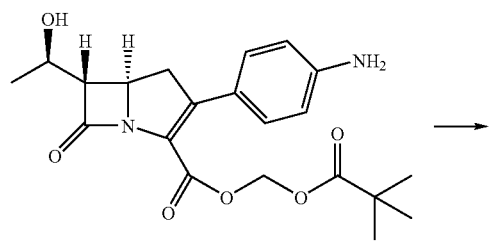

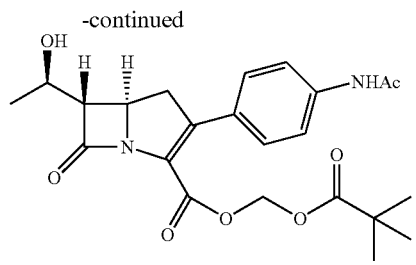

A mixture of [(2,2-dimethylpropanoyl)oxy]methyl (5R, 6S)-3-(4-aminophenyl)-6-[(1R)-1-hydroxyethyl]-7-oxo-1-azabicyclo[3.2.0]hept-2-ene-2-carboxylate prepared by example 26, diisopropylethylamine and dichloromethane was cooled at 0° C., and thereto was dropped acetyl chloride. After stirring, the reaction mixture was poured into ice water. The mixture was extracted with ethyl acetate. The organic layer was washed with a saturated aqueous sodium hydrogencarbonate solution and a saturated aqueous sodium chloride solution in the order, and dried over anhydrous sodium sulfate. The solvent was removed under reduced pressure to give a crude product. The crude product was purified by silica gel chromatography, to give [(2,2-dimethylpropanoyl)oxymethyl (5R,6S)-3-[4-(acetylamino)phenyl]-6-[(1R)-1-hydroxyethyl]-7-oxo-1-azabicyclo[3.2.0] hept-2-ene-2-carboxylate.
LC/MS (EI) 459 (M+1)

Example 45

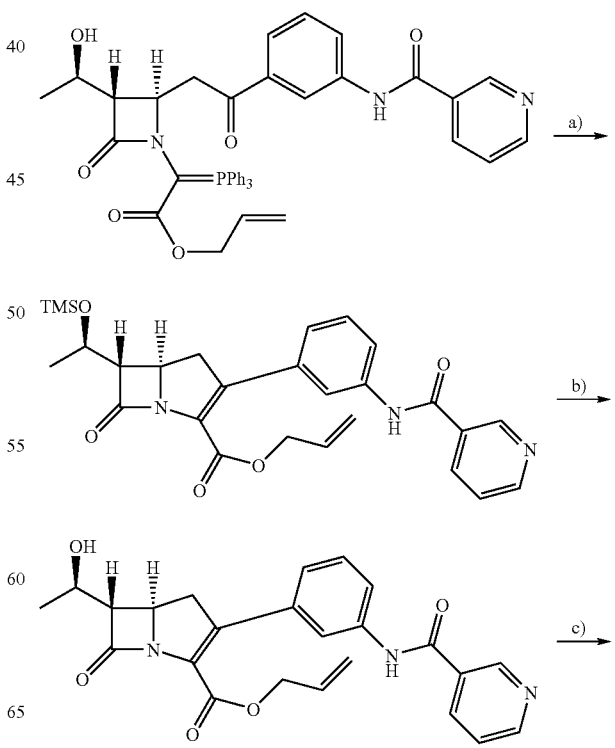

-continued

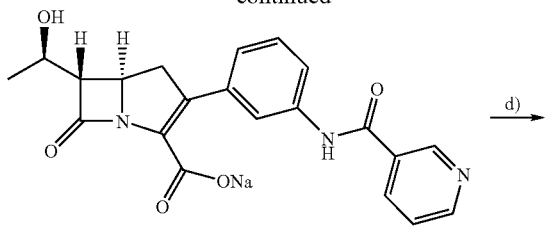

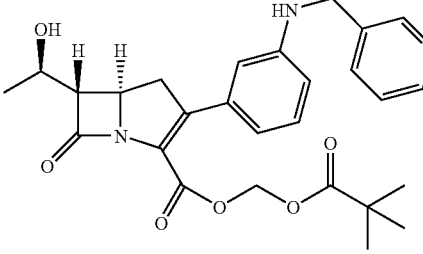

Step a)

In the same manner as step b) of example 2, from allyl [(3S,4R)-3-[(1R)-1-hydroxyethyl]-2-oxo-4-(2-oxo-2-{3-[(pyridin-3-ylcarbonyl)amino]phenyl}ethyl)azetidin-1-yl](triphenylphosphoranilidene)acetate prepared by reference example 38, there was obtained allyl ((3S,4R)-2-oxo-4-(2-oxo-2-{3-[(pyridin-3-ylcarbonyl)amino]phenyl}ethyl)-3-{(1R)-1-[(trimethylsilyl)oxy]ethyl}azetidin-1-yl)(triphenylphosphoranilidene)acetate. The product without purification was treated in the same manner as step b) of example 2 to give allyl (5R,6S)-7-oxo-3-{3-[(pyridin-3-ylcarbonyl)amino)phenyl)-6-{(1R)-1-[(-[(trimethylsilyl)oxy]ethyl)-1-azabicyclo[3.2.0]hept-2-ene-2-carboxylate.

LC/MS (EI) 506 (M+1)

Step b)

In the same manner as step b) of example 17, from the compound prepared in the above step, there was obtained allyl (5R,6S)-6-[(1R)-1-hydroxyethyl]-7-oxo-3-{3-[(pyridin-3-ylcarbonyl)amino]phenyl}-1-azabicyclo[3.2.0]hept-2-ene-2-carboxylate.

¹H NMR (400 MHz, CDCl₃) δ 1.37 (d, 3H, J=6.0 Hz), 3.20–3.38 (m, 3H), 4.26–4.38 (m, 2H), 4.60–4.78 (m, 2H), 5.16–5.30 (m, 2H), 5.82–5.89 (m, 1H), 7.16 (d, 1H, J=6.8 Hz), 7.37 (t, 1H, J=8.0 Hz), 7.44–7.48 (m, 1H), 7.48 (s, 1H), 7.72 (s, 1H), 8.07 (s, 1H), 8.22 (d, 1H, J=8.0 Hz), 8.78 (d, 1H, J=6.4 Hz), 9.09(s, 1H).

Step c)

In the same manner as step b) of example 17, from the compound prepared in the above step, there was obtained sodium (5R,6S)-6-[(1R)-1-hydroxyethyl]-7-oxo-3-{3-[(pyridin-3-ylcarbonyl)amino]phenyl}-1-azabicyclo[3.2.0]hept-2-ene-2-carboxylate.

¹H NMR (400 MHz, D₂O) δ 1.13 (d, 3H, J=6.4 Hz), 2.94 (dd, 1H, J=17.6 Hz, 7.6 Hz), 3.28 (dd, 1H, J=17.2 Hz, 8.8 Hz), 3.33–3.35 (m, 1H), 4.06–4.16 (m, 2H), 7.08 (d, 2H, J=8.4 Hz), 7.25 (d, 1H, J=8.0 Hz), 7.29 (s, 3H), 7.34 (d, 1H, J=7.6 Hz), 7.42–7.45 (m, 1H), 8.12 (s, 1H), 8.54 (d, 1H, J=4.4 Hz), 8.81 (s, 1H).

Step d)

In the same manner as example 3, from the compound prepared in the above step, there was obtained [(2,2-dimethylpropanoyl)oxymethyl (5R,6S)-6-[(1R)-1-hydroxyethyl]-7-oxo-3-{3-[(pyridin-3-ylcarbonyl)amino]phenyl}-1-azabicyclo[3.2.0]hept-2-ene-2-carboxylate.

¹H NMR (400 MHz, CDCl₃) δ 1.14 (s, 9H), 1.37 (d, 3H, J=6.4 Hz), 3.24–3.42 (m, 3H), 4.26–4.33 (m, 2H), 5.75 (d, 1H, J=5.6 Hz), 5.82 (d, 1H, J=5.6 Hz), 7.09 (d, 1H, J=6.8 Hz), 7.38–7.46 (m, 3H), 8.32 (d, 1H, J=6.0 Hz), 8.71 (s, 1H), 8.78 (d, 1H, J=6.0 Hz), 9.24 (s, 1H).

Example 46

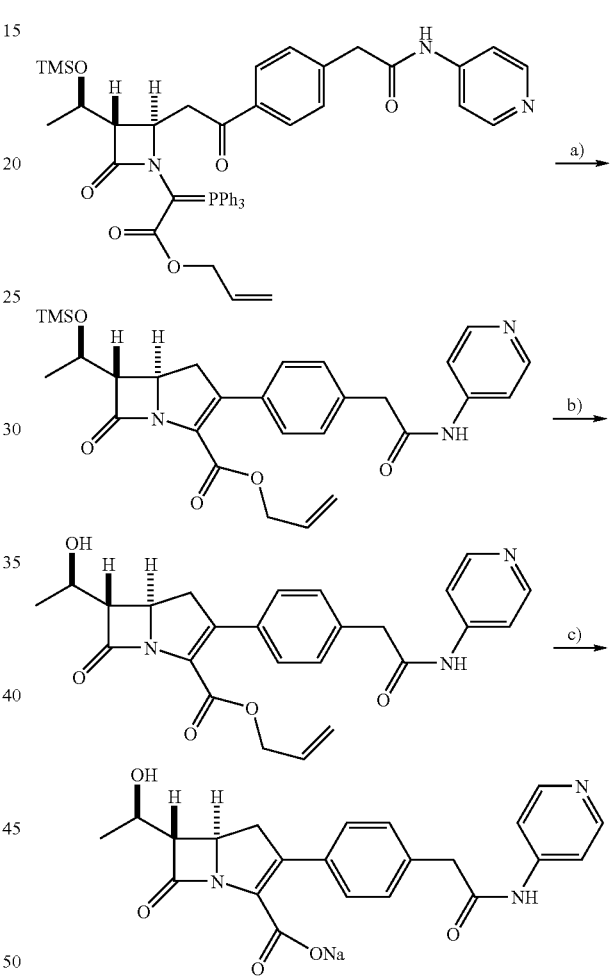

In the same manner as step b) of example 2, by using bistrimethylsilylamide as an additive and from allyl ((3S,4R)-2-oxo-4-(2-oxo-2-{4-[2-oxo-2-(pyridin-4-ylamino)ethyl]phenyl}ethyl)-3-{(1R)-1-[(trimethylsilyl)oxy]ethyl}azetidin-1-yl)(triphenylphosphoranilidene)acetate (0.62 g) prepared by reference example 39, there was obtained allyl (5R,6S)-7-oxo-3-{4-[2-oxo-2-(pyridin-4-ylamino) ethyl]phenyl}-6-{(1R)-1-[(trimethylsilyl)oxy]ethyl}-1-azabicyclo[3.2.0]hept-2-ene-2-carboxylate. In the same manner as step b) of example 17, by using this compound, there was obtained sodium (5R,6S)-6-[(1R)-1-hydroxyethyl]-7-oxo-3-{4-[2-oxo-2-(pyridin-4-ylamino)ethyl]phenyl}-1-azabicyclo[3.2.0]hept-2-ene-2-carboxylate (54.4 mg).

¹H NMR (400 MHz, D₂O) δ 1.25 (d, 3H, J=6.4 Hz), 2.95 (dd, 1H, J=17.0 Hz, 9.8 Hz), 3.32–3.42 (m, 1H), 3.42–3.47 (m, 1H), 3.77 (s, 2H), 4.17–4.24 (m, 2H), 7.47–7.52 (m, 2H), 8.34–8.38 (m, 2H).

Example 47

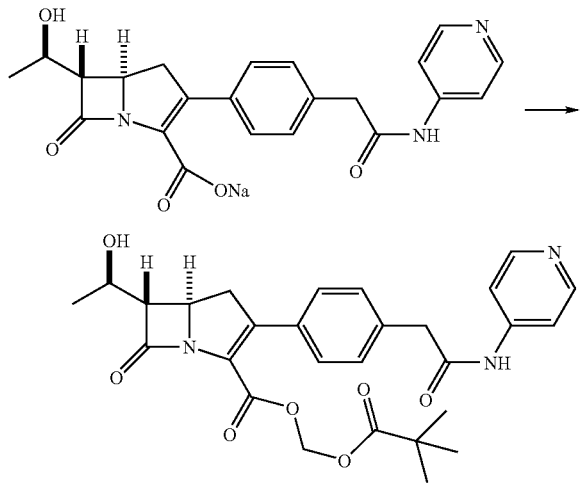

In the same manner as example 3, by using sodium (5R,6S)-6-[(1R)-1-hydroxyethyl]-7-oxo-3-{4-[2-oxo-2-(pyridin-4-ylamino)ethyl]phenyl}-1-azabicyclo[3.2.0]hept-2-ene-2-carboxylate prepared by example 46, there was obtained [(2,2-dimethylpropanoyl)oxy]methyl (5R,6S)-6-[(1R)-1-hydroxyethyl]-7-oxo-3-{4-[2-oxo-2-(pyridin-4-ylamino)ethyl]phenyl}-1-azabicyclo[3.2.0]hept-2-ene-2-carboxylate.

LC/MS (EI) 522 (M+1)

Example 48

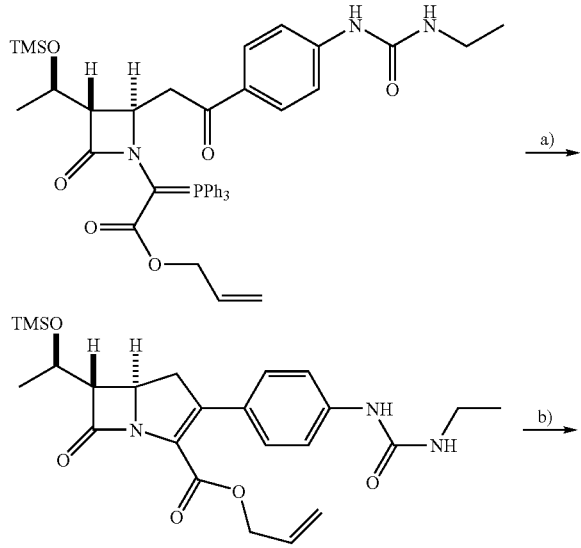

-continued

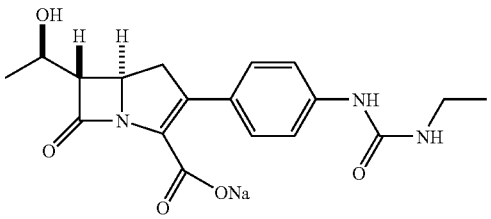

Step a)

In the same manner as step b) of example 2, by using bistrimethylsilylamide as an additive and from allyl ((2R,3S)-2-[2-(4-{[(ethylamino)carbonyl]amino}phenyl)-2-oxoethyl]-4-oxo-3-{(1R)-1-[(trimethylsilyl)oxy]ethyl}azetidin-1-yl)(triphenylphosphoranilidene)acetate prepared by reference example 42, there was obtained allyl (5R,6S)-3-(4-{[(ethylamino)carbonyl]amino}phenyl)-7-oxo-6-{(1R)-1-[(trimethylsilyl)oxy]ethyl}-1-azabicyclo[3.2.0]hept-2-ene-2-carboxylate.

LC/MS (EI) 472 (M+1)

Step b)

In the same manner as step b) of example 17, by using the compound prepare in the above step, there was obtained sodium (5R,6S)-3-(4-{[(ethylamino)carbonyl]amino}phenyl)-6-[(1R)-1-hydroxyethyl]-7-oxo-1-azabicyclo[3.2.0]hept-2-ene-2-carboxylate.

¹H NMR (400 MHz, D₂O) δ 0.98 (t, 3H, J=7.2 Hz), 1.17 (d, 3H, J=6.4 Hz), 2.94 (dd, 1H, J=16.9 Hz, 9.8 Hz), 3.06 (q, 2H, J=7.2 Hz), 3.29 (dd, 1H, J=16.9 Hz, 8.5 Hz), 3.32–3.39 (m, 1H), 4.08–4.20 (m, 2H), 7.09–7.15 (m, 2H), 7.16–7.22 (m, 2H).

Example 49

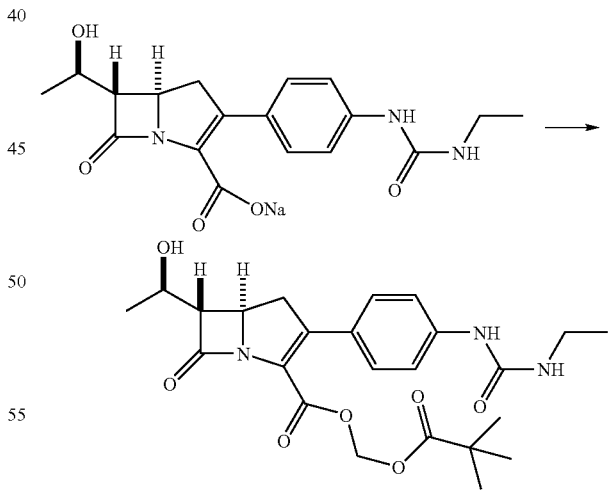

In the same manner as example 3, from sodium (5R,6S)-3-(4-{[(ethylamino)carbonyl]amino}phenyl)-6-[(1R)-1-hydroxyethyl]-7-oxo-1-azabicyclo[3.2.0]hept-2-ene-2-carboxylate prepared by example 48, there was obtained [(2,2-dimethylpropanoyl)oxy]methyl (5R,6S)-3-(4-{[(ethylamino)carbonyl]amino}phenyl)-6-[(1R)-1-hydroxyethyl]-7-oxo-1-azabicyclo[3.2.0]hept-2-ene-2-carboxylate.

¹H NMR (400 MHz, CDCl₃) δ 1.19 (s, 9H), 1.10–1.19 (m, 3H), 1.36 (d, 3H, J=6.3 Hz), 3.12–3.38 (m, 5H), 4.11–4.28 (m, 2H), 4.92 (brs, 1H), 5.77 (d, 1H, J=5.5 Hz), 5.87 (d, 1H, J=5.5 Hz), 6.51 (s, 1H), 7.20–7.35 (m, 4H).

Example 50

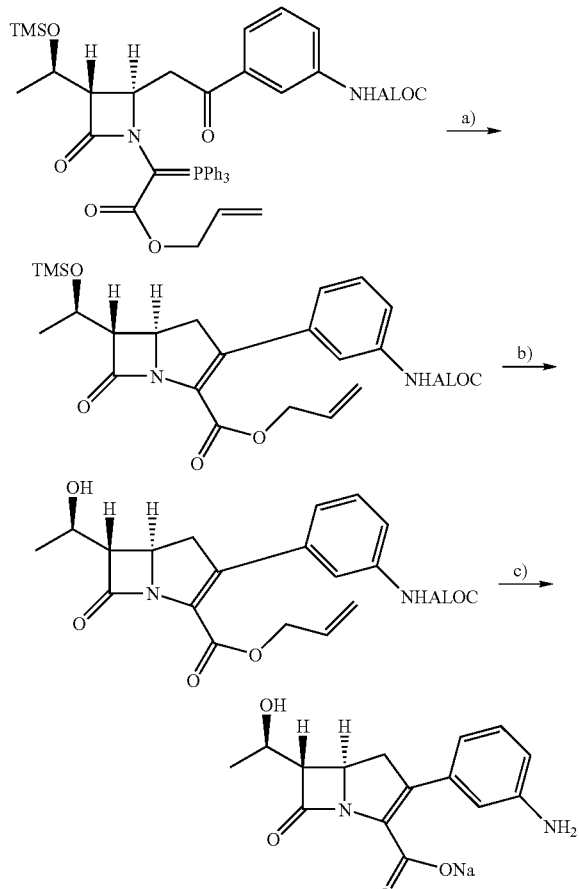

Step a)
In the same manner as step b) of example 2, from allyl [(2R,3S)-2-[2-(3-{[(allyloxy)carbonyl]amino}phenyl)-2-oxoethyl]-3-((1R)-1-[(trimethylsilyl)oxy]ethyl}-4-oxoazetidin-1-yl](triphenylphosphoranilidene)acetate prepared by reference example 44, there was obtained allyl (5R,6S)-3-(3-{[(allyloxy)carbonyl]amino}phenyl)-7-oxo-6-{(1R)-1-[(trimethylsilyl)oxy]ethyl}-1-azabicyclo[3.2.0]hept-2-ene-2-carboxylate.

¹H NMR (400 MHz, CDCl₃) δ 0.15 (s, 9H), 1.29 (d, 3H, J=6.1 Hz), 3.16–3.28 (m, 3H), 4.17–4.25 (m, 2H), 4.57–4.78 (m, 4H), 5.13–5.44 (m, 4H), 5.80–6.06 (m, 2H), 6.65 (brs, 1H), 7.03–7.09 (m, 1H), 7.24–7.31 (m, 2H), 7.47 (brs, 1H).

Step b)
Allyl (5R,6S)-3-(3-{[(allyloxy)carbonyl]amino}phenyl)-7-oxo-6-{(1R)-1-[(trimethylsilyl)oxy]ethyl}-1-azabicyclo[3.2.0]hept-2-ene-2-carboxylate was subjected to detrimethylsilyl etherification in the same manner as step b) of example 17 to give allyl (5R,6S)-3-(3-{[(allyloxy)carbonyl]amino}phenyl)-6-[(1R)-1-hydroxyethyl]-7-oxo-1-azabicyclo[3.2.0]hept-2-ene-2-carboxylate.

¹H NMR (400 MHz, CDCl₃) δ 1.36 (d, 3H, J=6.3 Hz), 3.13–3.38 (m, 3H), 4.19–4.35 (m, 2H), 4.54–4.77 (m, 4H), 5.12–5.42 (m, 4H), 5.74–6.04 (m, 2H), 6.75 (brs, 1H), 7.02–7.09 (m, 1H), 7.24–7.32 (m, 2H), 7.47 (brs, 1H).

Step c)
In the same manner as step b) of example 16, from the compound prepared in the above step, there was obtained sodium (5R,6S)-3-(3-aminophenyl)-6-[(1R)-1-hydroxyethyl]-7-oxo-1-azabicyclo[3.2.0]hept-2-ene-2-carboxylate.

¹H NMR (400 MHz, D₂O) δ 1.19 (d, 3H, J=6.4 Hz), 2.94 (dd, 1H, J=17.0 Hz, 9.8 Hz), 3.28 (dd, 1H, J=17.0 Hz, 8.5 Hz), 3.35–3.42 (m, 1H), 4.10–4.20 (m, 2H), 6.62–6.73 (m, 3H), 7.03–7.11 (m, 1H).

Example 51

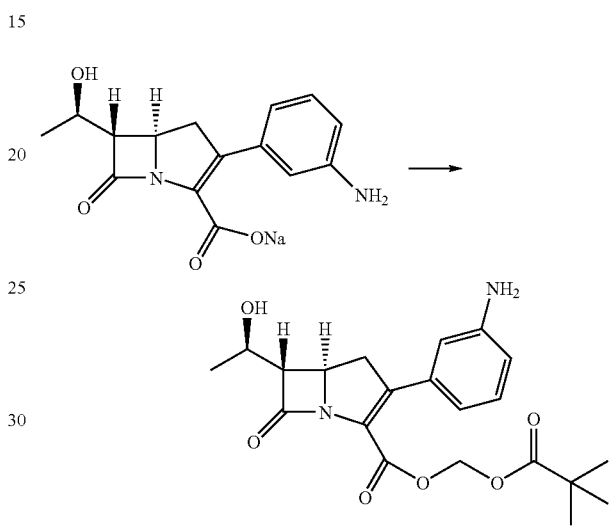

In the same manner as example 3, from sodium (5R,6S)-3-(3-aminophenyl)-6-[(1R)-1-hydroxyethyl]-7-oxo-1-azabicyclo[3.2.0]hept-2-ene-2-carboxylate prepared by example 50, there was obtained [(2,2-dimethylpropanoyl)oxy]methyl (5R,6S)-3-(3-aminophenyl)-6-[(1R)-1-hydroxyethyl]-7-oxo-1-azabicyclo[3.2.0]hept-2-ene-2-carboxylate.

¹H NMR (400 MHz, CDCl₃) δ 1.19 (s, 9H), 1.36 (d, 3H, J=6.3 Hz), 3.12–3.28 (m, 3H), 4.20–4.31 (m, 2H), 5.72–5.78 (m, 1H), 5.79–5.84 (m, 1H), 6.62–6.73 (m, 3H), 7.07–7.16 (m, 1H).

Example 52

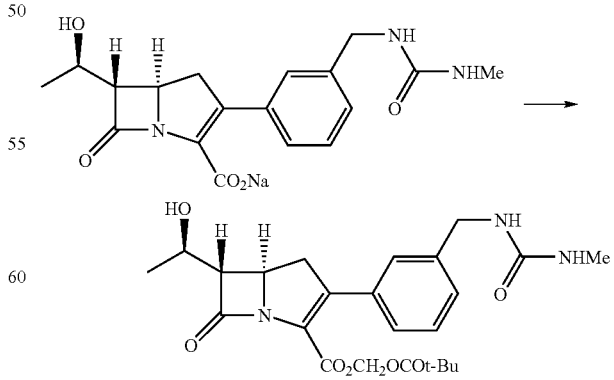

In the same manner as example 3, from sodium (5R,6S)-6-[(1R)-1-hydroxyethyl]-3-[3-({[(methylamino)carbonyl]

amino}methyl)phenyl]-7-oxo-1-azabicyclo[3.2.0]hept-2-ene-2-carboxylate prepared by example 16, there was obtained [(2,2-dimethylpropanoyl)oxy]methyl (5R,6S)-6-[(1R)-1-hydroxyethyl]-3-[3-({[(methylamino)carbonyl]amino}methyl)phenyl]-7-oxo-1-azabicyclo[3.2.0]hept-2-ene-2-carboxylate.

$^1$H NMR (400 MHz, CDCl$_3$) δ 1.15 (s, 9H), 1.33 (d, 3H, J=6.3 Hz), 2.75 (s, 3H), 3.20–3.28 (m, 2H), 4.13–4.27 (m, 2H), 4.30–4.38 (m, 2H), 5.70 (d, 1H, J=5.6 Hz), 5.79 (d, 1H, J=5.6 Hz), 7.15–7.17 (m, 1H), 7.19–7.30 (m, 3H).

Example 53

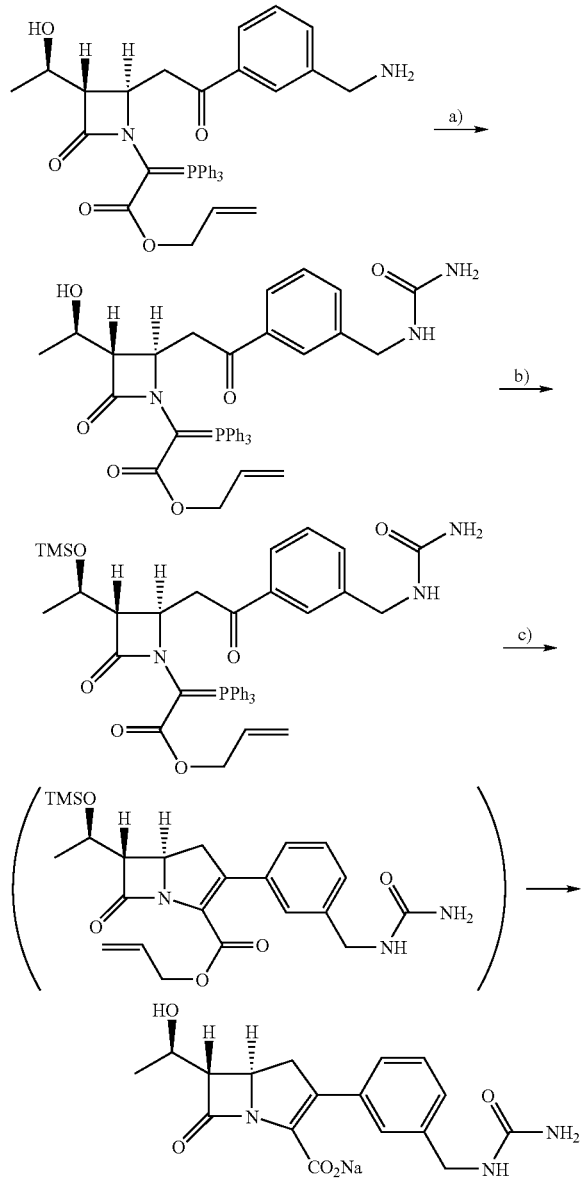

Step a)

In the same manner as reference example 11, from allyl {(2R,3S)-2-{2-[3-(aminomethyl)phenyl]-2-oxoethyl}-3-[(1R)-1-hydroxyethyl]-4-oxoazetidin-1-yl}(triphenylphosphoranilidene)acetate prepared by reference example 6, there was obtained allyl {(2R,3S)-2-[2-(3-{[(aminocarbonyl)amino]methyl}phenyl)-2-oxoethyl]-3-[(1R)-1-hydroxyethyl]-4-oxoazetidin-1-yl}(triphenylphosphoranilidene)acetate. This product was used in the next step without further purification.

Step b)

In the same manner as step a) of example 2, by using the compound prepared in the above step, there was obtained allyl {(2R,3S)-2-[2-(3-{[(aminocarbonyl)amino]methyl}phenyl)-2-oxoethyl]-3-[(1R)-1-({trimethylsilyl}oxy)ethyl]-4-oxoazetidin-1-yl}(triphenylphosphoranilidene)acetate. This product was used in the next step without further purification.

Step c)

In the same manner as step b) of example 2, by using the compound prepared in the above step, there was obtained allyl (5R,6S)-3-(3-{[(aminocarbonyl)amino]methyl}phenyl)-7-oxo-6-{(1R)-1-[(trimethylsilyl)oxy]ethyl}-1-azabicyclo[3.2.0]hept-2-ene-2-carboxylate. The product was further treated in the same manner as step b) of example 8 to give sodium (5R,6S)-3-(3-{[(aminocarbonyl)amino]methyl}phenyl)-6-[(1R)-1-hydroxyethyl]-7-oxo-1-azabicyclo[3.2.0]hept-2-ene-2-carboxylate.

$^1$H NMR (400 MHz, DMSO-d6) δ 1.09 (d, 3H, J=6.3 Hz), 2.78 (dd, 1H, J=9.8, 15.6 Hz), 3.01 (dd, 1H, J=8.5, 15.6 Hz), 3.07 (dd, 1H, J=2.8, 6.5 Hz), 3.80–3.88 (m, 1H), 3.91–3.96 (m, 1H), 4.03, (d, 2H, J=5.9 Hz), 4.93 (d, 1H, J=5.0 Hz), 6.32 (t, 1H, J=5.9 Hz), 6.92 (br.d, 1H, J=7.7 Hz), 7.07 (br.t, 1H, J=7.7 Hz), 7.19 (br.s, 1H), 7.33 (br.d, 1H, J=8.0 Hz). IR (ATR) 3338(br), 2972, 1743, 1649, 1570, 1489, 1389, 1340, 1308, 1246, 1223, 1132, 1092, 1039, 999, 978, 951, 887, 783, 696 cm$^{-1}$.

Example 54

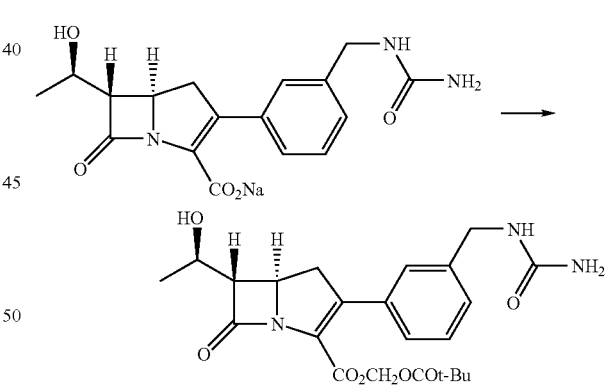

In the same manner as example 3, from sodium (5R,6S)-3-(3-{[(aminocarbonyl)amino]methyl}phenyl)-6-[(1R)-1-hydroxyethyl]-7-oxo-1-azabicyclo[3.2.0]hept-2-ene-2-carboxylate prepared by example 53, there was obtained [(2,2-dimethylpropanoyl)oxy]methyl (5R,6S)-3-(3-{[(aminocarbonyl)amino]methyl}phenyl)-6-[(1R)-1-hydroxyethyl]-7-oxo-1-azabicyclo[3.2.0]hept-2-ene-2-carboxylate.

$^1$H NMR (400 MHz, CD$_3$CN) δ 1.14 (s, 9H), 1.31 (d, 3H, J=6.3 Hz), 3.12 (dd, 1H, J=18.5, 9.9 Hz), 3.20–3.28 (m, 2H), 4.09–4.25 (m, 2H), 4.31 (br. s, 2H), 5.69 (d, 1H, J=5.6 Hz), 5.79 (d, 1H, J=5.6 Hz), 5.95 (br. s, 1H), 7.16–7.18 (m, 1H), 7.23–7.28 (m, 3H).

Example 55

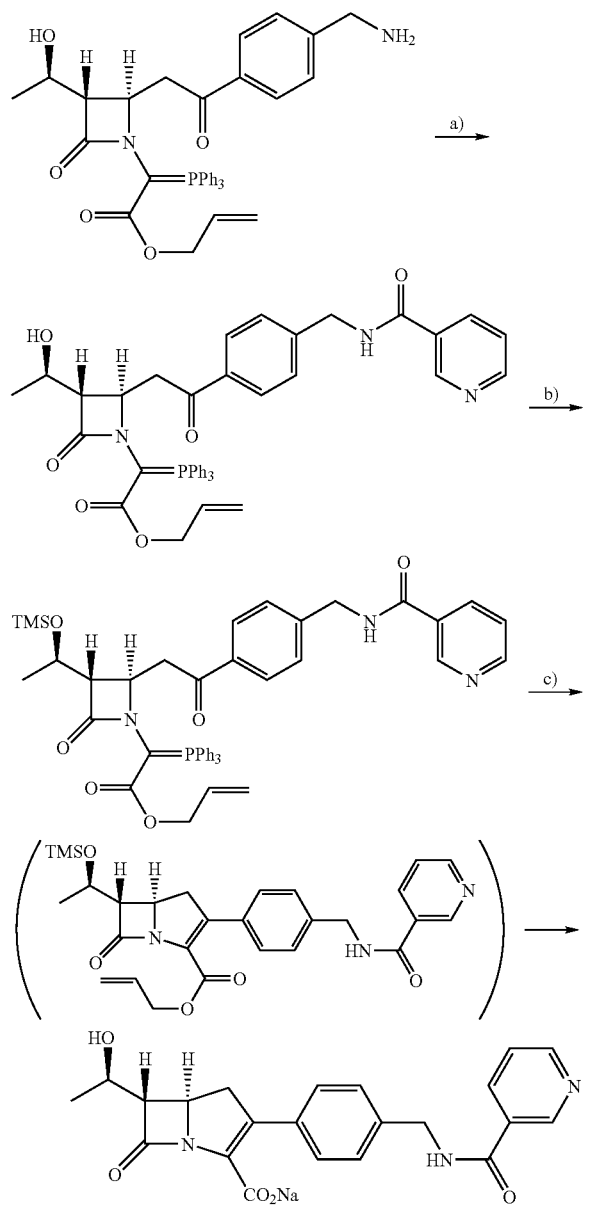

Step a)

To allyl {(2R,3S)-2-{12-[4-(aminomethyl)phenyl]-2-oxoethyl}-3-[(1R)-1-hydroxyethyl]-4-oxoazetidin-1-yl}(triphenylphosphoranilidene)acetate (3.05 g) prepared by reference example 9 and a solution of triethylamine (1.26 ml) in THF (45 ml) was added at room temperature a suspension of nicotinoyl chloride hydrochloride (1.19 g) in pyridine (10 mL), and the mixture was stirred for 10 minutes. Thereto was added ethyl acetate (100 ml) and the mixture was washed with a saturated aqueous sodium chloride solution (100 ml respectively, three times), dried over sodium sulfate and filtered. The solvent was removed under reduced pressure and the residue was purified by column chromatography (SiO₂ 150 g, chloroform/methanol=97:3~91:9) to give allyl {(3S,4R)-3-[(1R)-1-hydroxyethyl]-2-oxo-4-[2-oxo-2-(4-{[(pyridin-3-ylcarbonyl)amino]methyl}phenyl)ethyl]azetidin-1-yl}(triphenylphosphoranilidene)acetate.

Step b)

In the same manner as in step a) of example 2, by using the compound prepared in the above step, there was obtained allyl ((3S,4R)-2-oxo-4-[2-oxo-2-(4-{[(pyridin-3-ylcarbonyl)amino]methyl]}phenyl)ethyl]-3-{(1R)-1-[(trimethylsilyl)oxy]ethyl}azetidin-1-yl)(triphenylphosphoranylidene)acetate. This product was used in the next step without further purification.

Step c)

In the same manner as step b) of example 2, by using a compound prepared in the above step, there was obtained allyl (5R,6S)-7-oxo-3-(4-{[(pyridin-3-yl-carbonyl)amino]methyl}phenyl)-6-{(1R)-1-[(trimethylsilyl)oxy]ethyl}-1-azabicyclo[3.2.0]hept-2-ene-2-carboxylate. The product was further treated in the same manner as step b) of example 8 to give sodium (5R,6S)-6-[(1R)-1-hydroxyethyl]-7-oxo-3-(4-{[(pyridin-3-yl-carbonyl)amino]methyl}phenyl)-1-azabicyclo[3.2.0]hept-2-ene-2-carboxylate.

¹H NMR (400 MHz, DMSO-d6) δ 1.14 (d, 3H, J=6.3 Hz), 2.86 (dd, 1H, J=15.7, 9.9 Hz), 3.08 (dd, 1H, J=15.7, 8.5 Hz), 3.13 (dd, 1H, J=6.6, 2.8 Hz), 3.90 (br, 1H), 4.00 (td, 1H, J=8.9, 2.7 Hz), 4.44 (d, 2H, J=5.9 Hz), 5.01 (br. d, 1H, J=3.7 Hz), 7.17 (d, 2H, J=8.4 Hz), 7.42 (d, 2H, J=8.4 Hz), 7.49 (ddd, 1H, J=0.8, 4.8, 7.9 Hz), 8.22 (td, 1H, J=2.0, 7.9 Hz), 8.69 (dd, 1H, J=1.7, 4.8 Hz), 9.03 (dd, 1H, J=0.8, 2.2 Hz), 9.31 (t, 1H, J=5.9 Hz). IR (ATR) 3267, 1747, 1643, 1589, 1547, 1477, 1392, 1308, 1246, 1223, 1158, 1130, 1092, 1030, 987, 945, 879, 802, 787, 706, 675, 621 cm⁻¹.

Example 56

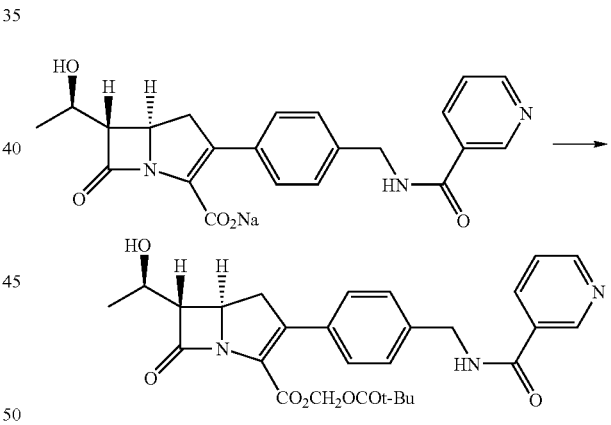

In the same manner as example 3, from sodium (5R,6S)-6-[(1R)-1-hydroxyethyl]-7-oxo-3-(4-{[(pyridin-3-ylcarbonyl)amino]methyl}phenyl)-1-azabicyclo[3.2.0]hept-2-ene-2-carboxylate prepared by example 55, there was obtained [(2,2-dimethylpropanoyl)oxy]methyl (5R,6S)-6-[(1R)-1-hydroxyethyl]-7-oxo-3-(4-{[(pyridin-3-ylcarbonyl)amino]methyl}phenyl)-1-azabicyclo[3.2.0]hept-2-ene-2-carboxylate.

¹H NMR (400 MHz, CDCl₃) δ 1.15 (s, 3H), 1.37 (d, 3H, J=3.6 Hz), 3.21 (dd, 1H, J=9.9 Hz, 18.5 Hz), 3.27 (dd, 1H, J=2.8 Hz, 6.6 Hz), 3.31 (dd, 1H, J=8.9 Hz, 18.5 Hz), 4.21–4.37 (m, 2H), 4.67 (d, 2H, J=5.5 Hz), 5.73 (d, 1H, J=5.5 Hz), 5.81 (d, 1H, J=5.5 Hz), 6.74 (br. t, 1H), 7.30–7.36 (m, 4H), 7.40 (ddd, 1H, J=0.7 Hz, 4.8 Hz, 8.0 Hz), 8.18 (dt, 1H, J=8.0 Hz, 2.0 Hz), 8.73 (dd, 1H, J=1.7 Hz, 4.8 Hz), 9.02 (d, 1H, J=1.7 Hz).

Reference Example 1

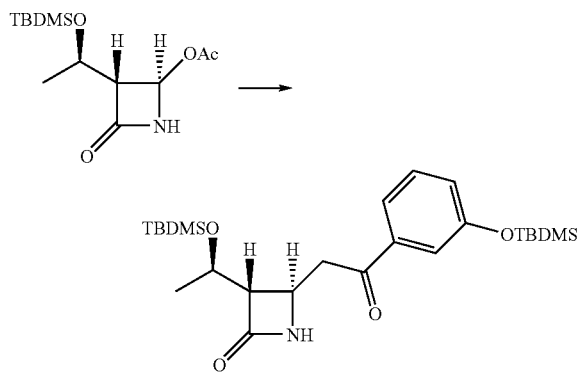

To a solution of (2R,3R)-3-((1R)-1-{[tert-butyl(dimethyl)silyl]oxy}ethyl)-4-oxo-2-azetidinylacetate (5.75 g) and a solution of tert-butyl(dimethyl)(3-{1-[(trimethylsilyl)oxy]vinyl}phenoxy)silane (about 20 mmol) in dry dichloromethane (36 ml) was added at room temperature zinc iodide (6.38 g, 20 mmol) and the mixture was reacted at the same temperature overnight. The reaction mixture was poured into ice water, diluted and extracted with ethyl acetate. The mixture was separated by a separating funnel. The organic layer was washed with a saturated aqueous sodium chloride solution (twice), an aqueous sodium hydrogencarbonate solution, and a saturated aqueous sodium chloride solution in the order, and dried over anhydrous magnesium sulfate. The solvent was removed under reduced pressure and the residue was crystallized from hexane, collected by filtration, washed and dried under reduced pressure to give (3S,4R)-3-((1R)-1-{[tert-butyl(dimethyl)silyl]oxy}ethyl)-4-[2-(3-{[tert-butyl(dimethyl)silyl]oxy}phenyl)-2-oxoethyl]azetidin-2-one (7.161 g).

$^1$H NMR (400 MHz, CDCl$_3$) δ 0.078 (6H, s), 0.084 (6H, s), 0.22 (9H, s), 0.88 (9H, s), 1.00 (9H, s), 1.25 (3H, d, J=6.2 Hz), 2.89 (1H, dd, J=2.3 Hz, 5.4 Hz), 3.07–3.18 (1H, m), 3.37–3.49 (1H, m), 4.07–4.16 (1H, m), 4.17–4.28 (1H, m), 6.11 (1H, s), 7.03–7.12 (1H, m), 7.30–7.44 (2H, m), 7.52 (1H, d, J=7.8 Hz).

Reference Example 2

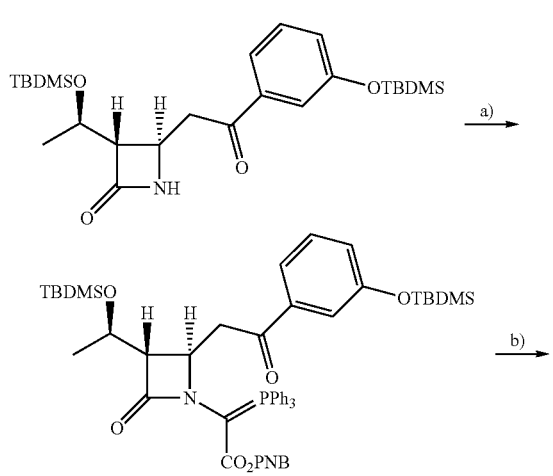

-continued

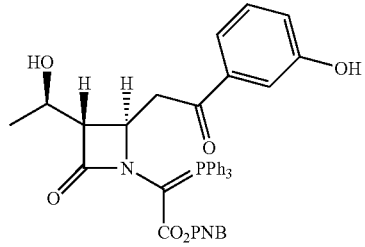

Step a)

A solution of p-nitrobenzyl glyoxalate monohydrate (2.73 g) in toluene (100 ml) was subjected to azeotropic dehydration under refluxing. After cooled to room temperature once, therein was dissolved (3S,4R)-3-((1R)-1-{[tert-butyl(dimethyl)silyl]oxy}ethyl)-4-[2-(3-{[tert-butyl(dimethyl)silyl]oxy}phenyl)-2-oxoethyl]azetidin-2-one (4.78 g) and the solution was azeotropicly dehydrated under refluxing. After disappearance of a starting material, the solvent was removed under reduced pressure. The residue was dried and dissolved in THF (40 ml). Thereto was added 2,6-lutidine (1.61 g) and the mixture was cooled at –20~–30° C. At the same temperature thereto was dropped thionyl chloride (1.78 g). After filtration of insoluble materials and washing with dry THF, the filtrate was concentrated in a bath at less than 35° C. under reduced pressure. The residue was dissolved in dry 1,4-dioxane (40 ml) and thereto were added triphenylphosphine (5.77 g) and 2,6-lutidine (2.36 g). The mixture was stirred in a bath at 50° C. for two hours. After the mixture was cooled to room temperature, thereto were added ethyl acetate and a cold saturated aqueous sodium chloride solution. The mixture was extract and separated with a separating funnel. The organic layer was washed with a cold aqueous potassium hydrogensulfate solution (twice), a cold saturated aqueous sodium chloride solution (twice), a cold aqueous sodium hydrogencarbonate solution and a cold saturated aqueous sodium chloride solution in the order, and dried over anhydrous sodium sulfate. After the solvent was removed under reduced pressure, the residue was purified by silica gel column chromatography (hexane/ethyl acetate) to give 4-nitrobenzyl {(2R,3S)-3-((1R)-1-{[tert-butyl(dimethyl)silyl]oxy}ethyl)-2-[2-(3-{[tert-butyl(dimethyl)silyl]oxy}phenyl)-2-oxoethyl]-4-oxoazetidin-1-yl}(triphenylphosphoranilidene)acetate (7.310 g).

Step b)

To a solution of 4-nitrobenzyl {(2R,3S)-3-((1R)-1-{[tert-butyl(dimethyl)silyl]oxy}ethyl)-2-[2-(3-{[tert-butyl(dimethyl)silyl]oxy}phenyl)-2-oxoethyl]-4-oxoazetidin-1-yl}(triphenylphosphoranilidene)acetate (1.89 g) and acetic acid (2.40 g) in THF (20 ml) was dropped at room temperature 1M tetrabutylammonium fluoride in THF (12 ml) and then, the mixture was stirred for 7.5 hours in a bath at 50° C. The reaction mixture was cooled to room temperature, and thereto were added ethyl acetate and a cold saturated aqueous sodium chloride solution. The mixture was extracted and separated by a separating funnel. The organic layer was washed with a cold aqueous sodium hydrogencarbonate solution and a cold (three times) in the order, and dried over anhydrous sodium sulfate. The solvent was removed under reduced pressure and the residue was crystallized from diethyl ether, filtered, washed and dried under reduced pressure to give 4-nitrobenzyl {(2R,3S)-3-[(1R)-1-hydroxyethyl]-2-[2-(3-hydroxyphenyl)-2-oxoethyl]-4-oxoazetidin-1-yl}(triphenylphosphoranilidene)acetate (1.168 g).

IR (KBr) 3423 (broad), 1727, 1604, 1256, 750, 720, 692 cm$^{-1}$.

Reference Example 3

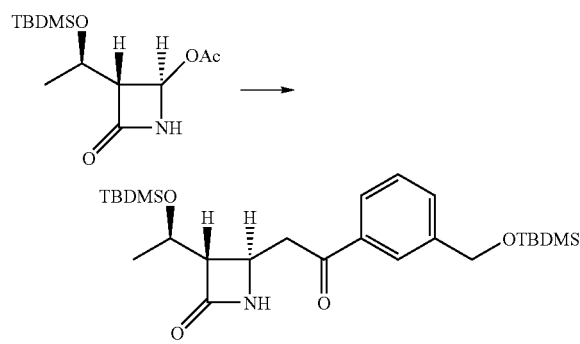

In the same manner as reference example 1, by using tert-butyl(dimethyl)[(3-{1-[(trimethylsilyl)oxy]vinyl}benzyl)oxy]silane instead of tert-butyl(dimethyl) (3-{1-[(trimethylsilyl)oxy]vinyl}phenoxy)silane, there was obtained (3S,4R)-3-((1R)-1-{[tert-butyl(dimethyl)silyl]oxy}ethyl)-4-{2-[3-({[tert-butyl(dimethyl)silyl]oxy}methyl)phenyl]-2-oxoethyl}azetidin-2-one.

$^1$H NMR (400 MHz, CDCl$_3$) δ 0.08 (s, 6H), 0.12 (s, 6H), 0.87 (s, 9H), 0.95 (s, 9H), 1.25 (d, 3H, J=5.6 Hz), 2.87–2.89 (m, 1H), 3.13–3.20 (m, 1H), 3.46 (dd, 1H, J=17.7, 3.0 Hz), 4.21–4.24 (m, 1H), 4.80 (s, 2H), 6.11 (s, 1H), 7.46 (t, 1H, J=7.7 Hz), 7.57 (d, 1H, J=7.7Hz), 7.82 (d, 1H, J=7.7Hz), 7.90 (s, 1H).

Reference Example 4

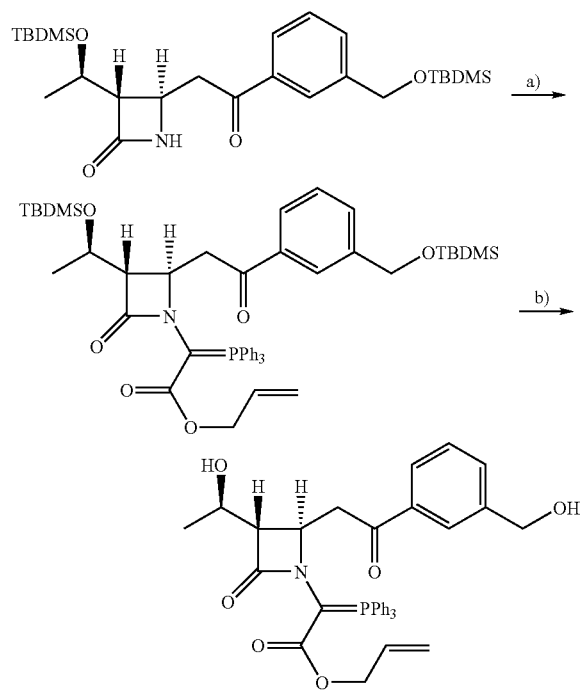

In the same manner as reference example 2, by using allyl glyoxalate monohydrate instead of p-nitrobenzyl glyoxalate monohydrate, there was obtained allyl ((2R,3S)-3-[(1R)-1-hydroxyethyl]-2-{2-[3-(hydroxymethyl)phenyl]-2-oxoethyl}-4-oxoazetidin-1-yl)(triphenylphosphoranilidene)acetate.

IR (KBr) 3324 (broad), 1767, 1738, 1671, 1439, 1373, 1245, 1124, 1107, 1084, 692 cm$^{-1}$.

Reference Example 5

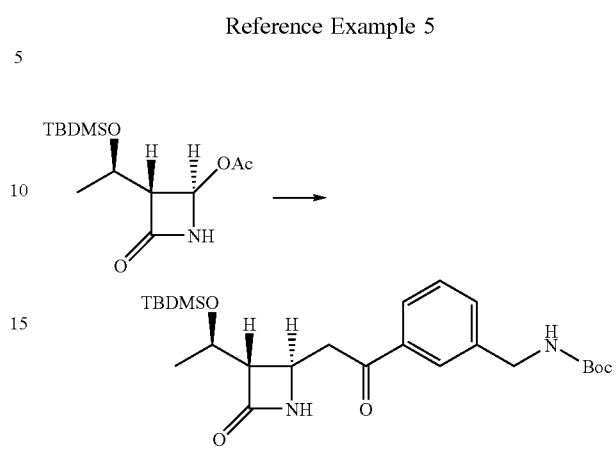

In the same manner as reference example 1, by using tert-butyl (3-{1-[(trimethylsilyl)oxy]vinyl}benzyl) carbamate instead of tert-butyl(dimethyl)(3-{1-[(trimethylsilyl)oxy]vinyl}phenoxy)silane, there was obtained tert-butyl-3-{[(2R,3S)-3-((1R)-1-{[tert-butyl(dimethyl)silyl]oxy}ethyl)-4-oxoazetidin-2-yl]acetyl}benzyl carbamate.

$^1$H NMR (400 MHz, CDCl$_3$) δ 0.08 (s, 3H), 0.09 (s, 3H), 0.88 (s, 9H), 1.25 (d, 3H, J=6.3 Hz), 1.47 (s, 9H), 2.89 (dd, 1H, J=2.2 Hz, 5.3 Hz), 3.17 (dd, 1H, J=10.1 Hz, 17.8 Hz), 3.46 (dd, 1H, J=3.0 Hz, 17.8 Hz), 4.09–4.16 (m, 1H), 4.19–4.27 (m, 1H), 4.38 (d, 2H, J=6.2 Hz), 4.96 (broad s, 1H), 6.14 (broad s, 1H), 7.43–7.48 (m, 1H), 7.52–7.55 (m, 1H), 7.82–7.87 (m, 2H).

Reference Example 6

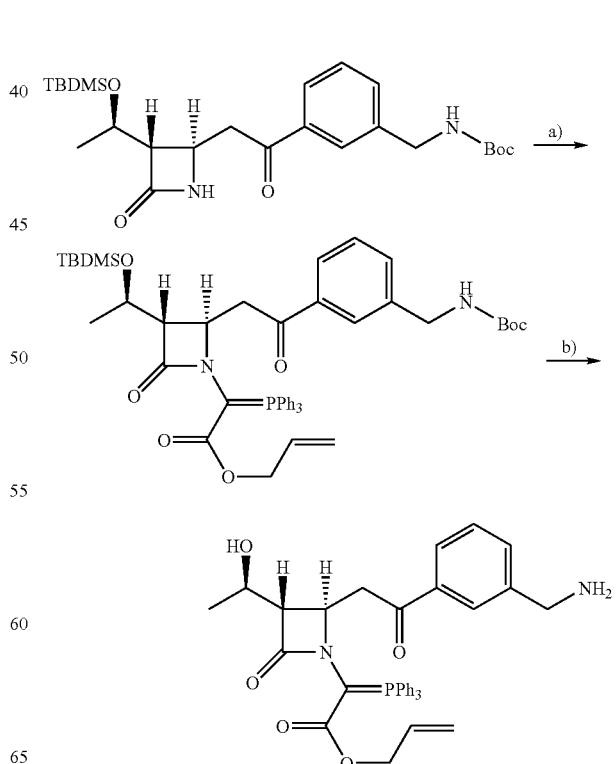

Step a)

In the same manner as reference example 2, by using tert-butyl-(3-{[(2R,3S)-3-((1R)-1-{[tert-butyl(dimethyl)silyl]oxy}ethyl)-4-oxoazetidin-2-yl]acetyl}benzyl carbamate (4.75 g) prepared by reference example 5 and by using allyl glyoxalate monohydrate instead of p-nitrobenzyl glyoxalate monohydrate, there was obtained allyl [(2R,3S)-2-[2-(3-{[(tert-butoxycabonyl)amino]methyl}phenyl)-2-oxoethyl]-3-((1R)-1-{[tert-butyl(dimethyl)silyl]oxy}ethyl)-4-oxoazetidin-1-yl](triphenylphosphoranilidene)acetate.

Step b)

The compound (1.0 g) prepared in the above step a) was dissolved in an aqueous 70% trifluoroacetic acid solution and the solution was stirred at room temperature for 1 hour. Thereto was added 0.1M phosphate buffer (pH6.86, 10 ml) and the solution was extracted with ethyl acetate (3×10 ml). The organic layers were combined, dried and filtered. The solvent was removed under reduced pressure to give allyl {(2R,3S)-2-{2-[3-(aminomethyl)phenyl]-2-oxoethyl}-3-[(1R)-1-hydroxyethyl]-4-oxoazetidin-1-yl}(triphenylphosphoranilidene)acetate.

Reference Example 7

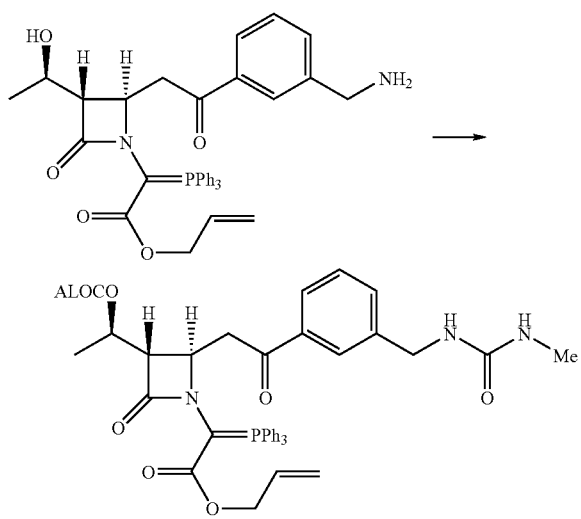

To a solution of allyl {(2R,3S)-2-{2-[3-(aminomethyl)phenyl]-2-oxoethyl}-3-[(1R)-1-hydroxyethyl]-4-oxoazetidin-1-yl}(triphenylphosphoranilidene)acetate (0.7 g) prepared by reference example 6 in THF (2 ml) were added 4-nitrophenyl methyl carbamate (196 mg) and N,N-diisopropylethylamine (0.17 ml). The mixture was stirred for 1 hour and additional 4-nitrophenyl methyl carbamate (50 mg) and N,N-diisopropylethylamine (0.17 ml) were added thereto. The mixture was stirred for 1 hour. Thereto was added 0.1M phosphate buffer (pH6.86, 10 ml) and the mixture was extracted with ethyl acetate (3×10 ml), dried over sodium sulfate and filtered. The solvent was removed under reduced pressure. The residue, triethylamine (0.17 ml) and 4-dimethylaminopyridine (7.3 mg) were dissolved in THF (2 mL) and thereto was added at 0° C. allyl chloroformate (0.095 ml). The mixture was reacted at room temperature for 14 hours. Thereto was added 0.1M phosphate buffer (pH6.86, 10 ml) and the mixture was extracted with ethyl acetate (3×10 ml), dried over sodium sulfate and filtered. The solvent was removed under reduced pressure and the residue was purified by silica gel column chromatography (ethyl acetate/methanol=100:0~10:1) to give allyl ((2R,3S)-3-((1R)-1-{[(allyloxy)carbonyl]oxy}ethyl)-2-{2-[3-({[(methylamino)carbonyl]amino}methyl)phenyl]-2-oxoethyl}-4-oxoazetidin-1-yl)(triphenylphosphoranilidene)acetate as a pale yellow oil (94 mg).

Reference Example 8

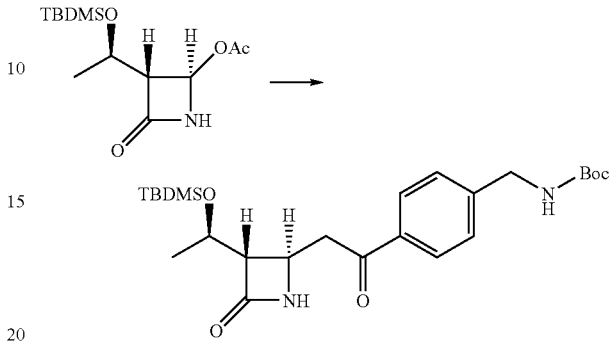

In the same manner as reference example 1, by using tert-butyl(4-{1-[(trimethylsilyl)oxy]vinyl}benzyl) carbamate instead of tert-butyl(dimethyl)(3-{1-[(trimethylsilyl)oxy]vinyl}phenoxy)silane, there was obtained tert-butyl-4-{[(2R,3S)-3-((1R)-1-{[tert-butyl(dimethyl)silyl]oxy}ethyl)-4-oxoazetidin-2-yl]acetyl}benzyl carbamate (5.53 g).

$^1$H NMR (400 MHz, CDCl$_3$) δ 0.06 (s, 3H), 0.07 (s, 3H), 0.86 (s, 9H), 1.24 (d, 3H, J=6.2 Hz), 1.45 (br, 9H), 2.87 (dd, 1H, J=2.3 Hz, 5.4 Hz), 3.14 (dd, 1H, J=10.2 Hz, 17.7 Hz), 3.43 (dd, 1H, J=3.0 Hz, 17.7 Hz), 4.08–4.12 (m, 1H), 4.18–4.24 (m, 1H), 4.37 (d, 2H, J=5.9 Hz), 4.95 (broad s, 1H), 6.11 (broad s, 1H), 7.37–7.39 (m, 2H), 7.89–7.91 (m, 2H).

Reference Example 9

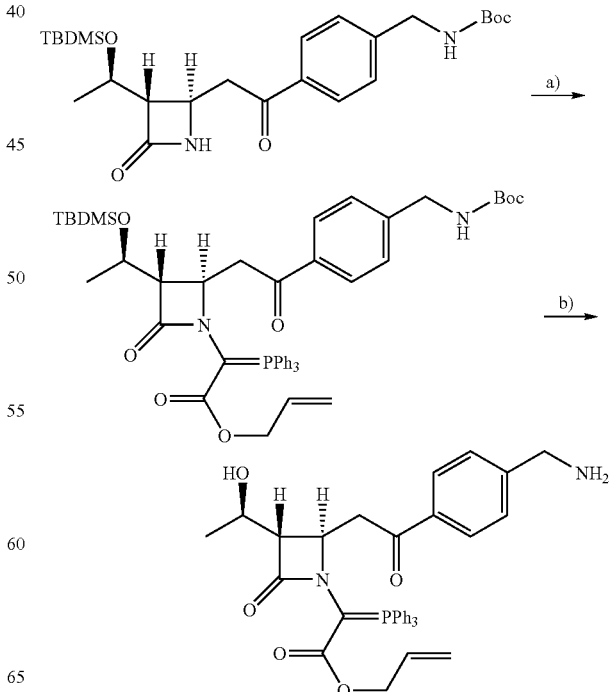

Step a)

In the same manner as reference example 2, by using tert-butyl-4-{[(2R,3S)-3-((1R)-1-{[tert-butyl(dimethyl)silyl]oxy}ethyl)-4-oxoazetidin-2-yl]acetyl}benzyl carbamate (18.7 g) prepared by reference example 8, and using allyl glyoxalate monohydrate instead of p-nitrobenzyl glyoxalate monohydrate, there was obtained allyl [(2R,3S)-2-[2-(4-{[(tert-butoxycarbonyl)amino]methyl}phenyl)-2-oxoethyl]-3-((1R)-1-{[tert-butyl(dimethyl)silyl]oxy}ethyl)-4-oxoazetidin-1-yl](triphenylphosphoranilidene)acetate.

Step b)

The compound (2.0 g) prepared in Step a) was dissolved in an aqueous 70% trifluoroacetic acid solution and the solution was reacted overnight. The solution was neutralized with an aqueous saturated sodium hydrogencarbonate solution (10 ml) and sodium hydrogencarbonate, and the mixture was extracted with chloroform (3×20 ml). The organic layers were combined, dried over magnesium sulfate and filtered. The solvent was removed under reduced pressure to give allyl {(2R,3S)-2-{2-[4-(aminomethyl)phenyl]-2-oxoethyl}-3-[(1R)-1-hydroxyethyl]-4-oxoazetidin-1-yl}(triphenylphosphoranilidene)acetate.

Reference Example 10

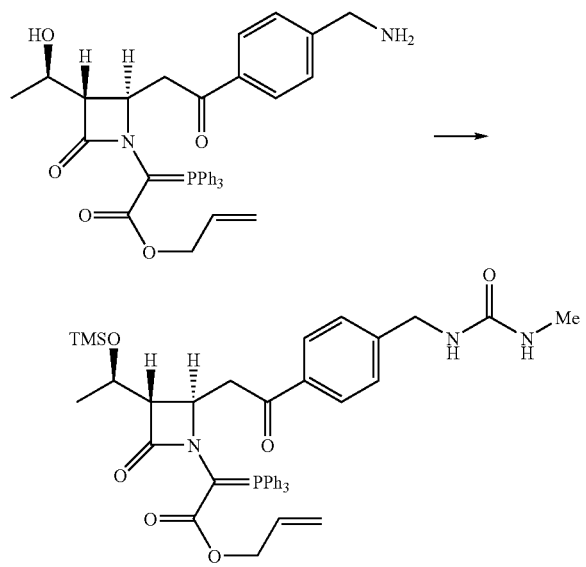

To a solution of allyl {(2R,3S)-2-{2-[4-(aminomethyl)phenyl]-2-oxoethyl}-3-[(1R)-1-hydroxyethyl]-4-oxoazetidin-1-yl}(triphenylphosphoranilidene)acetate (1.8 g) prepared by reference example 9 in THF (10 ml) were added 4-nitrophenyl methyl carbamate (565 mg) and triethylamine (0.34 ml), and the mixture was reacted overnight. Then, thereto were added triethylamine (0.34 ml), triethylamine (0.68 ml) and chlorotrimethylsilane (0.74 ml), and the mixture was stirred for 3 hours. Thereto was added 0.1M phosphate buffer (pH6.86, 30 ml) and the mixture was extracted with ethyl acetate (3×20 ml), dried over, magnesium sulfate and filtered. The solvent was removed under reduced pressure, and the residue was purified by silica gel column chromatography (chloroform/methanol=10:1) to give allyl ((2R,3S)-2-{2-[4-({[(methylamino)carbonyl]amino}methyl)phenyl]-2-oxoethyl}-4-oxo-3-{(1R)-1-[(trimethylsilyl)oxy]ethyl}azetidin-1-yl)(triphenylphosphoranilidene)acetate (0.74 g).

Reference Example 11

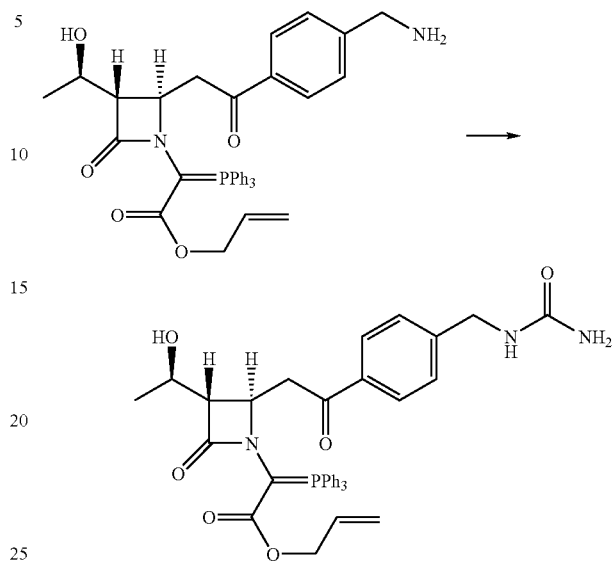

To a solution of allyl {(2R,3S)-2-{2-[4-(aminomethyl)phenyl]-2-oxoethyl}-3-[(1R)-1-hydroxyethyl]-4-oxoazetidin-1-yl}(triphenylphosphoranilidene)acetate (1.7 g) prepared by reference example 9 in THF (5 ml) was added trimethylsilylisocyanate (0.57 ml) and the solution was stirred for 2 hours. The solvent was removed under reduced pressure and the residue was purified by silica gel column chromatography (chloroform/methanol=95:5~100:20) to give allyl {(2R,3S)-2-[2-(4-{[(aminocarbonyl)amino]methyl}phenyl)-2-oxoethyl]-3-[(1R)-1-hydroxyethyl]-4-oxoazetidin-1-yl}(triphenylphosphoranilidene)acetate.

Reference Example 12

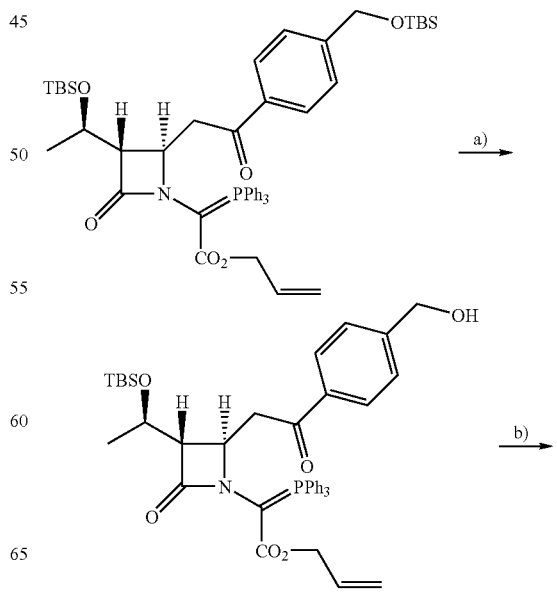

-continued

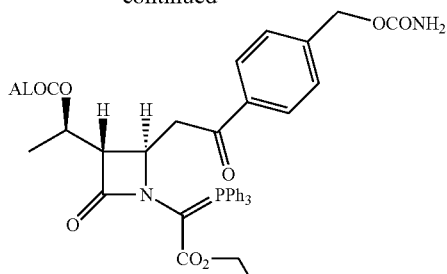

Step a)

Starting from allyl ((2R,3S)-3-((1R)-1-{[tert-butyl(dimethyl)silyl]oxy}ethyl)-2-{2-[4-({[tert-butyl(dimethyl)silyl]oxy}methyl)phenyl]-2-oxoethyl}-4-oxoazetidin-1-yl)(triphenylphosphoranilidene)acetate in the same manner as step b) of reference example 2 except for reacting under ice cooling, there was obtained allyl ((2R,3S)-3-((1R)-1-{[tert-butyl(dimethyl)silyl]oxy}ethyl)-2-{2-[4-(hydroxymethyl)phenyl]-2-oxoethyl}-4-oxoazetidin-1-yl)(triphenylphosphoranilidene)acetate.

Step b)

Allyl ((2R,3S)-3-((1R)-1-{[tert-butyl(dimethyl)silyl]oxy}ethyl)-2-{2-[4-(hydroxymethyl)phenyl]-2-oxoethyl}-4-oxoazetidin-1-yl)(triphenylphosphoranilidene)acetate (900 mg) and pyridine (a catalytic amount) were dissolved in dichloromethane (7.5 ml), and thereto was added trichloroacetyl isocyanate (345 mg). The mixture was stirred for 1 hour under ice cooling. The reaction mixture was poured into ice water, and the mixture was diluted, extracted with ethyl acetate and separated by a separating funnel. The organic layer was washed with an aqueous 5% potassium hydrogensulfate solution, water and a saturated aqueous sodium chloride solution in the order, and dried over anhydrous magnesium sulfate. The solvent was removed under reduced pressure. The residue was dissolved in acetonitrile (21 ml) and thereto was added under ice cooling borontrifluoride-diethyl ether complex (519 mg). The mixture was stirred for 15 minutes. The reaction mixture was poured into ice water, diluted, extracted with ethyl acetate, and separated with a separating funnel. The organic layer was washed with a saturated aqueous sodium chloride solution and dried over anhydrous magnesium sulfate. The solvent was removed under reduced pressure. 92/100 (by weight %) of the residue were dissolved in dichloromethane (6 ml) under ice cooling and thereto were added 4-dimethylaminopyridine (410 mg) and allyl chloroformate (270 mg). The mixture was stirred for 3 hours. The reaction mixture was poured into ice water and diluted with ethyl acetate. After the aqueous layer was acidified with an aqueous 5% potassium hydrogensulfate solution, the mixture was extracted and separated with a separating funnel. The organic layer was washed with a saturated aqueous sodium chloride solution, an aqueous sodium hydrogencarbonate solution and a saturated aqueous sodium chloride solution in the order, and dried over anhydrous magnesium sulfate. The solvent was removed under reduced pressure. The residue was dissolved in methanol (30 ml), and thereto was added a silica gel (10.5 g). The mixture was left to stand at room temperature for 3 days. To the reaction mixture was added chloroform (150 ml) and silica gel was filtered off. The filtrate was washed with chloroform/methanol. The filtrate was concentrated under reduced pressure and the residue was purified by silica gel column chromatography (hexane/ethyl acetate, followed by ethyl acetate/acetone) to give allyl {(2R,3S)-3-((1R)-1-{[(allyloxy)carbonyl]oxy}ethyl)-2-[2-(4-{[(aminocarbonyl)oxy]methyl}phenyl)-2-oxoethyl]-4-oxoazetidin-1-yl}(triphenylphosphoranilidene)acetate (409 mg).

Reference Example 13

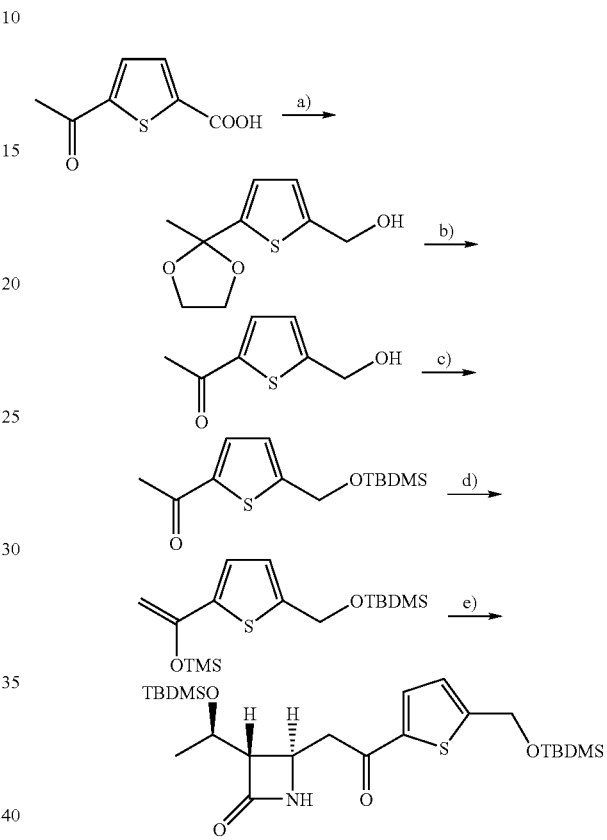

Step a)

A mixture of 5-acetylthiophene-2-carboxylic acid (41.44 g), p-toluenesulfonic acid monohydrate (926 mg), ethylene glycol (226 g) and toluene (500 ml) was refluxed under heating for 13 hours and subjected to azeotropic dehydration. The reaction mixture was washed with a saturated aqueous sodium hydrogencarbonate solution and a saturated aqueous sodium chloride solution, and dried over anhydrous sodium sulfate. The solvent was removed under reduced pressure to give a brawn solution. This product was dissolved in THF (500 ml) and the solution was gradually dropped to a mixture of lithium aluminum hydride (19.22 g) and THF (750 ml) under ice cooling. Two hours later, thereto was added a 10% aqueous sodium hydroxide solution (1000 ml). After the removal of insoluble materials, the filtrate was extracted with ethyl acetate. The organic layer was washed with water (twice) and was dried over anhydrous sodium sulfate. The solvent was removed under reduced pressure to give [5-(2-methyl-1,3-dioxolan-2-yl)thien-2-yl]methanol. This product was used in the next step without purification.

Step b)

To a solution of [5-(2-methyl-1,3-dioxolan-2-yl)thien-2-yl]methanol prepared in the above step in THF (240 ml) was added 1N hydrochloric acid (48 ml) and the mixture was stirred for 2 hours at room temperature. Thereto was added sodium hydrogencarbonate (4.04 g) and the mixture was extracted with ethyl acetate. The organic layer was washed with a saturated aqueous sodium chloride solution and dried over anhydrous sodium sulfate. The solvent was removed under reduced pressure to give 1-[5-(hydroxymethyl)thien-2-yl]ethanone. This product was used in the next step without purification.

Step c)

To a solution of 1-[5-(hydroxymethyl)thien-2-yl]ethanone prepared in the above step in DMF (84 ml) was added imidazole (27.11 g) and thereto was dropped under ice cooling tert-butyldimethylchlorosilane (30.01 g). Thirty minutes later, thereto was added ice water (250 ml) and the mixture was extracted with ethyl acetate. The organic layer was washed with a saturated aqueous sodium chloride solution, and dried over anhydrous sodium sulfate. The solvent was removed under reduced pressure and the residue was purified by silica gel column chromatography (hexane/ethyl acetate) to give 1-[5-({[tert-butyl(dimethyl)silyl]oxy}methyl)thien-2-yl]ethanone (46.53 g).

$^1$H NMR (400 MHz, CDCl$_3$) δ 0.11 (s, 6H), 0.93 (s, 9H), 2.53 (s, 3H), 4.87 (d, 2H, J=0.9 Hz), 6.92 (d, 1H, J=3.8 Hz), 7.56 (d, 1H, J=3.8 Hz).

Step d)

To a solution of 1-[5-({[tert-butyl(dimethyl)silyl]oxy}methyl)thien-2-yl]ethanone (19.75 g) in THF (200 ml) was added triethylamine (11.08 g). To the mixture was dropped at −78° C. 1N-lithium hexamethyldisilazane (87.63 ml), followed by chlorotrimethylsilane (9.52 g) and the mixture was stirred for 1 hour. Thereto was added hexane (200 ml) and the mixture was poured into water (300 ml) and extracted with hexane. The organic layer was washed with a saturated aqueous sodium chloride solution, and dried over anhydrous sodium sulfate. The solvent was removed under reduced pressure to give tert-butyl(dimethyl)[(5-{1-[(trimethylsilyl)oxy]vinyl}thien-2-yl)methoxy]silane. This product was used in the next step without purification.

Step e)

In the same manner as reference example 3, from tert-butyl(dimethyl)[(5-{1-[(trimethylsilyl)oxy]vinyl}thien-2-yl)methoxy]silane prepared in the above step and (2R,3R)-3-((1R)-1-{[tert-butyl(dimethyl)silyl]oxy}ethyl)-4-oxo-2-azetidinyl acetate (20.99 g), there was obtained (3S,4R)-3-((1R)-1-{[tert-butyl(dimethyl)silyl]oxy}ethyl)-4-{2-[5-({[tert-butyl(dimethyl)silyl]oxy}methyl) thien-2-yl]-2-oxoethyl}azetidin-2-one (10.32 g).

$^1$H NMR (400 MHz, CDCl$_3$) δ 0.069 (s, 3H), 0.075 (s, 3H), 0.12 (s, 3H+3H), 0.87 (s, 9H), 0.94 (s, 9H), 1.24 (d, 3H, J=6.2 Hz), 2.87 (dd, 1H, J=5.4 Hz, 2.2 Hz), 3.07 (dd, 1H, J=16.9 Hz, 10.1 Hz), 3.34 (dd, 1H, J=6.9 Hz, 3.3 Hz), 4.07–4.11 (m, 1H), 4.18–4.24 (m, 1H), 4.89 (d, 2H, J=0.7Hz), 6.08 (s, 1H), 6.94 (s, 1H, J=3.9 Hz), 7.58 (d, 1H, J=3.9 Hz).

Reference Example 14

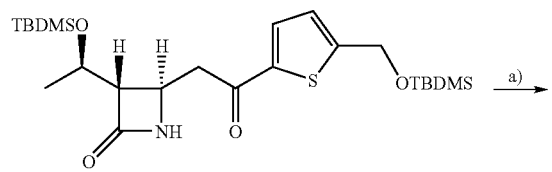

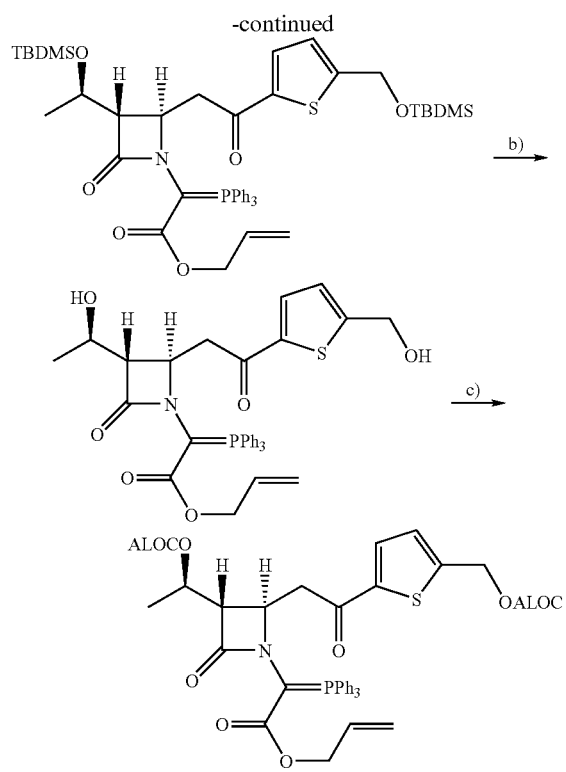

Step a)

In the same manner as reference example 4, from (3S,4R)-3-((1R)-1-{[tert-butyl(dimethyl)silyl]oxy}ethyl)-4-{2-[5-({[tert-butyl(dimethyl)silyl]oxy}methyl)thien-2-yl]-2-oxoethyl}azetidin-2-one (4.92 g) prepared by reference example 12, there was obtained allyl ((2R,3S)-3-((1R)-1-{[tert-butyl(dimethyl)silyl]oxy}ethyl)-2-{2-[5-({[tert-butyl(dimethyl)silyl]oxy}methyl)thien-2-yl]-2-oxoethyl}-4-oxoazetidin-1-yl)(triphenylphosphoranilidene)acetate (2.90 g).

LC-MS (m/e): 856 (M+1).

Step b)

To a solution of allyl ((2R,3S)-3-((1R)-1-{[tert-butyl(dimethyl)silyl]oxy}ethyl)-2-{2-[5-({[tert-butyl(dimethyl)silyl]oxy}methyl)thien-2-yl]-2-oxoethyl}-4-oxoazetidin-1-yl)(triphenylphosphoranilidene)acetate (2.90 g) prepared in the above step in acetonitrile (58 ml) was added at 0° C. borontrifluoride diethyl ether (2.89 g) and the mixture was stirred at room temperature for 24 hours. Thereto was added 0.1M phosphate buffer (pH6.86, 87 ml) and the solution was extracted with ethyl acetate. The organic layer was washed with a saturated aqueous sodium chloride solution and dried over anhydrous sodium sulfate. The solvent was removed under reduced pressure to give allyl ((2R,3S)-3-[(1R)-1-hydroxyethyl]-2-{2-[5-hydroxymethyl)thien-2-yl]-2-oxoethyl}-4-oxoazetidin-1-yl)(triphenylphosphoranilidene)acetate. This product was used in the next step without purification.

Step c)

To a solution of allyl ((2R,3S)-3-[(1R)-1-hydroxyethyl]-2-{2-[5-(hydroxymethyl)thien-2-yl]-2-oxoethyl}-4-oxoazetidin-1-yl)(triphenylphosphoranilidene)acetate prepared in the above step in dichloromethane (30 ml) was added N,N-dimethylaminopyridine (2.98 g) and to the mixture was added at under ice cooling allyl chloroformate (2.45 g). The mixture was stirred at room temperature overnight and diluted with chloroform and a cold aqueous potassium hydrogensulfate, and separated with a separating funnel. The organic layer was washed successively with a saturated aqueous sodium chloride solution, an aqueous sodium hydrogencarbonate solution and a saturated aqueous sodium chloride solution and dried over anhydrous sodium sulfate. The solvent was removed under reduced pressure and the residue was purified by silica gel column chromatography (hexane/ethyl acetate) to give allyl ((2R,3S)-3-((1R)-1-{[(allyloxy)carbonyl]oxy}ethyl)-2-{2-[5-({[(allyloxy)carbonyl]oxy}methyl)thien-2-yl]-2-oxoethyl}-4-oxoazetidin-1-yl)(triphenylphosphoranilidene)acetate (2. 56 g).

Reference Example 15

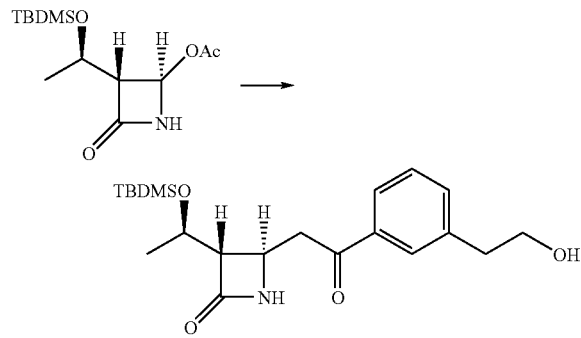

In the same manner as reference example 1, by using triethyl [2-(3-{1n-[(trimethylsilyl)oxy]vinyl}phenyl)ethoxy]silane instead of tert-butyl(dimethyl)(3-(1-[(trimethylsilyl)oxy]vinyl}phenoxy)silane, there was obtained (3S,4R)-3-((1R)-1-{[tert-butyl(dimethyl)silyl]oxy}ethyl)-4-{2-[3-(2-hydroxyethyl)phenyl]-2-oxoethyl}azetidin-2-one.

¹H NMR (400 MHz, CDCl₃) δ 0.08 (s, 3H), 0.09 (s, 3H), 0.88 (s, 9H), 1.26 (d, 3H, J=6.2 Hz), 1.46 (br. t, 1H, J=4.8 Hz), 2.89 (dd, 1H, J=2.3 Hz, 5.4 Hz), 2.95 (t, 2H, J=6.5 Hz), 3.18 (dd, 1H, J=10.2 Hz, 17.7 Hz), 3.46 (dd, 1H, J=3.0 Hz, 17.7 Hz), 3.91 (broad dt, 2H, J=4.8 Hz, 6.5 Hz), 4.10–4.14 (m, 1H), 4.20–4.26 (m, 1H), 6.13 (broad s, 1H), 7.42–7.52 (m, 2H), 7.80–7.83 (m, 2H).

Reference Example 16

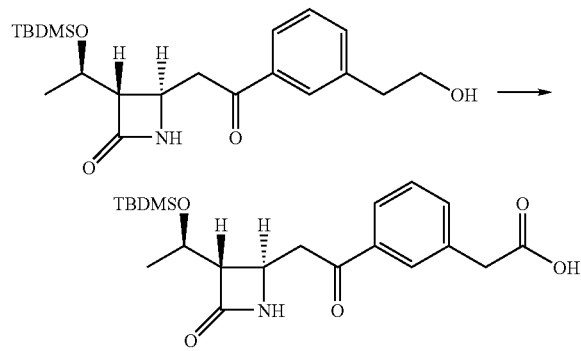

(3S,4R)-3-((1R)-1-{[tert-Butyl(dimethyl)silyl]oxy}ethyl)-4-{2-[3-(2-hydroxyethyl)phenyl]-2-oxoethyl}azetidin-2-one (3.0 g) prepared by reference example 15 and ruthenium trichloride (79 mg) were dissolved in acetone (77 ml) and to the solution was added at room temperature a solution of sodium periodate (3.3 g) in water (40 ml). The solution was stirred for 30 minutes. Further, a solution of sodium periodate (0.66 g) in water (4 ml) was added thereto and the solution was stirred for 3 hours. After removal of insoluble materials by filtration with celite, acetone was removed under reduced pressure. To the aqueous layer (about 50 ml) was added a saturated aqueous sodium chloride solution (100 ml) and the mixture was extracted with ethyl acetate (3×50 ml). The organic layers were combined, dried over magnesium sulfate and filtered. The solvent was removed under reduced pressure to give (3-{[(2R,3S)-3-((1R)-1-{[tert-butyl(dimethyl)silyl]oxy}ethyl)-4-oxoazetidin-2-yl]acetyl}phenyl)acetic acid (2.72 g).

¹H NMR (400 MHz, CDCl₃) δ 0.07 (s, 3H), 0.08 (s, 3H), 0.87 (s, 9H), 1.24 (d, 3H, J=6.2 Hz), 2.91 (dd, 1 H, J=2.2, 5.2 Hz), 3.19 (dd, 1H, J=10.0 Hz, 17.7 Hz), 3.43 (dd, 1H, J=3.1 Hz, 17.7 Hz), 3.72 (s, 2H), 4.11–4.19 (m, 1H), 4.20–4.26 (m, 1H), 6.39 (broad s, 1H), 7.44–7.53 (m, 2H), 7.84–7.88 (m, 2H).

Reference Example 17

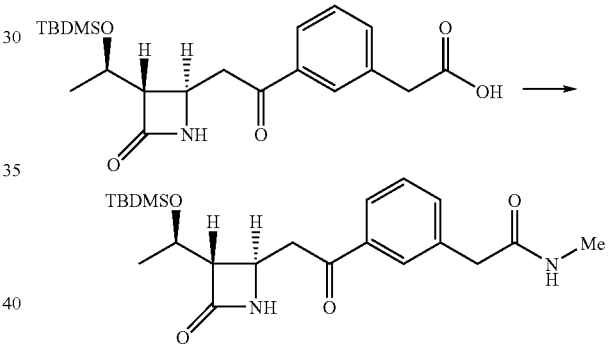

To a solution of (3-{[(2R,3S)-3-((1R)-1-{[tert-butyl(dimethyl)silyl]oxy}ethyl)-4-oxoazetidin-2-yl]acetyl}phenyl)acetic acid (2.62 g) prepared in reference example 16, 4-dimethylaminopyridine (78 mg) and 2.0M methylamine/THF (3.3 ml) in dichloromethane (25 ml) was added at 0° C. 1-ethyl-3-(dimethylaminopropyl)carbodiimide hydrochloride (1.24 g) and the mixture was stirred for 6 hours. Further, 1-ethyl-3-(dimethylaminopropyl)carbodiimide hydrochloride (0.13 g) and 2.0M methylamine/THF (0.33 ml) were added thereto and the mixture was reacted overnight. To the mixture was added an aqueous saturated ammonium chloride solution (50 ml) and the mixture was extracted with ethyl acetate.(100 ml). The organic layer was washed with a saturated aqueous sodium chloride solution (2×50 ml), dried over magnesium sulfate and filtered. The solvent was removed under reduced pressure and the residue was purified by silica gel column chromatography (chloroform/methanol) to give 2-(3-{[(2R,3S)-3-((1R)-1-{[tert-butyl(dimethyl)silyl]oxy}ethyl)-4-oxoazetidin-2-yl]acetyl}phenyl)-N-methylacetamide (1.96 g).

¹H NMR (300 MHz, CDCl₃) δ 0.08 (s, 3H), 0.09 (s, 3H), 0.88 (s, 9), 1.26 (d, 3H, J=6.3 Hz), 2.79 (d, 3H, J=5.0 Hz), 2.89 (dd, 1H, J=2.3, 5.4 Hz), 3.17 (dd, 1H, J=10.1 Hz, 17.8 Hz), 3.47 (dd, 1H, J=2.9 Hz, 17.8 Hz), 3.62 (s, 2H), 4.12–4.16 (m, 1H), 4.20–4.28 (m, 1H), 5.62 (broad s, 1H), 6.33 (broad s, 1H), 7.45–7.50 (m, 1H), 7.54–7.57 (m, 1H), 7.84–7.87 (m, 2H).

Reference Example 18

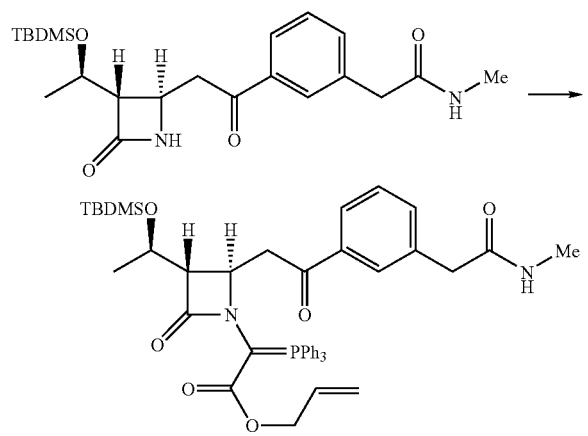

By using 2-(3-{[(2R,3S)-3-((1R)-1-{[tert-butyl(dimethyl)silyl]oxy}ethyl)-4-oxoazetidin-2-yl]acetyl}phenyl)-N-methylactetamide (1.96 g) prepared by reference example 17 and by using allyl glyoxalate monohydrate instead of p-nitrobenzyl glyoxalate monohydrate in the same manner as step a) of reference example 2, there was obtained allyl [(2R,3S)-3-((1R)-1-{[tert-butyl(dimethyl)silyl]oxy}ethyl)-2-(2-{3-[2-(methylamino)-2-oxoethyl]phenyl}-2-oxoethyl)-4-oxoazetidin-1-yl](triphenylphosphoranilidene)acetate (2.73 g).

Reference Example 19

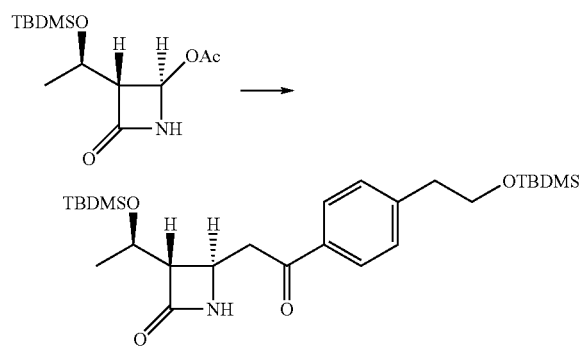

By using tert-butyl(dimethyl)[2-(4-{1-[(trimethylsilyl)oxy]vinyl}phenyl)ethoxy]silane in stead of tert-butyl(dimethyl) (3-{ 1-[(trimethylsilyl)oxy]vinyl}phenoxy) silane in the same manner as reference example 1, there was obtained (3S,4R)-3-((1R)-1-{[tert-butyl(dimethyl)silyl]oxy}ethyl)-4-{2-[4-(2-{[tert-butyl(dimethyl)silyl]oxy}ethyl)phenyl]-2-oxoethyl}azetidin-2-one (16.3 g).

$^1$H NMR (300 MHz, CDCl$_3$) δ 0.00 (s, 6H), 0.11 (s, 3H), 0.12 (s, 3H), 0.89 (s, 9H), 0.91 (s, 9H), 1.29 (d, 3H, J=6.0 Hz), 2.87–2.94 (m, 3H), 3.19 (dd, 1H, J=10.2 Hz, 17.6 Hz), 3.49 (dd, 1H, J=3.0 Hz, 17.6 Hz), 3.85–3.89 (m, 2H), 4.13–4.18 (m, 1H), 4.24–4.28 (m, 1H), 6.16 (broad s, 1H), 7.32–7.38 (m, 2H), 7.89–7.93 (m, 2H).

Reference Example 20

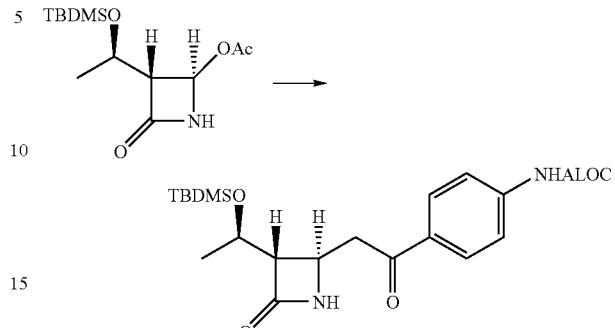

There was obtained allyl 4-{[(2R,3S)-3-((1R)-1-{[tert-butyl(dimethyl)silyl]oxy}ethyl)-4-oxoazetidin-2-yl]acetyl}phenyl carbamate in the same manner as reference example 1.

$^1$H NMR (400 MHz, CDCl$_3$) δ 0.07 (s, 6H), 0.87 (s, 9H), 1.24 (d, 3H, J=6.2 Hz), 2.86–2.89 (m, 1H), 3.08–3.16 (m, 1H), 3.39–3.45 (m, 1H), 4.09–4.13 (m, 1H), 4.18–4.25 (m, 1H), 4.69 (d, 2H, J=5.8 Hz),5.25–5.42 (m, 2H), 5.92–6.01 (m, 1H), 6.15 (s, 1H), 7.52 (d, 2H, J=8.7 Hz), 7.91 (d, 2H, J=8.7 Hz)

Reference Example 21

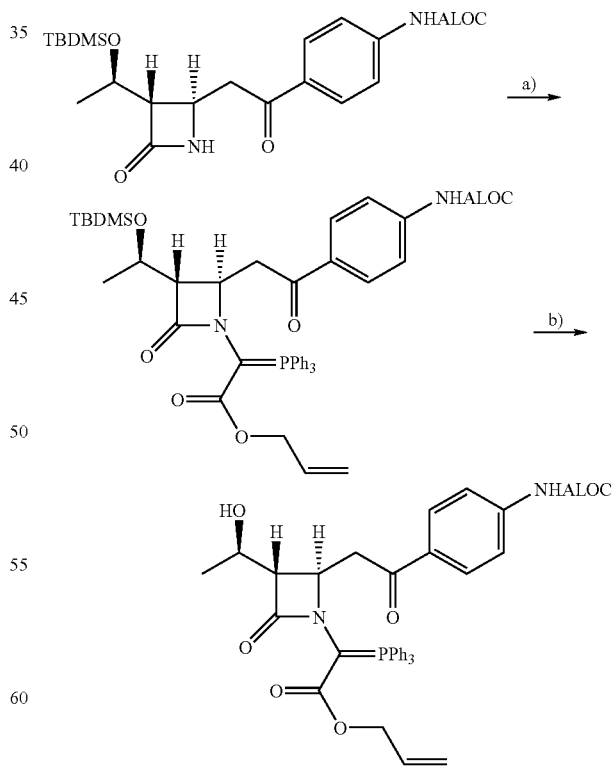

Step a)

By using allyl 4-{[(2R,3S)-3-((1R)-1-{[tert-butyl(dimethyl)silyl]oxy}ethyl)-4-oxoazetidin-2-yl]

acetyl}phenylcarbamate in the same manner as step a) of reference example 9, there was obtained allyl [(2R,3S)-2-[2-(4-{[(allyloxy)carbonyl]amino}phenyl)-2-oxoethyl]-3-((1R)-1-{[tert-butyl(dimethyl)silyl]oxy}ethyl)-4-oxoazetidin-1-yl](triphenylphosphoranilidene)acetate.

LC/MS (EI) 805 (M+1)

Step b)

There was obtained allyl [(2R,3S)-2-[2-(4-{[(allyloxy)carbonyl]amino}phenyl)-2-oxoethyl]-3-[(1R)-1-hydroxyethyl]-4-oxoazetidin-1-yl](triphenylphosphoranilidene)acetate in the same manner as step b) of reference example 9.

LC/MS (EI) 691 (M+1)

Reference Example 22

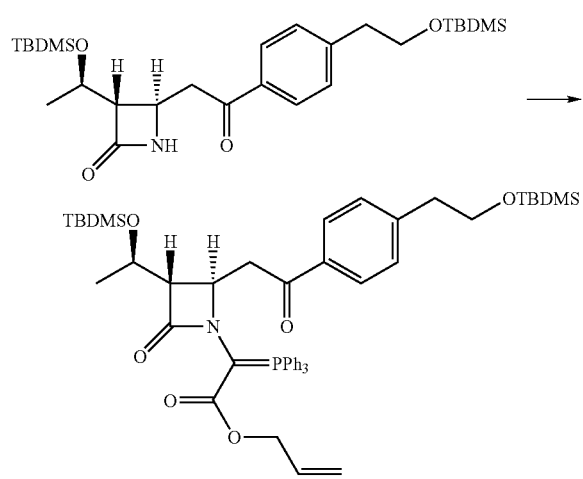

Step a)

In the same manner as step a) of reference example 9, by using (3S,4R)-3-((1R)-1-{[tert-butyl(dimethyl)silyl]oxy}ethyl)-4-{2-[4-(2-{tert-butyl(dimethyl)silyl]oxy}ethyl)phenyl]-2-oxoethyl}azetidin-2-one, there was obtained allyl ((2R,3S)-3-((1R)-1-{[tert-butyl(dimethyl)silyl]oxy}ethyl)-2-{2-[4-(2-{[tert-butyl(dimethyl)silyl]oxy}ethyl)phenyl]-2-oxoethyl}-4-oxoazetidin-1-yl)(triphenylphosphoranilidene)acetate.

LC/MS (EI) 865 (M+1)

Reference Example 23

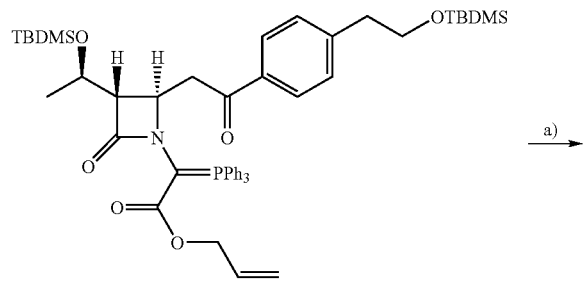

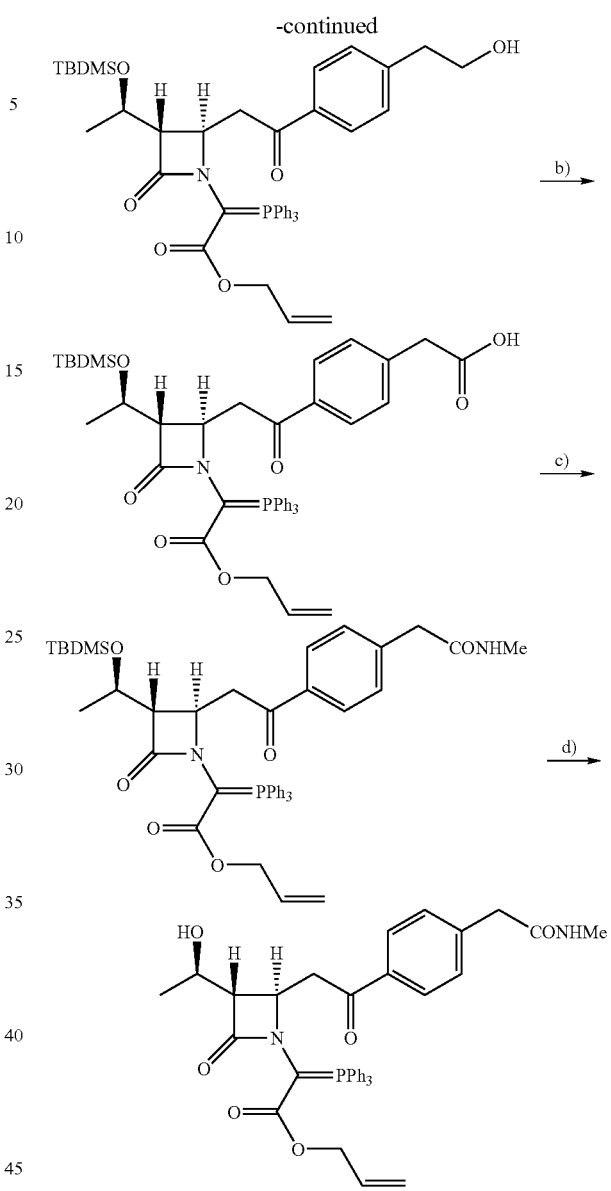

Step a)

To a solution of allyl ((2R,3S)-3-((1R)-1-{[tert-butyl(dimethyl)silyl]oxy}ethyl)-2-{2-[4-(2-{[tert-butyl(dimethyl)silyl]oxy}ethyl)phenyl]-2-oxoethyl}-4-oxoazetidin-1-yl)(triphenylphosphoranilidene)acetate (25.7 g) in THF (300 ml) were added acetic acid (2.95 ml) and a solution of 1M tetrabutylammonium fluoride/THF (26 ml), and the mixture was stirred for 24 hours. The solution was diluted with ethyl acetate and washed with a saturated aqueous sodium chloride solution. The organic layer was dried and concentrated, and the residue was purified by silica gel column chromatography (ethyl acetate) to give allyl ((2R,3S)-3-((1R)-1-{[tert-butyl(dimethyl)silyl]oxy}ethyl)-2-{2-[4-(2-hydroxyethyl)phenyl]-2-oxoethyl}-4-oxoazetidin-1-yl)(triphenylphosphoranilidene)acetate (15.3 g).

LC/MS (EI) 750 (M+1)

Step b)

To a solution of the compound (3 g) prepared in the above step in acetone (30 ml) was added Jones reagent (3 ml).

Thirty minutes later, the mixture was diluted with ethyl acetate and washed with water. The organic layer was dried and concentrated to give (4-{[(2R,3S)-1-[2-(allyloxy)-2-oxo-1-(triphenylphosphoranilidene)ethyl]-3-((1R)-1-{[tert-butyl(dimethyl)silyl]oxy}ethyl)-4-oxoazetidin-2-yl]acetyl}phenyl)acetic acid (3.17 g).

LC/MS (EI) 764 (M+1)

Step c)

To a solution of the compound (3.17 g) prepared in the above step in dichloromethane (30 ml) were added N,N-dimethylformamide (0.04 ml) and thionyl chloride (0.37 ml). One and a half hours later, the reaction mixture was dropped to a mixture of an aqueous 40% methylamine solution (30 ml) and dichloromethane (101 ml). The reaction mixture was diluted with ethyl acetate and washed with an aqueous sodium hydrogencarbonate solution and a saturated aqueous sodium chloride solution. The organic layer was dried and concentrated to give allyl [(2R,3S)-3-((1R)-1-{[tert-butyl(dimethyl)silyl]oxy}ethyl)-2-(2-{4-[2-(methylamino)-2-oxoethyl]phenyl}-2-oxoethyl)-4-oxoazetidin-1-yl](triphenylphosphoranilidene)acetate.

LC/MS (EI) 777 (M+1)

Step d)

A solution of the compound prepared in the above step in an aqueous 70% trifluoroacetic acid (45 ml) was stirred for 1 hour. After concentrating the reaction solution, the mixture was diluted with ethyl acetate and washed with a saturated aqueous sodium hydrogencarbonate solution and a saturated aqueous sodium chloride solution. The organic layer was dried, concentrated and the residue was purified by silica gel column chromatography (ethyl acetate: ethanol=5:1) to give allyl [(2R,3S)-3-[(1R)-1-hydroxyethyl]-2-(2-{4-[2-(methylamino)-2-oxoethyl]phenyl}-2-oxoethyl)-4-oxoazetidin-1-yl](triphenylphosphoranilidene)acetate (1.82 g).

LC/MS (EI) 663 (M+1)

Reference Example 24

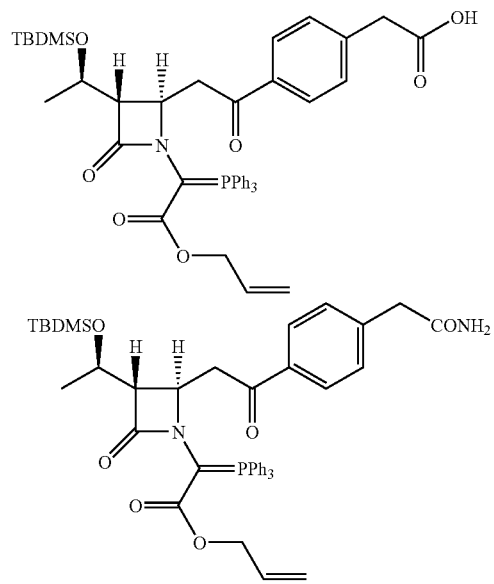

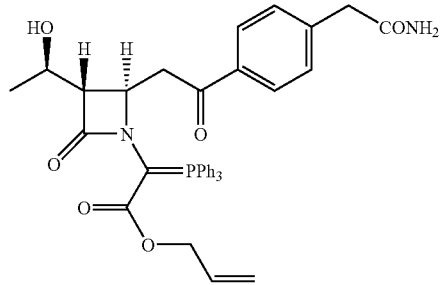

Step a)

In the same manner as step c) of reference example 23, from (4-{[(2R,3S)-1-[2-(allyloxy)-2-oxo-1-(triphenylphosphoranilidene)ethyl]-3-((1R)-1-{[tert-butyl(dimethyl)silyl]oxy}ethyl)-4-oxoazetidin-2-yl]acetyl}phenyl)acetic acid, there was obtained allyl [(2R,3S)-2-{2-[4-(2-amino-2-oxoethyl)phenyl]-2-oxoethyl}-3-((1R)-1-{[tert-butyl(dimethyl)silyl]oxy}ethyl)-4-oxoazetidin-1-yl](triphenylphosphoranilidene)acetate.

LC/MS (EI) 763 (M+1)

Step b)

In the same manner as step d) of reference example 23, from allyl [(2R,3S)-2-{2-[4-(2-amino-2-oxoethyl)phenyl]-2-oxoethyl}-3-((1R)-1-butyl(dimethyl)silyl]oxy}ethyl)-4-oxoazetidin-1-yl](triphenylphosphoranilidene)acetate, there was obtained allyl [(2R,3S)-2-{2-[4-(2-amino-2-oxoethyl)phenyl]-2-oxoethyl}-3-[(1R)-1-hydroxyethyl]-4-oxoazetidin-1-yl](triphenylphosphoranilidene)acetate.

LC/MS (EI) 649 (M+1)

Reference Example 25

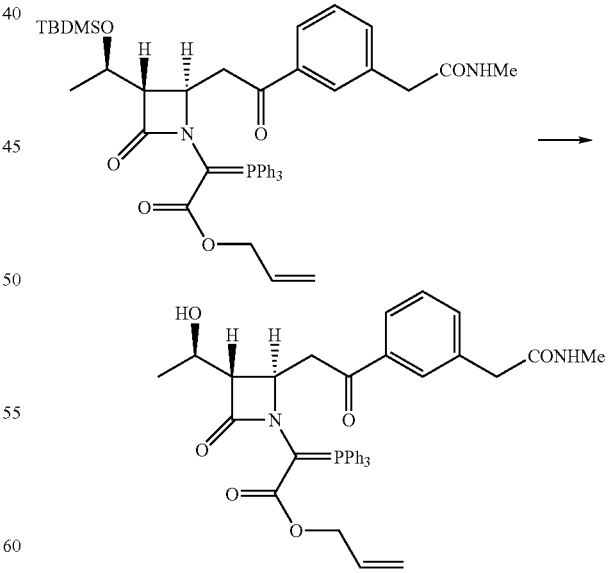

In the same manner as step d) of reference example 23, from allyl [(2R,3S)-3-((1R)-1-{[tert-butyl(dimethyl)silyl]oxy}ethyl)-2-(2-{3-[2-(methylamino)-2-oxoethyl]phenyl}-2-oxoethyl)-4-oxoazetidin-1-yl](triphenylphosphoranilidene)acetate, there was obtained allyl [(2R,3S)-3-[(1R)-1- hydroxyethyl]-2-(2-{3-[2-(methylamino)-2-oxoethyl]phenyl}-2-oxoethyl)-4-oxoazetidin-1-yl](triphenylphosphoranilidene)acetate.

LC/MS (EI) 663 (M+1)

Reference Example 26

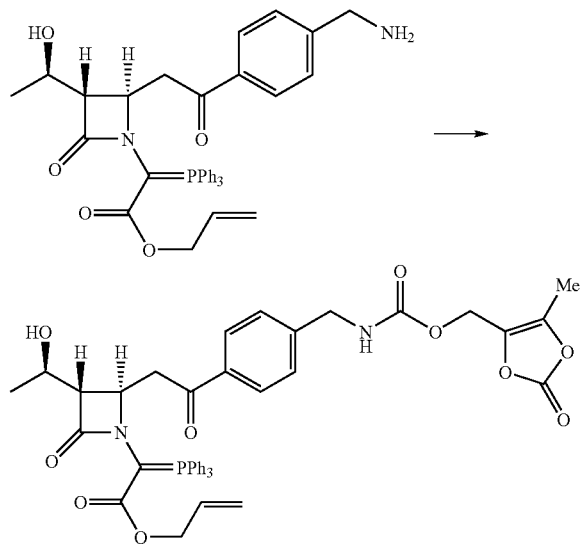

To a solution of allyl {(2R,3S)-2-{2-[4-(aminomethyl)phenyl]-2-oxoethyl}-3-[(1R)-1-hydroxyethyl]-4-oxoazetidin-1-yl}(triphenylphosphoranilidene)acetate (1.6 g) prepared by reference example 9 and triethylamine (0.35 ml) in THF (13 ml) was added at 0° C. (5-methyl-2-oxo-1,3-dioxol-4-yl)methyl 4-nitrophenylcarbonate (0.40 g) and the mixture was stirred for 2 hours. Further, thereto were added (5-methyl-2-oxo-1,3-dioxol-4-yl)methyl 4-nitrophenylcarbonate (0.80 g) and triethylamine (0.35 ml), and the mixture was reacted at room temperature for 34 hours. To the reaction mixture was added a saturated aqueous sodium chloride solution (50 ml) and the mixture was extracted with ethyl acetate (3×50 ml). The organic layers were combined and dried over anhydrous magnesium sulfate. The solvent was removed under reduced pressure and the residue was purified by silica gel column chromatography (chloroform/methanol=10:1) to give allyl [(2R,3S)-3-[(1R)-1-hydroxyethyl]-2-(2-{4-[({[(5-methyl-2-oxo-1,3-dioxol-4-yl)methoxy]carbonyl}amino)methyl]phenyl}-2-oxoethyl)-4-oxoazetidin-1-yl](triphenylphosphoranilidene)acetate (0.52 g).

Reference Example 27

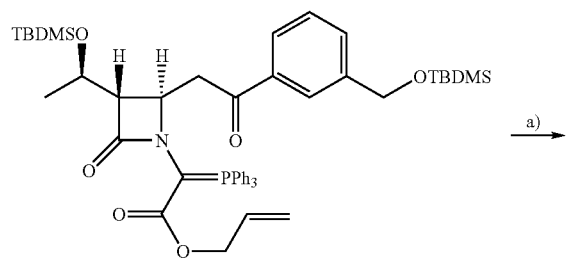

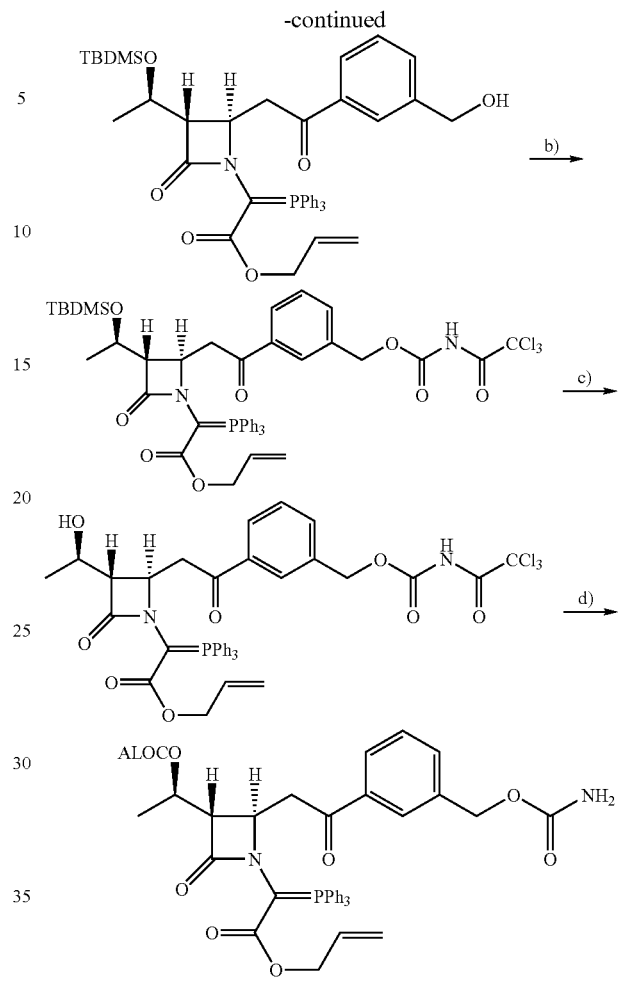

Step a)

In the same manner as step a) of reference example 12, from allyl ((2R,3S)-3-((1R)-1-{[tert-butyl(dimethyl)silyl]oxy}ethyl)-2-{2-[3-({[tert-butyl(dimethyl)silyl]oxy}methyl)phenyl]-2-oxoethyl}-4-oxoazetidin-1-yl)(triphenylphosphoranilidene)acetate (1.978 g), there was obtained allyl ((2R,3S)-3-((1R)-1-{[tert-butyl(dimethyl)silyl]oxy}ethyl)-2-{2-[3-(hydroxymethyl)phenyl]-2-oxoethyl}-4-oxoazetidin-1-yl)(triphenylphosphoranilidene)acetate (1.358 g, pale yellow amorphous). Allyl ((2R,3S)-3-((1R)-1-{[tert-butyl(dimethyl)silyl]oxy}ethyl)-2-{2-[3-({[tert-butyl(dimethyl)silyl]oxy}methyl)phenyl]-2-oxoethyl}-4-oxoazetidin-1-yl)(triphenylphosphoranilidene)acetate (0.308 g), the starting material was recovered.

Allyl ((2R,3S)-3-((1R)-1-{[tert-butyl(dimethyl)silyl]oxy}ethyl)-2-{2-[3-({[tert-butyl(dimethyl)silyl]oxy}methyl)phenyl]-2-oxoethyl}-4-oxoazetidin-1-yl)(triphenylphosphoranilidene)acetate IR(ATR) 2953, 2927, 2885, 2856, 1743, 1682, 1620, 1437, 1371, 1252, 1103, 833, 775, 690 cm$^{-1}$. LC/MS (EI) 851 (M+1)+.

Allyl ((2R,3S)-3-((1R)-1-{[tert-butyl(dimethyl)silyl]oxy}ethyl)-2-{2-[3-(hydroxymethyl)phenyl]-2-oxoethyl}-4-oxoazetidin-1-yl)(triphenylphosphoranilidene)acetate IR(ATR) 3417(broad), 2951, 2927, 1740, 1678, 1620, 1439, 1373, 1242, 1103, 833, 775, 752, 717, 690 cm$^{-1}$. LC/MS (EI) 737 (M+1)+.

Step b)

To a solution of allyl ((2R,3S)-3-((1R)-1-{[tert-butyl(dimethyl)silyl]oxy}ethyl)-2-{2-[3-(hydroxymethyl)phenyl]-2-oxoethyl}-4-oxoazetidin-1-yl)(triphenylphosphoranilidene)acetate(1.341 g) and pyridine (a catalytic amount) in dichloromethane (11 ml) was added trichloroacetyl isocyanate (514 mg) and the mixture was stirred under ice cooling for 1 hour. The reaction mixture was poured into ice water, diluted, extracted with ethyl acetate and separated by a separating funnel. The organic layer was washed with a cold aqueous 5% potassium hydrogensulfate solution, a saturated aqueous sodium chloride solution, a saturated aqueous sodium hydrogencarbonate solution and a saturated aqueous sodium chloride solution, and dried over anhydrous magnesium sulfate. The solvent was removed under reduced pressure to give allyl [(3S,4R)-3-((1R)-1-{[tert-butyl(dimethyl)silyl]oxy}ethyl)-2-oxo-4-(2-oxo-2-{3-[({[(trichloroacetyl)amino]carbonyl}oxy)methyl]phenyl}ethyl)azetidin-1-yl](triphenylphosphoranilidene)acetate (pale yellow amorphous).

LC/MS (EI) 925.5 (M+1)+. IR(ATR) 2951, 2931, 1797, 1724, 1605, 1439, 1246, 1169, 1103, 829, 690 cm$^{-1}$.

Step c)

Allyl [(3S,4R)-3-((1R)-1-{[tert-butyl(dimethyl)silyl]oxy}ethyl)-2-oxo-4-(2-oxo2-{3-[({[(trichloroacetyl)amino]carbonyl}oxy)methyl]phenyl}ethyl)azetidin-1-yl](triphenylphosphoranilidene)acetate prepared in step b) without purification, was dissolved in acetonitrile (31 ml), and thereto was added under ice cooling boron trifluoride-diethyl ether (568 mg). The mixture was stirred at room temperature for 20 hours. The reaction mixture was poured into ice water, diluted, extracted with ethyl acetate and separated by a separating funnel. The organic layer was washed with a saturated aqueous sodium chloride solution and died over anhydrous magnesium sulfate. The solvent was removed under reduced pressure to give allyl [(3S,4R)-3-[(1R)-1-hydroxyethyl]-2-oxo-4-(2-oxo-2-{3-[({[(trichlorocetyl)amino]carbonyl}oxy)methyl]phenyl}ethyl)azetidin-1-yl](triphenylphosphoranilidene)acetate (yellowish white amorphous).

LC/MS (EI) 811 (M+1)+. IR(ATR) 3286(broad), 1794, 1767, 1728, 1508, 1439, 1246, 1169, 1103, 1045, 999, 825, 748, 690, 667 cm$^{-1}$.

Step d)

Allyl [(3S,4R)-3-[(1R)-1-hydroxyethyl]-2-oxo-4-(2-oxo-2-{3-[({[(trichloroacetyl)amino]carbonyl}oxy)methyl]phenyl}ethyl)azetidin-1-yl](triphenylphosphoranilidene)acetate prepared in the above step c) without purification, was dissolved in dichloromethane (15 ml), and thereto were added 4-dimethylaminopyridine (1.00 g) and allyl chloroformate (921 mg). The mixture was stirred for 5 days. The reaction mixture was poured into ice water and diluted with chloroform. The aqueous layer was acidified with an aqueous 5% potassium hydrogensulfate solution, extracted and separated by a separating funnel. The organic layer was washed successively with a saturated aqueous sodium chloride solution, a saturated aqueous sodium hydrogencarbonate solution and a saturated aqueous sodium chloride solution, and dried over anhydrous magnesium sulfate. The solvent was removed under reduced pressure and the residue was purified by silica gel column chromatography (chloroform, followed by chloroform/methanol=100/1~100/4) to give allyl {(2R,3S)-3-((1R)-1-{[(allyloxy)carbonyl]oxy}ethyl)-2-[2-(3-{[(aminocarbonyl)oxy]methyl}phenyl)-2-oxoethyl]-4-oxoazetidin-1-yl}(triphenylphosphoranilidene)acetate (553 mg, yellowish brown oil).

LC/MS (EI) 750 (M+1)+. IR(ATR) 3359(broad), 2974, 2939, 1736, 1616, 1250, 1103, 1053, 752, 717, 690 cm$^{-1}$.

Reference Example 28

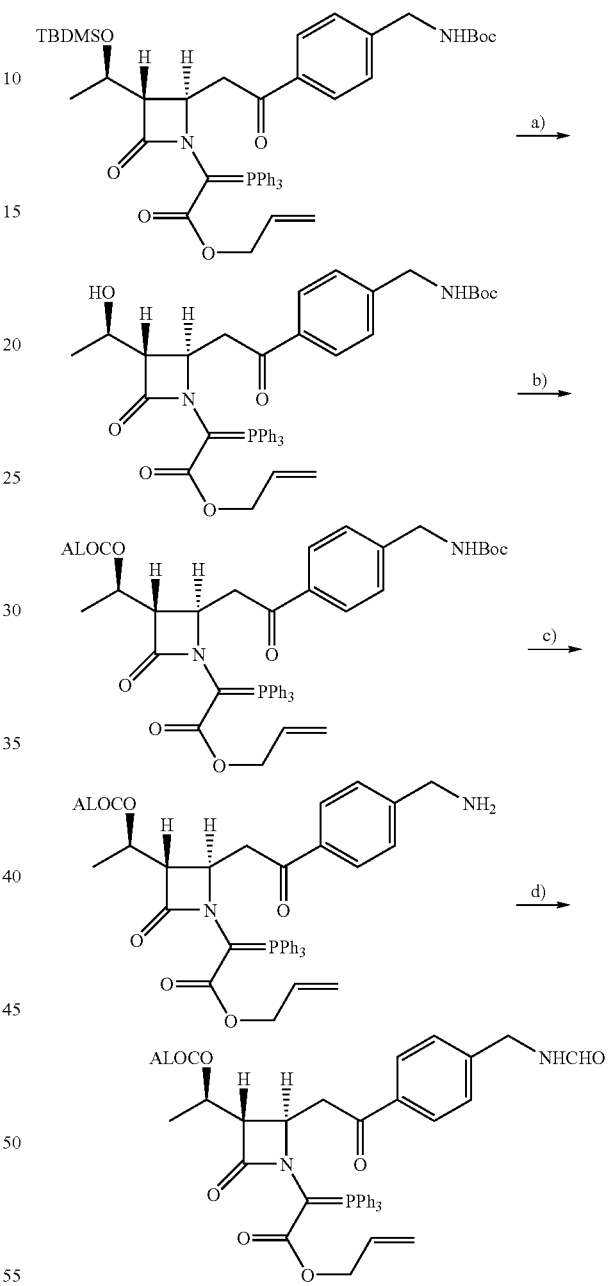

Step a)

To a solution of allyl [(2R,3S)-2-[2-(4-{[(tert-butoxycarbonyl)amino]methyl}phenyl)-2-oxoethyl]-3-((1R)-1-{[tert-butyl(dimethyl)silyl]oxy}ethyl)-4-oxoazetidin-1-yl](triphenylphosphoranilidene)acetate (10.06 g) prepared by step a) of reference example 9 and acetic acid (5.79 g) in THF (30 ml) was dropped 1M tetrabutylammonium fluoride/THF (60 ml). The mixture was heated for 7 hours in a bath at 40° C. and stirred at room temperature for 20 hours. To the reaction solution were added ethyl acetate and a cold saturated aqueous sodium chloride solution and the mixture was extracted and separated by a separating funnel. The organic layer was washed successively with a cold aqueous sodium hydrogencarbonate and a cold saturated aqueous sodium chloride solution and dried over anhydrous sodium sulfate. The solvent was removed under reduced pressure. The residue was purified by silica gel column chromatography (hexane/ethyl acetate=1/1~1/2, followed by only ethyl acetate) to give allyl {(2R,3S)-2-[2-(4-{[(tert-butoxycarbonyl)amino]methyl}phenyl)-2-oxoethyl]-3-[(1R)-1-hydroxyethyl]-4-oxoazetidin-1-yl}(triphenylphosphoranilidene)acetate (7.185 g, brown amorphous).

IR(ATR) 3348(broad), 2978, 1736, 1709, 1682, 1608, 1439, 1365, 1250, 1165, 1103, 752, 717, 690 cm$^{-1}$. LC/MS (EI) 722 (M+1)+.

Step b)

To a solution of the compound (7.17 g) prepared in the above step a) and 4-dimethylaminopyridine (3.64 g) in dichloromethane (70 ml) was added allyl chloroformate (3.36 g) and the mixture was stirred for 5 days. The reaction solution was poured into ice water and diluted with chloroform. The aqueous layer was acidified with an aqueous 5% potassium hydrogensulfate solution, extracted and separated by a separating funnel. The organic layer was washed successively with a saturated aqueous sodium chloride solution, a saturated aqueous sodium hydrogencarbonate solution and a saturated aqueous sodium chloride solution, and dried over anhydrous magnesium sulfate. The solvent was removed under reduced pressure and the residue was purified by silica gel column chromatography (hekane/ethyl acetate=2/1~1/5, followed by only ethyl acetate and then ethyl acetate/acetone=500/15~500/20) to give allyl {(2R,3S)-3-((1R)-1-{[(allyloxy)carbonyl]oxy}ethyl)-2-[2-(4-{[(tert-butoxycarbonyl)amino]methyl}phenyl)-2-oxoethyl]-4-oxoazetidin-1-yl}(triphenylphosphoranilidene)acetate (5.866 g, yellowish brown amorphous).

IR(ATR) 3329(broad), 2981, 2935, 1740, 1709, 1682, 1608, 1439, 1365, 1250, 1165, 1107, 752, 717, 690 cm$^{-1}$. LC/MS (EI) 806 (M+1)+.

Step c)

To the compound (1.10 g) prepared in the above step b) was added under ice cooling trifluoroacetic acid (3 ml) and the mixture was warmed to room temperature. After the mixture was stirred for 1 hour, thereto was added toluene and the solution was concentrated under reduced pressure. The residue was dissolved in chloroform and to the solution was added under ice cooling an aqueous sodium hydrogencarbonate solution. The aqueous layer was extracted three times with chloroform. The organic layers were combined, washed with a saturated aqueous sodium chloride solution and dried over anhydrous magnesium sulfate. The solvent was removed under reduced pressure to give allyl ((2R,3S)-3-((1R)-1-{[(allyloxy)carbonyl]oxy}ethyl)-2-{2-[4-(aminomethyl)phenyl]-2-oxoethyl}-4-oxoazetidin-1-yl)(triphenylphosphoranilidene)acetate (yellow amorphous).

IR(ATR) 1743, 1674, 1142, 1107 cm$^{-1}$. LC/MS (EI) 706 (M+1)+.

Step d)

In accordance with a method described in the literature (Synthesis, 1992, 1058), a total amount of the compound prepared in the above step c) was dissolved in dichloromethane (20 ml) and thereto was added N-(diethylcarbamoyl)-N-methoxyformamide (310 mg). After stirred at room temperature for 16 hours, the reaction mixture was concentrated under reduced pressure and the residue was dissolved in chloroform. The solution was washed with an aqueous sodium hydrogencarbonate solution, and a saturated aqueous sodium chloride solution in the order, and dried over anhydrous magnesium sulfate. The solvent was removed under reduced pressure and the residue was purified by silica gel column chromatography (chloroform, followed by chloroform/methanol=100/1~100/5) to give allyl [(2R,3S)-3-((1R)-1-{[(allyloxy)carbonyl]oxy}ethyl)-2-(2-{4-[(formylamino)methyl]phenyl}-2-oxoethyl)-4-oxoazetidin-1-yl](triphenylphosphoranilidene)acetate (721 mg, yellow amorphous).

IR(ATR) 3298(broad), 3059, 2935, 1740, 1678, 1608, 1439, 1377, 1450, 1103, 752, 717, 690 cm$^{-1}$. LC/MS (EI) 733 (M+1)+.

Reference Example 29

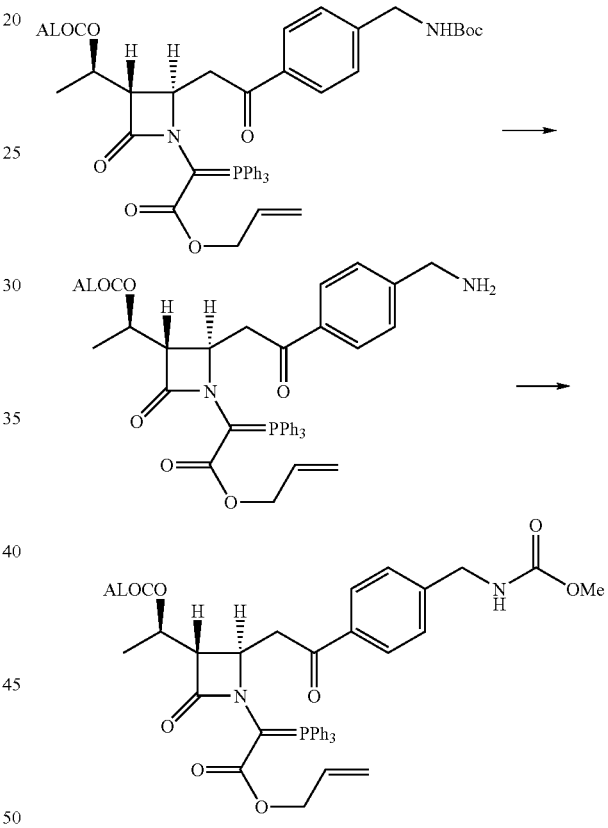

Allyl {(2R,3S)-3-((1R)-1-{[(allyoxy)carbonyl]oxy}ethyl)-2-[2-(4-{[(tert-butoxycarbonyl)amino]methyl}phenyl)-2-oxoethyl]-4-oxoazetidin-1-yl}(triphenylphosphoranilidene)acetate (1.258 g) prepared by step b) of reference example 28, was treated in the same manner as step c) of reference example 9xxx1 to give allyl ((2R,3S)-3-((1R)-1-{[(allyloxy)carbonyl]oxy}ethyl)-2-{2-[4-(aminomethyl)phenyl]-2-oxoethyl}-4-oxoazetidin-1-yl)(triphenylphosphoranilidene)acetate and this product was dissolved in THF (20 ml). Thereto was added triethylamine (1.0 ml), followed by methyl chloroformate (151 mg) and the mixture was stirred for 5 hours. The reaction mixture was poured into ice water, extracted with ethyl acetate and separated by a separating funnel. The organic layer was washed with a saturated aqueous sodium chloride solution and dried over anhydrous magnesium sulfate. The solvent was removed under reduced pressure and the residue was purified by silica gel column chromatography (hexane/ethyl acetate=1/1~1/2, followed with ethyl acetate alone) to give allyl {(2R,3S)-3-((1R)-1-{[(allyloxy)carbonyl]oxy}ethyl)-2-[2-(4-{[(methoxycarbonyl)amino]methyl}phenyl)-2-oxo-ethyl]-4-oxoazetidin-1-yl}(triphenylphosphoranilidene)acetate (801 mg, yellowish white amorphous).

IR(ATR) 3305(broad), 3059, 2942, 1740, 1250, 1103, 752, 717, 690 cm$^{-1}$. LC/MS (EI) 764 (M+1)+.

Reference Example 30

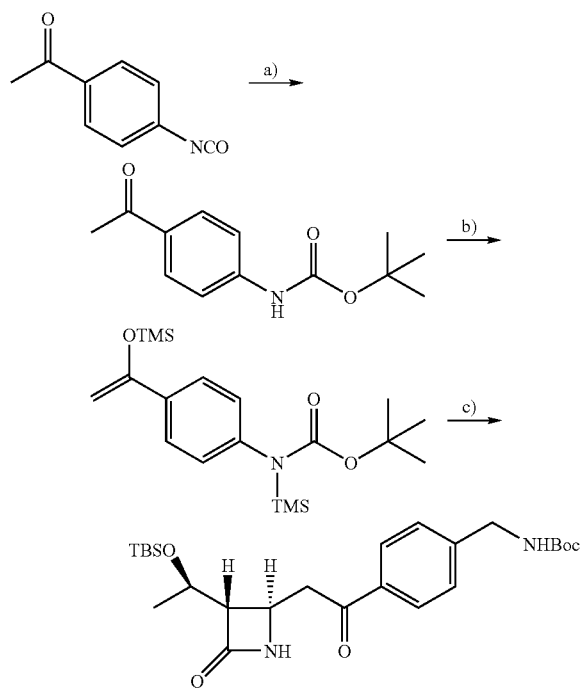

Step a)

A mixture of 4-acetylphenylisocyanate (20.00 g), t-butyl alcohol (31.00 g) and dioxane (60 mL) was heated at 60° C. and thereto was dropped triethylamine (20.40 g). After stirring for 6 hours, the reaction mixture was poured into ice water, diluted with ethyl acetate, extracted and separated. The organic layer was washed successively with a saturated aqueous sodium hydrogencarbonate solution and a saturated aqueous sodium chloride solution, and dried over anhydrous sodium sulfate. The solvent was removed under reduced pressure to give a pale yellow powder. Thereto was added hexane (100 mL) and the solution was stirred for 20 minutes, filtered, washed and dried under reduced pressure to give p-(N-tert-butoxycarbonyl)aminoacetophenone (24.61 g).

$^1$H NMR (400 MHz, CDCl$_3$) δ 1.47 (s, 9H), 2.56 (s, 3H), 7.42 (d, 2H, J=20 Hz), 7.90 (d, 2H, J=20 Hz).

Step b)

A solution of p-(N-t-butoxycarbonyl)aminoacetophenone (23.20 g) prepared in the above step in dichloromethane (116 mL) was cooled at −10° C. to −15° C. Thereto were gradually dropped triethylamine (20.98 g) and trifluoromethanesulfonic acid trimethylsilyl ester (43.84 g) in the order and the mixture was stirred at the same temperature for 1.5 hours. The reaction mixture was diluted with hexane, washed successively with a saturated aqueous sodium hydrogencarbonate solution and a saturated aqueous sodium chloride solution, and dried over anhydrous sodium sulfate. The solvent was removed under reduced pressure to give tert-butyl trimethylsilyl(4-{1-[(trimethylsilyl)oxy]vinyl}phenyl) carbamate (36.4 g).

$^1$H NMR (400 MHz, CDCl$_3$) δ 0.17 (s, 9H), 60.24 (s, 9H),. 61.48 (s, 9H), 4.38 (s, 1H), 4.86 (s, 1H), 6.98 (d, 2H, J=16 Hz), 7.52 (d, 2H, J=16 Hz).

Step c)

To a solution of the compound (about 98.60 mmol) prepared in the above and (2R,3R)-3-((1R)-1-{[tert-butyl(dimethyl)silyl]oxy}ethyl)-4-oxo-2-azetidinyl acetate (28.34 g) in dichloromethane (727 mL) was added at room temperature zinc iodide (9.44 g) and the mixture was stirred at the same temperature for 4 hours. The reaction mixture was poured into ice water, diluted with ethyl acetate, extracted and separated. The organic layer was washed successively with a saturated aqueous sodium hydrogencarbonate solution and a saturated aqueous sodium chloride solution, and dried over anhydrous sodium sulfate. The solvent was removed under reduced pressure to give a crude product. The product was purified by silica gel column chromatography to give tert-butyl 4-{[(2R,3S)-3-((1R)-1-{[tert-butyl(dimethyl)silyl]oxy}ethyl)-4-oxoazetidin-2-yl]acetyl}phenyl carbamate (24.60 g).

$^1$H NMR (400 MHz, CDCl$_3$) δ 0.07 (s, 6H), 0.87 (s, 9H), 1.24 (d, 3H, J=6.0 Hz), 2.87 (dd, 1H, J=2.4 Hz, 5.2 Hz), 3.11 (dd, 1H, J=10.0 Hz, 17.6 Hz), 3.41 (dd, 1H, J=2.8 Hz, 17.2 Hz), 4.08–4.12 (m, 1H), 4.20–4.23 (m, 1H), 6.11 (s, 1H), 6.71 (s, 1H), 7.47 (d, 2H, J=8.0 Hz), 7.89 (d, 2H, J=8.0 Hz).

Reference Example 31

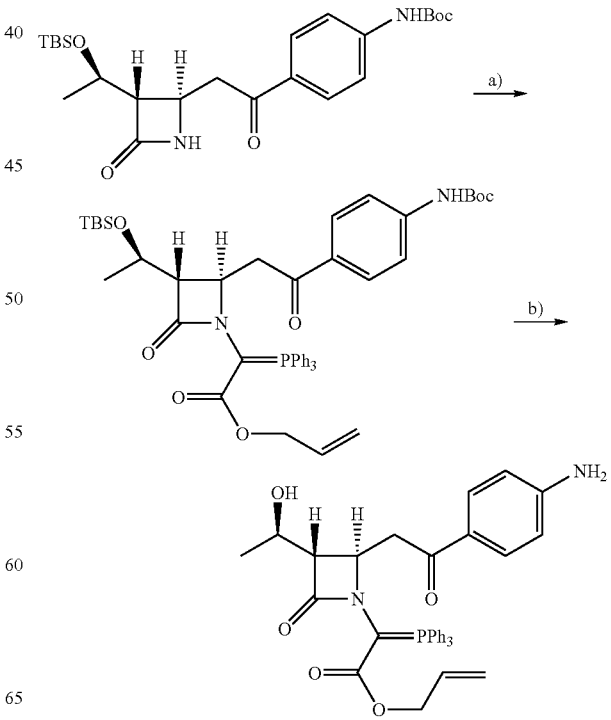

Step a)

In the same manner as step a) of reference example 9, from tert-butyl 4-{[(2R,3S)-3-((1R)-1-{[tert-butyl(dimethyl)silyl]oxy}ethyl)-4-oxoazetidin-2-yl]acetyl}phenylcarbamate prepared by step c) of reference example 30, there was obtained allyl [(2R,3S)-2-(2-{4-[(tert-butoxycarbonyl)amino]phenyl}-2-oxoethyl)-3-((1R)-1-{[tert-butyl(dimethyl)silyl]oxy}ethyl)-4-oxoazetidin-1-yl](triphenylphosphoranilidene)acetate (30.3 g).

LC/MS (EI) 822 (M+1)

Step b)

In the same manner as step b) of reference example 9, from the compound (3.0 g) prepared in the above step, there was obtained allyl {(2R,3S)-2-[2-(4-aminophenyl)-2-oxoethyl]-3-[(1R)-1-hydroxyethyl]-4-oxoazetidin-1-yl}(triphenylphosphoranilidene)acetate (2.53 g).

LC/MS (EI) 607 (M+1)

Reference Example 32

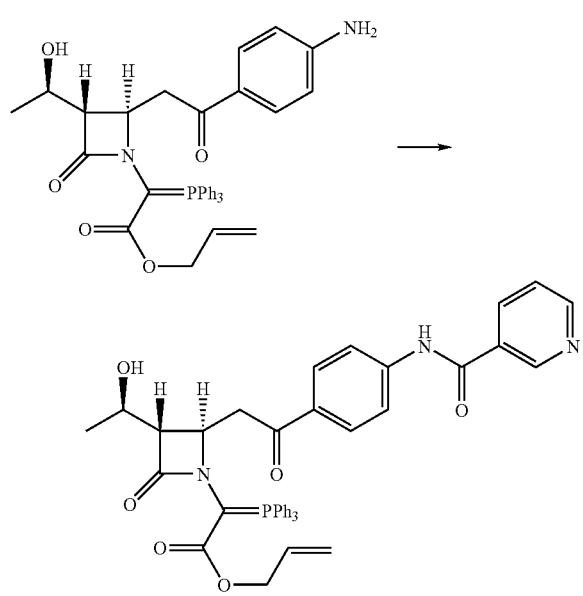

Allyl {(2R,3S)-2-[2-(4-aminophenyl)-2-oxoethyl]-3-[(1R)-1-hydroxyethyl]-4-oxoazetidin-1-yl}(triphenylphosphoranilidene)acetate (2.51 g) prepared by step b) of reference example 31 was dissolved in pyridine (50 mL) and the solution was cooled at 0° C. Thereto was gradually dropped a solution of nicotinoyl chloride hydrochloride (0.85 g) in pyridine (50 mL). The mixture was stirred at the same temperature for 10 minutes and then, diluted with ethyl acetate. The reaction mixture was poured into ice water, extracted with ethyl acetate and separated. The organic layer was washed successively with a saturated aqueous sodium hydrogencarbonate solution and a saturated aqueous sodium chloride solution, and dried over anhydrous sodium sulfate. The solvent was removed under reduced pressure to give allyl [(3S,4R)-3-[(1R)-1-hydroxyethyl]-2-oxo-4-(2-oxo-2-{4-[(pyridin-3-ylcarbonyl)amino]phenyl}ethyl)azetidin-1-yl](triphenylphosphoranilidene)acetate (3.32 g).

LC/MS (EI) 712 (M+1)

Reference Example 33

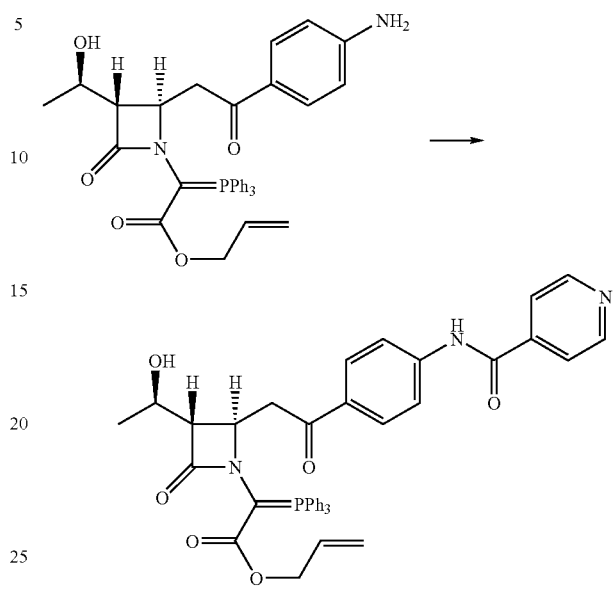

In the same manner as reference example 32 and at the reaction temperature of 50° C., from allyl {(2R,3S)-2-[2-(4-aminophenyl)-2-oxoethyl]-3-[(1R)-1-hydroxyethyl]-4-oxoazetidin-1-yl}(triphenylphosphoranilidene)acetate prepared by step b) of reference example H2, there was obtained allyl ((2R,3S)-3-[(1R)-1-hydroxyethyl]-2-{2-[4-(isonicotinoylylamino)phenyl]-2-oxoethyl}-4-oxoazetidin-1-yl)(triphenylphosphoranilidene)acetate.

LC/MS (EI) 712 (M+1)

Reference Example 34

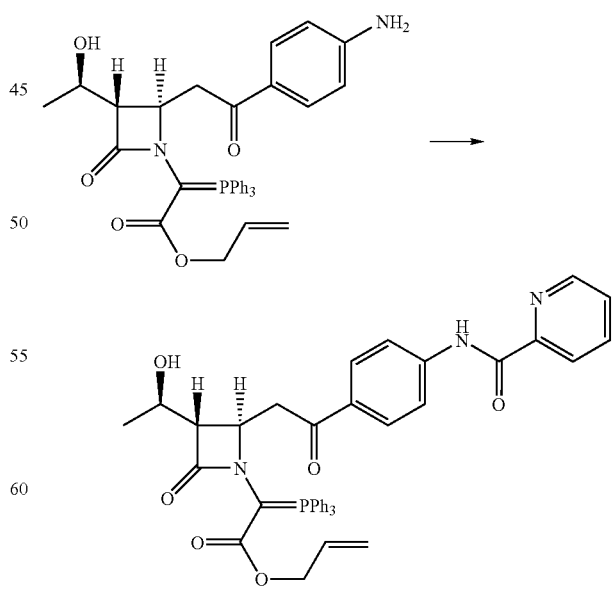

In the same manner as reference example 32, from allyl {(2R,3S)-2-[2-(4-aminophenyl)-2-oxoethyl]-3-[(1R)-1-hydroxyethyl]-4-oxoazetidin-1-yl}(triphenylphosphoranilidene)acetate (2.50 g) prepared by step b) of reference example 31, there was obtained allyl [(3S,4R)-3-[(1R)-1-hydroxyethyl]-2-oxo-4-(2-oxo-2-{4-[(pyridin-2-ylcarbonyl)amino]phenyl}ethyl)azetidin-1-yl](triphenylphosphoranilidene)acetate (2.69 g).

LC/MS (EI) 712 (M+1)

Reference Example 35

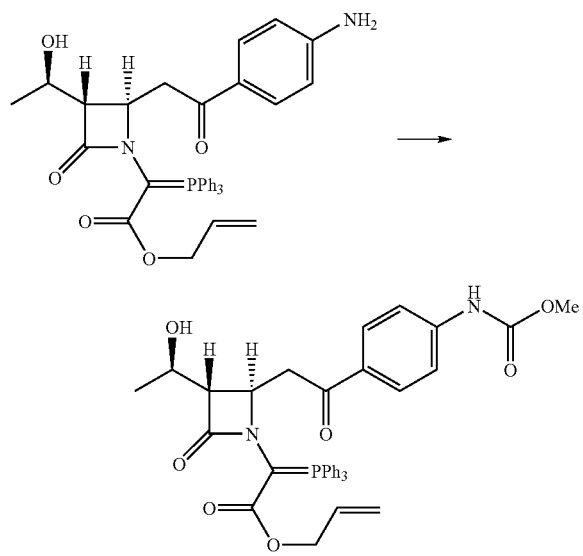

In the same manner as reference example 32, from allyl {(2R,3S)-2-[2-(4-aminophenyl)-2-oxoethyl]-3-[(1R)-1-hydroxyethyl]-4-oxoazetidin-1-yl}(triphenylphosphoranilidene)acetate prepared by step b) of reference example 31, there was obtained allyl [(2R,3S)-3-[(1R)-1-hydroxyethyl]-2-(2-{4-[(methoxycarbonyl)amino]phenyl}-2-hydroxyethyl)-4-oxoazetidin-1-yl](triphenylphosphoranilidene)acetate.

LC/MS (EI) 665 (M+1)

Reference Example 36

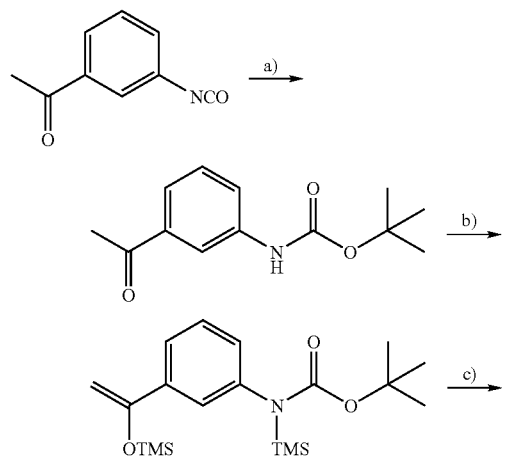

-continued

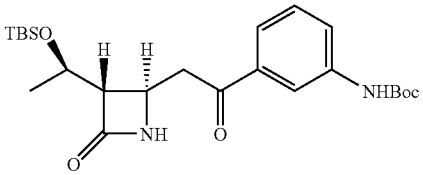

Step a)

In the same manner as step a) of reference example 30, from 3-acetylphenyl isocyanate (25.00 g) and tert-butyl alcohol (38.75 g), there was obtained m-(N-tert-butoxycarbonyl)-aminoacetophenone (33.78 g).

$^1$H NMR (400 MHz, CDCl$_3$) δ 1.52 (s, 9H), 2.60 (s, 3H), 6.58 (s, 1H), 7.38 (t, 1H, J=8.0 Hz), 7.60–7.65 (m, 2H), 7.91 (s, 1H).

Step b)

In the same manner as step b) of reference example 30, from m-(N-tert-butoxycarbonyl)aminoacetophenone (33.78 g) prepared in the above step, there was obtained tert-butyl trimethylsilyl(3-{1-[(trimethylsilyl)oxy]vinyl}phenyl)carbamate (55.7 g).

$^1$H NMR (400 MHz, CDCl$_3$) δ 0.17 (s, 9H), 60.24 (s, 9H), 81.48 (s, 9H), 4.42 (s, 1H), 4.89 (s, 1H), 6.96 (d, 1H, J=8.0 Hz), 7.20 (s, 1H), 7.26 (t, 1H, J=8.0 Hz), 7.43 (d, 1H, J=8.0 Hz).

Step c)

In the same manner as step c) of reference example 30, from the compound prepared in the above step, there was obtained tert-butyl 3-{[(2R,3S)-3-((1R)-1-{[tert-butyl(dimethyl)silyl]oxy}ethyl)-4-oxoazetidin-2-yl]acetyl}phenyl carbamate (52.9 g).

$^1$H NMR (400 MHz, CDCl$_3$) δ 0.08 (s, 6H), 0.87 (s, 9H), 1.25 (d, 3H, J=6.4 Hz), 2.89 (dd, 1H, J=2.4 Hz, 5.2 Hz), 3.16 (dd, 1H, J=10.4 Hz, 17.6 Hz), 3.45 (dd, 1H, J=3.2 Hz, 18.0 Hz), 4.09–4.14 (m, 1H), 4.21–4.23 (m, 1H), 6.10 (s, 1H), 6.60 (s, 1H), 7.40 (t, 1H, J=8.0 Hz), 7.60 (t, 2H, J=8.0 Hz), 7.97 (s, 1H).

Reference Example 37

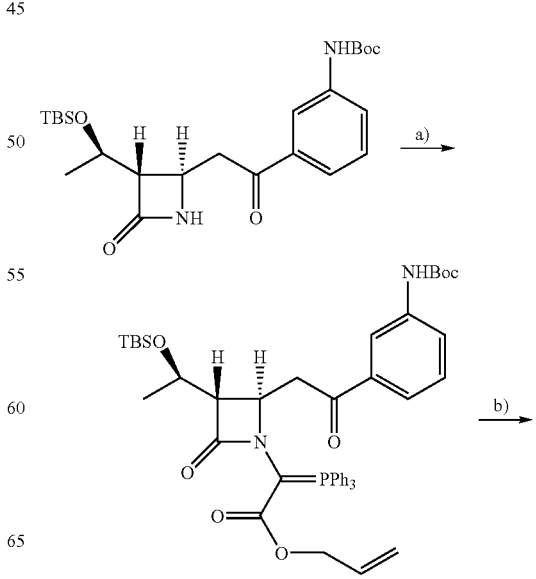

-continued

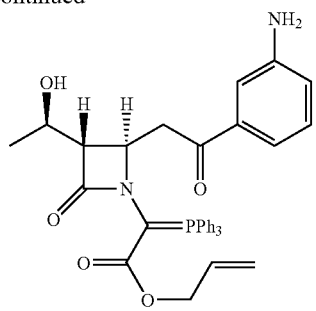

Step a)
In the same manner as step a) of reference example 9, from tert-butyl 3-{[(2R,3S)-3-((1R)-1-{[tert-butyl(dimethyl)silyl]oxy}ethyl)-4-oxoazetidin-2-yl]acetyl}phenyl carbamate (34.49 g) prepared by reference example 36, there was obtained allyl [(2R,3S)-2-(2-{3-[(tert-butoxycarbonyl)amino]phenyl}-2-oxoethyl)-3-((1R)-1-{[tert-butyl(dimethyl)silyl]oxy}ethyl)-4-oxoazetidin-1-yl](triphenylphosphoranilidene)acetate (40.90 g).
LC/MS (EI) 822 (M+1)

Step b)
In the same manner as step b) of reference example 9, from the compound (10.0 g) prepared in the above step, there was obtained allyl {(2R,3S)-2-[2-(3-aminophenyl)-2-oxoethyl]-3-[(1R)-1-hydroxyethyl]-4-oxoazetidin-1-yl}(triphenylphosphoranilidene)acetate (8.01 g).
LC/MS (EI) 607 (M+1)

Reference Example 38

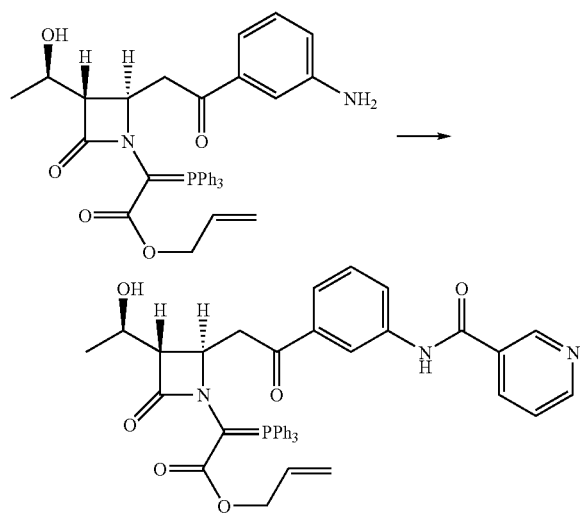

In the same manner as reference example 32, from allyl {(2R,3S)-2-[2-(3-aminophenyl)-2-oxoethyl]-3-[(1R)-1-hydroxyethyl]-4-oxoazetidin-1-yl}(triphenylphosphoranilidene)acetate prepared by step b) of reference example 37, there was obtained allyl [(3S,4R)-3-[(1R)-1-hydroxyethyl]-2-oxo-4-(2-oxo-2-{3-[(pyridin-3-ylcarbonyl)amino]phenyl}ethyl)azetidin-1-yl](triphenylphosphoranilidene)acetate.
LC/MS (EI) 712 (M+1)

Reference Example 39

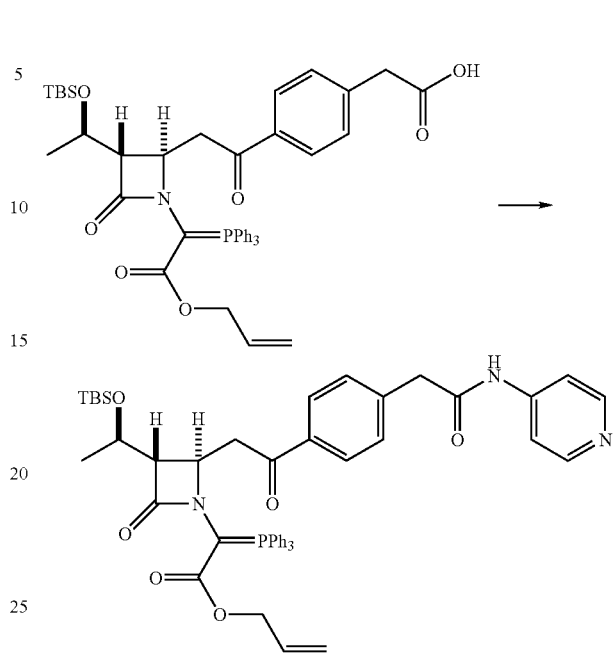

To a solution of (4-{[(2R,3S)-1-[2-(allyloxy)-2-oxo-1-(triphenylphosphoranilidene)ethyl]-3-((1R)-1-{[tert-butyl(dimethyl)silyl]oxy}ethyl)-4-oxoazetidin-2-yl]acetyl}phenyl)acetic acid (3.76 g) prepared by step b) of reference example 23 in dichloromethane (40 ml) were added dimethylformamide (1 drop) and thionyl chloride (0.43 ml) and the mixture was stirred for 2 hours. The reaction mixture was concentrated and dissolved in dichloromethane (40 ml). Thereto were added triethylamine (3.43 ml), 4-dimethylaminopyridine (1.8 g) and 4-aminopyridine (0.93 g), and the mixture was stirred for 4 hours. To the reaction mixture was added ethyl acetate and the mixture was washed with an aqueous sodium hydrogencarbonate solution and a saturated aqueous sodium chloride solution. After the organic layer was dried and concentrated, the residue was purified by silica gel column chromatography (chloroform: methanol=30:1) to give allyl [(3S,4R)-3-((1R)-1-{[tert-butyl(dimethyl)silyl]oxy}ethyl)-2-oxo-4-(2-oxo-2-{4-[2-oxo-2-(pyridin-4-ylamino)ethyl]phenyl}ethyl)azetidin-1-yl](triphenylphosphoranilidene)acetate (1.0 g).
LC/MS (EI) 841 (M+1)

Reference Example 40

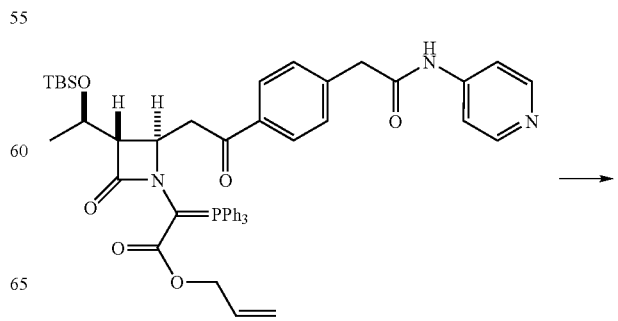

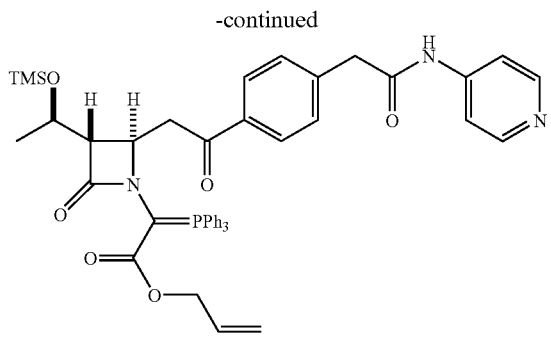

In the same manner as step d) of reference example 23 and step a) of Example 2, from allyl [(3S,4R)-3-((1R)-1-{[tert-butyl(dimethyl)silyl]oxy}ethyl)-2-oxo-4-(2-oxo-2-{4-[2-oxo-2-(pyridin-4-ylamino)ethyl]phenyl}ethyl)azetidin-1-yl](triphenylphosphoranilidene)acetate (1.0 g) prepared by reference example 39, there was obtained allyl ((3S,4R)-2-oxo-4-(2-oxo-2-{4-[2-oxo-2-(pyridin-4-ylamino)ethyl]phenyl}ethyl)-3-{(1R)-1-[(trimethylsilyl)oxy]ethyl}azetidin-1-yl)(triphenylphosphoranilidene)acetate (0.72 g).

Reference Example 41

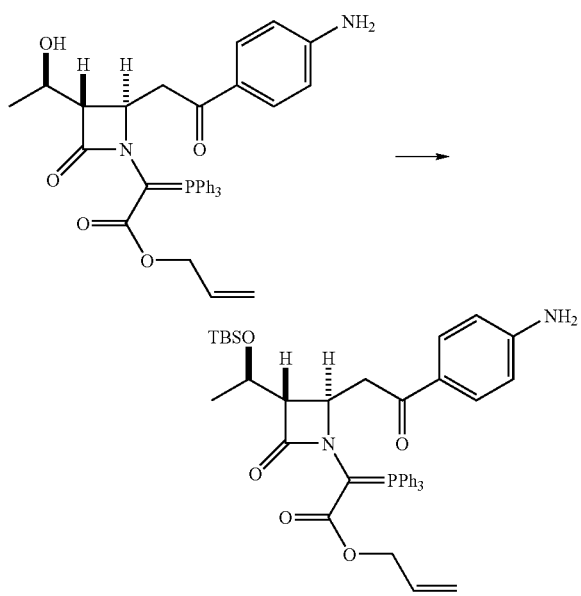

To a solution of allyl {(2R,3S)-2-[2-(4-aminophenyl)-2-oxoethyl]-3-[(1R)-1-hydroxyethyl]-4-oxoazetidin-1-yl}(triphenylphosphoranilidene)acetate prepared by step b) of reference example 31 in dimethylformamide was added imidazole and the solution was stirred for 12 hours. The reaction mixture was diluted with ethyl acetate, washed with a saturated aqueous ammonium chloride solution and a saturated aqueous sodium chloride solution. The organic layer was dried, concentrated and the residue was purified by silica gel column chromatography (hexane: ethyl acetate=1:3) to give allyl [(2R,3S)-2-[2-(4-aminophenyl)-2-oxoethyl]-3-((1R)-1-{[tert-butyl(dimethyl)silyl]oxy}ethyl)-4-oxoazetidin-1-yl](triphenylphosphoranilidene)acetate (2.13 g).

LC/MS (EI) 763 (M+1)

Reference Example 42

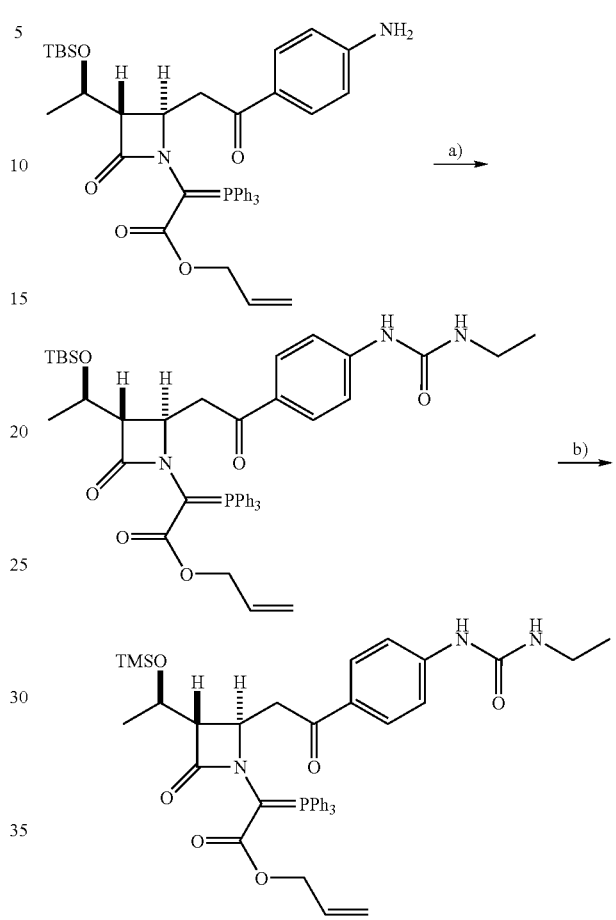

Step a)

To a solution of allyl [(2R,3S)-2-[2-(4-aminophenyl)-2-oxoethyl]-3-((1R)-1-{[tert-butyl(dimethyl)silyl]oxy}ethyl)-4-oxoazetidin-1-yl](triphenylphosphoranilidene)acetate (1.92 g) prepared by reference example 41 in tetrahydrofuran were added triethylamine (2.43 g) and ethyl isocyanate (0.84 g) and the mixture was stirred at 50° C. for 30 hours. To the reaction mixture was added ethyl acetate and the mixture was washed with an aqueous sodium hydrogencarbonate solution and a saturated aqueous sodium chloride solution. The organic layer was dried and concentrated to give allyl {(2R,3S)-3-((1R)-1-{[tert-butyl(dimethyl)silyl]oxy}ethyl)-2-[2-(4-{[(ethylamino)carbonyl]amino}phenyl)-2-oxoethyl]-4-oxoazetidin-1-yl}(triphenylphosphoranilidene)acetate (2.06 g).

LC/MS (EI) 792 (M+1)

Step b)

In the same manner as step d) of reference example 23 and step a) of example 2, from allyl {(2R,3S)-3-((1R)-1-{[tert-butyl(dimethyl)silyl]oxy}ethyl)-2-[2-(4-{[(ethylamino)carbonyl]amino}phenyl)-2-oxoethyl]-4-oxoazetidin-1-yl}(triphenylphosphoranilidene)acetate, there was obtained allyl ((2R,3S)-2-[2-(4-{[(ethylamino)carbonyl]amino}phenyl)-2-oxoethyl]-4-oxo-3-{((1R)-1-[(trimethylsilyl)oxy]ethyl}azetidin-1-yl)(triphenylphosphoranilidene)acetate.

LC/MS (EI) 750 (M+1)

Reference Example 43

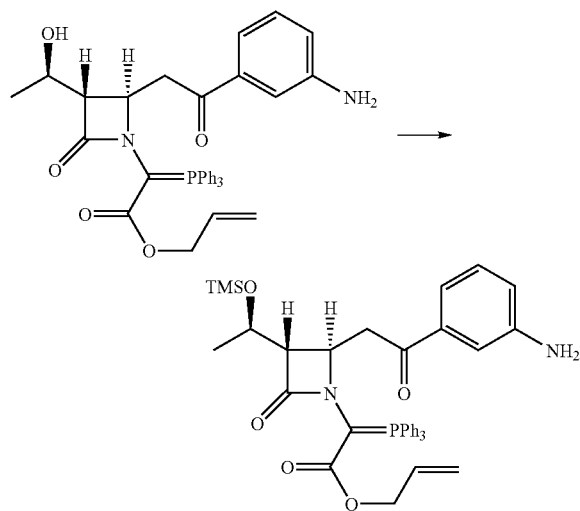

In the same manner as step b) of reference example 2, from allyl {(2R,3S)-2-[2-(3-aminophenyl)-2-oxoethyl]-3-[(1R)-1-hydroxyethyl]-4-oxoazetidin-1-yl}(triphenylphosphoranilidene)acetate prepared by step b) of reference example 37, there was obtained allyl ((2R,3S)-2-[2-(3-aminophenyl)-2-oxoethyl]-4-oxo-3-{(1R)-1-[(trimethylsilyl)oxy]ethyl}azetidin-1-yl)(triphenylphosphoranilidene)acetate.

LC/MS (EI) 679 (M+1)

Reference Example 44

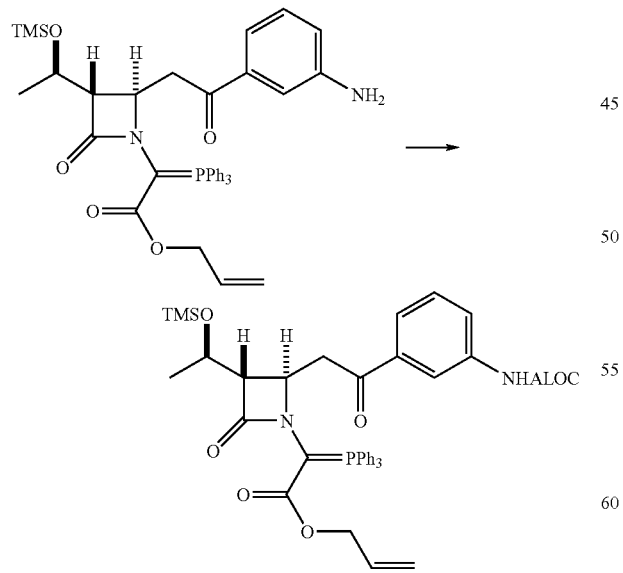

To a solution of allyl ((2R,3S)-2-[2-(3-aminophenyl)-2-oxoethyl]-4-oxo3-{(1R)-1-[(trimethylsilyl)oxy]ethyl}azetidin-1-yl)(triphenylphosphoranilidene)acetate (2.24 g) prepared by reference example 43 in dichloromethane, were added 4-dimethylaminopyridine (2.04 g) and allyl chloroformate (1.06 g). The mixture was stirred for 2 hours. The reaction mixture was diluted with ethyl acetate and washed with an aqueous sodium hydrogencarnonate solution and a saturated aqueous sodium chloride solution. The organic layer was dried, concentrated and the residue was purified with silica gel column chromatography (hexane: ethyl acetate=1:3) to give allyl [(2R,3S)-2-[2-(3-{[(allyloxy)carbonyl]amino}phenyl)-2-oxoethyl]-3-{(1R)-1-[(trimethylsilyl)oxy]ethyl}-4-oxoazetidin-1-yl](triphenylphosphoranilidene)acetate (1.65 g).

LC/MS (EI) 763 (M+1)

INDUSTRIAL APPLICABILITY

By the present invention, it becomes possible to provide a β-lactam antibiotic with a high oral absorbability showing an excellent antibacterial activity over a broad range of Gram-positive and Gram-negative bacteria, in particular, penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-regisant (BLNAR) *Haemophilus influenzae*.

The invention claimed is:

1. A carbapenem compound represented by the formula [1]:

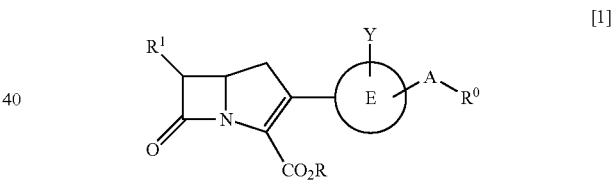

wherein ring E is benzene or thiophene;
$R^1$ is $C_1$ to $C_3$ alkyl or $C_1$ to $C_3$ alkyl substituted by hydroxy;
A is —$CH_2$—O— and $R^0$ is the formula [2]:

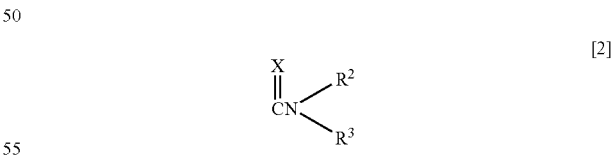

wherein X is oxygen atom, $R^2$ is (1) hydrogen atom, (2) $C_1$ to $C_6$ alkyl, (3) $C_3$ to $C_7$ cycloalkyl, (4) aryl which may optionally contain heteroatom(s) therein, (5) aralkyl in which ring may optionally contain heteroatom(s), or (6) 3 to 7 membered hetero ring, $R^3$ is (2) $C_1$ to $C_6$ alkyl, (3) $C_3$ to $C_7$ cycloalkyl, (4) aryl which may optionally contain heteroatom(s) therein, (5) aralkyl in which ring may optionally contain heteroatom(s), or (6) 3 to 7 membered hetero ring; or $R^2$ and $R^3$ are combined together with the N atom to form a 3 to 7 membered hetero ring, or A is —CH$_2$—NH— and R$^0$ is the formula [3]:

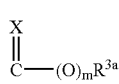

[3]

wherein X is oxygen atom, m is 1, R$^{3a}$ is C$_1$ to C$_6$ alkyl, C$_3$ to C$_7$ cycloalkyl, aryl which may optionally contain heteroatom(s) therein, aralkyl in which ring may optionally contain heteroatom(s), or 3 to 7 membered hetero ring;

R is hydrogen atom,

C$_1$ to C$_6$ alkyl, C$_2$ to C$_{12}$ alkyloxyalkyl, (2-oxo-1,3-dioxol-4-yl)methyl, (5-methyl-2-oxo-1,3-dioxol-4-yl)methyl, (5-tert-butyl-2-oxo-1,3-dioxol-4-yl)methyl, (5-phenyl-2-oxo-1,3-dioxol-4-yl)methyl, or the formula [4]:

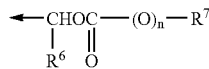

[4]

wherein R$^6$ is hydrogen atom or C$_1$ to C$_6$ alkyl, R$^7$ is C$_1$ to C$_6$ alkyl, or C$_3$ to C$_7$ cycloalkyl and n is 0 or 1, and Y is hydrogen atom, or its pharmaceutically acceptable salt.

2. A carbapenem compound represented by the formula [1d]:

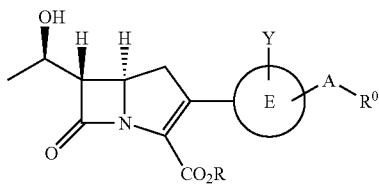

[1d]

wherein ring E is benzene or thiophene;

A is —CH$_2$—O— and R$^0$ the formula [2]:

[2]

wherein X is oxygen atom, R$^2$ is (1) hydrogen atom, (2) C$_1$ to C$_6$ alkyl, (3) C$_3$ to C$_7$ cycloalkyl, (4) aryl which may optionally contain heteroatom(s) therein, (5) aralkyl in which ring may optionally contain heteroatom(s), or (6) 3 to 7 membered hetero ring, R$^3$ is (2) C$_1$ to C$_6$ alkyl, (3) C$_3$ to C$_7$ cycloalkyl, (4) aryl which may optionally contain heteroatom(s) therein, (5) aralkyl in which ring may optionally contain heteroatom(s), or (6) 3 to 7 membered hetero ring; or R$^2$ and R$^3$ are combined together with the N atom to form a 3 to 7 membered hetero ring, or A is —CH$_2$—NH— and R$^0$ is the formula [3]:

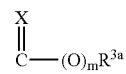

[3]

wherein X is oxygen atom, m is 1, R$^{3a}$ is C$_1$ to C$_6$ alkyl, C$_3$ to C$_7$ cycloalkyl, aryl which may optionally contain heteroatom(s) therein, aralkyl in which ring may optionally contain heteroatom(s), or 3 to 7 membered hetero ring;

R is hydrogen atom, C$_1$ to C$_6$ alkyl, C$_2$ to C$_{12}$ alkyloxyalkyl, (2-oxo-1,3-dioxol-4-yl)methyl, (5-methyl-2-oxo-1,3-dioxol-4-yl)methyl, (5-tert-butyl-2-oxo-1,3-dioxol-4-yl)methyl, (5-phenyl-2-oxo-1,3-dioxol-4-yl)methyl, or the formula [4]:

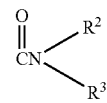

[4]

wherein R$^6$ is hydrogen atom or C$_1$ to C$_6$ alkyl, R$^7$ is C$_1$ to C$_6$ alkyl or C$_3$ to C$_7$ cycloalkyl, and n is 0 or 1;

Y is hydrogen atom, or its pharmaceutically acceptable salt.

3. The carbapenem compound or its pharmaceutically acceptable salt according to claim 2, wherein ring E is benzene, A is —CH$_2$O— and R$^0$ is the formula [2a]:

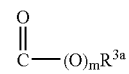

[2a]

wherein R$^2$ is hydrogen atom or C$_1$ to C$_6$ alkyl, and R$^3$ is C$_1$ to C$_6$ alkyl, or A is —CH$_2$NH— and R$^0$ is the formula [3a]:

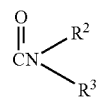

[3a]

wherein m is 1, and R$^{3a}$ is C$_1$ to C$_6$ alkyl.

4. The carbapenem compound or its pharmaceutically acceptable salt according to claim 2, wherein ring E is benzene, A is —CH$_2$O— and R$^0$ is the formula [2a]:

[2a]

wherein R$^2$ is hydrogen atom or C$_1$ to C$_6$ alkyl and R$^3$ is C$_1$ to C$_6$ alkyl, or A is —CH$_2$NH— and R$^0$ is the formula [3a]:

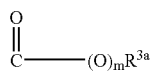

[3a]

wherein m is 1, and R$^{3a}$ is C$_1$ to C$_6$ alkyl,

R is hydrogen atom, (5-methyl-2-oxo-1,3-dioxol-4-yl) methyl, or the formula [4]:

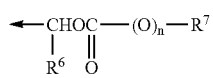

[4]

wherein R$^6$, R$^7$ and n are the same as defined in claim 2.

5. The carbapenem compound or its pharmaceutically acceptable salt according to claim 2, wherein ring E is benzene, A is —CH$_2$O— and R$^0$ is the formula [2a]:

[2a]

wherein R$^2$ is hydrogen atom and R$^3$ is C$_1$ to C$_6$ alkyl, or A is —CH$_2$NH— and R$^0$ is the formula [3a]:

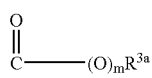

[3a]

wherein m is 1, and R$^{3a}$ is C$_1$ to C$_6$ alkyl,

R is hydrogen atom, (5-methyl-2-oxo-1,3-dioxol-4-yl) methyl, or the formula [4]:

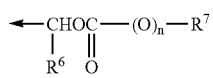

[4]

wherein R$^6$, R$^7$ and n are the same as defined in claim 2, and wherein the A is bound to the benzene ring at a meta or para position with respect to the position where 7-oxo-1-azabicyclo[3.2.0]hept-2-ene is bound to the benzene ring.

6. A pharmaceutical composition comprising the carbapenem compound or its pharmaceutically acceptable salt according to claim 1 as an active ingredient together with a pharmaceutically acceptable carrier, excipient, binder or stabilizer.

7. A pharmaceutical composition comprising the carbapenem compound or its pharmaceutically acceptable salt according to claim 2 as an active ingredient together with a pharmaceutically acceptable carrier, excipient, binder or stabilizer.

8. The carbapenem compound or its pharmaceutically acceptable salt according to claim 2, wherein ring E is benzene, R is hydrogen atom, (5-methyl-2-oxo-1,3-dioxol-4-yl)methyl, or pivaloyloxymethyl; A is —CH$_2$O— and R$^0$ is CONHCH$_3$.

9. The carbapenem compound or its pharmaceutically acceptable salt according to claim 2, wherein ring E is benzene, R is hydrogen atom, (5-methyl-2-oxo-1,3-dioxol-4-yl)methyl, or pivaloyloxymethyl; A is —CH$_2$NH— and R$^0$ is COOCH$_3$.

10. The carbapenem compound or its pharmaceutically acceptable salt according to claim 2, wherein ring E is benzene, R is hydrogen atom, (5-methyl-2-oxo-1,3-dioxol-4-yl)methyl, or pivaloyloxymethyl; A is —CH$_2$O— and R$^0$ is CONHCH$_3$, and wherein the A is bound to the benzene ring at a meta or para position with respect to the position where 7-oxo-1-azabicyclo[3.2.0]hept-2-ene is bound to the benzene ring.

11. The carbapenem compound or its pharmaceutically acceptable salt according to claim 2, wherein ring E is benzene, R is hydrogen atom, (5-methyl-2-oxo-1,3-dioxol-4-yl)methyl, or pivaloyloxymethyl; A is —CH$_2$NH— and R$^0$ is COOCH$_3$, and wherein the A is bound to the benzene ring at a meta or para position with respect to the position where 7-oxo-1-azabicyclo[3.2.0]hept-2-ene is bound to the benzene ring.

12. The carbapenem compound or its pharmaceutically acceptable salt according to claim 2, wherein ring E is benzene, R is hydrogen atom, (5-methyl-2-oxo-1,3-dioxol-4-yl)methyl, or pivaloyloxymethyl, A is —CH$_2$O— and R$^0$ is CONHCH$_3$ and wherein the A is bound to the benzene ring at a para position with respect to the position where 7-oxo-1-azabicyclo[3.2.0]hept-2-ene is bound to the benzene ring.

13. The carbapenem compound or its pharmaceutically acceptable salt according to claim 2, wherein ring E is benzene, R is hydrogen atom, (5-methyl-2-oxo-1,3-dioxol-4-yl)methyl, or pivaloyloxymethyl, A is —CH$_2$NH— and R$^0$ is COOCH$_3$, and wherein the A is bound to the benzene ring at a para position with respect to the position where 7-oxo-1-azabicyclo[3.2.0]hept-2-ene is bound to the benzene ring.

* * * * *